United States Patent
Warner et al.

(10) Patent No.: US 11,040,038 B2
(45) Date of Patent: Jun. 22, 2021

(54) METHODS FOR TREATING DISEASES ASSOCIATED WITH ABNORMAL ACVR1 EXPRESSION AND ACVR1 INHIBITORS FOR USE IN THE SAME

(71) Applicant: Sumitomo Dainippon Pharma Oncology, Inc., Cambridge, MA (US)

(72) Inventors: Steven L. Warner, Sandy, UT (US); David J. Bearss, Alpine, UT (US); Adam Siddiqui-Jain, South Jordan, UT (US); Clifford J. Whatcott, West Jordan, UT (US); Jason Marc Foulks, Sandy, UT (US); Stephen Patrick Anthony, Heber City, UT (US); Paul Flynn, Citrus Heights, CA (US); Yuji Fujiwara, Draper, UT (US); Yuka Arikawa, Minoh (JP)

(73) Assignee: SUMITOMO DAINIPPON PHARMA ONCOLOGY, INC., Cambridge, MA (US)

( * ) Notice: Subject to any disclaimer, the term of this patent is extended or adjusted under 35 U.S.C. 154(b) by 0 days.

(21) Appl. No.: 16/523,829

(22) Filed: Jul. 26, 2019

(65) Prior Publication Data
US 2020/0085823 A1    Mar. 19, 2020

Related U.S. Application Data

(60) Provisional application No. 62/703,862, filed on Jul. 26, 2018.

(51) Int. Cl.
| | |
|---|---|
| C07D 401/14 | (2006.01) |
| A61K 31/506 | (2006.01) |
| A61P 35/00 | (2006.01) |
| A61K 9/00 | (2006.01) |
| A61K 9/16 | (2006.01) |
| A61K 9/48 | (2006.01) |
| A61K 45/06 | (2006.01) |

(52) U.S. Cl.
CPC .......... *A61K 31/506* (2013.01); *A61K 9/0053* (2013.01); *A61K 9/1623* (2013.01); *A61K 9/1652* (2013.01); *A61K 9/4825* (2013.01); *A61P 35/00* (2018.01); *C07D 401/14* (2013.01); *A61K 45/06* (2013.01)

(58) Field of Classification Search
CPC .................................................. C07D 401/14
See application file for complete search history.

(56) References Cited

U.S. PATENT DOCUMENTS

| | | |
|---|---|---|
| 2,779,780 A | 1/1957 | Middleton |
| 5,310,763 A | 5/1994 | Campion et al. |
| 5,521,173 A | 5/1996 | Venkatesan et al. |
| 5,587,458 A | 12/1996 | King et al. |
| 5,621,002 A | 4/1997 | Bosslet et al. |
| 5,747,498 A | 5/1998 | Schnur et al. |
| 5,792,783 A | 8/1998 | Tang et al. |
| 5,795,909 A | 8/1998 | Shashoua et al. |
| 5,834,504 A | 11/1998 | Tang et al. |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,932,595 A | 8/1999 | Bender et al. |

(Continued)

FOREIGN PATENT DOCUMENTS

| | | |
|---|---|---|
| CN | 1429222 A | 7/2003 |
| CN | 101657431 A | 2/2010 |

(Continued)

OTHER PUBLICATIONS

Ahn et al., "Synthesis and Antiproliferative Activity of Pyridinylcarbonylpyrimidines Against Melanoma Cell Line," *Bull. Korean Chem. Soc.* 32(4):1209-1214, 2011.

(Continued)

*Primary Examiner* — Brian E McDowell
(74) *Attorney, Agent, or Firm* — Seed Intellectual Property Law Group LLP

(57) ABSTRACT

Methods for treating a disease in a subject in need thereof by administering an ACVR1 inhibitor having the following formula (I) are disclosed:

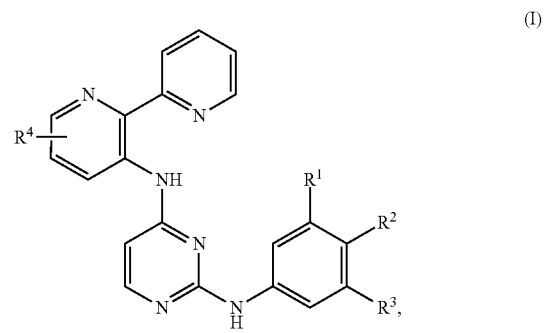

(I)

including stereoisomers, tautomers, pharmaceutically acceptable salts and prodrugs thereof, wherein $R^1$, $R^2$, $R^3$, and $R^4$ are as defined herein. Subjects that may benefit from treatment may have mutations in their ACVR1 gene. Various diseases may be treated using the described methods, including cancers (e.g., diffuse intrinsic pontine glioma (DIPG)) and genetic disorders (e.g., fibrodysplasia ossificans progressiva (FOP)).

11 Claims, 42 Drawing Sheets

(56) References Cited

U.S. PATENT DOCUMENTS

| | | |
|---|---|---|
| 5,958,935 A | 9/1999 | Davis et al. |
| 5,962,458 A | 10/1999 | Lohmann et al. |
| 6,017,919 A | 1/2000 | Inaba et al. |
| 6,077,864 A | 6/2000 | Burgess et al. |
| 6,087,392 A | 7/2000 | Reiter |
| 6,090,852 A | 7/2000 | Dack et al. |
| 6,110,964 A | 8/2000 | Robinson |
| 6,114,361 A | 9/2000 | Robinson et al. |
| 6,147,061 A | 11/2000 | Reiter |
| 6,153,609 A | 11/2000 | Robinson et al. |
| 6,174,889 B1 | 1/2001 | Cockerill et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,235,764 B1 | 5/2001 | Larson et al. |
| 6,258,824 B1 | 7/2001 | Yang |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,391,874 B1 | 5/2002 | Cockerill et al. |
| 6,395,734 B1 | 5/2002 | Tang et al. |
| 6,440,207 B1 | 8/2002 | Shulz |
| 6,492,383 B1 | 12/2002 | Munchhof et al. |
| 6,495,568 B1 | 12/2002 | Dack et al. |
| 6,511,993 B1 | 1/2003 | Dack et al. |
| 6,587,123 B2 | 7/2003 | Ando et al. |
| 6,596,726 B1 | 7/2003 | Bridges et al. |
| 6,599,890 B1 | 7/2003 | McClure et al. |
| 6,599,904 B2 | 7/2003 | Bromidge et al. |
| 6,713,485 B2 | 3/2004 | Carter et al. |
| 6,897,208 B2 | 5/2005 | Edwards et al. |
| 6,939,874 B2 | 9/2005 | Harmange et al. |
| 7,005,449 B2 | 2/2006 | Hawley et al. |
| 7,030,242 B2 | 4/2006 | Noe et al. |
| 7,163,921 B1 | 1/2007 | Ishiyama et al. |
| 7,282,504 B2 | 10/2007 | Armistead et al. |
| 7,348,318 B2 | 3/2008 | Abe et al. |
| 7,348,339 B2 | 3/2008 | Bailey et al. |
| 7,411,001 B2 | 8/2008 | Barrett et al. |
| 7,414,072 B2 | 8/2008 | Sato et al. |
| 7,514,446 B2 | 4/2009 | Davis-Ward et al. |
| 7,528,143 B2 | 5/2009 | Noronha et al. |
| 7,612,094 B2 | 11/2009 | Lee et al. |
| 7,625,903 B2 | 12/2009 | Johnson et al. |
| 7,655,649 B2 | 2/2010 | Bilodeau et al. |
| 7,691,865 B2 | 4/2010 | Lee et al. |
| 7,741,330 B1 | 6/2010 | Chen et al. |
| 7,834,024 B2 | 11/2010 | Li et al. |
| 7,943,627 B2 | 5/2011 | Baenteli et al. |
| 7,964,592 B2 | 6/2011 | Garcia-Echeverria et al. |
| 7,998,966 B2 | 8/2011 | Bearss et al. |
| 8,067,395 B2 | 11/2011 | Jankowski et al. |
| 8,133,900 B2 | 3/2012 | Hood et al. |
| 8,138,199 B2 | 3/2012 | Noronha et al. |
| 8,263,772 B2 | 9/2012 | Arnold et al. |
| 8,268,850 B2 | 9/2012 | Li et al. |
| 8,288,425 B2 | 10/2012 | Edwards et al. |
| 8,324,279 B2 | 12/2012 | Anziano |
| 8,329,742 B2 | 12/2012 | Boivin et al. |
| 8,338,439 B2 | 12/2012 | Singh et al. |
| 8,354,407 B2 | 1/2013 | Djung et al. |
| 8,431,694 B1 | 4/2013 | Babu et al. |
| 8,513,293 B2 | 8/2013 | Wallace et al. |
| 8,552,186 B2 | 10/2013 | Ahmed et al. |
| 8,563,549 B2 | 10/2013 | Burger et al. |
| 8,604,014 B2 | 12/2013 | Belvin et al. |
| 8,604,042 B2 | 12/2013 | Noronha et al. |
| 8,642,624 B2 | 2/2014 | Chen et al. |
| 8,722,663 B2 | 5/2014 | Takasu et al. |
| 8,853,369 B2 | 10/2014 | Pei et al. |
| 8,901,120 B2 | 12/2014 | Bearss et al. |
| 8,987,233 B2 | 3/2015 | Pan et al. |
| 9,040,549 B2 | 5/2015 | Bourke et al. |
| 9,133,134 B2 | 9/2015 | Chen et al. |
| 9,199,944 B2 | 12/2015 | Lee et al. |
| 9,206,176 B2 | 12/2015 | Bearss et al. |
| 9,295,664 B2 | 3/2016 | Adams et al. |
| 9,409,911 B2 | 8/2016 | Honigberg et al. |
| 9,469,642 B2 | 10/2016 | Chen et al. |
| 9,481,654 B2 | 11/2016 | Li et al. |
| 9,540,385 B2 | 1/2017 | Chen et al. |
| 9,556,426 B2 | 1/2017 | Singh et al. |
| 9,597,329 B2 | 3/2017 | Sebti et al. |
| 9,617,243 B2 | 4/2017 | McMillen et al. |
| 9,624,224 B2 | 4/2017 | Chen et al. |
| 9,637,487 B2 | 5/2017 | Chen et al. |
| 9,708,326 B2 | 7/2017 | Chen et al. |
| 9,714,247 B2 | 7/2017 | Zeng et al. |
| 9,724,338 B2 | 8/2017 | Michelson |
| 9,745,319 B2 | 8/2017 | Ren et al. |
| 9,758,539 B2 | 9/2017 | Siddiqui-Jain et al. |
| 9,795,605 B2 | 10/2017 | Buggy et al. |
| 9,862,722 B2 | 1/2018 | Chen et al. |
| 9,913,842 B2 | 3/2018 | Singh et al. |
| 9,980,964 B2 | 5/2018 | Haq et al. |
| 9,987,276 B2 | 6/2018 | Singh et al. |
| 10,016,435 B2 | 7/2018 | Buggy et al. |
| 10,125,140 B1 | 11/2018 | Purro et al. |
| 10,137,136 B2 | 11/2018 | Adams et al. |
| 10,155,763 B2 | 12/2018 | Lee et al. |
| 10,179,777 B2 | 1/2019 | Dorsch et al. |
| 10,202,356 B2 | 2/2019 | Mollard et al. |
| 10,233,186 B2 | 3/2019 | Brooijmans et al. |
| 10,752,594 B2 | 8/2020 | Mollard et al. |
| 2003/0166620 A1 | 9/2003 | Lee et al. |
| 2004/0242655 A1 | 12/2004 | Anziano |
| 2005/0012070 A1 | 1/2005 | Inoue et al. |
| 2005/0171134 A1 | 8/2005 | Davis et al. |
| 2006/0111357 A1 | 5/2006 | Frimurer et al. |
| 2006/0223820 A1 | 10/2006 | Brand et al. |
| 2006/0270694 A1 | 11/2006 | Wong |
| 2007/0032514 A1 | 2/2007 | Zahn et al. |
| 2007/0105839 A1 | 5/2007 | Imbach et al. |
| 2007/0191405 A1 | 8/2007 | Noronha et al. |
| 2008/0182852 A1 | 7/2008 | Johnson et al. |
| 2008/0214558 A1 | 9/2008 | Vankayalapati et al. |
| 2009/0054428 A1 | 2/2009 | Barlaam et al. |
| 2009/0298830 A1 | 12/2009 | Mann et al. |
| 2010/0029675 A1 | 2/2010 | Hwang |
| 2010/0190770 A1 | 7/2010 | Li et al. |
| 2010/0204221 A1 | 8/2010 | Vankayalapati et al. |
| 2010/0331350 A1 | 12/2010 | Honigberg et al. |
| 2011/0028405 A1 | 2/2011 | Harrison et al. |
| 2011/0230476 A1 | 9/2011 | Niu et al. |
| 2011/0257171 A1 | 10/2011 | Damour et al. |
| 2011/0269721 A1 | 11/2011 | Hood |
| 2012/0040955 A1 | 2/2012 | Harrison et al. |
| 2012/0238540 A1 | 9/2012 | Holcomb et al. |
| 2012/0252821 A1 | 10/2012 | Honigberg et al. |
| 2012/0277254 A1 | 11/2012 | Honigberg et al. |
| 2012/0283261 A1 | 11/2012 | Bearss et al. |
| 2012/0283276 A1 | 11/2012 | Honigberg et al. |
| 2012/0283277 A1 | 11/2012 | Honigberg et al. |
| 2013/0012525 A1 | 1/2013 | Honigberg et al. |
| 2013/0035334 A1 | 2/2013 | Honigberg et al. |
| 2013/0102681 A1 | 4/2013 | Anziano |
| 2013/0197014 A1 | 8/2013 | Chen et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0039168 A1 | 2/2014 | Birau et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0128413 A1 | 5/2014 | Honigberg et al. |
| 2014/0128414 A1 | 5/2014 | Honigberg et al. |
| 2014/0135347 A1 | 5/2014 | Honigberg et al. |
| 2014/0142123 A1 | 5/2014 | Honigberg et al. |
| 2014/0142126 A1 | 5/2014 | Chen et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |

(56) References Cited

U.S. PATENT DOCUMENTS

| | | |
|---|---|---|
| 2014/0187565 A1 | 7/2014 | Honigberg et al. |
| 2014/0194446 A1 | 7/2014 | Buggy et al. |
| 2014/0212485 A1 | 7/2014 | Honigberg et al. |
| 2014/0243355 A1 | 8/2014 | Honigberg et al. |
| 2014/0336206 A1 | 11/2014 | Honigberg et al. |
| 2015/0018336 A1 | 1/2015 | Chen et al. |
| 2015/0184249 A1 | 7/2015 | Chang et al. |
| 2015/0374694 A1 | 12/2015 | Boden et al. |
| 2016/0022683 A1 | 1/2016 | Fardis et al. |
| 2016/0115167 A1 | 4/2016 | Yu et al. |
| 2016/0214944 A1 | 7/2016 | Mollard et al. |
| 2016/0287592 A1 | 10/2016 | Chang et al. |
| 2017/0174691 A1 | 6/2017 | Singh et al. |
| 2017/0246167 A1 | 8/2017 | Singh et al. |
| 2017/0266186 A1 | 9/2017 | Buggy et al. |
| 2017/0369451 A1 | 12/2017 | Allwein et al. |
| 2019/0105333 A1 | 4/2019 | Adams et al. |
| 2019/0119221 A1 | 4/2019 | Mollard et al. |
| 2020/0323851 A1 | 10/2020 | Bearss et al. |

FOREIGN PATENT DOCUMENTS

| | | |
|---|---|---|
| EP | 0 606 046 A1 | 7/1994 |
| EP | 0 780 386 B1 | 12/1996 |
| EP | 0 606 046 B1 | 10/1997 |
| EP | 0 818 442 A2 | 1/1998 |
| EP | 0 931 788 B1 | 11/2002 |
| EP | 1 132 434 B1 | 12/2003 |
| EP | 1 004 578 B1 | 2/2004 |
| EP | 2 970 205 B1 | 5/2019 |
| JP | 2003-512358 A | 4/2003 |
| JP | 2003-532635 A | 11/2003 |
| JP | 2005-505535 A | 2/2005 |
| JP | 2005-516046 A | 6/2005 |
| JP | 2006-518386 A | 8/2006 |
| JP | 2007-505858 A | 3/2007 |
| JP | 2009-528378 A | 8/2009 |
| JP | 2010-520222 A | 6/2010 |
| JP | 2011-526299 A | 10/2011 |
| JP | 2011-530517 A | 12/2011 |
| JP | 2016-513661 A | 5/2016 |
| RU | 2 343 148 C2 | 1/2009 |
| WO | 90/05719 A1 | 5/1990 |
| WO | 95/19970 A1 | 7/1995 |
| WO | 95/21613 A1 | 8/1995 |
| WO | 96/27583 A1 | 9/1996 |
| WO | 96/33172 A1 | 10/1996 |
| WO | 1996/033980 A1 | 10/1996 |
| WO | 97/13760 A1 | 4/1997 |
| WO | 97/19065 A1 | 5/1997 |
| WO | 97/22596 A1 | 6/1997 |
| WO | 97/29079 A1 | 8/1997 |
| WO | 97/32856 A1 | 9/1997 |
| WO | 98/02434 A1 | 1/1998 |
| WO | 98/02437 A1 | 1/1998 |
| WO | 98/03516 A1 | 1/1998 |
| WO | 1998/002438 A1 | 1/1998 |
| WO | 98/07697 A1 | 2/1998 |
| WO | 98/14451 A1 | 4/1998 |
| WO | 98/30566 A1 | 7/1998 |
| WO | 98/33768 A1 | 8/1998 |
| WO | 98/34915 A1 | 8/1998 |
| WO | 98/34918 A1 | 8/1998 |
| WO | 98/50356 A1 | 11/1998 |
| WO | 98/54093 A1 | 12/1998 |
| WO | 99/07675 A1 | 2/1999 |
| WO | 99/10349 A1 | 3/1999 |
| WO | 99/16755 A1 | 4/1999 |
| WO | 99/24440 A1 | 5/1999 |
| WO | 99/29667 A1 | 6/1999 |
| WO | 99/35132 A1 | 7/1999 |
| WO | 99/35146 A1 | 7/1999 |
| WO | 99/52889 A1 | 10/1999 |
| WO | 99/52910 A1 | 10/1999 |
| WO | 99/61422 A1 | 12/1999 |
| WO | 99/62890 A1 | 12/1999 |
| WO | 00/35436 A2 | 6/2000 |
| WO | 01/60816 A1 | 8/2001 |
| WO | 2001/060814 A2 | 8/2001 |
| WO | 01/79263 A1 | 10/2001 |
| WO | 02/06213 A2 | 1/2002 |
| WO | 02/066470 A1 | 8/2002 |
| WO | 02/094766 A1 | 11/2002 |
| WO | 03/003009 A1 | 1/2003 |
| WO | 03/018021 A1 | 3/2003 |
| WO | 03/035065 A1 | 5/2003 |
| WO | 03/055477 A1 | 7/2003 |
| WO | 03/063794 A2 | 8/2003 |
| WO | 03/076424 A1 | 9/2003 |
| WO | 03/077914 A1 | 9/2003 |
| WO | 03/080610 A1 | 10/2003 |
| WO | 03/080633 A1 | 10/2003 |
| WO | 2003/087304 A3 | 10/2003 |
| WO | 03/095448 A1 | 11/2003 |
| WO | 2004/014931 A1 | 2/2004 |
| WO | 2004/022054 A1 | 3/2004 |
| WO | 2004/046118 A2 | 6/2004 |
| WO | 2004/052370 A3 | 6/2004 |
| WO | 2004/074244 A2 | 9/2004 |
| WO | 2004/077007 A2 | 9/2004 |
| WO | 2004/078163 A2 | 9/2004 |
| WO | 2005/021551 A1 | 3/2005 |
| WO | 2005/026130 A1 | 3/2005 |
| WO | 2005/082892 A2 | 9/2005 |
| WO | 2006/026306 A1 | 3/2006 |
| WO | 2006/124874 A2 | 11/2006 |
| WO | 2007/014011 A2 | 2/2007 |
| WO | 2007/053452 A1 | 5/2007 |
| WO | 2007/084786 A1 | 7/2007 |
| WO | 2007/087068 A2 | 8/2007 |
| WO | 2007/098507 A2 | 8/2007 |
| WO | 2007/146981 A2 | 12/2007 |
| WO | 2008/039218 A2 | 4/2008 |
| WO | 2008/054827 A3 | 5/2008 |
| WO | zoos/092049 A1 | 7/2008 |
| WO | 2008/092199 A1 | 8/2008 |
| WO | 2008/106635 A1 | 9/2008 |
| WO | 2008/121742 A2 | 10/2008 |
| WO | 2008/124085 A2 | 10/2008 |
| WO | 2008/128072 A2 | 10/2008 |
| WO | 2009/010794 A1 | 1/2009 |
| WO | 2009/036082 A2 | 3/2009 |
| WO | 2009/055730 A1 | 4/2009 |
| WO | 2009/080638 A2 | 7/2009 |
| WO | 2009/143389 A1 | 11/2009 |
| WO | 2009/158571 A1 | 12/2009 |
| WO | 2010/007317 A1 | 1/2010 |
| WO | 2010/009342 A2 | 1/2010 |
| WO | 2010/011349 A2 | 1/2010 |
| WO | 2010/017122 A2 | 1/2010 |
| WO | 2020/023910 A1 | 1/2010 |
| WO | 2010/118986 A1 | 10/2010 |
| WO | 2011/034907 A2 | 3/2011 |
| WO | 2011/046964 A2 | 4/2011 |
| WO | 2011/046970 A1 | 4/2011 |
| WO | 2011/093524 A1 | 8/2011 |
| WO | 2011/106168 A1 | 9/2011 |
| WO | 2011/121223 A1 | 10/2011 |
| WO | 2011/153514 A2 | 12/2011 |
| WO | 2012/135641 A2 | 10/2012 |
| WO | 2012/135800 A1 | 10/2012 |
| WO | 2012/135801 A1 | 10/2012 |
| WO | 2012/170546 A1 | 12/2012 |
| WO | 2013/010136 A2 | 1/2013 |
| WO | 2013/059738 A2 | 4/2013 |
| WO | 2013/064068 A1 | 5/2013 |
| WO | 2013/102059 A1 | 7/2013 |
| WO | 2013/116382 A1 | 8/2013 |
| WO | 2013/173518 A1 | 11/2013 |
| WO | 2013/184572 A1 | 12/2013 |
| WO | 2014/018567 A1 | 1/2014 |
| WO | 2014/025128 A1 | 2/2014 |
| WO | 2014/025486 A1 | 2/2014 |
| WO | 2014/052365 A1 | 4/2014 |

(56) References Cited

FOREIGN PATENT DOCUMENTS

| WO | 2014/078578 A1 | 5/2014 |
|---|---|---|
| WO | 2014/124230 A2 | 8/2014 |
| WO | 2014/130411 A1 | 8/2014 |
| WO | 2014/130693 A1 | 8/2014 |
| WO | 2014/138088 A1 | 9/2014 |
| WO | 2014/143659 A1 | 9/2014 |
| WO | 2014/151871 A9 | 9/2014 |
| WO | 2014/152588 A1 | 9/2014 |
| WO | 2014/159745 A1 | 10/2014 |
| WO | 2014/168975 A1 | 10/2014 |
| WO | 2015/002894 A1 | 1/2015 |
| WO | 2015/048689 A1 | 4/2015 |
| WO | 2015/054572 A1 | 4/2015 |
| WO | 2016/187316 A1 | 11/2016 |
| WO | 2017/181117 A1 | 10/2017 |
| WO | 2018/124001 A1 | 7/2018 |
| WO | 2018/0232094 A1 | 12/2018 |
| WO | 2016/146651 A1 | 9/2019 |
| WO | 2016/165808 A1 | 10/2019 |
| WO | 2019/195753 A1 | 10/2019 |
| WO | 2020/146819 A1 | 7/2020 |

OTHER PUBLICATIONS

Alessi et al., "Mechanism of Activation of Protein Kinase B by Insulin and IGF-1," *The Embo Journal* 15(23):6541-6551, 1996.
Anderton et al., "Induction of Heart Valve Lesions by Small-Molecule ALK5 Inhibitors," *Toxicologic Pathology* 39(6):916-924, 2011.
Angelillo-Scherrer et al., "Role of Gas6 in Erythropoiesis and Anemia in Mice," *J. Clin. Invest.* 118(2):583-596, 2008.
Barlaam et al., "Inhibitors of the tyrosine kinase EphB4. Part 4: Discovery and optimization of a benzylic alcohol series," *Bioorganic & Medicinal Chemistry Letters* 21:2207-2211, 2011.
Baxter et al., "Acquired mutation of the tyrosine kinase JAK2 in human myeloproliferative disorders," *Lancet* 36:1054-1061, 2005.
Bellido-Martin et al., "Vitamin K-dependent actions of Gas6," *Vitam. Horm.* 78:185-209, 2008.
Bellosta et al., "Signaling Through the ARK Tyrosine Kinase Receptor Protects From Apoptosis in the Absence of Growth Stimulation," *Oncogene* 15:2387-2397, 1997.
Bellosta et al., "The Receptor Tyrosine Kinase ARK mediates Cell Aggregation by Homophilic Binding," *Molecular and Cellular Biology* 15(2):614-625, 1995.
Benekli et al., "Signal transducer and activator of transcription proteins in leukemias," *Blood* 101(8):2940-2954, 2003.
Blume-Jensen et al., "Oncogenic Kinase Signaling," *Nature* 411:355-365, 2001.
Braunger et al., "Intracellular Signaling of the Ufo/Axl Receptor Tyrosine Kinase Is Mediated Mainly by a Multi-Substrate Docking-Site," *Oncogene* 14:2619-2631, 1997.
Breslin et al., "Design, Synthesis, and Anaplastic Lymphoma Kinase (ALK) Inhibitory Activity for a Novel Series of 2,4,8,22-Tetraazatetracyclo[14.3.1.1$^{3,7}$.1$^{9,13}$]-docosa-1(20),3(22),4,6,9(21),10,12,16,18-nonaene Macrocycles," *Journal of Medicinal Chemistry* 55:449-464, 2012.
Brunetto et al., "First-in-human, Pharmacokinetic and Pharmacodynamic Phase I Study of Resminostat, an Oral Histone Deacetylase Inhibitor, in Patients with Advanced Solid Tumors," *Clin. Cancer Res.* 19(19):5494-5504, 2013. (Author Manuscript, 20 pages).
Buchanan et al., "Discovery of 2,4-bis-arylamino-1,3-pyrimidines as insulin-like growth factor-1 receptor (IGF-1R) inhibitors," *Bioorganic & Medicinal Chemistry Letters* 21:2394-2399, 2011.
Buggy et al., "CRA-024781: a novel synthetic inhibitor of histone deacetylase enzymes with antitumor activity in vitro and in vivo," *Mol. Cancer Ther.* 5(5):1309-1317, 2006.
CAS Registry No. 1192474-26-2, "Benzeneethanol, 3-bromo-5-[[5-chloro-4-[(3-hydroxyphenyl)amino]-2-pyrimidinyl]amino]-," Feb. 7, 2010, 67 pages.

CAS Registry No. 1251954-86-5, "Benzamide, 3-[[4-[2-amino-3-flurophenyl)amino]-5-chloro-2-pyrimidinyl]amino]-N-ethyl-4-fluoro-," Nov. 9, 2010, 11 pages.
CAS Registry No. 698998-35-5, "2,4-Pyrimidinediamine, 5-bromo-N2-(3,4-dimethoxyphenyl)-N4-[4-(1H-pyrazol-3-yl)phenyl]-," Jun. 25, 2004, 1 page.
CAS Registry No. 794466-29-8, "2,4-Pyrimidinediamine, 5-bromo-N4-[2-(4-morpholinyl)phenyl]-N2-(3,4,5-trimethoxyphenyl)-," Dec. 8, 2004, 1 page.
Choi et al., "Design and synthesis of 7H-pyrrolo[2,3-d]pyrimidines as focal adhesion kinase inhibitors. Part 1," *Bioorganic & Medicinal Chemistry Letters* 16:2173-2176, 2006.
Compound Summary for CID 49702158, Pub Chem, Dec. 23, 2015, 10 pages.
Compound Summary for CID 69861127, PubChem, Dec. 23, 2015, 11 pages.
Compound Summary for CID 69898605, PubChem, Dec. 23, 2015, 11 pages.
Ember et al., "Acetyl-lysine Binding Site of Bromodomain-Containing Protein 4 (BRD4) Interacts with Diverse Kinase Inhibitors," *ACS Chem. Biol.* 9:1160-1171, 2014.
Filippakopoulos et al., "Selective inhibition of BET bromodomains," *Nature* 468:1067-1073, 2010.
Fish et al., "Identification of a Chemical Probe for Bromo and Extra C-Terminal Bromodomain Inhibition through Optimization of a Fragment-Derived Hit," *J. Med. Chem.* 55:9831-9837, 2012.
Fridell et al., "GAS6 Induces Axl-mediated Chemotaxis of Vascular Smooth Muscle Cells," *The Journal of Biological Chemistry* 273(12):7123-7126, 1998.
Fruman et al., "Xid-like phenotypes: a B Cell Signalosome Takes Shape," *Immunity* 13:1-3, 2000.
Fry, "Phosphoinositide 3-kinase signalling in breast cancer: how big a role might it play?" *Breast Cancer Res* 3:304-312, 2001.
Giles et al., "A Phase I Study of Intravenous LBH589, a Novel Cinnamic Hydroxamic Acid Analogue Histone Deacetylase Inhibitor, in Patients with Refractory Hematologic Malignancies," *Clin. Cancer Res.* 12(15):4628-4635, 2006.
Goldberg et al., "Rapid generation of a high quality lead for transforming growth factor-beta (TGF-beta) type I receptor (ALK5)," *J. Med. Chem* 52:7901-7905, 2009.
Göttlicher et al., "Valproic acid defines a novel class of HDAC inhibitors inducing differentiation of transformed cells," *The EMBO Journal* 20(24):6969-6978, 2001.
Gould et al., "Gas6 receptors Axl, Sky and Mer enhance platelet activation and regulate thrombotic responses," *Journal of Thrombosis and Haemostasis* 3:733-741, 2005.
Graham et al., "Cloning and mRNA expression analysis of a novel human protooncogene, c-mer," *Cell Growth and Differentiation* 5:647-657, 1994.
Green et al., "Overexpression of the Axl tyrosine kinase receptor in cutaneous SCC-derived cell lines and tumours," *British Journal of Cancer* 94(10):1446-1451, 2006.
Gura, "Systems for identifying new drugs are often faulty," *Science* 278:1041-1042, 1997.
Hafizi et al., "Gas6 and protein S Vitamin K-dependent ligands for the Axl receptor tyrosine kinase subfamily," *FEBS Journal* 273:5231-5244, 2006.
Hafizi et al., "Interaction of Axl receptor tyrosine kinase with C1-TEN, a novel C1 domain-containing protein with homology to tensin," *Biochemical and Biophysical Research Communications* 299:793-800, 2002.
Hafizi et al., "Signalling and functional diversity within the Axl subfamily of receptor tyrosine kinases," *Cytokine & Growth Factor Reviews* 17:295-304, 2006.
Hallek et al., "iwCLL guidelines for diagnosis, indications for treatment, response assessment and supportive management of CLL," *Blood* 131(25):2745-2760, 2018.
Hanada et al., "Structure, regulation and function of PKB/AKT—a major therapeutic target," *Biochimica et Biophysica Acta* 1697:3-16, 2004.
Hendriks, "Drug discovery: New Btk inhibitor holds promise," *Nat. Chem. Biol* 7:4-5, 2011.

(56) References Cited

OTHER PUBLICATIONS

Hubbard et al., "Protein Tyrosine Kinase Structure and Function," *Annual Review of Biochemistry* 69:373-398, 2000.
Hughes et al., "4-Aryl-5-cyano-2-aminopyrimidines as VEGF-R2 inhibitors: Synthesis and biological evaluation," *Bioorganic & Medicinal Chemistry Letters* 17:3266-3270, 2007.
James et al., "A unique clonal JAK2 mutation leading to constitutive signalling causes polycythaemia vera," *Nature* 434:1144-1148, 2005.
Johnson et al., "Relationships between drug activity in NCI preclinical in vitro and in vivo models and early clinical trials," *British Journal of Cancer* 84(10):1424-1431, 2001.
Keating et al., "Lymphoblastic leukemia/lymphoma in mice overexpressing the Mer (MerTK) receptor tyrosine kinase," *Oncogene* 25:6092-6100, 2006.
Knutson et al., "Synergistic Anti-Tumor Activity of EZH2 Inhibitors and Glucocorticoid Receptor Agonists in Models of Germinal Center Non-Hodgkin Lymphomas," *PLoS One* 9(12):e111840, 2014. (22 pages).
Korshunov et al., "Axl mediates vascular remodeling induced by deoxycorticosterone acetate-salt hypertension," *Hypertension* 50:1057-1062, 2007.
Korshunov et al., "Axl, a receptor tyrosine kinase, mediates flow-induced vascular remodeling," *Circulation Research* 98:1446-1452, 2006.
Kurosaki, "Functional dissection of BCR signaling pathways," *Curr. Opin. Immunol.* 12:276-281, 2000.
Lemke et al., "Immunobiology of the TAM receptors," *Nature Reviews Immunology* 8:327-336, 2008.
Levine et al., "Activating mutation in the tyrosine kinase JAK2 in polycythemia vera, essential thrombocythemia and myeloid metaplasia with myelofibrosis," *Cancer Cell* 7:387-397, 2005.
U.S. National Library of Medicine, "Compound Summary, CID 86290265, 2-N-[3-Methoxy-4-(4-methylpiperazin-1-yl)phenyl]-4-N-(2-pyridin-2-ylpyridin-3-yl)pyrimidine-2,4-diamine" Dec. 22, 2014, URL=https://pubchem.ncbi.nlm.nih.gov/compound/86290265, retrieved Sep. 25, 2019, 15 pages.
Roland, "Diffuse Intrinsic Pontine Glioma (DIPG)," Healthline, May 5, 2018, retrieved from https://www.healthline.com/health/cancer/dipg, 13 pages.
Li et al., "Axl as a potential therapeutic target in cancer: role of Axl in tumor growth, metastasis and angiogenesis," *Oncogene* 28:3442-3455, 2009.
Linger et al., "TAM receptor tyrosine kinases: biologic functions, signaling, and potential therapeutic targeting in human cancer," *Advanced Cancer Research* 100:35-83, 2008. (Author Manuscript, 41 pages).
Malani et al., "Synthesis, characterization and in vitro screening on bacterial, fungal and malarial strain of piprazinyl cyano biphenyl based compounds," *Bioorg Chemistry* 51:16-23, 2013.
Manfioletti et al., "The protein encoded by a growth arrest-specific gene (gas6) is a new member of the vitamin K-dependent proteins related to protein S, a negative coregulator in the blood coagulation cascade," *Molecular and Cellular Biology* 13(8):4976-4985, 1993.
Manning et al., "Evolution of protein kinase signaling from yeast to man," *TRENDS in Biochemical Sciences* 27(10):514-520, 2002.
Mark et al., "rse, a novel receptor-type tyrosine kinase with homology to Axl/Ufo, is expressed at high levels in the brain," *Journal of Biological Chemistry* 269:10720-10728, 1994.
Mazzacurati et al., "The PIM inhibitor AZD1208 synergizes with ruxolitinib to induce apoptosis of ruxolitinib sensitive and resistant JAK2-V617F-driven cells and inhibit colony formation of primary MPN cells," *Oncotarget* 6(37):40141-40157, 2015.
Mollard et al., "Design, Synthesis and Biological Evaluation of a Series of Novel AXL Kinase Inhibitors," *ACS Medicinal Chemistry Letters* 2:907-912, 2011.
Myers et al., "AXL Inhibitors in Cancer: A Medicinal Chemistry Perspective," *J. Med. Chem.* 59(8):3593-3608, 2016.
Noel et al., "Abstract C244: Development of the BET bromodomain inhibitor OTX015," *Mol. Cancer Ther.* 12(11), 2013. (4 pages).
Paquin et al., "Design and synthesis of 4-[(s-triazin-2-ylamino)methyl]-N-(2-aminophenyl)-benzamides and their analogues as a novel class of histone deacetylase inhibitors," *Bioorg. Med. Chem. Lett.* 18:1067-1071, 2008.
Parry et al., "Dinaciclib (SCH 727965), a Novel and Potent Cyclin-Dependent Kinase Inhibitor," *Mol. Cancer Ther.* 9(8):2344-2353, 2010.
Paruch et al., "Discovery of Dinaciclib (SCH 727965): A Potent and Selective Inhibitor of Cyclin-Dependent Kinases," *ACS Med. Chem. Lett.* 1:204-208, 2010.
Pearce et al., "18. Failure modes in anticancer drug discovery and development," in Neidle (ed.), *Cancer Drug Design and Discovery*, Elsevier, 2008, pp. 424-435.
Peeters et al., "Fusion of TEL, the ETS-Variant Gene 6 (ETV6), to the Receptor-Associated Kinase JAK2 as a Result of t(9; 12) in a Lymphoid and t(9; 15; 12) in a Myeloid Leukemia," *Blood* 90(7):2535-2540, 1997.
Picaud et al., "PFI-1, a highly selective protein interaction inhibitor, targeting BET Bromodomains," *Cancer Res.* 73(11):3336-3346, 2013. (Author Manuscript, 20 pages).
Piekarz et al., "Inhibitor of histone deacetylation, depsipeptide (FR901228), in the treatment of peripheral and cutaneous T-cell lymphoma: a case report," *Blood* 98(9):2865-2868, 2001.
Plumb et al., "Pharmacodynamic Response and Inhibition of Growth of Human Tumor Xenografts by the Novel Histone Deacetylase Inhibitor PXD101," *Mol. Cancer Ther.* 2:721-728, 2003.
Reiter et al., "The t(8;9)(p22;p24) Is a Recurrent Abnormality in Chronic and Acute Leukemia that Fuses PCM1 to JAK2," *Cancer Res* 65(7):2662-2667, 2005.
Rescigno et al., "A putative receptor tyrosine kinase with unique structural topology," *Oncogene* 6:1909-1913, 1991.
Richon et al., "A class of hybrid polar inducers of transformed cell differentiation inhibits histone deacetylases," *Proc. Natl. Acad. Sci. USA* 95:3003-3007, 1998.
Robinson et al., "The protein tyrosine kinase family of the human genome," *Oncogene* 19:5548-5557, 2000.
Rothlin et al., "TAM receptors are pleiotropic inhibitors of the innate immune response," *Cell.* 131:1124-1136, 2007.
Sainaghi et al., "Gas6 induces proliferation in prostate carcinoma cell lines expressing the Axl receptor," *Journal of Cell Physiology* 204:36-44, 2005.
Alexander, et al., "Tumor-Specific Expression and Alternate Splicing of Messenger Ribonucleic Acid Encoding Activin/Transforming Growth Factor-β Receptors in Human Pituitary Adenomas" *Journal of Clinical Endocrinology and Metabolism*, vol. 81, No. 2, pp. 783-790, 1996.
Herrera, et al. "Autocrine Bone Morphogenetic Protein-9 Signals through Activin Receptor-like Kinase-2/Smad1/Smad4 to Promote Ovarian Cancer Cell Proliferation" *Cancer Research*, 2009; 69: (24), pp. 9254-9262 Dec. 8, 2009.
Jung, et al., "Activin Type 2 Receptor Restoration in MSI-H Colon Cancer Suppresses Growth and Enhances Migration With Activin" *Gastroenterology*, vol. 132, Issue 2, pp. 633-644, Feb. 2007.
Langenfeld, et al., "Expression of Bone Morphogenetic Proteins in Human Lung Carcinomas" *The Annals of Thoracic Surgery*, vol. 80, Issue 3, pp. 1028-1032, 2005.
Langenfeld, et al., "Bone Morphogenetic Protein Type I Receptor Antagonists Decrease Growth and Induce Cell Death of Lung Cancer Cell Lines" *PLoS ONE* vol. 8, Issue 4, pp. 1-15, Apr. 2013.
Liu, et al., "Human Type II Receptor for Bone Morphogenic Proteins (BMPs): Extension of the Two-Kinase Receptor Model to the BMPs" *Mollecular and Cellular Biology*, vol. 15, No. 7, pp. 3479-3486, Jul. 1995.
Romero, et al., "Endoglin phosphorylation by ALK2 contributes to the regulation of prostate cancer cell migration" *Carcinogenesis*, vol. 31, No. 3, pp. 359-366, 2010.
Weber, et al., "A Limited Set of Human MicroRNA Is Deregulated in Follicular Thyroid Carcinoma" *The Journal of Clinical Endocrinology & Metabolism*, 91(9): 3584-3591, 2006.
Saito et al., "A synthetic inhibitor of histone deacetylase, MS-27-275, with marked in vivo antitumor activity against human tumors," *Proc. Natl. Acad. Sci. USA* 96:4592-4597, 1999.

(56) References Cited

OTHER PUBLICATIONS

Sawabu et al., "Growth arrest-specific gene 6 and Axl signaling enhances gastric cancer cell survival via Akt pathway," *Mol. Carcinog.* 46:155-164, 2007.
Schaeffer et al., "Tec family kinases in lymphocyte signaling and function," *Curr. Opin. Immunol.* 12:282-288, 2000.
Seal et al., "Identification of a novel series of BET family bromodomain inhibitors: binding mode and profile of I-BET151 (GSK1210151A)," *Bioorg. Med. Chem. Lett.* 22:2968-2972, 2012.
Shankar et al., "Gas6/Axl signaling activates the phosphatidylinositol 3-kinase/Akt1 survival pathway to protect oligodendrocytes from tumor necrosis factor alpha-induced apoptosis," *The Journal of Neuroscience* 26(21):5638-5648, 2006.
Shannon et al., "JAKing up hematopoietic proliferation," *Cancer Cell* 7(4):291-293, 2005.
Sharif et al., "Twist mediates suppression of inflammation by type I IFNs and Axl," *The Journal of Experimental Medicine* 203(8):1891-1901, 2006.
Shieh et al., "Expression of axl in lung adenocarcinoma and correlation with tumor progression," *Neoplasia* 7(12):1058-1064, 2005.
Simone, *Oncology: Introduction*, Cecil Textbook of Medicine, 20th Edition, vol. 1, pp. 1004-1010, 1996.
Sinha et al., "Targeted Axl Inhibition Primes Chronic Lymphocytic Leukemia B Cells to Apoptosis and Shows Synergistic/Additive Effects in Combination with BTK Inhibitors," *Clin. Cancer Res.* 21(9):2115-2126, 2015.
Sun et al., "Clinical implications of coexpression of growth arrest-specific gene 6 and receptor tyrosine kinases Axl and Sky in human uterine leiomyoma," *Molecular Human Reproduction* 9(11):701-707, 2003.
Takemoto et al., "Proliferation of adult T cell leukemia/lymphoma cells is associated with the constitutive activation of JAK/STAT proteins," *Proc. Natl Acad. Sci. USA* 94:13897-13902, 1997.
Thompson et al., "Minimal Residual Disease in Chronic Lymphocytic Leukemia in the Era of Novel Agents," *JAMA Oncol.* 4(3):394-400, 2018.
Toogood et al., "Discovery of a potent and selective inhibitor of cyclin-dependent kinase 4/6," *J. Med. Chem.* 48(7):2388-2406, 2005.
Traxler, "Protein Tyrosine Kinase Inhibitors in Cancer Treatment," *Exp. Opin. Ther. Patents* 7(6):571-588, 1997.
Ulrich, "Crystallization," *Kirk-Othmer Encyclopedia of Chemical Technology*, 2002. (7 pages).
Vajkoczy et al., "Dominant-negative inhibition of the Axl receptor tyrosine kinase suppresses brain tumor cell growth and invasion and prolongs survival," *PNAS* 103(15):5799-5804, 2006.
Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," *Clin. Cancer Res.* 19(15):4262-4272, 2013.
Vippagunta et al., "Crystalline solids," *Advanced Drug Delivery Reviews* 48:3-26, 2001.
Walz et al., "Activated JAK2 with the V617F Point Mutation Promotes $G_1$/S Phase Transition," *J. Biol Chem* 281(26):18177-18183, 2006.
Wang et al., "TIG1 Promotes the Development and Progression of Inflammatory Breast Cancer through Activation of Axl Kinase," *Cancer Res.* 73(21):6516-6525, 2013. (Author Manuscript, 22 pages).
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," *J. Med. Chem.* 51(16):4986-4999, 2008.
Zenkl et al., "Sugar-responsive fluorescent nanospheres," *Macromol. Biosci.* 8:146-152, 2008.
Zhao et al., "The Making of I-BET762, a BET Bromodomain Inhibitor Now in Clinical Development," *J. Med. Chem.* 56:7498-7500, 2013.

U.S. Appl. No. 16/376,452, filed Apr. 5, 3029.
U.S. Appl. No. 17/092,521, filed Nov. 9, 2020.
"Guideline on Clinical Trials in Small Populations," European Medicines Agency, London, 2006. (10 Pages).
Ahmed et al., "In vitro and in vivo characterization of SGI-1252, a small molecule inhibitor of JAK2," *Experimental Hematology* 39:14-25, 2011.
Almarsson et al., "Crystal engineering of the composition of pharmaceutical phases. Do pharmaceutical co-crystals represent a new path to improved medicines?," *Chem. Commun.* 17:1889-1896, 2004.
Alsamarah et al., "Uncovering Molecular Bases Underlying Bone Morphogenetic Protein Receptor Inhibitor Selectivity," *PLoS One* 10(7):e0132221, 20 pages, 2015.
Argetsinger et al., "Identification of JAK2 as a growth hormone receptor-associated tyrosine kinase," *Cell* 74(2):237-244, 1993.
Aringer et al., "Janus kinases and their role in growth and disease," *Life Sci.* 64(24):2173-2186, 1999.
Asshoff et al., "Momelotinib inhibits ACVR1/ALK2, decreases hepcidin production and ameliorates anemia of chronic disease in rodents," *Blood* 129(13):1823-1830, 2017.
Babb et al., "Cancer phase I clinical trials: efficient dose escalation with overdose control," *Statistics in Medicine* 17(10):1103-1120, 1998.
Bach et al., "The Dual Role of Bone Morphogenetic Proteins in Cancer," *Molecular Therapy: Oncolytics* 8:1-13, 2018.
Bagarova et al., "Constitutively Active ALK2 Receptor Mutants Require Type II Receptor Cooperation," *Molecular and Cellular Biology* 33(12):2413-2424, 2013.
Ballester et al., "Morphologic characteristics and immunohistochemical profile of diffuse intrinsic pontine gliomas," *Am. J. Surg. Pathol.* 37 (9):1357-64, 2013.
Becher et al., "Preclinical evaluation of radiation and perifosine in a genetically and histologically accurate model of brainstem glioma," *Cancer Res.* 70(6):1-16, 2010.
Besarab et al., "Roxadustat (FG-4592): Correction of Anemia in Incident Dialysis Patients," *J. Am. Soc. Nephrol.* 27:1-9, 2015.
Bobinac et al., "Expression of bone morphogenetic proteins in human metastatic prostate and breast cancer," *Croat. Med. J.* 46(3):389-396, 2005.
Briscoe et al., "JAKs, STATs and signal transduction in response to the interferons and other cytokines," *Philos. Trans. R. Soc. Lond. B. Biol. Sci.* 351(1336):167-71, 1996.
Buczkowicz et al., "Genomic analysis of diffuse intrinsic pontine gliomas identifies three molecular subgroups and recurrent activating ACVR1 mutations," *Nature Genet.* 46(5):451-456, 2014.
Buczkowicz et al., "Histopathological spectrum of paediatric diffuse intrinsic pontine glioma: diagnostic and therapeutic implications," *Acta Neuropathol.* 128(4):573-581, 2014.
CAS Registry No. 1029712-80-8, "Benzamide, 2-fluoro-N-methyl-4-[7-(6-quinolinylmethyl)imidazo[1,2-b][1,2,4]triazin-2-yl]-" Entered STN Jun. 22, 2008, 1 page.
CAS Registry No. 1035555-63-5, "Pyrido[2,3-d]pyrimidine-4,7(3H,8H)-dione, 3-[(2R)-2,3-dihydroxypropyl]-6-fluoro-5-[(2-fluoro-4-iodophenyl)amino]-8-methyl-" Entered STN Jul. 23, 2008, 1 page.
CAS Registry No. 1211441-98-3, "7H-Pyrrolo[2,3-d]pyrimidine-6-carboxamide, 7-cyclopentyl-N,N-dimethyl-2-[[5-(1-piperazinyl)-2-pyridinyl]amino]-" Entered STN Mar. 18, 2010, 1 page.
CAS Registry No. 1236699-92-5 (Deleted CAS Registry No. 1204531-26-9, "4-Pyridinecarboxamide, N-[(2S)-2,3-dihydroxypropyl]-3-[(2-fluoro-4-iodophenyl)amino]-" Entered STN Aug. 19, 2010, 1 page.
CAS Registry No. 1246560-33-7, "2-Pyrimidinamine, 5-[8-methyl-9-(1-methylethyl)-2-(4-morpholinyl)-9H-purin-6-yl]-" Entered STN Oct. 19, 2010, 1 page.
CAS Registry No. 212141-51-0, "1-Phthalazinamine, N-(4-chlorophenyl)-4-(4-pyridinylmethyl)-, hydrochloride (1:2)" Entered STN Oct. 4, 1998, 1 page.
CAS Registry No. 2457-80-9, "Adenosine, 5'-S-methyl-5'-thio-" Entered STN Nov. 16, 1984, 1 page.
CAS Registry No. 332012-40-5, "2-Pyridinecarboxamide, 4-[[[4-[(4-chlorophenyl)amino]furo[2,3-d]pyridazin-7-yl]oxy]methyl]-N-methyl-" Entered STN Apr. 22, 2001, 1 page.

(56) References Cited

OTHER PUBLICATIONS

CAS Registry No. 475108-18-0, "Urea, N-[2-chloro-4-[(6,7-dimethoxy-4-quinolinyl)oxy]phenyl]-N'-(5-methyl-3-isoxazolyl)-" Entered STN Dec. 4, 2002, 1 page.
CAS Registry No. 602306-29-6, "2-Pyrimidinamine, 4-[2-methyl-1-(1-methylethyl)-1H-imidazol-5-yl]-N-[4-(methylsulfonyl)phenyl]-" Entered STN Oct. 10, 2003, 1 page.
CAS Registry No. 653592-04-2, "3-Pyrrolidinol, 1-[(4-amino-5H-pyrrolo[3,2-d]pyrimidin-7-yl)methyl]-4-[(methylthio)methyl]-, (3R,4S)-" Entered STN Feb. 24, 2004, 1 page.
CAS Registry No. 656247-17-5 (Deleted STN Registry No. 928326-83-4, "1H-Indole-6-carboxylic acid, 2,3-dihydro-3-[[[4-[methyl[2-(4-methyl-1-piperazinyl)acetyl]amino]phenyl]amino]phenylmethylene]-2-oxo-, methyl ester, (3Z)-" Entered STN Mar. 1, 2004, 1 page.
CAS Registry No. 755037-03-7, "2-Pyridinecarboxamide, 4-[4-[[[[4-chloro-3-(trifluoromethyl)phenyl]amino]carbonyl]amino]-3-fluorophenoxy]-N-methyl-" Entered STN Oct. 1, 2004, 1 page.
CAS Registry No. 837364-57-5, "3-Pyridinemethanamine, 5-[3-(5,7-difluoro-1H-benzimidazol-2-yl)-1H-indazol-5-yl]-N-ethyl-4-methyl-" Entered STN Feb. 25, 2005, 1 page.
CAS Registry No. 844442-38-2, "1H-Pyrazole-3-carboxamide, 4-[(2,6-dichlorobenzoyl)amino]-N-4-piperidinyl-" Entered STN Mar. 8, 2005, 1 page.
CAS Registry No. 857876-30-3, "3-Pyridinecarboxamide, N-(2,3-dihydro-3,3-dimethyl-1H-indo1-6-yl)-2-[(4-pyridinylmethyl)amino]-, phosphate (1:2)" Entered STN Aug. 1, 2005, 1 page.
CAS Registry No. 869363-13-3, "Benzoic acid, 4-[[9-chloro-7-(2,6-difluorophenyl)-5H-pyrimido[5,4-d][2]benzazepin-2-yl]amino]-" Entered STN Dec. 6, 2005, 1 page.
CAS Registry No. 877399-52-5, "2-Pyridinamine, 3-[(1R)-1-(2,6-dichloro-3-fluorophenyl)ethoxy]-5-[1-(4-piperidinyl)-1H-pyrazol-4-yl]-" Entered STN Mar. 21, 2006, 1 page.
CAS Registry No. 905281-76-7, "1H-Inden-1-one, 2,3-dihydro-5-[1-(2-hydroxyethyl)-3-(4-pyridinyl)-1H-pyrazol-4-yl]-, oxime" Entered STN Aug. 29, 2006, 1 page.
CAS Registry No. 918504-65-1, "1-Propanesulfonamide, N-[3-[[5-(4-chlorophenyl)-1H-pyrrolo[2,3-b]pyridin-3-yl]carbonyl]-2,4-difluorophenyl]-" Entered STN Jan. 26, 2007, 1 page.
CAS Registry No. 920113-03-7, "4H-1-Benzopyran-4-one, 2-(2-chlorophenyl)-5,7-dihydroxy-8-[(2R,3S)-2-(hydroxymethyl)-1-methyl-3-pyrrolidinyl]-, hydrochloride (1:1)" Entered STN Feb. 8, 2007, 1 page.
CAS Registry No. 927880-90-8, "1H-Benzimidazol-2-amine, 1-methyl-5-[[2-[5-(trifluoromethyl)-1H-imidazol-2-yl]-4-pyridinyl]oxy]-N-[4-(trifluoromethyl)phenyl]-" Entered Stn Mar. 22, 2007, 1 page.
CAS Registry No. 934660-93-2 (Deleted CAS Registry No. 1029872-29-4), "Methanone, [3,4-difluoro-2-[(2-fluoro-4-iodophenyl)amino]phenyl][3-hydroxy-3-(2S)-2-piperidinyl-1-azetidinyl]-" Entered STN May 13, 2007, 1 page.
CAS Registry No. 950769-58-1, "Urea, N-[5-(1,1-dimethylethyl)-3-isoxazolyl]-N'-4[4-[7-[2-(4-morpholinyl)ethoxy]imidazo[2,1-b]benzothiazol-2-yl]phenyl]-" Entered STN Oct. 16, 2007, 1 page.
CAS Registry No. 951209-71-5, "IRX 2" Entered STN Oct. 23, 2007, 1 page.
CAS Registry No. 958852-01-2, "2,4-Thiazolidinedione, 5-[[4-(4-pyridinyl)-6-quinolinyl]methylene]-, (5Z)-" Entered STN Dec. 19, 2007, 1 page.
Chaikuad et al., "Structure of the Bone Morphogenetic Protein Receptor ALK2 and Implications for Fibrodysplasia Ossificans Progressiva," *J. Bio. Chem*, 287(44):36990-36998, 2012.
Chao et al., "Tumor Stress-Induced Phosphoprotein 1 (STIP1) as a Prognostic Biomarker in Ovarian Cancer," *Plos One* 8(2):e57084, 9 pages, 2013.
Chen et al., "Transforming growth factor β1 (TGF-β1) activates hepcidin mRNA expression in hepatocytes," *J. Bio. Chem.* 291(25):13160-13174, 2016.

Cohen et al., "Diffuse intrinsic pontine gliomas-current management and new biologic insights. Is there a glimmer of hope?," *Neuro-Oncology* 19(8):1025-1034, 2017.
Compound Summary for CID 20615641, Pub Chem, Dec. 5, 2007, 6 pages.
Compound Summary for CID 3025986 (CAS Registry No. 345627-80-7), Pub Chem, Created Aug. 8, 2005, 25 pages.
Compound Summary for CID 50992434 (Deprecated CAS Registry No. 1204531-25-8), Pub Chem, Created Apr. 4, 2011, 24 pages.
Compound Summary for CID 56839178, Pub Chem, Mar. 19, 2012, 21 pages.
Compound Summary for CID 132131624, Pub Chem, Jan. 29, 2018, 10 pages.
Coutant et al, "Early Development GMPs for Small-Molecule Specifications: An Industry Perspective (Part V)," *Pharmaceutical Technology* 36(10):86-94, 2012.
Coyne, "Hepcidin: clinical utility as a diagnostic tool and therapeutic target," *Kidney Int*, 80(3):240-244, 2011.
Cullis, "Diagnosis and management of anaemia of chronic disease: current status," *Br J Haematol*, 154(3):289-300, 2011.
Dixon et al., "The role of iron and reactive oxygen species in cell death," *Nature Chemical Biology* 10:9-17, 2014.
Eisenhauer et al., "New response evaluation criteria in solid tumours: Revised RECIST guideline (version 1.1)," *Eur. J. Cancer* 45:228-247, 2009.
Engers et al., "Synthesis and structure-activity relationships of a novel and selective bone morphogenetic protein receptor (BMP) inhibitor derived from the pyrazolo[1.5-a]pyrimidine scaffold of Dorsomorphin: The discovery of ML347 as an ALK2 versus ALK3 selective MLPCN probe," *Bioorganic & Medicinal Chemistry Letters* 23(11):3248-3252, 2013.
Frazier et al., "Inhibition of ALK5 Signaling Induces Physeal Dysplasia in Rats," *Toxicologic Pathology* 35:284-295, 2007.
Fu et al., "SM16, an Orally Active TGF-β Type I Receptor Inhibitor Prevents Myofibroblast Induction and Vascular Fibrosis in the Rat Carotid Injury Model," *Arterioscler. Thromb. Vasc. Biol.* 28:665-671, 2008.
Galesloot et al., "Serum hepcidin: reference ranges and biochemical correlates in the general population," *Blood* 117(25):e218-e225, 2011.
Ganz et al., "Hepcidin and Iron Homeostasis," *Biochim. Biophys. Acta*, 1823(9):1434-1443, 2012.
Grasso et al., "Functionally-defined Therapeutic Targets in Diffuse Intrinsic Pontine Glioma: A Report of the Children's Oncology Group DIPG Preclinical Consortium," *Nature Medicine* 21(6):555-559, 2015.
Greenberg et al., "Revised international prognostic scoring system for myelodysplastic syndromes," Blood 120(12):2454-2465, 2012.
Griesinger et al., "A BCR-JAK2 fusion gene as the result of a t(9;22)(p24;q11.2) translocation in a patient with a clinically typical chronic myeloid leukemia," Genes Chromosomes Cancer 44(3):329-333, 2005.
Hamasaki et al., "Pathogenic Mutation of ALK2 Inhibits Induced Pluripotent Stem Cell Reprogramming and Maintenance: Mechanisms of Reprogramming and Strategy for Drug Identification," *Stem Cells* 30:2437-2449, 2012.
Hamilton et al., "Characterization of a xenograft model of human ovarian carcinoma which produces ascites and intraabdominal carcinomatosis in mice," *Cancer Res.* 44(11):5286-5290, 1984.
Han et al., "Shared ACVR1 mutations in FOP and DIPG: Opportunities and challenges in extending biological and clinical implications across rare diseases," *Bone* 109:91-100, 2018.
Hanada et al, "Regulation of Bcl-2 Oncoprotein Levels with Differentiation of Human Neuroblastoma Cells," *Cancer Res.* 53.4978-4986, 1993.
Hashizume et al., "Pharmacologic inhibition of histone demethylation as a therapy for pediatric brainstem glioma," *Nature Medicine* 20(12):1394-1396, 2014.
Hinck et al., "Structural Biology and Evolution of the TGf-β Family," *Cold Spring Harb. Perspect. Biol.* 8(12):1-51, 2017.
Hino et al., "Neofunction of ACVR1 in fibrodysplasia ossificans progressiva," *Proc. Natl. Acad. Sci. USA* 112(50):15438-15443, 2015.

(56) References Cited

OTHER PUBLICATIONS

Hoeman et al., "ACVR1 R206H cooperates with H3.1K27M in promoting diffuse intrinsic pontine glioma pathogenesis," Nature Communications, 10:1-15, 2019.
Hu et al. "Vascular Endothelial Growth Factor Immunoneutralization Plus Paclitaxel Markedly Reduces Tumor Burden and Ascites in Athymic Mouse Model of Ovarian Cancer," *The American Journal of Pathology* 161(5): 1917-1924, 2002.
Ihle, "Janus kinases in cytokine signaling," *Philos. Trans. R. Soc. Lond. B. Biol. Sci.* 351(1336):159-166, 1996.
Ihle, "The Janus protein tyrosine kinases in hematopoietic cytokine signaling," *Semin. Immunol.* 7(4): 247-254, 1995.
Ikushima et al., "Biology of Transforming Growth Factor-beta Signaling," *Curr. Pharm. Biotechnol*, 12(12):2099-2107,2011.(Abstract Only).
Inman et al., "SB-431542 Is a Potent and Specific Inhibitor of Transforming Growth Factor-β Superfamily Type I Activin Receptor-Like Kinase (ALK) Receptors ALK4, ALK5, and ALK7," *Molecular Pharmacology* 62:65-74, 2002.
Jones et al., "Paediatric and adult malignant glioma: close relatives or distant cousins?," *Nat. Rev. Clin. Oncol.* 9(7):400-413, 2012.
Kaplan et al., "Classic and atypical fibrodysplasia ossificans progressiva (FOP) phenotypes are caused by mutations in the bone morphogenetic protein (BMP) type I receptor ACVR1," *Hum Mutat.* 30(3):379-390, 2009.
Kaplan et al., "From mysteries to medicines: drug development for fibrodysplasia ossificans progressive," *Expert Opin. Orphan Drugs* 1(8):637-649, 2014.
Kaplan et al., "Investigations of activated ACVR1/ALK2, a bone morphogenetic protein type I receptor, that causes fibrodysplasia ossificans progressiva," *Methods Enzymol* 484:357-373,2010.
Kim et al., "Identification of novel ALK2 inhibitors and their effect on cancer cells," *Biochemical and Biophysical Research Communications* 492:121-127, 2017.
Kirson et al., "Disruption of Cancer Cell Replication by Alternating Electric Fields," *Cancer Research* 64:3288-3295, 2004.
Kokatla et al., "Reduction of Amine N-Oxides by Diboron Reagents," *J. Org. Chem.* 76(19):7842-7848, 2011.
Lacronique et al., "A TEL-JAK2 Fusion Protein with Constitutive Kinase Activity in Human Leukemia," Science 278(5341):1309-1312, 1997.
Lewis et al., "Inhibition of PRC2 Activity by a Gain-of-Function H3 Mutation Found in Pediatric Glioblastoma," *Science* 340(6134):857-861, 2013.
Liu et al., "Progress in Brain Penetration Evaluation in Drug Discovery and Development," *J. Pharmacology and Exper. Therapeutics* 325(2):349-356, 2008.
Louis et al., "The 2016 World Health Organization Classification of Tumors of the Central Nervous System: a summary," *Acta Neuropathol* 131(6):803-820, 2016.
Macdougall, "Iron management: new strategies currently under investigation," presentation at the Controversies Conference on Iron Management in Chronic Kidney Disease, San Francisco, CA Mar. 27-30, 48 pages, 2014.
Mandal et al., "An Update of Bone Morphogenetic Proteins as Biomarker and Therapy for Cancer," *J. Carcinog. Mutagen.* 6(1):1000e114, 4 pages, 2015.
Martelotto et al., "Whole-genome single-cell copy number profiling from formalin-fixed paraffin-embedded samples," *Nature Med.* 23(3):376-385, 2017.
Massague et al., "Smad transcription factors", Genes Dev,X19(23): 2783-2810 (2005).
Misuraca et al., "Pre-clinical models of diffuse intrinsic pontine glioma," *Frontiers in Oncology*, Article 172, 5:1-7, 2015.
Misuraca et al., "A Novel Mouse Model of Diffuse Intrinsic Pontine Glioma Initiated in Pax3-Expressing Cells," *Neoplasia* 18(1):60-70, 2016.
Mohedas et al., "Development of an ALK2-biased BMP type I receptor kinase inhibitor," *ACS Chem. Biol.* 8(6):1291-1302, 2013.

Monje, et al., "Hedgehog-responsive candidate cell of origin for diffuse intrinsic pontine glioma," Proc. Natl. Acad. Sci. USA 108(11):4453-4458 (2011).
Nayak et al., "Novel Approaches in Erythropoietin," *J. Chem. Pharm. Res.* 2(2):13-26, 2010.
NCBI "AXL receptor tyrosine kinase [ *Homo sapiens* (human) ]" Gene ID 558, updated Feb. 3, 2021, 11 pages.
NCBI "growth arrest specific 6 [ *Homo sapiens* (human) ]" Gene ID 2621, Feb. 3, 2021, 10 pages.
Neuenschwander et al., "Critical aspects of the Bayesian approach to phase I cancer trials," *Statistics in Medicine* 27(13):2420-2439, 2008.
Nicholson et al., "Tyrosine kinase JAK1 is associated with the granulocyte-colony-stimulating factor receptor and both become tyrosine-phosphorylated after receptor activation," *Proc. Natl. Acad. Sci. U.S.A.* 91(8):2985-2988, 1994.
Oliveira et al., "Oral Administration of GW788388, an Inhibitor of Transforming Growth Factor Beta Signaling, Prevents Heart Fibrosis in Chagas Disease," *Plos* 6(6):e1696, 14 pages, 2012.
Pacifici et al., "Common mutations in ALK2/ACVR1, a multifaceted receptor, have roles in distinct pediatric musculoskeletal and neural orphan disorders," *Cytokine Growth Factor Rev.* 27:93-104, 2016.
Peterson et al., "Abstract 3647: Targeting Cancer-Induced Anemia with Hepcidin Lowering ALK2 Inhibitors," AACR; Cancer Res., 75(15 Suppl): 3647, 2 pages (2015) presented at the 106th AACR Annual Meeting, Apr. 18-22, 2015,Philadelphia, PA (Mar. 18, 2015).
Peterson et al., "Targeting Cancer-Induced Anemia with Hepcidin Lowering ALK2 Inhibitors," poster presentation on Apr. 21, 2015 at the 106th AACR Annual Meeting, Apr. 18-22, 2015,Philadelphia, PA.
Peterson et al., "ALK2 Inhibition Via TP-0184 Abrogates Inflammation-Induced Hepcidin Expression and is a Potential Therapeutic for Anemia of Chronic Disease," Blood, 126:Abstract 273, 5 pages (2015) presented at the American Society of Hematology 57th Annual Meeting & Exposition, Dec. 5-8, 2015, Orlando, FL. Dec. 3, 2015.
Peterson et al., "ALK2 Inhibition Via TP-0184 Abrogates Inflammation-Induced Hepcidin Expression and is a Potential Therapeutic for Anemia of Chronic Disease," presentation on Dec. 6, 2015 at the American Society of Hematology 57th Annual Meeting & Exposition, Dec. 5-8, 2015, Orlando, FL.
Peterson et al., "The ALK-2 inhibitor, TP-0184, Demonstrates High Distribution to the Liver Contributing to Significant Preclinical Efficacy in Mouse Models of Anemia of Chronic Disease," Blood, 128: 263, 5 pages (2016) as presented at the American Society of Hematology 58th Annual Meeting & Exposition, Dec. 3-6, 2016, San Diego, CA.
Peterson et al., "The ALK-2 inhibitor, TP-0184, Demonstrates High Distribution to the Liver Contributing to Significant Preclinical Efficacy in Mouse Models of Anemia of Chronic Disease," presentation at the American Society of Hematology 58th Annual Meeting & Exposition, Dec. 3-6, 2016, San Diego, CA.
Peterson et al., "TP-0184 is an Inhibitor of ALK2 and a Potential Therapeutic for the Treatment of Anemia of Chronic Disease," Poster Abstract #112 presented at: 7th Congress of the International BioIron Society, May 7-11, 2017, Los Angeles, CA (Jun. 24, 2017).
Peterson et al., "TP-0184 is an Inhibitor of ALK2 and a Potential Therapeutic for the Treatment of Anemia of Chronic Disease," Poster #112 presented on May 8, 2017 at the 7th Congress of the International BioIron Society, May 7-11, 2017, Los Angeles, CA.
Peterson et al., "TP-0184 Inhibits ALK2/ACVR1, Decreases Hepcidin Levels, and Demonstrates Activity in Preclinical Mouse Models of Functional Iron Deficiency," Blood, 130:937, 6 pages (2017) presented at the American Society of Hematology 59th Annual Meeting, Dec. 9-12, 2017 at Atlanta, GA (Dec. 7, 2017).
Peterson et al., "TP-0184 Inhibits ALK2/ACVR1, Decreases Hepcidin Levels, and Demonstrates Activity in Preclinical Mouse Models of Functional Iron Deficiency," poster presentation at the American Society of Hematology 59th Annual Meeting, Dec. 9-12, 2017 at Atlanta, GA.

(56) References Cited

OTHER PUBLICATIONS

Pignolo et al., "Fibrodysplasia Ossificans Progressiva: Diagnosis, Management, and Therapeutic Horizons," *Pediatr. Endocrinol. Rev.* 10(2):437-448, 2013.
Rawlings et al., "The JAK/STAT signalling pathway," *J. Cell Sci.* 117(Pt 8):1281-1283, 2004.
Sanvitale et al., "A New Class of Small Molecule Inhibitor of BMP Signaling," *PlosOne* 8(4):e62721, 11 pages, 2013.
Schanz et al., "New comprehensive cytogenetic scoring system for primary myelodysplastic syndromes (MDS) and oligoblastic acute myeloid leukemia after MDS derived from an international database merge," *J. Clin. Oncol.* 30(8):820-829, 2012.
Schroeder et al., "Children are not just little adults: recent advances in understanding of diffuse intrinsic pontine glioma biology," *Pediatric Res.* 75(1):205-209, 2014.
Schwartz et al., "RECIST 1.1-Update and Clarification: From the RECIST Committee," *Eur. J. Cancer* 62:132-137, 2016.
Seymour et al., "iRECIST: guidelines for response criteria for use in trials testing immunotherapeutics," *Lancet Oncol.* 18(3):e143-e152, 2017.
Shen et al., "The fibrodysplasia ossificans progressiva R206H ACVR1 mutation activates BMP-independent chondrogenesis and zebrafish embryo ventralization," *J. Clin. Invest.* 119:3462-3472, 2009.
Shore et al., "A recurrent mutation in the BMP type I receptor ACVR1 causes inherited and sporadic fibrodysplasia ossificans progressiva," *Nat Genet.* 38(5):525-527, 2006.
Silvennoinen et al., "Structure of the JAK2 protein tyrosine kinase and its role in IL-3 signal transduction," *Proc. Natl. Acad. Sci. U.S.A.* 90(18):8429-8433, 1993.
Singh et al., "Hepcidin: A novel peptide hormone regulating iron metabolism," *Clinica. Chimica. Acta.* 412:823-830, 2011.
Slattery et al., "Genetic Variation in Bone Morphogenetic Proteins and Breast Cancer Risk in Hispanic and non-Hispanic white women: the Breast Cancer Health Disparities Study," *Int. J. Cancer* 132(12):2928-2939, 2013.
Stauber et al., "Nonclinical Safety Evaluation of a Transforming Growth Factor β Receptor I Kinase Inhibitor in Fischer 344 Rats and Beagle Dogs," *J. Clin. Pract.* 4(3):1-10,2014.
Steinbicker et al., "Inhibition of bone morphogenetic protein signaling attenuates anemia associated with inflammation," *Blood* 117:4915-4923, 2011.
Steinbicker et al., "Perturbation of hepcidin expression by BMP type I receptor deletion induces iron overload in mice," *Blood* 118(15):4224-4230, 2011.
Sun et al, "A Hepcidin Lowering Agent Mobilizes Iron for Incorporation into Red Blood Cells in an Adenine-Induced Kidney Disease Model of Anemia in Rats," *Nephrol. Dial. Transplant.* 28:1733-1743, 2013.
Sun et al., "Targeting the hepcidin-ferroportin axis to develop new treatment strategies for anemia of chronic disease and anemia of inflammation," *American Journal of Hematology* 87(4):392-400, 2012.
Tahara et al., "Electronic Tongues—A Review," *IEEE Sensors Journal* 13(8):3001-3011, 2013.
Taylor et al., "ACVR1 Mutations in DIPG: Lessons Learned from FOP," *Cancer Res.* 74(17):1-6, 2014.
Taylor et al., "Recurrent activating ACVR1 mutations in diffuse intrinsic pontine glioma," *Nat. Genet.* 45(5):457-461, 2014.
Theurl, I. et al., "Pharmacologic inhibition of hepcidin expression reverses anemia of chronic inflammation in rats," *Blood*118(18):4977-4984, 2011.
Tolero Pharmaceuticals (Jul. 25, 2018), Tolero Pharmaceuticals Announces First Patient Dosed with Investigational Agent TP-0184, an Activin A Receptor Type 1 (ACVR1) Inhibitor, in Phase 1 Study of Patients with Advanced Solid Tumors [Press Release]. Originally published at https://www.toleropharma.com/our-news/press-releases/press07252018.
Tolero Pharmaceuticals (Feb. 27, 2019), Tolero Pharmaceuticals to Present New Data Evaluating Investigational Agents TP-0903 and TP-0184 at AACR Annual Meeting 2019 [Press Release]. Originally published at https://www.toleropharma.com/our-news/press-releases/press02272019.
Truffaux et al., "Preclinical evaluation of dasatinib alone and in combination with cabozantinib for the treatment of diffuse intrinsic pontine glioma," *Neuro-Oncology* 17(7):953-964, 2015.
Tsai et al., "Secreted Stress-Induced Phosphoprotein 1 Activates the ALK2-SMAD Signaling Pathways and Promotes Cell Proliferation of Ovarian Cancer Cells," *Cell Reports* 2:283-293, 2012.
Tumilowicz et al., "Definition of a Continuous Human Cell Line Derived from Neuroblastoma," *Cancer Res.* 30:2110-2118, 1970.
Vadhan-Raj et al., "A first-in-human phase 1 study of a hepcidin monoclonal antibody, LY2787106, in cancer-associated anemia," *J. Hematology & Oncology* 10:73, 2017.
Vialaret et al., "Nano-Flow vs Standard-Flow: which is the more suitable LC/MS method for quantifying hepcidin-25 in human serum in routine clinical settings?" *J. Chrom. B.*, p. 110-117, 2018.
Wade et al., "Abstract 3166: Evaluation of Genetic Modulation of *ACVR1* (aka *ALK2*) Kinase Gene as a Clinical Biomarker of the ACVR1 Inhibitor TP-0184" abstract presented at AACR Annual Meeting, Mar. 29-Apr. 3, 2019, Atlanta, GA (Feb. 27, 2019).
Wade et al., "Evaluation of Genetic Modulation of *ACVR1* (aka ALK2) Kinase Gene as a Clinical Biomarker of the *ACVR1* Inhibitor TP-0184" poster presentation on Apr. 2, 2019 at the AACR Annual Meeting, Mar. 29-Apr. 3, 2019, Atlanta, GA.
Warner, "Targeting Novel Kinases in Hematological Malignancies", [abstract from the 9th International Conference on Leukemia and Hematologic Oncology, Oct. 5-6, 2017, London UK]abstract taken from J. Hematol Thrombo Dis., 5:5(Suppl) (2017).
Wang et al., "Iron Metabolism in Cancer," *Int. J Molecular Sciences* 20(95), 22 pages, 2019.
Warren, "Diffuse intrinsic pontine glioma: poised for progress," *Front. Oncol.* 2:Article 205, 9 pages, 2012.
Wentworth et al., "Therapeutic Advances for Blocking Heterotopic Ossification in Fibrodysplasia Ossificans Progressiva," *British Journal of Clinical Pharmacology* 85:1180-1187, 2018.
Wilks, "Cloning members of protein-tyrosine kinase family using polymerase chain reaction," *Methods Enzymol.* 200:533-546, 1991.
Witthuhn et al., "JAK2 associates with the erythropoietin receptor and is tyrosine phosphorylated and activated following stimulation with erythropoietin," *Cell* 74(2):227-236, 1993.
Worthen et al., "The role of hepatic transferrin receptor 2 in the regulation of iron homeostasis in the body," *Frontiers in Pharmacology* 5:1-8, 2014.
Ye et al., "Bone morphogenetic protein and bone metastasis, implication and therapeutic potential," *Front. Biosci* 16:865-897, 2011.
Zhao et al., "Inherited Disease Genetics Improves the Identification of Cancer-Associated Genes," *PLoS Genetics* 12(6):e1006081, 16 pages, 2016.
Zhao et al., "Iron regulation by hepcidin," *J. Clinical Investigation* 123(6):2337-2343, 2013.
Zhou et al., "Inhibition of the TGF-B receptor I kinase promotes hematopoiesis in MDS," *Blood* 112(8):3434-3443, 2008.
Zhou et al., "Reduced SMAD7 Leads to Overactivation of TGF-b Signaling in MDS that Can Be Reversed by a Specific Inhibitor of TGF-b Receptor I Kinase," *Cancer Res.* 71(3):955-63, 2011.
U.S. Appl. No. 16/930,261, filed Jul. 15, 2020.

| Group | Number of Cases, Total | Number of Cases, Deceased | Median Months Survival |
|---|---|---|---|
| Cases with Alteration(s) in Query Gene(s) | 40 | 9 | 20.25 |
| Cases without Alteration(s) in Query Gene(s) | 7534 | 2216 | 26.2 |

| Molecule | myMPO | Name | molLogP | molWeight | nof_HBD | molPSA | pKa-mb |
|---|---|---|---|---|---|---|---|
|  | 4.547702 | codeine | 1.745722 | 299.15213 | 1 | 34.287369 | 6.212182 |
|  | 4.5 | acetaminophen | 1.136226 | 151.063324 | 2 | 41.117363 | -0.291551 |
|  | 4.5 | lorazepam | 2.699728 | 320.011932 | 2 | 50.452785 | 1.29082 |
|  | 4.456232 | risperidone | 3.618627 | 410.211792 | 0 | 51.678829 | 8.264673 |
|  | 4.12689 | olanzapine | 2.434614 | 312.140869 | 1 | 25.911329 | 7.492568 |

| Molecule | myMPO | Name | molLogP | molWeight | n of HBD | molPSA | pKa-mb |
|---|---|---|---|---|---|---|---|
| | 3.833333 | aspirin | 1.181602 | 180.042252 | 1 | 49.484238 | 0 |
| | 3.807585 | baclofen | 1.199816 | 213.055649 | 3 | 50.282619 | 8.718163 |
| | 3.640617 | paroxetine | 4.022516 | 329.142731 | 1 | 36.39378 | 9.002295 |
| | 3.389315 | Compound 2 | 3.660375 | 468.238617 | 2 | 70.923172 | 8.196222 |
| | 3.344511 | aripiprazole | 4.94291 | 447.148041 | 1 | 39.147327 | 8.006507 |

FIG. 32B

| Molecule | myMPO | Name | molLogP | molWeight | nof_HBD | molPSA | pKa-mb |
|---|---|---|---|---|---|---|---|
| [ibuprofen structure] | 3.106473 | ibuprofen | 3.318373 | 206.130676 | 1 | 28.646532 | 0 |
| [sertraline structure] | 2.453356 | sertraline | 5.337157 | 305.073792 | 1 | 11.789347 | 8.759954 |

*FIG. 32C*

METHODS FOR TREATING DISEASES ASSOCIATED WITH ABNORMAL ACVR1 EXPRESSION AND ACVR1 INHIBITORS FOR USE IN THE SAME

CROSS-REFERENCE

This application claims the benefit of U.S. Provisional Application Ser. No. 62/703,862, filed Jul. 26, 2018, herein incorporated by reference in its entirety.

FIELD OF THE INVENTION

The present disclosure provides therapeutic uses and methods of treatment comprising administering a compound having activity as an ACVR1 inhibitor. The present disclosure also provides pharmaceutical compositions comprising a compound having activity as an ACVR1 inhibitor. Moreover, the present disclosure provides novel forms of a compound having activity as an ACVR1 inhibitor.

BACKGROUND OF THE INVENTION

Bone morphogenetic proteins (BMPs) are pleiotropic growth factors playing essential roles in coordinating tissue architecture throughout various organs in the body. BMP ligands interact with bone morphogenetic protein receptors (BMPRs), which belong to the transforming growth factor beta (TGF-b) superfamily of serine/threonine kinase receptors (Ikushima, H. and K. Miyazono, *Biology of Transforming Growth Factor-beta Signalin*. Curr Pharm Biotechnol, 2011), hereby incorporated by reference with regard to such background teaching. The ligands bind to type-II receptors, which then recruit type-I receptors forming a heteromeric complex. As a complex, the type-II receptor phosphorylates the type-I receptor, which allows the type-I receptor to become active and phosphorylate downstream signaling molecules. The downstream effects of activating these receptors are primarily carried out by the SMAD family of proteins. SMADs become phosphorylated and transduce the signal from the cell membrane to the nucleus where they function as transcription factors to regulated gene expression (Massague, J., J. Seoane, and D. Wotton, *Smad transcription factors*. Genes Dev, 2005. 19(23): p. 2783-810), hereby incorporated by reference with regard to such background teaching.

In individuals with chronic diseases, such as cancer and inflammation, BMP signaling is constitutively activated leading to anemia. This condition is commonly referred to as anemia of chronic disease (ACD) and is a debilitating symptom associated with cancer patients (Cullis, J. O., *Diagnosis and management of anaemia of chronic disease: current status*. Br J Haematol, 2011. 154(3): p. 289-300), hereby incorporated by reference with regard to such background teaching. Chronic anemia in cancer patients leads to extreme weakness and fatigue, which leads to a poor quality of life for these individuals. In these patients, BMP signaling through two BMP type-I receptors, ALK2 (as noted, also known as ACVR1) and ALK3 induces the hepatic expression of the peptide hormone, called hepcidin (Steinbicker, A. U., et al., *Perturbation of hepcidin expression by BMP type I receptor deletion induces iron overload in mice*. Blood, 2011. 118(15): p. 4224-30), hereby incorporated by reference with regard to such background teaching.

Hepcidin reduces serum iron levels by promoting the degradation of the iron exporter, ferroportin, resulting in the increase of iron stored away in macrophages and other cell types and making the iron unavailable for hemoglobin and red blood cell (RBC) function. Supplementing a patient's intake of iron does not reverse ACD because the ingested iron simply is stored away due to the activated BMP pathway and high serum hepcidin levels. Currently, ACD in cancer is managed by limiting the physical activity of patients and blood transfusions are used in the most severe cases. Inhibition of BMP signaling in these patients has the potential to provide a real difference in their quality of life and ultimately, may positively impact how they respond to therapy, radiation, or surgery (Steinbicker, A. U., et al., *Inhibition of bone morphogenetic protein signaling attenuates anemia associated with inflammation*. Blood, 2011. 117(18): p. 4915-23; Coyne, D. W., *Hepcidin: clinical utility as a diagnostic tool and therapeutic target*. Kidney Int, 2011. 80(3): p. 240-4; Theurl, I., et al., *Pharmacologic inhibition of hepcidin expression reverses anemia of chronic disease in rats*. Blood, 2011), each hereby incorporated by reference with regard to such background teaching.

In addition to its function in ACD, BMP signaling plays pivotal roles in the growth and metastasis of cancer cells, particularly in breast, prostate, and other cancers that frequently metastasize to the bone (Ye, L., M. D. Mason, and W. G. Jiang, *Bone morphogenetic protein and bone metastasis, implication and therapeutic potential*. Front Biosci, 2011. 16: p. 865-97). BMPs and BMPRs are more highly expressed in metastatic breast cancer cells compared to less metastatic ones and also in prostate cancer cells that generate osteosclerotic bone metastases (Bobinac, D., et al., *Expression of bone morphogenetic proteins in human metastatic prostate and breast cancer*. Croat Med J, 2005. 46(3): p. 389-96). In addition to affecting the invasiveness and metastasis of cancer cells, the BMP pathway has also been shown to influence the bone microenvironment. Studies have shown that the inhibition of BMP signaling significantly reduces bone tumor burden and osteolytic disease in a preclinical model of prostate cancer bone metastasis. These results suggest that a BMP inhibitor may have application in preventing bone metastases.

Furthermore, a BMP inhibitor has the potential to treat multiple disease indications outside of cancer. ACD is a devastating condition that affects individuals suffering from other diseases, including rheumatoid arthritis, systemic lupus, chronic kidney disease, and many other inflammatory diseases. Additionally, a rare childhood genetic disease, called fibrodysplasia ossificans progressive (FOP) has been shown to be caused by activating mutations in the alk2 gene (Kaplan, F. S., et al., *Investigations of activated ACVR1/ALK2, a bone morphogenetic protein type I receptor, that causes fibrodysplasia ossificans progressiva*. Methods Enzymol, 2010. 484: p. 357-73). The mutation in ALK2 in this disease causes fibrous tissue (muscle, tendon, ligament, etc.) to be ossified when damaged. Studies performed in animal models of FOP suggest that inhibiting ALK2 decreases the "flare-ups" associated with FOP and prevents the ossification of repaired tissue in the model.

SUMMARY OF THE DISCLOSURE

In one embodiment, the present disclosure provides a method of treating diffuse intrinsic pontine glioma (DIPG)

in a subject in need thereof, the method comprising: administering a therapeutically effective amount of a compound of formula (2):

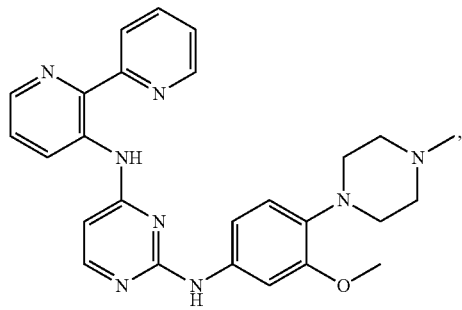

(2)

or a crystalline salt thereof.

In one aspect, the crystalline salt is an acid addition salt. In one aspect, the acid addition salt is a hydrochloric acid salt. In one aspect, the hydrochloric acid salt is monovalent. In one aspect, the crystalline salt form is anhydrous. In one aspect, the subject is a pediatric patient. In one aspect, the subject is about 1 week of age to about 22 years of age. In one aspect, the subject is about 18 years of age or less. In one aspect, the subject is about 10 years of age or less. In one aspect, the subject is about 8 years of age or less. In one aspect, the subject is about 6 years of age or less. In one aspect, the DIPG is newly diagnosed or recurrent. In one aspect, the DIPG is characterized as a pontine tumor with a histologic diagnosis of infiltrating glioma, grades II to IV. In one aspect, the method further comprises administering radiation therapy. In one aspect, the administration of radiation occurs prior to administration of the compound or crystalline salt thereof. In one aspect, the administration of radiation occurs after the administration of the compound or crystalline salt thereof. In one aspect, the administration of radiation occurs both prior to and after administration of the compound or crystalline salt thereof. In one aspect, the method further comprises administering one or more additional therapeutic agent. In one aspect, the radiation may be administered as a component agent. In one aspect, the administration of the compound or crystalline salt thereof reduces or alleviates one or more signs or symptoms associated with DIPG. In one aspect, the one or more signs or symptoms are selected from the group consisting of modifications of speech or speech patterns, loss of ability to move one side of the subject's face or body, loss of balance, loss of coordination, trouble with walking or movement, vision problems, hearing problems, headache, nausea, vomiting, unusual sleepiness, modification in energy level, behavioral changes, and change in performance in school. In one aspect, the administration of the compound or crystalline salt thereof achieves progression free survival. In one aspect, the progression free survival is one month or more, two months or more, three months or more, four months or more, five months or more, six months or more, seven months or more, eight months or more, nine months or more, ten months or more, eleven months or more, one year or more, two years or more, three years or more, or five years or more. In one aspect, the method further comprises one or more of debulking of tumor growth or cerebrospinal fluid diversion. In one aspect, the subject has a predetermined genetic profile comprising one or more mutations in an ACVR1 gene. In one aspect, the one or more mutations in an ACVR1 gene is an activating mutation. In one aspect, the one or more mutations in the ACVR1 gene encode an ACVR1 polypeptide comprising an amino acid substitution at one or more amino acid residues selected from R206H, G328V, R258G, or a combination thereof. In one aspect, the amino acid substitution in the ACVR1 polypeptide comprises R206H. In one aspect, the compound or crystalline salt thereof is administered orally. In one aspect, the compound or crystalline salt thereof is administered in a dose ranging from about 10 mg to about 320 mg per week. In one aspect, the dose ranges from about 30 mg to about 240 mg per week. In one aspect, the dose ranges from about 60 mg to about 180 mg per week. In one aspect, the dose ranges from about 30 mg to about 120 mg per week. In one aspect, the dose ranges from about 60 mg to about 120 mg per week. In one aspect, the dose is about 60 mg per week. In one aspect, the dose is about 90 mg per week. In one aspect, the dose is about 120 mg per week. In one aspect, the dose is about 180 mg per week. In one aspect, the dose is about 210 mg per week. In one aspect, the dose is about 240 mg per week. In one aspect, the compound or crystalline salt thereof is administered in a weekly dose of about 320 mg or less, about 240 mg or less, about 210 or less, about 180 or less, about 120 or less, about 90 or less, about 60 or less, or about 30 or less. In one aspect, the dose is about 60 mg or less per week. In one aspect, the dose is about 90 mg or less per week. In one aspect, the dose is about 120 mg or less per week. In one aspect, the dose is about 180 mg or less per week. In one aspect, the dose is about 210 mg or less per week. In one aspect, the dose is about 240 mg or less per week. In one aspect, the dose is administered once a week. In one aspect, the dose is administered in two or more sub-doses, three or more sub-doses, four or more sub-doses, five or more sub-doses, six or more sub-doses, or daily sub-doses over the course of a week. In one aspect, the subject is a pediatric patient and the dose is between about 80% to 100% of the dose range. In one aspect, the dose is adjusted to 80%, 85%, 90%, or 95% of the dose range. In one aspect, the dose ranges from about 8 mg to about 320 mg per week. In one aspect, the dose ranges from about 24 mg to about 240 mg per week. In one aspect, the dose ranges from about 24 mg to about 120 mg per week. In one aspect, the dose ranges from about 48 mg to about 120 mg per week. In one aspect, the dose ranges from about 72 mg to about 120 mg per week. In one aspect, the dose ranges from about 96 mg to about 120 mg per week. In one aspect, the subject has a predetermined hepcidin level of at least about 0.1 ng/mL. In one aspect, the predetermined hepcidin level ranges from about 10 ng/mL to about 200 ng/mL. In one aspect, the method further comprises determining a hepcidin level in the subject after the compound or crystalline salt thereof is administered. In one aspect, the method further comprises determining a transferrin saturation level in the subject after the compound or crystalline salt thereof is administered. In one aspect, the transferrin saturation level is less than about 50%. In one aspect, the transferrin saturation level is less than about 45%. In one aspect, the transferrin saturation level is less than about 40%. In one aspect, the compound or crystalline salt thereof is administered over one or more treatment cycles, wherein each cycle comprises four weeks. In one aspect, the method further comprises one or more treatment holidays between treatment cycles. In one aspect, the treatment holiday is selected from one day, two days, three days, four days, five days, six days, one week, two weeks, three weeks, or four weeks.

In one embodiment, the present disclosure provides a method for treating a disease or disorder susceptible to inhibition of ACVR1 comprising administering to a subject in need thereof a therapeutically effective amount of a compound of formula (2):

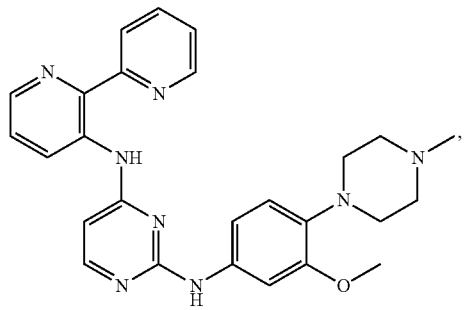

(2)

or a crystalline salt thereof, wherein the compound is administered in a dose ranging from about 10 mg to about 320 mg per week. In one aspect, the dose ranges from about 30 mg to about 240 mg per week. In one aspect, the dose ranges from about 60 mg to about 180 mg per week. In one aspect, the dose ranges from about 30 mg to about 120 mg per week. In one aspect, the dose ranges from about 60 mg to about 120 mg per week. In one aspect, the dose is about 60 mg per week. In one aspect, the dose is about 90 mg per week. In one aspect, the dose is about 120 mg per week. In one aspect, the dose is about 180 mg per week. In one aspect, the dose is about 210 mg per week. In one aspect, the dose is about 240 mg per week. In one aspect, the compound or crystalline salt thereof is administered in a weekly dose of about 320 mg or less, about 240 mg or less, about 210 or less, about 180 or less, about 120 or less, about 90 or less, about 60 or less, or about 30 or less. In one aspect, the dose is about 60 mg or less per week. In one aspect, the dose is about 90 mg or less per week. In one aspect, the dose is about 120 mg or less per week. In one aspect, the dose is about 180 mg or less per week. In one aspect, the dose is about 210 mg or less per week. In one aspect, the dose is about 240 mg or less per week. In one aspect, the subject is a pediatric patient and the dose is between about 80% to 100% of the dose range. In one aspect, the dose is 80%, 85%, 90%, or 95% of the dose range. In one aspect, the dose ranges from about 8 mg to about 320 mg per week. In one aspect, the dose ranges from about 24 mg to about 240 mg per week. In one aspect, the dose ranges from about 24 mg to about 120 mg per week. In one aspect, the dose ranges from about 48 mg to about 120 mg per week. In one aspect, the dose ranges from about 72 mg to about 120 mg per week. In one aspect, the dose ranges from about 96 mg to about 120 mg per week. In one aspect, the dose is administered once a week. In one aspect, the dose is administered in two sub-doses over the course of a week. In one aspect, the dose is administered in three sub-doses over the course of a week. In one aspect, the dose is administered in four sub-doses over the course of a week. In one aspect, the dose is administered in five sub-doses over the course of a week. In one aspect, the dose is administered in six sub-doses over the course of a week. In one aspect, the dose is administered in daily sub-doses. In one aspect, the subject has a predetermined genetic profile comprising one or more mutations in an ACVR1 gene. In one aspect, the one or more mutations in an ACVR1 gene is an activating mutation. In one aspect, the one or more mutations in the ACVR1 gene encode an ACVR1 polypeptide comprising an amino acid substitution at one or more amino acid residues selected from R206H, G328V, R258G, or a combination thereof. In one aspect, the amino acid substitution in the ACVR1 polypeptide comprises R206H. In one aspect, the compound or crystalline salt thereof is administered orally. In one aspect, the disease or disorder is selected from one or more of diffuse intrinsic pontine glioma, a pontine tumor with a histologic diagnosis of infiltrating glioma of grades II to IV, a solid tumor, fibrodysplasia ossificans progressiva, and anemia of chronic disease. In one aspect, the disease or disorder is diffuse intrinsic pontine glioma. In one aspect, the disease or disorder is a pontine tumor with a histologic diagnosis of infiltrating glioma—grades II to IV. In one aspect, the disease or disorder is a solid tumor. In one aspect, the disease or disorder is fibrodysplasia ossificans progressiva. In one aspect, the disease or disorder is anemia of chronic disease. In one aspect, the compound or crystalline salt thereof is administered as a solid dose formulation. In one aspect, the compound or crystalline salt thereof is administered as a liquid dose formulation. In one aspect, the subject is monitored for hepcidin levels to determine any modification of dose. In one aspect, the subject is monitored for accumulation of the compound in one or more organ. In one aspect, the crystalline salt is an acid addition salt. In one aspect, the acid addition salt is a hydrochloric acid salt. In one aspect, the hydrochloric acid salt is monovalent. In one aspect, the crystalline salt form is anhydrous.

In one embodiment, the present disclosure provides an oral solid pharmaceutical composition comprising one or more pharmaceutically acceptable excipient and a compound of formula (2):

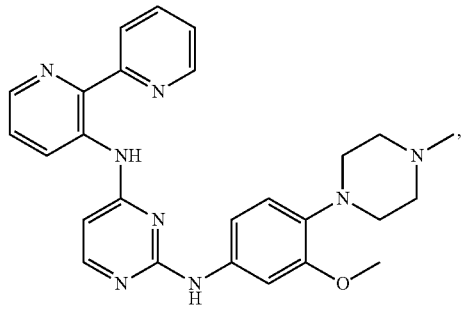

(2)

or a crystalline salt thereof, wherein the compound is formulated in a strength of between about 5 mg to about 125 mg based on free base weight.

In one aspect, the crystalline salt is an acid addition salt. In one aspect, the acid addition salt is a hydrochloric acid salt. In one aspect, the hydrochloric acid salt is monovalent. In one aspect, the crystalline salt form is anhydrous. In one aspect, the pharmaceutical composition is a gelatin capsule. In one aspect, the gelatin capsule is (i) 5 mg, (ii) 25 mg, or (iii) 125 mg strength, based on free base weight. In one aspect, the gelatin capsule is (i) 30 mg, (ii) 60 mg, (iii) 90 mg, or (iv) 120 mg strength, based on free base weight. In one aspect, the one or more pharmaceutical excipients are selected from microcrystalline cellulose, lactose monohydrate, croscarmellose sodium, magnesium stearate, or a combination thereof.

In one embodiment, the present disclosure provides an oral liquid pharmaceutical composition comprising a compound of formula (2):

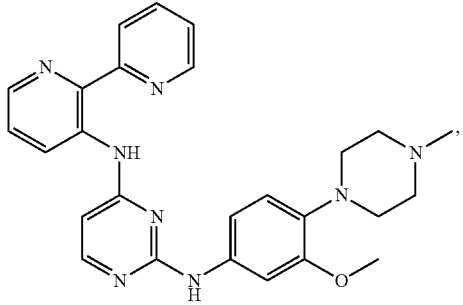

(2)

or a crystalline salt thereof; and
a) one or more buffering agents;
b) optionally, one or more preservatives;
c) optionally, one or more solvents;
d) optionally, one or more taste masking agents; and
e) optionally, one or more further pH-adjusting agent.

In one aspect, the crystalline salt is an acid addition salt. In one aspect, the acid addition salt is a hydrochloric acid salt. In one aspect, the hydrochloric acid salt is monovalent. In one aspect, the crystalline salt form is anhydrous. In one aspect, the composition has a pH of between about 2.0 and about 5.0. In one aspect, the composition has a pH of between about 2.0 and about 3.5. In one aspect, the composition has a pH of about 2.0. In one aspect, the buffering agent is selected from citric acid, tartaric acid, malic acid, or acetic acid. In one aspect, the buffering agent is malic acid. In one aspect, the malic acid is DL-malic acid. In one aspect, the composition comprises one or more preservatives. In one aspect, the preservative is selected from benzoic acid, sodium benzoate, methyl para-hydroxy benzoate, propyl para-hydroxy benzoate, or propylene glycol. In one aspect, the preservative is benzoic acid. In one aspect, the benzoic acid is a preservative and a buffering agent. In one aspect, the composition comprises one or more taste masking agent. In one aspect, the taste masking agent is selected from sucralose, glycerin, cyclodextrin, HP-β-cyclodextrin, α-cyclodextrin, β-cyclodextrin, or a combination thereof. In one aspect, the taste masking agent is a combination of HP-β-cyclodextrin and sucralose. In one aspect, the composition comprises a compound of formula (2) or a crystalline salt thereof in a concentration of about 10 mg/mL. In one aspect, the composition comprises malic acid in a concentration up to about 6.7 mg/mL. In one aspect, the composition comprises malic acid in a concentration of about 1.3 mg/mL. In one aspect, the composition comprises HP-β-cyclodextrin in a concentration of up to about 300 mg/mL. In one aspect, the composition comprises HP-β-cyclodextrin in a concentration of up to about 150 mg/mL. In one aspect, the composition comprises sucralose in a concentration of up to about 2.0 mg/mL. In one aspect, the composition comprises sucralose in a concentration of about 1.0 mg/mL. In one aspect, the composition comprises benzoic acid in a concentration of up to about 3.0 mg/mL. In one aspect, the composition comprises benzoic acid in a concentration of up to about 2.0 mg/mL. In one aspect, the pH is adjusted to about 2.0 with hydrochloric acid. In one aspect, the solvent is water.

In one embodiment, the present disclosure provides a crystalline form of a salt of compound (2)

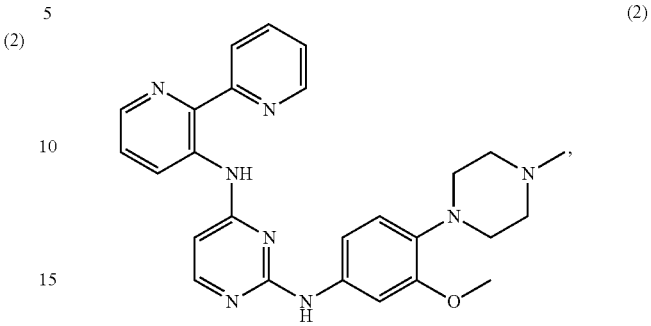

(2)

$N^4$-(2,2'-bipyridin-3-yl)-$N^2$-(3-methoxy-4-(4-methylpiperazin-1-yl)phenyl)pyrimidine-2,4-diamine.

In one aspect, the salt is a pharmaceutically acceptable salt. In one aspect, the pharmaceutically acceptable salt is an HCl salt. In one aspect, the crystalline form comprises Form A. In one aspect, the crystalline form consists essentially of Form A. In one aspect, the Form A is substantially free from impurities.

In one embodiment, the present disclosure provides Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt.

In one embodiment, the present disclosure provides Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) comprising one or more 2θ values selected from: 13.53, 16.14, 17.67, 18.38, 24.96, and 28.18.

In one aspect, the form is characterized by two or more of the listed 2θ values. In one aspect, the form is characterized by three or more of the listed 2θ values. In one aspect, the form is characterized by four or more of the listed 2θ values. In one aspect, the form is characterized by five or more of the listed 2θ values. In one aspect, the form is characterized by all six of the listed 2θ values. In one aspect, the form is further characterized by one or more 2θ values selected from: 6.71, 19.25, 23.98, and 29.60. In one aspect, the form is characterized by two or more of the listed 2θ values. In one aspect, the form is characterized by three or more of the listed 2θ values. In one aspect, the form is characterized by all four of the listed 2θ values. In one aspect, the X-ray powder diffractometer is used in reflection mode with an X-ray wavelength of Cu kα, Kα1 (Å): 1.540598, Kα2 (Å): 1.544426, with a Kα2/Kα1 intensity ratio of 0.50, and an X-ray tube setting of 45 kV, 40 mA. In one aspect, the 2θ values are within +/−0.2 2θ.

In one embodiment, the present disclosure provides Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) substantially the same as FIG. 12.

In one embodiment, the present disclosure provides Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an endotherm at one or more of 196.2° C., 214.8° C., and 274.0° C.

In one aspect, the form is further characterized by a peak endotherm at one or more of 198.9° C., 218.0° C., and 275.9° C. In one aspect, the form is further characterized by an onset temperature of 274.0° C. In one aspect, the form is further characterized by weight loss of 1.7% up to 150° C.

In one embodiment, the present disclosure provides Form A of N⁴-(2,2'-bipyridin-3-yl)-N²-(3-methoxy-4-(4-methylpiperazin-1-yl)phenyl)pyrimidine-2,4-diamine anhydrous hydrochloric acid salt characterized by a TGA-DSC thermogram substantially the same as FIG. 15.

In one embodiment, the present disclosure provides a pharmaceutical composition comprising the crystalline form of the present disclosure. In one aspect, the composition is a solid dose formulation. In a particular aspect, the solid dose formulation is an oral solid pharmaceutical composition of the present disclosure where the compound is the crystalline form of the present disclosure. In one aspect, the composition is a liquid dose formulation. In a particular aspect, the liquid dose formulation is an oral liquid pharmaceutical composition of the present disclosure where the compound is the crystalline form of the present disclosure.

In one embodiment, the present disclosure provides any method of the present disclosure where the compound is a crystalline form of the present disclosure.

In one embodiment, the present disclosure provides a pharmaceutical composition comprising the crystalline form of the present disclosure, either alone or in combination with either radiation or an additional therapeutic agent. In one aspect, the composition is a solid dose formulation. In one aspect, the composition is a liquid dose formulation.

One embodiment of the present disclosure includes any method of the present disclosure comprising administering any compound of the present disclosure.

One embodiment of the present disclosure includes the use of any compound of the present disclosure in one or more treatment of the present disclosure.

One embodiment of the present disclosure includes preparation of a medicament according to the present disclosure for the treatment of one or more disease or disorder as herein disclosed.

One embodiment of the present disclosure includes use of a compound of the present disclosure in therapy.

In brief, embodiments of the present disclosure provide methods for treating a disease in a subject in need thereof, the method comprising administering a treatment regimen comprising an ACVR1 inhibitor to the subject having a predetermined genetic profile comprising one or more mutations in an ACVR1 gene, the ACVR1 inhibitor having the following formula (I):

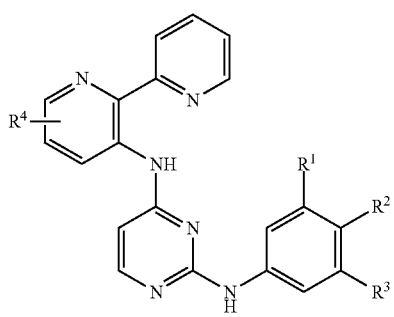

(I)

or a stereoisomer, pharmaceutically acceptable salt, tautomer or prodrug thereof, wherein $R^1$, $R^2$, $R^3$, and $R^4$ are as defined herein.

Further embodiments of the present disclosure provide methods for treating diffuse intrinsic pontine glioma (DIPG) in a subject in need thereof, the method comprising administering a treatment regimen comprising an ACVR1 inhibitor to the subject, the ACVR1 inhibitor having the following formula (I):

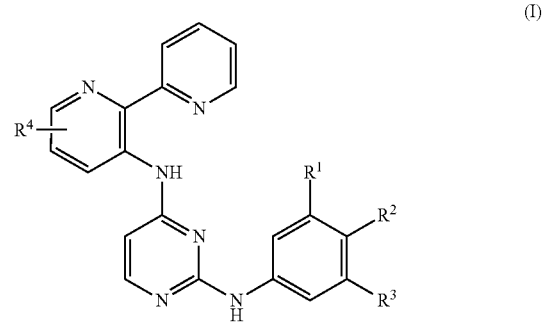

(I)

or a stereoisomer, pharmaceutically acceptable salt, tautomer or prodrug thereof, wherein $R^1$, $R^2$, $R^3$, and $R^4$ are as defined herein.

Additional embodiments of the present disclosure provide methods for treating fibrodysplasia ossificans progressiva (FOP) in a subject in need thereof, the method comprising administering a treatment regimen to the subject, the treatment regimen comprising an ACVR1 inhibitor and a therapeutic agent, the ACVR1 inhibitor having the following formula (I):

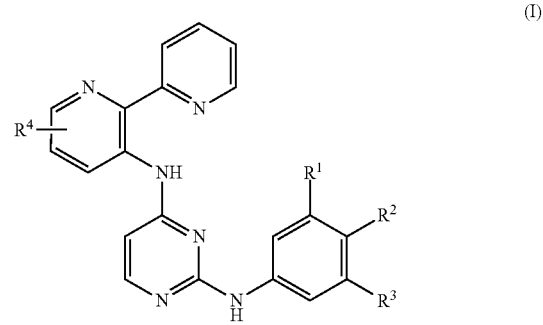

(I)

or a stereoisomer, pharmaceutically acceptable salt, tautomer or prodrug thereof, wherein $R^1$, $R^2$, $R^3$, and $R^4$ are as defined herein.

One embodiment of the present disclosure includes the use of an ACVR1 inhibitor of formula (I) for treatment of diseases associated with abnormal ACVR1 expression (e.g., mutations in the expressed protein), such as DIPG and FOP, is also provided.

One or more aspects and embodiments may be incorporated in a different embodiment although not specifically described. That is, all aspects and embodiments may be combined in any way or combination.

These and other aspects of the disclosure will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIGS. 32A, 32B, and 32C show a chart comparing Compound 2 to known CNS drugs as comparators. A multiple parameter score ("myMPO") factored physicochemical properties to predict BBB penetration. The higher the score (5 being ideal) the better the chance of CNS penetration.

DETAILED DESCRIPTION OF THE DISCLOSURE

Figure 1:
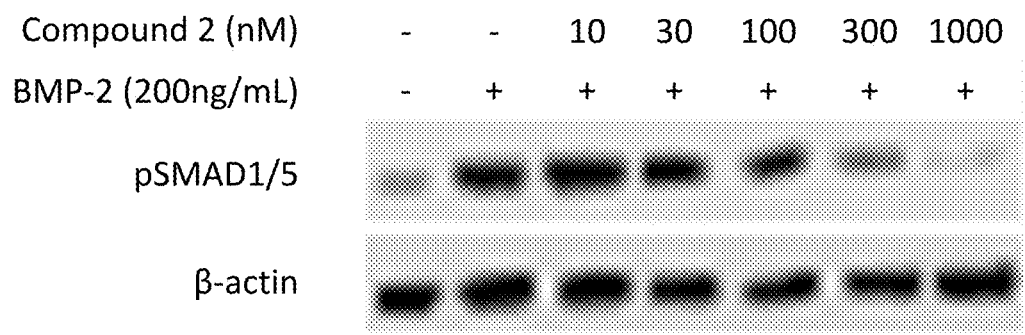
FIG. 1 presents data showing the inhibition of SMAD1/5 phosphorylation in BMP2 stimulated HepG2 cells by Compound 2.

The present disclosure relates to methods of treating diseases (e.g., cancer, for example, diffuse intrinsic pontine glioma (DIPG); genetic disorders (e.g., fibrodysplasia ossificans progressiva (FOP)); etc.) associated with abnormal ACVR1 expression (e.g., mutations in the expressed protein) by administering an ACVR1 inhibitor.

Prior to setting forth this disclosure in more detail, it may be helpful to an understanding thereof to provide definitions of certain terms to be used herein. Additional definitions are set forth throughout this disclosure.

"Amino" refers to the —$NH_2$ radical.
"Cyano" or "nitrile" refers to the —CN radical.
"Halo" refers to the —F, —Cl, —Br or —I radical.
"Hydroxy" or "hydroxyl" refers to the —OH radical.
"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double (alkenyl) and/or triple (alkynyl) bonds), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. An alkyl comprising one or more carbob-carbon double bonds is an alkenyl. An alkyl comprising one or more carbon-carbon triple bonds is an alkynyl. Unless stated otherwise specifically in the specification, an alkyl group is optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Fused" refers to any ring structure described herein which is fused to an existing ring structure in the ACVR1 inhibitors of the disclosure. When the fused ring is a heterocyclyl ring, any carbon atom on the existing ring structure which becomes part of the fused heterocyclyl ring or the fused heteroaryl ring may be replaced with a nitrogen atom.

"Heterocyclyl" or "heterocyclic ring" refers to a stable 3- to 18-membered non-aromatic ring radical which comprises two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

The term "substituted" used herein means any of the above groups (e.g., alkyl, alkoxy and/or heterocyclyl) wherein at least one hydrogen atom is replaced by a bond to a non-hydrogen radical such as amino, cyano, hydroxyl, imino, nitro, oxo, thioxo, halo, alkyl and alkoxy, each of the foregoing radicals may also be optionally substituted with one or more of the above substituents "Substituted" also includes any of the above groups in which one or more hydrogen atoms are replaced with NR$_g$R$_h$, NR$_g$C(=O)R$_h$, NR$_g$C(=O)NR$_g$R$_h$, NR$_g$C(=O)OR$_h$, NR$_g$SO$_2$R$_h$, OC(=O)NR$_g$R$_h$, OR$_g$, SR$_g$, SOR$_g$, SO$_2$R$_g$, OSO$_2$R$_g$, SO$_2$OR$_g$, NSO$_2$R$_g$, or SO$_2$NR$_g$R$_h$. "Substituted" also means any of the above groups in which one or more hydrogen atoms are replaced with C(=O)R$_g$, C(=O)OR$_g$, C(=O)NR$_g$R$_h$, CH$_2$SO$_2$R$_g$ or CH$_2$SO$_2$NR$_g$R$_h$. In the foregoing, R$_g$ and R$_h$ are the same or different and independently hydrogen or optionally substituted alkyl.

"Prodrug" is meant to indicate an ACVR1 inhibitor that may be converted under physiological conditions or by solvolysis to a biologically active salt described herein. Thus, the term "prodrug" refers to a precursor of a biologically active ACVR1 inhibitor that is pharmaceutically acceptable. In some aspects, a prodrug is inactive when administered to a subject, but is converted in vivo to an active ACVR1 inhibitor, for example, by hydrolysis. The prodrug ACVR1 inhibitor often offers advantages of solubility, tissue compatibility or delayed release in a subject organism (see, e.g., Bundgard, H., Design of Prodrugs (1985), pp. 7-9, 21-24 (Elsevier, Amsterdam). A discussion of prodrugs is provided in Higuchi, T., et al., "Pro drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active ACVR1 inhibitor in vivo when such prodrug is administered to a subject. Prodrugs of an active ACVR1 inhibitor, as described herein, are typically prepared by modifying functional groups present in the active ACVR1 inhibitor in such a way that the modifications are cleaved, either in routine manipulation or in vivo, to the parent active ACVR1 inhibitor. Prodrugs include ACVR1 inhibitors wherein a hydroxy, amino or mercapto group is bonded to any group that, when the prodrug of the active ACVR1 inhibitor is administered to a subject, cleaves to form a free hydroxy, free amino or free mercapto group, respectively. Examples of prodrugs include acetate, formate and benzoate derivatives of a hydroxy functional group, or acetamide, formamide and benzamide derivatives of an amine functional group in the active ACVR1 inhibitor and the like.

The disclosure herein is also meant to encompass all pharmaceutically acceptable ACVR1 inhibitors of formula (I) being isotopically-labelled by having one or more atoms replaced by an atom having a different atomic mass or mass number. Examples of isotopes that can be incorporated into the disclosed ACVR1 inhibitors include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled ACVR1 inhibitors could be useful to help determine or measure the effectiveness of the ACVR1 inhibitors, by characterizing, for example, the site or mode of action, or binding affinity to pharmacologically important site of action. Certain isotopically-labelled ACVR1 inhibitors of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled ACVR1 inhibitors of formula (I) can generally be prepared by conventional techniques known to those skilled in the art or by processes analogous to those described in the Preparations and Examples as set out below using an appropriate isotopically-labeled reagent in place of the non-labeled reagent previously employed.

The disclosure herein is also meant to encompass the in vivo metabolic products of the disclosed ACVR1 inhibitors. Such products may result from, for example, the oxidation, reduction, hydrolysis, amidation, esterification, and the like of the administered ACVR1 inhibitor, primarily due to enzymatic processes. Accordingly, the disclosure includes ACVR1 inhibitors produced by a process comprising administering an ACVR1 inhibitor of this disclosure to a subject for a period of time sufficient to yield a metabolic product thereof. Such products are typically identified by administering a radiolabelled ACVR1 inhibitor of the disclosure in a detectable dose to an animal, such as rat, mouse, guinea pig, monkey, or to human, allowing sufficient time for metabolism to occur, and isolating its conversion products from the urine, blood or other biological samples.

"Stable ACVR1 inhibitor" and "stable structure" are meant to indicate an ACVR1 inhibitor that is sufficiently robust to survive isolation to a useful degree of purity from a reaction mixture, and formulation into an efficacious therapeutic agent.

The use of the words "optional" or "optionally" means that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid (e.g., L-(+)-tartaric acid), thiocyanic acid, p-toluenesulfonic acid, trifluoroacetic acid, undecylenic acid, and the like.

"Pharmaceutically acceptable base addition salt" refers to those salts which are prepared from addition of an inorganic base or an organic base to the free acid. Salts derived from inorganic bases include the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

Often crystallizations produce a solvate of the ACVR1 inhibitor of the disclosure. As used herein, the term "solvate" refers to an aggregate that comprises one or more molecules of an ACVR1 inhibitor of the disclosure with one or more molecules of solvent. The solvent may be water, in which case the solvate may be a hydrate. Alternatively, the solvent may be an organic solvent. Thus, the ACVR1 inhibitors of the present disclosure may exist as a hydrate, including a monohydrate, dihydrate, hemihydrate, sesquihydrate, trihydrate, tetrahydrate and the like, as well as the corresponding solvated forms. The ACVR1 inhibitor of the disclosure may be true solvates, while in other cases, the ACVR1 inhibitor of the disclosure may merely retain adventitious water or be a mixture of water plus some adventitious solvent.

The ACVR1 inhibitors of the disclosure, or their pharmaceutically acceptable salts or tautomers may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the ACVR1 inhibitors described herein contain olefinic double bonds or other centres of geometric asymmetry, and unless specified otherwise, it is intended that the ACVR1 inhibitors include both E and Z geometric isomers. Likewise, all tautomeric forms are also intended to be included.

A "stereoisomer" refers to an ACVR1 inhibitor made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another.

The term "substantially" refers to a significant qualitative or quantitative extent. As an example, when used in the context to refer to a particular characterization of a compound, the term refers to an ability to identify a chemical substance based on material similarity with a referenced characterization method, such as, for example, XRPD, DSC, or TGA. Error ranges for such techniques, as are appreciated by those skilled in the art, are encompassed within the term "substantially." Moreover, as used herein, "substantially pure," when used in reference to a form, means a compound having a purity greater than 90 weight %, including greater than 90, 91, 92, 93, 94, 95, 96, 97, 98, 98.5, 99, 99.1, 99.2, 99.3, 99.4, 99.5. 99.6, 99.7, 99.8, 99.9 weight %, and also including equal to 100 weight % of an ACVR1 inhibitor, such as Compound 2, based on the weight of the compound. The remaining material comprises other form(s) of the compound, and/or reaction impurities and/or processing impurities arising from its preparation. For example, a crystalline form of Compound 2 may be deemed substantially pure in that it has a purity greater than 90 weight %, as measured by means that are at this time known and generally accepted in the art, where the remaining less than 10 weight % of material comprises other form(s) of Compound 2 and/or reaction impurities and/or processing impurities. Another way to define substantially pure is following: As used herein, the term "substantially pure" with reference to a particular polymorphic form means that the polymorphic form includes less than 10%, preferably less than 5%, more preferably less than 3%, most preferably less than 1% by weight of any other physical forms of the compound.

A "tautomer" refers to a proton shift from one atom of a molecule to another atom of the same molecule, for example, the conversion of a ketone to an enol via a proton shift. The present disclosure includes tautomers of any said ACVR1 inhibitors.

A "pharmaceutical composition" refers to a formulation of one or more therapeutic agents and a medium generally accepted in the art for the delivery of the biologically active agent to subjects, e.g., humans. Such a medium includes all pharmaceutically acceptable carriers, diluents, or excipients. "Pharmaceutically acceptable carrier, diluent, or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

A "chemotherapeutic agent" or "anti-cancer agent" is a chemical which destroys cancer cells, or stops or slows the growth of cancer cells.

A "cancer," including a "tumor," refers to an uncontrolled growth of cells and/or abnormal increased cell survival and/or inhibition of apoptosis which interferes with the normal functioning of the bodily organs and systems. "Cancer" (e.g., a tumor) includes solid and non-solid cancers. A subject that has a cancer or a tumor has an objectively measurable number of cancer cells present in the subject's body. "Cancers" include benign and malignant cancers (e.g., benign and malignant tumors, respectively), as well as dormant tumors or micro-metastases.

"Metastasis" refers to the spread of cancer from its primary site to other places in the body. "Metastases" are cancers which migrate from their original location and seed vital organs, which can eventually lead to the death of the subject through the functional deterioration of the affected organs. Metastasis is a sequential process, where cancer cells can break away from a primary tumor, penetrate into lymphatic and blood vessels, circulate through the bloodstream, and grow in a distant focus (metastasize) in normal tissues elsewhere in the body. At the new site, the cells establish a blood supply and can grow to form a life-threatening mass. Metastasis can be local or distant. Both stimulatory and inhibitory molecular pathways within the tumor cell regulate this behavior, and interactions between the tumor cell and host cells in the new site are also significant.

"Treating" or "treatment" as used herein refers to the administration of a medication or medical care to a subject, such as a human, having a disease or condition of interest, e.g., a cancer, including: (i) inhibiting the disease or condition, i.e., arresting its development; (ii) relieving the disease or condition, i.e., causing regression of the disease or condition; or (iii) relieving the symptoms resulting from the disease or condition, (e.g., pain, weight loss, cough, fatigue, weakness, etc.) without addressing the underlying disease or condition. As used herein, the terms "disease" and "condition" may be used interchangeably or may be different in that the particular malady or condition may not have a known causative agent (so that etiology has not yet been confirmed) and it is therefore not yet recognized as a disease but only as an undesirable condition or syndrome, wherein a more or less specific set of symptoms have been identified by clinicians.

"Subject" includes humans, domestic animals, such as laboratory animals (e.g., dogs, monkeys, rats, mice, etc.), household pets (e.g., cats, dogs, rabbits, etc.), and livestock (e.g., pigs, cattle, sheep, goats, horses, etc.), and non-domestic animals (e.g., bears, elephants, porcupines, etc.). In embodiments, the subject is a mammal. In embodiments, a subject is a human. The term "patient" may be used interchangeably with the term "subject."

The FD&C Act defines "pediatric" as a subject aged 21 or younger at the time of their diagnosis or treatment. Pediatric subpopulations are further characterized as: (i) neonates—from birth through the first 28 days of life; (ii) infants—from 29 days to less than 2 years; (iii) children—2 years to less than 12 years; and (iv) adolescents—aged 12 through 21. Despite the definition, depending on the susceptible patient population and clinical trial evaluation, an approved regulatory label may include phrasing that specifically modifies the range of a pediatric population, such as, for example, pediatric patients up to 22 years of age.

"Effective amount" or "therapeutically effective amount" refers to the amount of an ACVR1 inhibitor or composition which, when administered to a subject, such as a human, is sufficient to effect treatment of the subject's cancer. The amount of an ACVR1 inhibitor or composition that constitutes an "effective amount" will vary depending on the ACVR1 inhibitor or composition, the condition being treated and its severity, the manner of administration, the duration of treatment, and/or the age of the subject to be treated, but can be determined routinely by one of ordinary skill in the art based on his own knowledge and this disclosure. In embodiments, an "effective amount" effects treatment (e.g., treats, prevents, inhibits, relieves, promotes, improves, increases, reduces, and the like) as measured by a statistically significant change in one or more indications, symptoms, signs, diagnostic tests, vital signs, and the like. In other embodiments, an "effective amount" suppresses, manages, or prevents a condition as measured by a lack of a statistically significant change in one or more indications, symptoms, signs, diagnostic tests, vital signs, and the like.

As used herein, "statistically significant" refers to a p value of 0.050 or less when calculated using the Students t-test and indicates that it is unlikely that a particular event or result being measured has arisen by chance.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the term "about" means±20%, ±10%, ±5% or ±1% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives.

Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to," such that recitation of items in a list is not to the exclusion of other like items that may also be useful in the materials, compositions, devices, and methods of this technology. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Similarly, the terms "can" and "may" and their variants are intended to be non-limiting, such that recitation that an embodiment can or may comprise certain elements or features does not exclude other embodiments of the present technology that do not contain those elements or features. Furthermore, the particular features, structures, or characteristics may be combined in any suitable manner in one or more embodiments.

In the following description, certain specific details are set forth in order to provide a thorough understanding of various embodiments of this disclosure. However, one skilled in the art will understand that the disclosure may be practiced without these details.

Pharmacology

Diffuse intrinsic pontine glioma (DIPG) is a brain tumor found in a part of the brain stem called the pons. The pons controls essential bodily functions such as heartbeat, breathing, swallowing, eye movement, eyesight, and balance. Although considerably less frequent than histologically similar lesions occurring in adults, high grade gliomas in children represent a major unmet need in clinical neuro-oncology. See, Jones C et al., Paediatric and adult malignant glioma: close relatives or distant cousins?, Nat Rev Clin Oncol. 2012 May 29; 9(7):400-13, hereby incorporated by reference with regard to such background teaching of DIPG.

DIPG tumors are universally fatal, with a median overall survival of 9-12 months. DIPGs are diffusely infiltrating, and although may harbor regions of lower grade histology, are largely indistinguishable from WHO grade IV glioblastoma multiforme (GBM) of the cerebral cortex. Efforts to improve survival in these children have thus far failed. Surgical resection of these tumors is not possible due to their anatomical location and clinical trials based upon promising targets from the adult GBM literature have shown no benefit. See, e.g., Warren, Diffuse intrinsic pontine glioma: poised for progress, Front Oncol. 2012; 2:205, and Taylor et al., ACVR1 mutations in DIPG: lessons learned from FOP, Cancer Res., 2014 Sep. 1: 74(17): 4565-4570, each hereby incorporated by reference with regard to such background teaching of DIPG.

As noted, DIPG affects children almost exclusively. According to the Michael Mosier Defeat DIPG Foundation, approximately 200-400 children in the United States are diagnosed with DIPG each year. These children are typically between the ages of 4 and 11. DIPG accounts for roughly 10-15% of all brain tumors in children.

DIPG is an aggressive tumor that may interfere with bodily functions, depriving a child of the ability to move, to communicate, and even to eat and drink. As a DIPG tumor begins to grow, it may put pressure on the nerves that control the essential bodily functions regulated by the pons. Children with DIPG may experience double vision, reduced eye movement, facial weakness or asymmetry, and arm and leg weakness. They also may have problems with walking, coordination, speech, chewing, and swallowing. As the tumor progresses, it may also interfere with breathing and heartbeat, which ultimately results in the child's death.

Buczkowicz et al. demonstrated that clinically classic DIPGs represent a diverse histologic spectrum. See, Buczkowicz et al., Histopathological spectrum of paediatric diffuse intrinsic pontine glioma: diagnostic and therapeutic implications, *Acta Neuropathol.* 2014 October; 128(4):573-81. doi: 10.1007/s00401-014-1319-6. Epub 2014 Jul. 22, herein incorporated by reference with regard to background teaching of DIPG. In context, therefore, DIPG may be characterized as a pontine tumor with a histologic diagnosis of infiltrating glioma—grades II to IV. Primary tumors of the brain stem may be diagnosed on the basis of clinical findings and on neuroimaging studies using magnetic resonance imaging (MRI). A presumptive diagnosis of DIPG may be based on classic imaging features, in the absence of a histologic diagnosis. Increasingly, histologic confirmation may be obtained for both entry into research studies and molecular characterization of the tumor. New approaches with stereotactic needle biopsy also may make biopsy safer. Biopsy may be recommended for pontine tumors when the diagnosis is uncertain based on imaging findings. Thus, astrocytic tumors predominate in the brain stem. WHO grade 1 tumors, such as pilocytic astrocytomas and ganglio-gliomas, have a favorable prognosis and may arise throughout the brain stem, including the tectum of the midbrain, focally within the pons, or at the cervicomedullary junction where they are often exophytic. Low-grade diffuse astrocytomas (WHO grade 2) occurring outside the pons in other brain stem locations tend to be tumors with a more favorable prognosis. DIPGs are diffuse astrocytomas that, when biopsied at diagnosis, can range from diffuse astrocytomas (WHO grade 2) to glioblastomas (WHO grade 4). At post-mortem evaluation, DIPGs are also generally anaplastic astrocytomas (WHO grade 3) or glioblastomas (WHO grade 4) by morphological criteria, although WHO grade 2 regions may also be identified. Approximately 80% of DIPGs, regardless of histologic grade, may be classified by the WHO as diffuse midline gliomas. All diffuse midline gliomas, H3 K27M-mutant, are WHO grade 4, regardless of histologic grade, reflecting the poor prognosis of children with this diagnosis. See, e.g., Ballester et al., Morphologic characteristics and immunohistochemical profile of diffuse intrinsic pontine gliomas. Am J Surg Pathol 37 (9): 1357-64, 2013, and Louis D N et al., The 2016 World Health Organization Classification of Tumors of the Central Nervous System: a summary. Acta Neuropathol 131 (6): 803-20, 2016, each herein incorporated by reference with regard to characterization and diagnosis of DIPG and related diseases.

Taylor et al., published whole genome sequencing studies that identified a quarter of cases of DIPG to harbor somatic mutations in ACVR1. This gene encodes the type I bone morphogenetic protein (BMP) receptor ALK2, with the residues affected identical to those which, when mutated in the germline, give rise to the congenital malformation syndrome fibrodysplasia ossificans progressiva (FOP), resulting in the transformation of soft tissue into bone. This unexpected link points towards the importance of developmental biology processes in tumorigenesis, and provides an extensive experience in mechanistic understanding and drug development hard-won by FOP researchers to pediatric neuro-oncology. See, e.g., Taylor et al., ACVR1 mutations in DIPG: lessons learned from FOP, Cancer Res., 2014 Sep. 1: 74(17): 4565-4570, hereby incorporated by reference with regard to such background teaching.

Bone morphogenetic proteins (BMPs) are pleiotropic growth factors playing essential roles in coordinating tissue architecture throughout various organs in the body. BMP ligands interact with bone morphogenetic protein receptors (BMPRs), which belong to the transforming growth factor beta (TGF-b) superfamily of serine/threonine kinase receptors (Ikushima, H. and K. Miyazono, *Biology of Transforming Growth Factor-beta Signalin*. Curr Pharm Biotechnol, 2011), hereby incorporated by reference with regard to such background teaching. The ligands bind to type-II receptors, which then recruit type-I receptors forming a heteromeric complex. As a complex, the type-II receptor phosphorylates the type-I receptor, which allows the type-I receptor to become active and phosphorylate downstream signaling molecules. The downstream effects of activating these receptors are primarily carried out by the SMAD family of proteins. SMADs become phosporylated and transduce the signal from the cell membrane to the nucleus where they function as transcription factors to regulated gene expression (Massague, J., J. Seoane, and D. Wotton, *Smad transcription factors*. Genes Dev, 2005. 19(23): p. 2783-810), hereby incorporated by reference with regard to such background teaching.

In individuals with chronic diseases, such as cancer and inflammation, BMP signaling is constitutively activated leading to anemia. This condition is commonly referred to as anemia of chronic disease (ACD) and is a debilitating symptom associated with cancer patients (Cullis, J. O., *Diagnosis and management of anaemia of chronic disease: current status*. Br J Haematol, 2011. 154(3): p. 289-300), hereby incorporated by reference with regard to such background teaching. Chronic anemia in cancer patients leads to extreme weakness and fatigue, which leads to a poor quality of life for these individuals. In these patients, BMP signaling through two BMP type-I receptors, ALK2 (as noted, also known as ACVR1) and ALK3 induces the hepatic expression of the peptide hormone, called hepcidin (Steinbicker, A. U., et al., *Perturbation of hepcidin expression by BMP type I receptor deletion induces iron overload in mice*. Blood, 2011. 118(15): p. 4224-30), hereby incorporated by reference with regard to such background teaching.

Hepcidin reduces serum iron levels by promoting the degradation of the iron exporter, ferroportin, resulting in the increase of iron stored away in macrophages and other cell types and making the iron unavailable for hemoglobin and red blood cell (RBC) function. Supplementing a patient's intake of iron does not reverse ACD because the ingested iron simply is stored away due to the activated BMP pathway and high serum hepcidin levels. Currently, ACD in cancer is managed by limiting the physical activity of patients and blood transfusions are used in the most severe cases. Inhibition of BMP signaling in these patients has the potential to provide a real difference in their quality of life and ultimately, may positively impact how they respond to therapy, radiation, or surgery (Steinbicker, A. U., et al., *Inhibition of bone morphogenetic protein signaling attenuates anemia associated with inflammation*. Blood, 2011. 117(18): p. 4915-23; Coyne, D. W., *Hepcidin: clinical utility as a diagnostic tool and therapeutic target*. Kidney Int, 2011. 80(3): p. 240-4; Theurl, I., et al., *Pharmacologic inhibition of hepcidin expression reverses anemia of chronic disease in rats*. Blood, 2011), each hereby incorporated by reference with regard to such background teaching.

As noted above, fibrodysplasia ossificans progressive (FOP) is an autosomal dominant disorder of skeletal malformation and disabling heterotopic ossification that arises in 1 in 1,500,000 live births due to sporadic germline mutations in ACVR1. See, Shore E M et al., A recurrent mutation in the BMP type I receptor ACVR1 causes inherited and sporadic fibrodysplasia ossificans progressiva, Nat Genet. 2006 May; 38(5):525-7, hereby incorporated by reference with regard to such background teaching of FOP. FOP is a disorder in which muscle tissue and connective tissue such as tendons and ligaments are gradually replaced by bone (ossified), forming bone outside the skeleton (extra-skeletal or heterotopic bone) that constrains movement. This process generally becomes noticeable in early childhood, starting with the neck and shoulders and proceeding down the body and into the limbs. Extra-skeletal bone formation causes progressive loss of mobility as the joints become affected. Inability to fully open the mouth may cause difficulty in speaking and eating. Over time, people with this disorder may experience malnutrition due to their eating problems. They may also have breathing difficulties as a result of extra bone formation around the rib cage that restricts expansion of the lungs. Any trauma to the muscles of an individual with FOP, such as a fall or invasive medical procedures, may trigger episodes of muscle swelling and inflammation (myositis) followed by more rapid ossification in the injured area. Flare-ups may also be caused by viral illnesses such as influenza.

Five sites of mutation newly described in DIPG are also found in cases of FOP, as well as a further five sites across the GS and kinase domains of the encoded ALK2 protein. See, Kaplan F S et al., Classic and atypical fibrodysplasia ossificans progressiva (FOP) phenotypes are caused by mutations in the bone morphogenetic protein (BMP) type I receptor ACVR1, Hum Mutat. 2009 March; 30(3):379-90, hereby incorporated by reference with regard to such background teaching of FOP and DIPG.

There is a need for effective treatments to manage both FOP and DIPG. Radiation is the traditional therapy for newly diagnosed DIPGs. Conventional limited-field radiation produces responses in more than 90 percent of children with DIPGs. These responses are short-lived, however, lasting about six to nine months on average. Several trials to increase the dose of radiation therapy have been performed and none have improved survival. Surgery is precluded for both conditions and therapeutic antibodies appear unsuitable as the activating mutations found in ALK2/ACVR1 affect only the cytoplasmic portion of the receptor.

In certain embodiments, methods of the disclosure are useful for treating abnormal ACVR1 expression, including diffuse intrinsic pontine glioma (DIPG) and fibrodysplasia ossificans progressiva (FOP).

Certain methods disclosed herein serve to select a regimen of treatment for a subject in need thereof. That is, this disclosure provides methods for selecting treatment regimens as well as methods of treatment themselves. Other embodiments provide a method for selecting a treatment regimen and for treating a disease in a subject based on the subject having a predetermined genetic profile. In various embodiments, methods of the disclosure further comprise obtaining a sample from a subject and determining a genetic profile.

Embodiments provided herein include methods for selecting a treatment regimen for a subject based on the subject's genetic profile. Such genetic profiles may be produced in any suitable manner (e.g., microarrays, reverse transcription polymerase chain reaction (RT-PCR), RNA/DNA sequencing, etc.).

In some embodiments, the genetic profile comprises one or more mutations in an ACVR1 gene. The term "gene" can include not only coding sequences but also regulatory regions such as promoters, enhancers, and termination regions. The term further can include all introns and other DNA sequences spliced from the mRNA transcript, along with variants resulting from alternative splice sites. Gene sequences encoding the particular protein can be DNA or RNA that directs the expression of the particular protein. These nucleic acid sequences may be a DNA strand sequence that is transcribed into RNA or an RNA sequence that is translated into the particular protein. The nucleic acid sequences include both the full-length nucleic acid sequences as well as non-full-length sequences derived from the full-length protein.

In various embodiments, the subject receiving treatment has one or more mutations in an ACVR1 gene. In embodiments, the subject has a predetermined genetic profile comprising such mutation(s). In some embodiments, the one or more mutations in the ACVR1 gene comprise a missense mutation, a frameshift mutation, a duplication (i.e. copy number variation), a splice site mutation, or a combination thereof.

In embodiments, the one or more mutations comprise (P197F198)L, C509S, D185G, D185N, D433N, E38FS, F265S, G225D, G264S, G328E, G328R, G328V, G328W, G356D, G50C, H320Y, I323V, K31E, K345Q, L196P, L251S, M34I, N100D, N481I, P115S, P455A, Q207E, Q278P, R201I, R206C, R206H, R258G, R258S, R307Q, R325A, R375C, R375P, R401M, R490H, S130F, S226N, S41F, S440G, S469C, S56L, T298S, V234M, V91M, W98R, or a combination thereof. In embodiments, the one or more mutations in the ACVR1 gene comprise R206H, G328V, R258G, or a combination thereof. In certain embodiments, the one or more mutations in the ACVR1 gene comprise R206H.

In some embodiments, the one or more mutations in the ACVR1 gene comprise a missense mutation. In some embodiments, the missense mutation is C509S, D185N, D433N, F265S, G225D, H320Y, I323V, K31E, K345Q, M34I, N100D, N481I, P115S, P455A, Q278P, R206C, R401M, S130F, S226N, S41F, S41F, S440G, S469C, S56L, T298S, V234M, V91M, or W98R. In some embodiments, the one or more mutations in the ACVR1 gene comprise a frameshift mutation. In some embodiments, the frameshift mutation is E38fs. In some embodiments, the one or more mutations in the ACVR1 gene comprise a splice site mutation. In some embodiments, the splice site mutation is G264S.

As used herein, the shorthand reference to mutations indicates (the naturally occurring amino acid) (the position of that amino acid) (and the amino acid present in the mutant peptide). For example, P197L indicates that the proline at position 197 is replaced with leucine. In another example, (P197F198)L indicates that the proline at position 197 and the phenylalanine at position 198 are collectively replaced with a single leucine.

Such mutations may be detected using any suitable methods. In embodiments, a mutation is detected by contacting a sample with reagents (e.g., antibodies or nucleic acid primers), generating complexes of reagent and marker(s), and detecting the complexes. Antibodies can be conjugated to a solid support suitable for a diagnostic assay in accordance with known techniques, such as passive binding. Antibodies can be conjugated to cell surface antigens for a diagnostic assay in accordance with known techniques, such as flow cytometry, including multi-color flow cytometry. Antibodies can be conjugated to detectable labels or groups such as radiolabels, enzyme labels, and fluorescent labels in accordance with known techniques.

In various embodiments, effective amounts of an ACVR1 inhibitor is administered to a subject. In embodiments, the ACVR1 inhibitor is administered for treatment of cancer. A wide variety of cancers, including solid tumors and leukemias are amenable to the methods disclosed herein. In embodiments, the cancer is a solid cancer. In some embodiments, the cancer is a brain cancer. In some embodiments, the cancer is a uterine, ovarian, or cervical cancer. In some embodiments, the cancer is a uterine cancer. In some embodiments, the uterine cancer is an endometrial cancer. In some embodiments, the cancer is a lung cancer. In some embodiments, the cancer is a breast cancer. In some embodiments, the cancer is a colon cancer.

In some embodiments, the cancer comprises a solid tumor. In some embodiments, the cancer comprises an advanced solid tumor. In some embodiments, the cancer comprises an advanced metastatic or progressive solid tumor. In embodiments, the cancer comprises a brain or uterine tumor. In embodiments, the cancer is a non-solid cancer. In various embodiments, the cancer is a pre-metastatic cancer. In various embodiments, the cancer is a metastatic cancer.

Types of cancer that may be treated in various embodiments include: brain cancers, uterine cancers, ovarian cancers, cervical cancers, lung cancers, breast cancers, colon cancers, gastrointestinal cancers, hematopoietic or lymphoid cancers, skin cancers, and bone cancers.

In some embodiments, the cancer is a brain cancer (e.g. brainstem glioma, cerebellar astrocytoma, ependymoma, medulloblastoma, supratentorial primitive neuroectodermal tumors, visual pathway and hypothalamic glioma). In various embodiments, the brain cancer is a brain tumor. In various embodiments, the brain cancer is a glioma (e.g. brain stem, cerebral astrocytoma, visual pathway and hypothalamic). In some embodiments, the glioma is a high grade glioma. In some embodiments, the brain cancer is a brain stem glioma. In some embodiments, the brain cancer is DIPG. In some embodiments, the cancer is a central nervous system cancer (e.g., a central nervous system lymphoma). In some embodiments, the cancer is a neuroblastoma.

In some embodiments, the cancer is a uterine, ovarian, or cervical cancer. In some embodiments, the cancer is a uterine cancer. In some embodiments, the uterine cancer is an endometrial cancer. In some embodiments, the endometrial cancers is uterine corpus endometrial cancer. In embodiments, the cancer is an ovarian cancer (e.g., ovarian adenocarcinoma).

In some embodiments, the cancer is a lung cancer (e.g. non-small cell, small cell). In certain embodiments, the lung cancer is a small cell lung cancer. In some embodiments, the cancer is a breast cancer.

In some embodiments, the cancer is a gastrointestinal cancer. In some embodiments, the cancer is an upper aerodigestive tract cancer. In some embodiments, the cancer is a large intestine cancer. In some embodiments, the cancer is a colon cancer.

In some embodiments, the cancer is a urinary tract cancer. In some embodiments, the cancer is a prostate cancer.

In embodiments, the cancer is a hematopoietic or lymphoid cancer. In various embodiments, the cancer is a leukemia (e.g. acute lymphocytic leukemia, acute myelogenous leukemia, chronic lymphocytic leukemia, chronic myeloid leukemia, hairy cell, acute T cell leukemia, etc.) or a lymphoma (e.g. AIDS-related, Burkitt, cutaneous T-cell Hodgkin, non-Hodgkin, primary central nervous system).

In embodiments, the cancer is a skin cancer. In various embodiments, the cancer is a melanoma (e.g., a cutaneous melanoma). In embodiments, the cancer is a bone cancer. In some embodiments, the cancer is a bone tumor (e.g. osteosarcoma, malignant fibrous histiocytoma).

Illustrative mutations associated with particular types of cancer are shown in Table 1.

TABLE 1

| Tumor Sample | Variant Classification | Protein Change |
| --- | --- | --- |
| 639V_URINARY_TRACT | Missense_Mutation | p.F265S |
| CCK81_LARGE_INTESTINE | Missense_Mutation | p.W98R |
| CH157MN_CENTRAL_NERVOUS_SYSTEM | Missense_Mutation | p.S469C |
| CS1_BONE | Missense_Mutation | p.S56L |
| DU145_PROSTATE | Missense_Mutation | p.V91M |
| EM2_HAEMATOPOIETIC_AND_LYMPHOID_nTISSUE | Splice_Site | p.G264S |
| ESS1_ENDOMETRIUM | Missense_Mutation | p.S440G |
| FADU_UPPER_AERODIGESTIVE_TRACT | Missense_Mutation | p.K31E |
| HCC44_LUNG | Missense_Mutation | p.T298S |
| HEC108_ENDOMETRIUM | Missense_Mutation | p.S226N |
| HEC251_ENDOMETRIUM | Missense_Mutation | p.D185N |
| HEC251_ENDOMETRIUM | Missense_Mutation | p.D433N |
| HEC6_ENDOMETRIUM | Missense_Mutation | p.M34I |
| HT3_CERVIX | Missense_Mutation | p.N481I |
| IGROV1_OVARY | Missense_Mutation | p.P455A |
| JURKAT_HAEMATOPOIETIC_AND_LYMPHOID_TISSUE | Missense_Mutation | p.I323V |
| KE37_HAEMATOPOIETIC_AND_LYMPHOID_TISSUE | Splice_Site | |
| KE37_HAEMATOPOIETIC_AND_LYMPHOID_TISSUE | Missense_Mutation | p.H320Y |
| LB2518EBV_MATCHED_NORMAL_TISSUE | Missense_Mutation | p.S41F |
| LB2518MEL_SKIN | Missense_Mutation | p.S41F |
| MCC26_SKIN | Missense_Mutation | p.S130F |
| MHHPREB1_HAEMATOPOIETIC_AND_LYMPHOID_TISSUE | Frame_Shift_Ins | p.E38fs |
| MZ7MEL_SKIN | Missense_Mutation | p.P115S |
| NCIH1793_LUNG | Missense_Mutation | p.K345Q |
| NCIH1836_LUNG | Missense_Mutation | p.R401M |
| NCIH2291_LUNG | Missense_Mutation | p.C509S |
| PC9_LUNG | Missense_Mutation | p.G225D |
| SHP77_LUNG | Missense_Mutation | p.Q278P |
| SKMEL2_SKIN | Splice_Site | |
| SNU407_LARGE_INTESTINE | Missense_Mutation | p.V234M |
| T47D_BREAST | Missense_Mutation | p.N100D |
| TALL1_HAEMATOPOIETIC_AND_LYMPHOID_TISSUE | Missense_Mutation | p.R206C |

Effective amounts of the ACVR1 inhibitor can decrease the number of tumor cells, decrease the number of metastases, decrease tumor volume, induce apoptosis of cancer cells, induce cancer cell death, induce radio-sensitivity in cancer cells, inhibit angiogenesis near cancer cells, inhibit cancer cell proliferation, inhibit tumor growth, prevent metastasis, reduce the number of metastases, increase life expectancy, prolong a subject's life, reduce cancer-associated pain, and/or reduce relapse or re-occurrence of the cancer following treatment. In various embodiments, the effect of administering an ACVR1 inhibitor can be assessed by objective radiographic assessment.

In other embodiments, the disease is a genetic disorder. In some embodiments, the disease is FOP.

In embodiments, the methods of treatment described herein comprise administering an effective amount of an ACVR1 inhibitor to a subject. In various embodiments, the ACVR1 inhibitor is an ACVR1 inhibitor having the following formula (I):

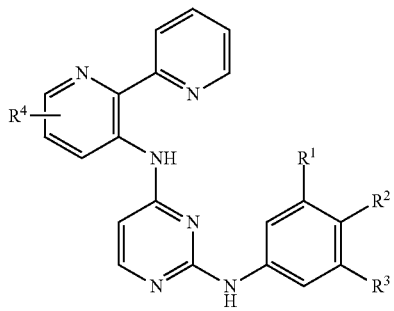

(I)

or a stereoisomer, pharmaceutically acceptable salt, tautomer or prodrug thereof,
wherein:
$R^1$ is H or $C_1$-$C_6$ alkoxy;
$R^2$ is $C_1$-$C_6$ alkoxy or heterocyclyl;
$R^3$ is halo or $C_1$-$C_6$ alkoxy; and
$R^4$ is H or $C_1$-$C_6$ alkyl.

Accordingly, in embodiments, methods of the disclosure comprise administering a treatment regimen comprising an ACVR1 inhibitor to the subject having a predetermined genetic profile comprising one or more mutations in an ACVR1 gene, the ACVR1 inhibitor having the following formula (I):

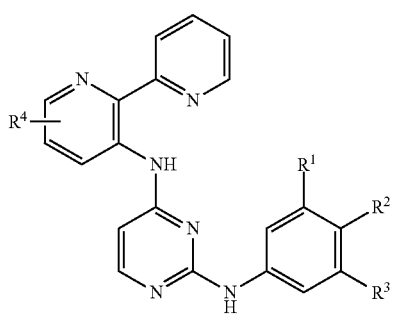

(I)

or a stereoisomer, pharmaceutically acceptable salt, tautomer or prodrug thereof, wherein $R^1$, $R^2$, $R^3$, and $R^4$ are as defined herein.

In further embodiments, methods of the disclosure include methods of treating diffuse intrinsic pontine glioma (DIPG) in a subject, the method comprising administering a treatment regimen comprising an ACVR1 inhibitor to the subject, the ACVR1 inhibitor having the following formula (I):

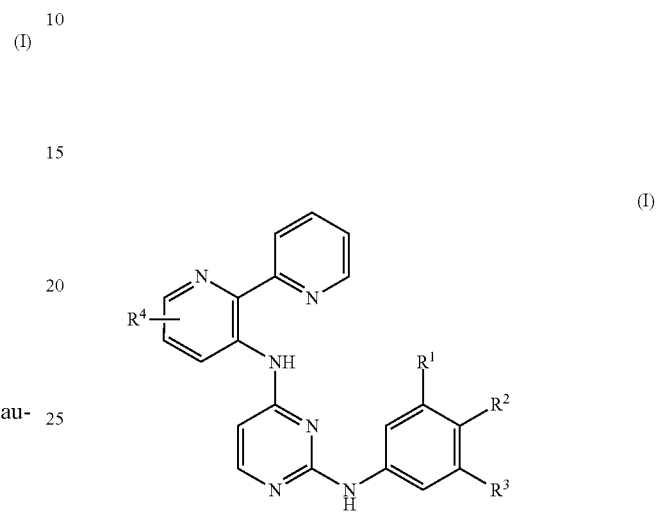

(I)

or a stereoisomer, pharmaceutically acceptable salt, tautomer or prodrug thereof, wherein $R^1$, $R^2$, $R^3$, and $R^4$ are as defined herein.

In certain embodiments of ACVR1 inhibitor (I), $R^1$ is H.

In some embodiments of ACVR1 inhibitor (I), $R^1$ is $C_1$-$C_6$ alkoxy. In some embodiments, the $C_1$-$C_6$ alkoxy is methoxy.

In embodiments of ACVR1 inhibitor (I), $R^2$ is $C_1$-$C_6$ alkoxy. In particular embodiments, the $C_1$-$C_6$ alkoxy is methoxy.

In other embodiments of ACVR1 inhibitor (I), $R^2$ is heterocyclyl. In certain embodiments, the heterocyclyl is optionally substituted piperazinyl. In particular embodiments, the optionally substituted piperazinyl is substituted with $C_1$-$C_6$ alkyl or $C_1$-$C_6$ hydroxylalkyl.

In some embodiments of ACVR1 inhibitor (I), $R^3$ is halo. In particular embodiments, the halo is chloro.

In further embodiments of ACVR1 inhibitor (I), $R^3$ is $C_1$-$C_6$ alkoxy. In certain embodiments, the $C_1$-$C_6$ alkoxy is methoxy.

In embodiments of ACVR1 inhibitor (I), $R^4$ is H. In some embodiments, $R^4$ is $C_1$-$C_6$ alkyl. In certain embodiments, the $C_1$-$C_6$ alkyl is methyl.

In other certain embodiments, the ACVR1 inhibitor is selected from an ACVR1 inhibitor in Table 2.

TABLE 2

Exemplary ACVR1 inhibitors

| Compound No. | Structure | ACVR1 Activity |
|---|---|---|
| 1 | 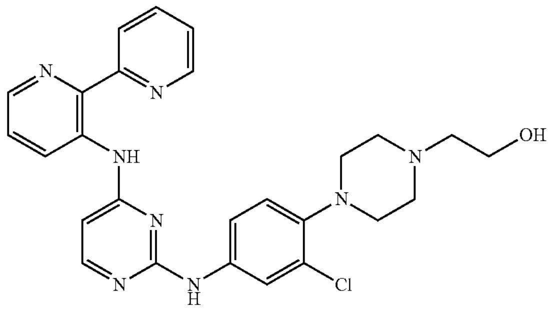 [SMILES: OCCN1CCN(c2ccc(Nc3nccc(Nc4cccnc4-c4ccccn4)n3)cc2Cl)CC1] | ++ |
| 2 | 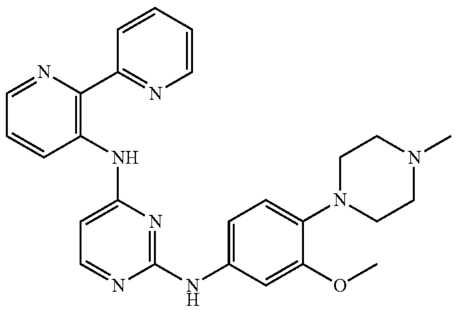 [SMILES: COc1cc(Nc2nccc(Nc3cccnc3-c3ccccn3)n2)ccc1N1CCN(C)CC1] | +++ |
| 3 | 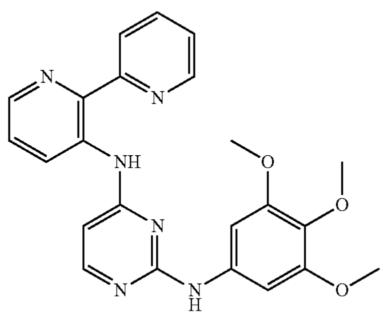 [SMILES: COc1cc(Nc2nccc(Nc3cccnc3-c3ccccn3)n2)cc(OC)c1OC] | +++ |
| 4 | 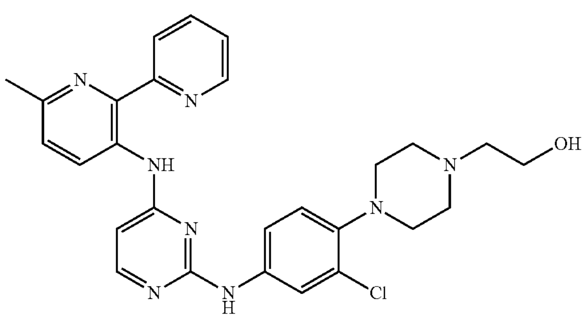 [SMILES: Cc1ccc(Nc2ccnc(Nc3ccc(N4CCN(CCO)CC4)c(Cl)c3)n2)c(-c2ccccn2)n1] | ++ |
| 5 | 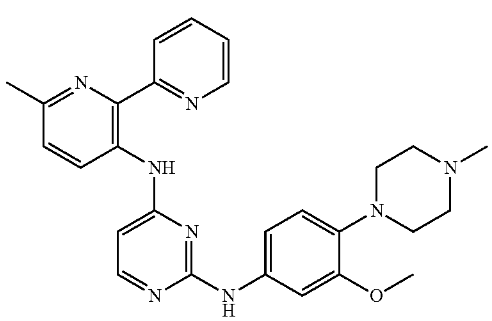 | ++ |

TABLE 2-continued

Exemplary ACVR1 inhibitors

| Compound No. | Structure | ACVR1 Activity |
|---|---|---|
| 6 | 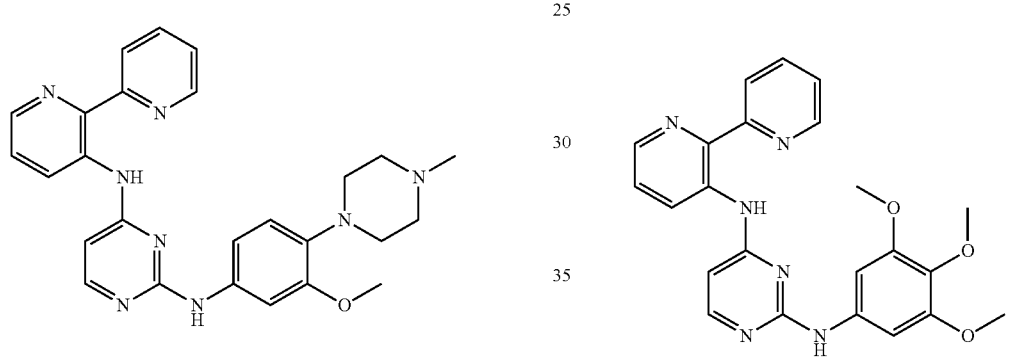 | ++ |

In particular embodiments, the ACVR1 inhibitor is or a pharmaceutically acceptable salt or prodrug thereof. For ease of reference with regard to Table 2, in particular embodiments, the ACVR1 inhibitor is a compound of formula (2) or a pharmaceutically acceptable salt thereof.

In particular embodiments, the ACVR1 inhibitor is

In particular embodiments, the ACVR1 inhibitor is or a pharmaceutically acceptable salt or prodrug thereof.

In particular embodiments, the ACVR1 inhibitor is

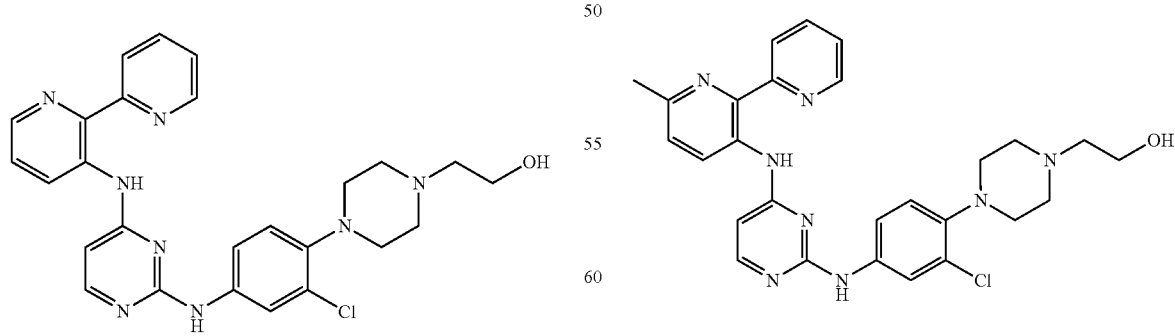

or a pharmaceutically acceptable salt or prodrug thereof.

or a pharmaceutically acceptable salt or prodrug thereof.

In particular embodiments, the ACVR1 inhibitor is

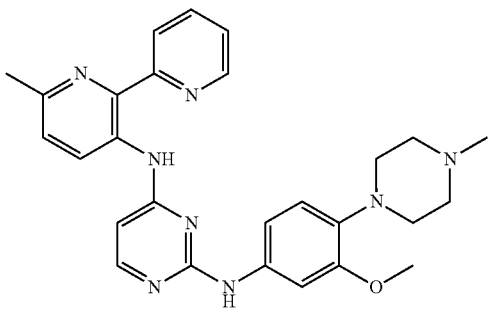

or a pharmaceutically acceptable salt or prodrug thereof.

In particular embodiments, the ACVR1 inhibitor is

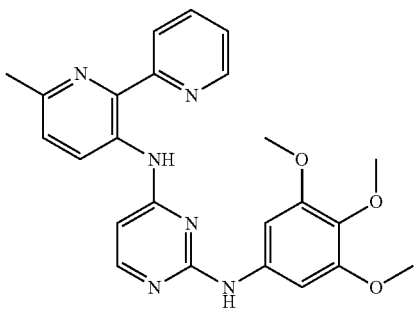

or a pharmaceutically acceptable salt or prodrug thereof.

In various embodiments, the pharmaceutically acceptable salt is an acid addition salt. In some embodiments, the acid addition salt is a hydrochloric acid salt.

It is understood that any embodiment of the ACVR1 inhibitors of formula (I), as set forth above, and any of the specific substituents set forth herein (e.g., $R^1$-$R^4$) in the ACVR1 inhibitors of formula (I), as set forth above, may be independently combined with other embodiments and/or substituents of ACVR1 inhibitors of formula (I) to form embodiments of the disclosure not specifically set forth above. In addition, in the event that a list of substituents is listed for any particular R group in a particular embodiment and/or claim, it is understood that each individual substituent may be deleted from the particular embodiment and/or claim and that the remaining list of sub stituents will be considered to be within the scope of the disclosure. It is understood that in the present description, combinations of sub stituents and/or variables of the depicted formulae are permissible only if such contributions result in stable ACVR1 inhibitors.

The ACVR1 inhibitors of the present disclosure can be prepared according to any number of methods known in the art, including methods described in US 2016/0214944, which is hereby incorporated by reference.

All ACVR1 inhibitors of the disclosure which exist in free base or acid form can be converted to their pharmaceutically acceptable salts by treatment with the appropriate inorganic or organic base or acid by methods known to one skilled in the art. Salts of the ACVR1 inhibitors of the disclosure can be converted to their free base or acid form by standard techniques.

The ACVR1 inhibitors described herein (i.e., ACVR1 inhibitors of formula (I)) can be used in combination with one or more other, additional, therapeutic agents. The dosage of the ACVR1 inhibitors may be adjusted for any drug-drug reaction.

Accordingly, in embodiments, methods of the disclosure include methods of treating solid tumors, DIPG, or FOP in a subject, the method comprising administering a treatment regimen to the subject, the treatment regimen comprising an ACVR1 inhibitor and an additional therapeutic agent, the ACVR1 inhibitor having the following formula (I):

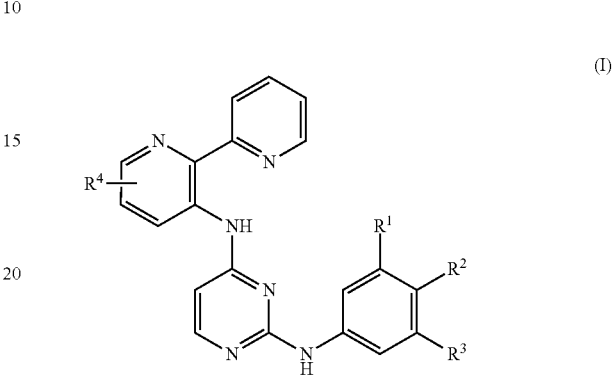

(I)

or a stereoisomer, pharmaceutically acceptable salt, tautomer or prodrug thereof, wherein $R^1$, $R^2$, $R^3$, and $R^4$ are as defined herein.

In various embodiments, the additional therapeutic agent comprises one or more of a retinoic acid receptor gamma agonist; an mTOR inhibitor; an Activin A antibody; a kinase inhibitor; an ACVR1 antibody; a TAK1 inhibitor; a phosphodiesterase inhibitor; a HDAC inhibitor; a chemotherapy agent; an immunotherapeutic agent; a cell therapy; a peptide or tumor lysate vaccine; irinotecan; a TTRNA-DC vaccine with GM-CSF, TTRNA-xALT; an integrin inhibitor; an IL-12 therapy; an antineoplaston therapy; Imiquimod; an oncolytic adenovirus; a WEE1 inhibitor; a WT1 protein derived peptide vaccine; a pegylated Interferon Alfa 2b; a kinase antibody; a smoothened inhibitor; a tubulin inhibitor; a telomerase inhibitor; a CD40 agonist; a GM-CSF agonist; an IDO inhibitor; and a radioactive Iodine labeled monoclonal antibody 8H9.64.

In embodiments, the additional therapeutic agent comprises one or more of a retinoic acid receptor gamma agonist; an mTOR inhibitor; an Activin A antibody; a kinase inhibitor; an ACVR1 antibody; a TAK1 inhibitor; and a phosphodiesterase inhibitor. In some embodiments, the additional therapeutic agent comprises one or more of a HDAC inhibitor; a chemotherapy agent; an immunotherapeutic agent; a cell therapy; a peptide or tumor lysate vaccine; irinotecan; a TTRNA-DC vaccine with GM-CSF, TTRNA-xALT; an integrin inhibitor; an IL-12 therapy; an antineoplaston therapy; Imiquimod; an oncolytic adenovirus; a WEE1 inhibitor; a WT1 protein derived peptide vaccine; a pegylated Interferon Alfa 2b; a kinase antibody; a kinase inhibitor; a smoothened inhibitor; a tubulin inhibitor; a telomerase inhibitor; a CD40 agonist; a GM-CSF agonist; an IDO inhibitor; and a radioactive Iodine labeled monoclonal antibody 8H9.

In embodiments, the kinase inhibitor inhibits cyclin dependent kinase (CDK). In some embodiments, the CDK is CDK9 or CDK7. In some embodiments, the CDK is CDK9. In various embodiments, the CDK9 inhibitor is a siRNA, alvocidib, or a prodrug thereof, dinaciclib, or a combination thereof. In particular embodiments, the CDK9 inhibitor is alvocidib, or a prodrug thereof. Examples of such prodrugs (e.g., phosphate prodrugs) are described in U.S. Pat. No. 9,758,539, which is hereby incorporated by reference). In embodiments, the kinase inhibitor inhibits phosphoinositide 3-kinase (PI3K).

In various embodiments, the immunotherapeutic agent is an immune checkpoint inhibitor. In some embodiments, the immune checkpoint inhibitor is a PD-1 inhibitor. In particular embodiments, the PD-1 inhibitor is Pembrolizumab, Nivolumab, or a combination thereof. In some embodiments, the immune checkpoint inhibitor is a PD-L1 inhibitor. In certain embodiments, the PD-L1 inhibitor is Atezolizumab, Avelumab, Durvalumab, or a combination thereof.

In some embodiments, the kinase antibody comprises a drug conjugate.

In particular embodiments, the retinoic acid receptor gamma agonist is Palovarotene. In particular embodiments, the mTOR inhibitor is Rapamycin or everolimus. In particular embodiments, the Activin A antibody is REGN2447. In particular embodiments, the kinase inhibitor is saracatinib, momelotinib, dorsomorphin, imatinib, Crizotinib, Dasatinib, bevacizumab, erlotinib, vandetanib, ribociclib, crenolanib, abemaciclib, ONC201, Cilengitide, alvocidib, or a prodrug thereof. In particular embodiments, the phosphodiesterase inhibitor is Dipyridamole. In particular embodiments, the HDAC inhibitor is SAHA, vorinostat, or panobinostat. In particular embodiments, the immunotherapeutic agent is MDV9300. In particular embodiments, the cell therapy comprises autologous dendritic cells. In particular embodiments, the peptide or tumor lysate vaccine comprises a K27M peptide or Rindopepimut. In particular embodiments, the irinotecan is administered with convection enhanced delivery. In particular embodiments, the integrin inhibitor is cilengitide. In particular embodiments, the antineoplaston therapy is Atengenal or Astugenal. In particular embodiments, the oncolytic adenovirus is DNX-2401. In particular embodiments, the WEE1 inhibitor is AZD1775. In particular embodiments, the WT1 protein derived peptide vaccine is DSP-7888. In particular embodiments, the kinase antibody is Nimotuzumab, erbitux, or ABT-414. In particular embodiments, the smoothened inhibitor is Vismodegib. In particular embodiments, the tubulin inhibitor is Mebendazole. In particular embodiments, the telomerase inhibitor is Imetelstat. In particular embodiments, the CD40 agonist is APX005M. In particular embodiments, the GM-CSF agonist is Sargramostim with reovirus. In particular embodiments, the IDO inhibitor is indoximod.

In one embodiment, the additional therapeutic agent is a chemotherapeutic agent. In particular embodiments, the chemotherapy agent is melphalan, gemcitabine, temozolomide, cyclophosphamide, fludarabine, doxorubicin, irinotecan, lenalidomide, valproic acid, chloroquine, carboplatin, etoposide, ifosfamide, pomalidomide, or lomustine.

The above methods can also be carried out in combination with radiation therapy, wherein the amount of an ACVR1 inhibitor in combination with the radiation therapy is effective in treating the above diseases.

In one embodiment, radiation is provided prior to the treatment with a compound of formula (I). In one embodiment, radiation is provided after the treatment with a compound of formula (I). In one embodiment, radiation is provided both prior to and after treatment with a compound of formula (I). In one embodiment, treatment with a compound of formula (I) allows for an prolonged period of time before a subject is re-irradiated thereby allowing for reduced side effects associated with radiation therapy.

Techniques for administering radiation therapy are known in the art, and these techniques can be used in the combination therapy described herein. The administration of the ACVR1 inhibitor of the disclosure in this combination therapy can be determined as described herein.

In some embodiments, treatment regimens described herein further comprise surgical resection. Such techniques are known in the art.

In various embodiments, a subject has received a previous treatment for their disease. In such embodiments, a subject may be refractory to or intolerant of the previous treatment. As used herein "refractory" indicates that a subject displayed progressive disease by RECIST, as described in Eur J Cancer. 2016 July; 62:132-7, which is incorporated by reference herein. A subject is considered to have "progressive disease" based on RECIST when there is at least a 20% increase in target lesions, as is understood by one of skill in the art. "Complete response" for DIPG refers to the disappearance of all target lesions. "Partial response" in DIPG refers to at least a 30% decrease in the sum of target lesions and "stable disease" is not sufficient shrinkage to qualify for PR nor sufficient increase to qualify for PD. As used herein "intolerant" means that the subject is unable or unwilling to tolerate the adverse effects of an effective amount of therapeutic agent. In some embodiments, a subject is intolerant to the prior treatment regimen.

For DIPG in particular, effectiveness of treatment with a compound of formula (I) may be measured based on overall survival (OS) or progression-free survival (PFS), which may be calculated based on weeks, months, or years. In one embodiment, treatment with a compound of formula (I) provides an OS of 6 months or more, 9 months or more, 1 year or more, or 5 years or more. In one embodiment, treatment with a compound of formula (I) provides for PFS of at least 6 months, at least 9 months, at least one year, or at least five years.

In embodiments, a subject being treated has a predetermined level of one or more markers. In some embodiments, the one or more markers are for iron regulation. In some embodiments, the one or more markers includes a hepcidin level, tumor burden, transferrin saturation, c-reactive protein (CRP), cardiac markers (B-type natriuretic peptide (BNP), N-terminal pro B-type natriuretic peptide (NT-proBNP)), serum iron, total iron, ferritin, transferrin, soluble transferrin receptor (STR), total iron binding capacity (TIBC), phospho-SMAD, or a combination thereof. In some embodiments, the one or more markers are assessed using an iron panel (i.e., serum iron, ferritin, transferrin, STR, and TIBC). In various embodiments, the one or more markers are in the phospho-signaling pathways downstream of ACVR1. In further embodiments, the one or more markers are gene expression markers downstream of ACVR1/SMAD signaling.

In various embodiments, a subject being treated has a predetermined marker (e.g., hepcidin) level above a threshold value.

A baseline level can be derived from a population. A "population" is any grouping of subjects or samples of like specified characteristics. The grouping could be according to, for example, clinical parameters, clinical assessments, therapeutic regimens, disease status, severity of condition, etc.

In some embodiments, the population is selected randomly. In some embodiments, the population is a group comprising about 2, about 5, about 10, about 25, about 50, about 75, or about 100 subjects. In some embodiments, the population is a group comprising about 200, about 300, about 500, about 1,000, about 1,500, about 2,000, about 3,000, about 5,000, or about 10,000 subjects. In some embodiments, the population is a group comprising less than about 10,000 subjects. In other embodiments, the population is a group comprising greater than about 10,000 subjects.

In some embodiments, the population includes individuals that have cancer and individuals that do not have cancer. In some embodiments, a portion of the population has a solid cancer. In some embodiments, a portion of the population has a brain cancer. In some embodiments, a portion of the population has a uterine cancer.

In some embodiments, the population is a group that does not have cancer. In some embodiments, the population does not have a solid cancer. In some embodiments, the population does not have brain cancer. In some embodiments, the population does not have uterine cancer.

In some embodiments, the population is a group that has cancer. In embodiments, the population has a solid cancer. In some embodiments, the population has a brain cancer. In some embodiments, the population has uterine cancer. In some embodiments, the population has a same type of cancer as the subject.

In embodiments, the expression level of a marker (e.g., hepcidin) is at least about 10% greater than the baseline expression level. In some embodiments, the expression level is at least about 1% greater, at least about 2% greater, at least about 3% greater, at least about 4% greater, at least about 5% greater, at least about 7% greater, at least about 12% greater, at least about 15% greater, at least about 17% greater, at least about 20% greater, at least about 22% greater, at least about 25% greater, at least about 27% greater, at least about 30% greater, at least about 32% greater, at least about 35% greater, at least about 37% greater, at least about 40% greater, at least about 45% greater, at least about 50% greater, at least about 75% greater, or at least about 90% greater. In certain embodiments, a marker (e.g., hepcidin) is up-regulated. "Up-regulation" or "up-regulated" refers to an increase in the presence of a protein and/or an increase in the expression of its gene.

In some embodiments, an expression level of a marker (e.g., hepcidin) is less than a baseline expression level. In embodiments, the expression level of the marker is at least 10% less than the baseline expression level. In some embodiments, the expression level is at least about 1% less, at least about 2% less, at least about 3% less, at least about 4% less, at least about 5% less, at least about 10% less, at least about 12% less, at least about 15% less, at least about 17% less, at least about 20% less, at least about 22% less, at least about 25% less, at least about 27% less, at least about 30% less, at least about 32% less, at least about 35% less, at least about 37% less, at least about 40% less, at least about 45% less, at least about 50% less, at least about 75% less, or at least about 90% less. In certain embodiments, a marker (e.g., hepcidin) is down-regulated. "Down-regulation" or "down-regulated" refers to a decrease in the presence of a protein and/or a decrease in the expression of its gene.

Measurement of expression of a marker (e.g., hepcidin) can be determined at the protein or nucleic acid level using any method known in the art. In some embodiments, marker expression is detected by contacting a sample with reagents (e.g., antibodies or nucleic acid primers), generating complexes of reagent and marker(s), and detecting the complexes. Antibodies can be conjugated to a solid support suitable for a diagnostic assay in accordance with known techniques, such as passive binding. Antibodies can be conjugated to cell surface antigens for a diagnostic assay in accordance with known techniques, such as flow cytometry, including multi-color flow cytometry. Antibodies can be conjugated to detectable labels or groups such as radiolabels, enzyme labels, and fluorescent labels in accordance with known techniques.

Examples of suitable immunoassays include immunoblotting, immunoprecipitation, immunofluorescence, chemiluminescence, electro-chemiluminescence (ECL), and ELISA. Up- or down-regulation of markers also can be detected using, for example, cDNA arrays, clone hybridization, differential display, differential screening, FRET detection, liquid microarrays, PCR, RT-PCR, Sanger sequencing, mass-parallel (next-generation) sequencing, molecular beacons, microelectric arrays, oligonucleotide arrays, polynucleotide arrays, serial analysis of gene expression (SAGE), and/or subtractive hybridization.

Expression may be determined in a sample collected from a subject prior to treatment. In such embodiments, expression levels may be used to predict responsiveness to a particular treatment. In some embodiments, expression levels may be used, at least in part, to determine a treatment administered to a subject. In some embodiments, a sample is collected about 28 days before a treatment regimen is administered. In some embodiments, a sample is collected about 14 days before a treatment regimen is administered. In some embodiments, a sample is collected about 7 days before a treatment regimen is administered. In some embodiments, a sample is collected about 72 hours before a treatment regimen is administered. In some embodiments, a sample is collected up to about 6 hours before a treatment regimen is administered.

In specific embodiments, a sample is collected on day 1 of a first cycle of treatment, pre-dose, 0.5 hours after dosing, two hours after dosing, four hours after dosing, six hours after dosing, eight hours after dosing, 12 hours after dosing, and/or 24 hours after dosing. In specific embodiments, a sample is collected on day 1 of a first cycle of treatment, pre-dose, 0.5 hours after dosing, two hours after dosing, four hours after dosing, six hours after dosing, and/or 24 hours after dosing. In specific embodiments, a sample is collected on day 1 of a first cycle of treatment, pre-dose, two hours after dosing, six hours after dosing, and/or 24 hours after dosing. In some embodiments, a sample may be collected after a dose of a treatment is administered to a subject. In another specific embodiment, a sample is also collected on day 8 of the first cycle of treatment, pre-dose. In some embodiments, a sample is collected on one or more of days 1, 7, 14, 21, and 28 of the first cycle of treatment, pre-dose. In specific embodiments, a sample is collected on day 21 of a first cycle of treatment, pre-dose, 0.5 hours after dosing, two hours after dosing, four hours after dosing, six hours after dosing, eight hours after dosing, 12 hours after dosing, and/or 24 hours after dosing. In specific embodiments, a sample is collected on day 21 of a first cycle of treatment, pre-dose, 0.5 hours after dosing, two hours after dosing, four hours after dosing, six hours after dosing, and/or 24 hours after dosing. In specific embodiments, a sample is collected on day 21 of the first cycle of treatment, at pre-dose, 2 hours, and 6 hours. In specific embodiments, a sample is collected on day 21 of a first cycle of treatment, pre-dose, two hours after dosing, six hours after dosing, and/or 48 hours after dosing. In specific embodiments, a sample is collected on days 8, 21, and 23 of a treatment cycle.

In another specific embodiment, a sample is also collected on day 1 of the second cycle of treatment, pre-dose. In some embodiments, a sample is collected within 7 days prior to day 1 of the second cycle. In another specific embodiment, a sample is also collected on day 1 of the second cycle of treatment at 4 hours post-treatment. In some embodiments, a sample is collected on one or more of days 1, 7, 14, 21, and 28 of the second cycle of treatment, pre-dose. In some embodiments, a sample is collected on one or more of days 1, 8, 15, 22, and 29 of the second cycle of treatment. In some embodiments, a sample is collected on day 21 of the second cycle of treatment, pre-dose. In further specific embodiment, a sample is also collected on day 1 of any additional cycles of treatment (e.g., third, fourth, fifth, etc.), pre-dose. In some specific embodiments, a sample is collected according to one of the schedules described herein for any additional cycles of treatment (e.g., third, fourth, fifth, etc.), pre-dose. In another specific embodiment, a sample is also collected after treatment is completed. In such embodiments, a sample may be collected within 14 days of the completion of treatment.

As is understood, the type of sample collected will be chosen based on the marker being tested. Any suitable samples (e.g., plasma, serum, peripheral blood mononuclear cells (PBMCs), etc.) may be used.

Up- or down-regulation can be assessed by comparing a value to a relevant reference level. For example, the quantity of one or more markers can be indicated as a value, which can be derived, e.g., by measuring level(s) of the marker(s) in the sample by an assay performed. In embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. Accordingly, the term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Alternatively, relative quantification can be accomplished by comparison of detected levels or amounts between two or more different markers to provide a relative quantification of each of the two or more markers, e.g., relative to each other.

In various embodiments, levels of the one or more markers are monitored after the ACVR1 inhibitor is administered.

In embodiments, a relationship between administration of the ACVR1 inhibitor and the one or more markers may be quantified using a Spearman rank correlation statistic.

In some embodiments, the one or more markers include hepcidin. In some embodiments, the subject has a predetermined hepcidin level of at least about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, about 1 ng/mL, about 1.5 ng/mL, about 2 ng/mL, about 2.5 ng/mL, about 3 ng/mL, about 4 ng/mL, about 5 ng/mL, about 6 ng/mL, about 7 ng/mL, about 8 ng/mL, about 9 ng/mL, about 10 ng/mL, about 12.5 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 0.1 ng/mL to about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 0.5 ng/mL to about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 1 ng/mL to about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 5 ng/mL to about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 10 ng/mL to about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 12.5 ng/mL to about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

In various embodiments, the subject has a predetermined hepcidin level of from about 25 ng/mL to about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

Hepcidin levels may also be measured in molar concentrations. In some embodiments, a predetermined hepcidin level is at least 4 nM. In some such embodiments, the subject is a female. In some embodiments, a predetermined hepcidin level is at least 4.1 nM. In some such embodiments, the subject is a female. In some embodiments, a predetermined hepcidin level is at least 8.5 nM. In some such embodiments, the subject is a female. In some embodiments, a predetermined hepcidin level is at least 7.5 nM. In some such embodiments, the subject is a male. In some embodiments, a predetermined hepcidin level is at least 7.8 nM. In some such embodiments, the subject is a male.

In various embodiments, a hepcidin level is monitored after the ACVR1 inhibitor is administered.

In various embodiments, a subject has a predetermined transferrin saturation that is lower than a threshold value. "Transferrin saturation" refers to the value of serum iron divided by the total iron-binding capacity, and may be determined using any technique known in the art.

In embodiments, a subject has a transferrin saturation of less than about 50%. In some such embodiments, the subject is male. In embodiments, a subject has a transferrin saturation of less than about 45%. In some such embodiments, the subject is female. In some embodiments, a subject has a transferrin saturation of less than about 40%. In some embodiments, a subject has a transferrin saturation of less than about 35%. In some embodiments, a subject has a transferrin saturation of less than about 30%. In some embodiments, a subject has a transferrin saturation of less than about 25%. In some embodiments, a subject has a transferrin saturation of less than about 20%. In some embodiments, a subject has a transferrin saturation of less than about 15%. In some such embodiments, the subject is female.

In some embodiments, a subject has a transferrin saturation ranging from about 12% to about 50%. In some embodiments, a subject has a transferrin saturation ranging from about 15% to about 50%. In some such embodiments, the subject is male. In some embodiments, a subject has a transferrin saturation ranging from about 12% to about 45%. In some such embodiments, the subject is female. In some embodiments, a subject has a transferrin saturation ranging from about 20% to about 40%. In some embodiments, a subject has a transferrin saturation ranging from about 30% to about 45%. In some embodiments, a subject has a transferrin saturation ranging from about 25% to about 35%. In some embodiments, a subject has a transferrin saturation ranging from about 15% to about 25%. In some embodiments, a subject has a transferrin saturation ranging from about 20% to about 30%.

In various embodiments, a transferrin saturation level is monitored after the ACVR1 inhibitor is administered.

In various embodiments, a subject has acceptable liver function. In such embodiments, a subject's bilirubin is ≤1.5× upper limit of normal (ULN) (unless associated with Gilbert's Syndrome), and the subject's aspartate aminotransferase (AST/SGOT), alanine aminotransferase (ALT/SGPT) and alkaline phosphatase are ≤2.5×ULN (if liver metastases are present, then ≤5×ULN is allowed).

In some embodiments, a subject has acceptable renal function. In such embodiments, the subject's calculated creatinine clearance is ≥30 mL/min.

In some embodiments, a subject has acceptable hematologic status. In such embodiments, the subject's granulocyte count is ≥1500 cells/mm$^3$, platelet count is ≥100,000 (plt/mm$^3$), and hemoglobin is ≥8 g/dL. In some embodiments, a subject has not received a transfusion within 14 days of the first administration of the ACVR1 inhibitor.

In some embodiments, a subject has an acceptable coagulation status. In such embodiments, the subject's prothrombin time (PT) is within 1.5× normal limits, and activated partial thromboplastin time (aPTT) is within 1.5× normal limits.

In certain embodiments, the subject is a patient of 22 years of age or younger, 21 years of age or younger, 20 years of age or younger, 19 years of age or younger, 18 years of age or younger, 17 years of age or younger, 16 years of age or younger, 15 years of age or younger, 14 years of age or younger, 13 years of age or younger, 12 years of age or younger, 11 years of age or younger, 10 years of age or younger, 9 years of age or younger, 8 years of age or younger, 7 years of age or younger, 6 years of age or younger, 5 years of age or younger, 4 years of age or younger, 3 years of age or younger, 2 years of age or younger, or 1 year of age or younger. In some embodiments, the patient is a pediatric patient, which may be defined as 22 years of age or younger or 18 years of age or younger. In other words, in some embodiments, the patient is pediatric up to age 22. In other embodiments, the patient is pediatric up to age 18. In some embodiments, the patient is from about 3 to about 10 years of age. In some embodiments, the patient is from about 3 to about 5 years of age. In some embodiments, the patient is from about 5 to about 10 years of age. In some embodiments, the patient is from about 6 to about 10 years of age. In some embodiments, the patient is from about 6 to about 8 years of age.

In various embodiments, the ACVR1 inhibitor is formulated as a pharmaceutical composition comprising an ACVR1 inhibitor of formula (I), or a pharmaceutically acceptable salt or prodrug thereof, and a pharmaceutically acceptable carrier, diluent or excipient.

Accordingly, the present disclosure provides compositions comprising an ACVR1 inhibitor for use in the methods described herein. In embodiments, an ACVR1 inhibitor is formulated for oral administration. In various embodiments, an ACVR1 inhibitor is formulated as a tablet, capsule (e.g., gelatin capsule), or solution. In particular embodiments, the ACVR1 inhibitor is formulated with an excipient. In certain embodiments, the ACVR1 inhibitor is formulated as a gelatin capsule. In some embodiments, the gelatin capsules are formulated in 5 mg, 25 mg, or 125 mg strengths. In some embodiments, the capsules are formulated in 30 mg, 90 mg, or 120 mg strengths. In certain embodiments, the ACVR1 inhibitor is formulated as an oral solution. In some embodiments, the solution is formulated in 5 mg/mL increments, 10 mg/mL increments, 20 mg/mL increments, or 30 mg/mL increments. In some embodiments, the solution is formulated to provide a pediatric dose of between about 80% to about 100% of an adult dose. In some embodiments, the solution is formulated in a strength of about 24 to about 30 mg, about 48 to about 60 mg, about 72 to about 90 mg, about 96 to about 120 mg. In some embodiments, the solution is formulated in 30 mg, 60 mg, 90 mg, or 120 mg strengths. In some embodiments, the solution is formulated in 24 mg, 48 mg, 72 mg, or 96 mg strengths.

The pharmaceutical compositions of the disclosure can be prepared by combining the ACVR1 inhibitor with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient.

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When a pharmaceutical composition is in the form of a capsule, for example, a gelatin capsule, it may contain, in addition to materials of the above type, a liquid carrier such as polyethylene glycol or oil.

A pharmaceutical composition for use in the present methods may be in the form of a liquid, for example, an elixir, syrup, solution, emulsion or suspension. The liquid may be for oral administration or for delivery by injection, for example. When intended for oral administration, pharmaceutical compositions contain, for example in addition to the therapeutic compound(s), one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions used in certain embodiments of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. Physiological saline is a preferred adjuvant. An injectable pharmaceutical composition is preferably sterile. In embodiments, the pharmaceutical composition is formulated for injection. In some embodiments, the pharmaceutical composition is formulated for bolus injection. In embodiments, the pharmaceutical composition is formulated for infusion.

A liquid pharmaceutical composition used in embodiments of the disclosure intended for either parenteral or oral administration should contain an amount of an ACVR1 inhibitor such that a suitable dosage will be obtained.

In certain embodiments, an ACVR1 inhibitor as described herein is administered in a local rather than systemic manner, for example, via injection of the ACVR1 inhibitor directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation.

A pharmaceutical composition to be used for certain embodiments of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

A pharmaceutical composition for use in certain embodiments of the disclosure (e.g., in solid or liquid form) may include an agent that binds to the therapeutic compound(s) and thereby assists in delivery. Suitable agents that may act in this capacity include a monoclonal or polyclonal antibody, a protein or a liposome.

Delivery systems for hydrophobic pharmaceutical compounds may be employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In embodiments, an ACVR1 inhibitor and an additional therapeutic agent are formulated together in a liposomal formulation.

A pharmaceutical composition used in certain embodiments of the disclosure may be prepared by methodology well known in the pharmaceutical art. For example, a pharmaceutical composition intended to be administered by injection can be prepared by combining the ACVR1 inhibitor with sterile, distilled water so as to form a solution. In some embodiments, pharmaceutical composition(s) for administration according to methods of the disclosure take the form of a liquid where the therapeutic agents are present in solution, in suspension, or both. In some embodiments, when a therapeutic agent is administered as a solution or suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also optionally include solubilizing agents to aid in the solubility of the ACVR1 inhibitor. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions also optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

A surfactant may be added to facilitate the formation of a homogeneous solution or suspension. Surfactants are compounds that non-covalently interact with the therapeutic compound(s) so as to facilitate dissolution or homogeneous suspension aqueous delivery system. In embodiments, a pharmaceutical composition includes one or more surfactants to enhance physical stability. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40, and the like.

Still other pharmaceutical compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

A pharmaceutical composition for use in some embodiments of the disclosure may be intended for rectal administration, in the form, for example, of a suppository, which will melt in the rectum and release the ACVR1 inhibitor. The composition for rectal administration may contain an oleaginous base as a suitable nonirritating excipient. Such bases include lanolin, cocoa butter and polyethylene glycol.

A pharmaceutical composition for use in embodiments of the disclosure may include various materials, which modify the physical form of a solid or liquid dosage unit. For example, the composition may include materials that form a coating shell around the ACVR1 inhibitor. The materials that form the coating shell are typically inert, and may be selected from, for example, sugar, shellac, and other enteric coating agents. Alternatively, the active ingredients may be encased in a gelatin capsule.

A pharmaceutical composition used in certain embodiments may consist of dosage units that can be administered as an aerosol. The term aerosol is used to denote a variety of systems ranging from those of colloidal nature to systems utilizing pressurized packages. Delivery may be by a liquefied or compressed gas or by a suitable pump system that dispenses the active ingredients. Aerosols of the ACVR1 inhibitor may be delivered in single phase, bi-phasic, or tri-phasic systems in order to deliver the active ingredient(s).

Delivery of the aerosol includes the necessary container, activators, valves, subcontainers, and the like, which together may form a kit. One skilled in the art, without undue experimentation may determine preferred aerosols.

In any of the foregoing embodiments, the ACVR1 inhibitor, or a pharmaceutically acceptable salt thereof, is administered in an effective amount, which will vary depending upon a variety of factors including the activity of the specific ACVR1 inhibitor employed; the metabolic stability and length of action of the ACVR1 inhibitor; the age, body weight, general health, sex, and diet of the patient; the mode and time of administration; the rate of excretion; the drug combination; the severity of the particular disorder or condition; and the subject undergoing therapy.

Toxicity and therapeutic efficacy of methods described herein can be determined by standard pharmaceutical procedures in cell cultures or experimental animals, e.g., by determining the $IC_{50}$ and the $LD_{50}$ for an administered ACVR1 inhibitor. For administration, effective amounts (also referred to as doses) can be initially estimated based on results from in vitro assays and/or animal model studies. For example, a dose can be formulated in animal models to achieve a circulating concentration range that includes an $IC_{50}$ as determined in cell culture against a particular target. The dosage may vary depending upon the dosage form employed and the route of administration utilized. The exact formulation, route of administration and dosage can be chosen by the individual physician in view of the patient's condition. (See, e.g., Goodman & Gilman's The Pharmacological Basis Of Therapeutics, Ch. 3, $9^{th}$ ed., Ed. by Hardman, J., and Limbard, L., McGraw-Hill, New York City, 1996, p. 46.)

Compositions that will be administered to a subject take the form of one or more dosage units, where for example, a tablet may be a single dosage unit, and a container of one or more therapeutic agents of the disclosure in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The pharmaceutical composition to be administered using certain embodiments of the methods of the disclosure will, in any event, contain an effective amount of the ACVR1 inhibitor, or a pharmaceutically acceptable salt thereof, for treatment of a disease in accordance with the teachings of embodiments of this disclosure.

The ACVR1 inhibitor described herein are effective over a wide dosage range. For example, in the treatment of adult humans, dosages from about 5 mg to about 500 mg, from about 10 mg to about 320 mg, from about 30 mg to about 240 mg per day, and from about 30 mg to about 180 mg per day are examples of dosages that are used in some embodiments. In some embodiments, the dose is about 30 mg to about 120 mg per day. In some embodiments, the dose is about 30 mg to about 60 mg per day. In some embodiments, the dose is about 60 mg to about 240 mg per day. In some embodiments, the dose is about 60 mg to about 180 mg per day. In some embodiments, the dose is about 60 mg to about 120 mg per day. In some embodiments, the dose is about 120 mg to about 240 mg per day. In some embodiments, the dose is about 120 mg to about 180 mg per day. In some embodiments, the dose is about 180 mg to about 240 mg per day.

In particular embodiments, the dose is about 5 mg per day. In particular embodiments, the dose is about 10 mg per day. In particular embodiments, the dose is about 25 mg per day. In other embodiments, the dose is about 30 mg per day. In other embodiments, the dose is about 60 mg per day. In other embodiments, the dose is about 120 mg per day. In particular embodiments, the dose is about 125 mg per day. In other embodiments, the dose is about 180 mg per day. In other embodiments, the dose is about 240 mg per day. In other embodiments, the dose is about 250 mg per day. In other embodiments, the dose is about 320 mg per day. In other embodiments, the dose is about 325 mg per day.

As another example, in the treatment of adult humans, dosages from about 5 mg to about 500 mg, from about 10 mg to about 320 mg, from about 30 mg to about 240 mg per week, and from about 30 mg to about 180 mg per week are examples of dosages that are used in some embodiments. In some embodiments, the dose is about 30 mg to about 120 mg per week. In some embodiments, the dose is about 30 mg to about 60 mg per week. In some embodiments, the dose is about 60 mg to about 240 mg per week. In some embodiments, the dose is about 60 mg to about 180 mg per week. In some embodiments, the dose is about 60 mg to about 120 mg per week. In some embodiments, the dose is about 120 mg to about 240 mg per week. In some embodiments, the dose is about 120 mg to about 180 mg per week. In some embodiments, the dose is about 180 mg to about 240 mg per week.

In particular embodiments, the dose is about 5 mg per week. In particular embodiments, the dose is about 10 mg per week. In particular embodiments, the dose is about 25 mg per week. In other embodiments, the dose is about 30 mg per week. In other embodiments, the dose is about 60 mg per week. In other embodiments, the dose is about 120 mg per week. In particular embodiments, the dose is about 125 mg per week. In other embodiments, the dose is about 180 mg per week. In other embodiments, the dose is about 240 mg per week. In other embodiments, the dose is about 250 mg per week. In other embodiments, the dose is about 320 mg per week. In other embodiments, the dose is about 325 mg per week.

As noted herein, a pediatric dose may be between about 80% to 100% of an adult dose.

In some embodiments, the dose is escalated. In one embodiment, the dose begins at 30 mg per week and escalates in 30 mg increments up to 120 mg per week. In one embodiment, the dose begins at 30 mg per week and remains level. In one embodiment, the dose begins at 30 mg per week and escalates to a final dose of 60 mg per week. In one embodiment, the dose begins at 30 mg per week and escalates to an interim dose of 60 mg per week, which further escalates to a final dose of 90 mg per week. In one embodiment, the dose begins at 30 mg per week and escalates to a first interim dose of 60 mg per week, a second interim dose of 90 mg per week, which further escalates to a final dose of 120 mg per week. In one embodiment, the dose begins at 60 mg per week and remains level. In one embodiment, the dose begins at 60 mg per week and escalates to a final dose of 90 mg per week. In one embodiment, the dose begins at 60 mg per week and escalates to an interim dose of 90 mg per week, which further escalates to a final dose of 120 mg per week.

In embodiments, an ACVR1 inhibitor is administered in a dose ranging from about 10 $mg/m^2$ to about 500 $mg/m^2$ per day. In embodiments, an ACVR1 inhibitor is administered in a dose ranging from about 150 $mg/m^2$ to about 350 $mg/m^2$ per day. In some embodiments, an ACVR1 inhibitor is administered in a dose ranging from about 200 $mg/m^2$ to about 300 $mg/m^2$ per day. In some embodiments, an ACVR1 inhibitor is administered in a dose ranging from about 220 $mg/m^2$ to about 260 $mg/m^2$ per day. In some embodiments, an ACVR1 inhibitor is administered in a dose ranging from about 230 mg/m$^2$ to about 250 mg/m$^2$ per day. In some embodiments, an ACVR1 inhibitor is administered in a dose ranging from about 235 mg/m$^2$ to about 245 mg/m$^2$ per day. In specific embodiments, an ACVR1 inhibitor is administered in a dose is about 240 mg/m$^2$ per day.

In embodiments, an ACVR1 inhibitor is administered in a dose ranging from about 10 mg/m$^2$ to about 500 mg/m$^2$ per week. In embodiments, an ACVR1 inhibitor is administered in a dose ranging from about 150 mg/m$^2$ to about 350 mg/m$^2$ per week. In some embodiments, an ACVR1 inhibitor is administered in a dose ranging from about 200 mg/m$^2$ to about 300 mg/m$^2$ per week. In some embodiments, an ACVR1 inhibitor is administered in a dose ranging from about 220 mg/m$^2$ to about 260 mg/m$^2$ per week. In some embodiments, an ACVR1 inhibitor is administered in a dose ranging from about 230 mg/m$^2$ to about 250 mg/m$^2$ per week. In some embodiments, an ACVR1 inhibitor is administered in a dose ranging from about 235 mg/m$^2$ to about 245 mg/m$^2$ per week. In specific embodiments, an ACVR1 inhibitor is administered in a dose is about 240 mg/m$^2$ per week.

The exact dosage will depend upon the ACVR1 inhibitor, the route of administration, the form in which the compound is administered, the subject to be treated, physical and physiological factors including target, body weight, severity of condition, type of cancer, previous or concurrent therapeutic interventions, idiopathy of the subject, and the preference and experience of the attending physician.

In some embodiments, an effective amount of an ACVR1 inhibitor is administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, an effective amount of an ACVR1 inhibitor is administered in multiple doses. In some embodiments, dosing is about once, twice, three times, four times, five times, six times, or more than six times per day. In some embodiments, dosing is about once, twice, three times, four times, five times, six times, or more than six times per week. In other embodiments, dosing is about once a month, once every two weeks, once a week, or once every other day. In yet another embodiment, the administration continues for more than about 6, 10, 14, 28 days, two months, six months, or one year. In some cases, continuous dosing is achieved and maintained as long as necessary. In some embodiments, an ACVR1 inhibitor is administered for 1, 7, 14, 21, or 28 consecutive days. In some embodiments, an ACVR1 inhibitor is administered weekly. In some embodiments, an ACVR1 inhibitor is administered on week 1, week 2, week 3, and week 4 of a four-week cycle. In some embodiments, a four-week cycle includes one or more holidays. In some embodiments, a four-week cycle does not include a holiday and dosing is continuous.

In various embodiments, the ACVR1 inhibitor is administered daily. In various embodiments, the ACVR1 inhibitor is administered weekly. In each of such embodiments, the ACVR1 inhibitor is taken substantially at the same time of day. In some embodiments, the ACVR1 inhibitor is administered after fasting (e.g., for at least six hours). In particular embodiments, a subject fasts for at least one hour after administration.

Administration of an ACVR1 inhibitor may continue as long as necessary. In some embodiments, an ACVR1 inhibitor is administered for more than 1, 2, 3, 4, 5, 6, 7, 14, or 28 days. In some embodiments, an ACVR1 inhibitor is administered for less than 28, 14, 7, 6, 5, 4, 3, 2, or 1 day. In some embodiments, an ACVR1 inhibitor is administered for more than 1, 4, 8, 12, 16, 20, 24, 28, 32, 36, 40, 44, 48, or 52 weeks. In some embodiments, an ACVR1 inhibitor is administered for less than 52, 48, 44, 40, 36, 32, 28, 24, 20, 16, 12, 8, 4, or 1 week.

In some embodiments, an ACVR1 inhibitor is administered chronically on an ongoing basis, e.g., for the treatment of chronic effects.

In some embodiments, the additional therapeutic agent may be administered chronically (e.g., as a maintenance therapy). In other such embodiments, the additional one or more therapeutic agents may be administered as a second treatment regimen.

In some embodiments, an ACVR1 inhibitor is administered in dosages. Due to intersubject variability in compound pharmacokinetics, individualization of dosing regimen is provided in certain embodiments. Dosing for a therapeutic agent may be found by routine experimentation in light of the instant disclosure and/or can be derived by one of ordinary skill in the art.

Dosage amount and interval may be adjusted individually to provide plasma levels of the active species which are sufficient to maintain desired pharmacological effects. These plasma levels are referred to as minimal effective concentrations (MECs). Dosages necessary to achieve the MEC will depend on individual characteristics and route of administration. HPLC assays or bioassays can be used to determine plasma concentrations.

Dosage intervals may also be determined using MEC value. In some embodiments, methods of treatment comprise maintaining plasma levels above the MEC for 10-90% of the time. In some embodiments, plasma levels are maintained above the MEC between 30-90% of the time. In some embodiments, plasma levels are maintained above the MEC between 50-90% of the time. For example, in certain embodiments, effective amounts of a therapeutic agent may range from approximately 2.5 mg/m$^2$ to 1500 mg/m$^2$ per day. For example, in certain embodiments, effective amounts of a therapeutic agent may range from approximately 2.5 mg/m$^2$ to 1500 mg/m$^2$ per week. Additional illustrative amounts range from 0.2-1000 mg, 2-500 mg, and 20-250 mg either daily or weekly.

In cases of local administration or selective uptake, the effective local concentration of the therapeutic agent may not be related to plasma concentration, and other procedures known in the art may be employed to determine the correct dosage amount and interval.

In some embodiments, the concentration an ACVR1 inhibitor provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of an ACVR1 inhibitor provided in the pharmaceutical compositions is greater than 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of an ACVR1 inhibitor provided in the pharmaceutical compositions is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% w/w, w/v or v/v.

In some embodiments, the concentration of an ACVR1 inhibitor provided in the pharmaceutical compositions is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

An ACVR1 inhibitor used in embodiments of the disclosure, or pharmaceutically acceptable derivatives thereof, may also be administered simultaneously with, prior to, or after administration of one or more other therapeutic agents. For example, a first therapeutic agent (e.g., an ACVR1 inhibitor) can be administered and after a sufficient period of time a second therapeutic agent is administered. In such embodiments, the period of time between the administration of the first therapeutic agent and the second therapeutic agent may be referred to as a "treatment break" or "holiday." A "treatment break" or "holiday" may also refer to a period of time between cycles of treatment. In some embodiments, such a treatment break or holiday ranges from about 12 hours to about 48 hours. In some embodiments, such a treatment break or holiday ranges from about 18 to about 36 hours. In some embodiments, such a treatment break or holiday ranges from about 24 to about 48 hours. In some embodiments, a treatment break or holiday ranges from about 2 to about 10 days. In some embodiments, a treatment break or holiday ranges from about 3 to about 5 days. In some embodiments, a treatment break or holiday ranges from about 5 to about 9 days. In some embodiments, a treatment break or holiday is about 7 days. In various embodiments, an ACVR1 inhibitor is administered for 21 consecutive days followed by a 7 day treatment break or holiday. In some embodiments, a treatment break or holiday is about 30 days. In various embodiments, an ACVR1 inhibitor is administered weekly for a cycle of 4 consecutive weeks without a treatment break or holiday between cycles. One of ordinary skill in the art can derive an appropriate dosing schedule based on common techniques and knowledge. In embodiments, an ACVR1 inhibitor and one or more of radiation therapy and an additional therapeutic agent are administered sequentially.

EXAMPLES

Example 1

Testing of an Exemplary ACVR1 Inhibitor

Inhibition of Wild Type and Mutant ACVR1

Compound 2 demonstrated potent biochemical inhibition of wild type ACVR1, the FOP/DIPG mutation R206H, and two additional mutant kinases found in DIPG (G328V and R258G), tested according to standard assay procedures.

In brief, casein-based substrates were prepared. The respective ACVR1 kinase was added to the substrate mixture and hot/cold 33P-ATP (10 µM) was added to initiate the reaction. The activity was then measured with a filter binding method.

The $IC_{50}$ values against the kinases are listed below in Table 3.

TABLE 3

| Target | Compound 2 ($IC_{50}$ nM) |
|---|---|
| ACVR1 Wild Type | 4.5 |
| ACVR1 R206H | 3.8 |
| ACVR1 R258G | 51.6 |
| ACVR1 G328V | 13.8 |

Inhibition of SMAD1/5 Phosphorylation

SMAD proteins are transcription factors involved in signaling downstream of TGFβ receptors. The TGFβ receptor ALK2 phosphorylates SMADs when activated by bone morphogenic proteins such as BMP2, which leads to SMAD nuclear translocation, transcriptional initiation and increased expression of genes like HAMP which codes for the peptide hormone hepcidin. Therefore, compounds that target ALK2 should inhibit BMP induced SMAD phosphorylation. In order to evaluate the in vitro potency of Compound 2, HepG2 cells were stimulated with the ALK2 ligand BMP2 in the presence or absence of various concentrations of Compound 2. The results shown in FIG. 1, reveal a clear concentration-dependent inhibition of SMAD1/5 phosphorylation by Compound 2 (EC50=162 nM).

Inhibition of Hepcidin Expression

Figure 2A:
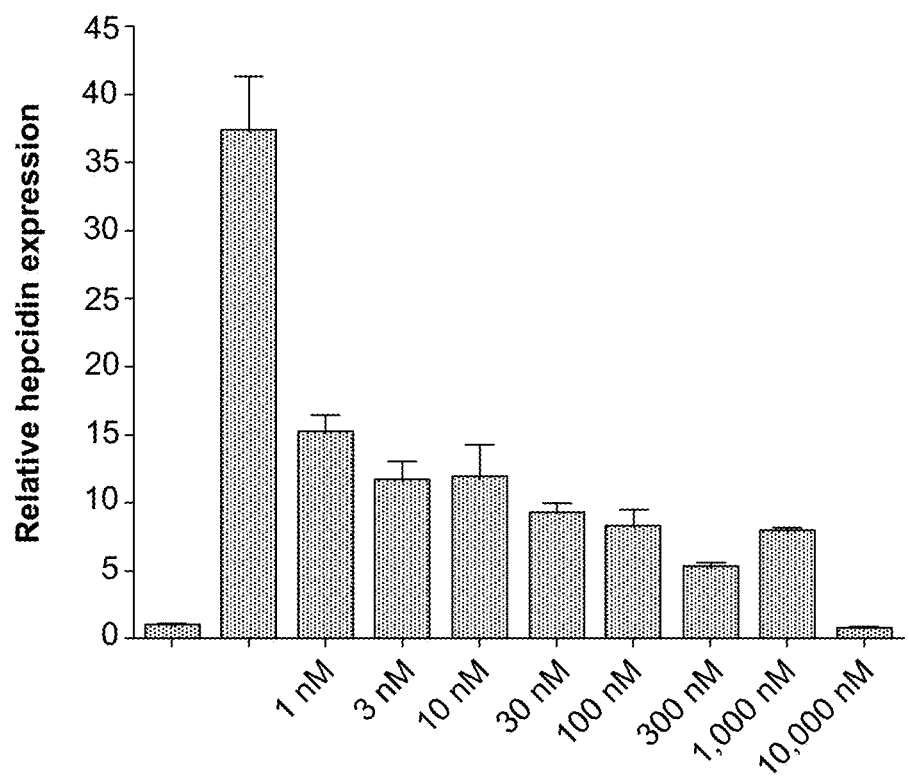
FIG. 2A and FIG. 2B show the inhibition of hepcidin expression in HepG2 cells by Compound 2 with BMP-2 stimulation (FIG. 2A) or without BMP-2 stimulation (FIG. 2B).
Figure 2B:
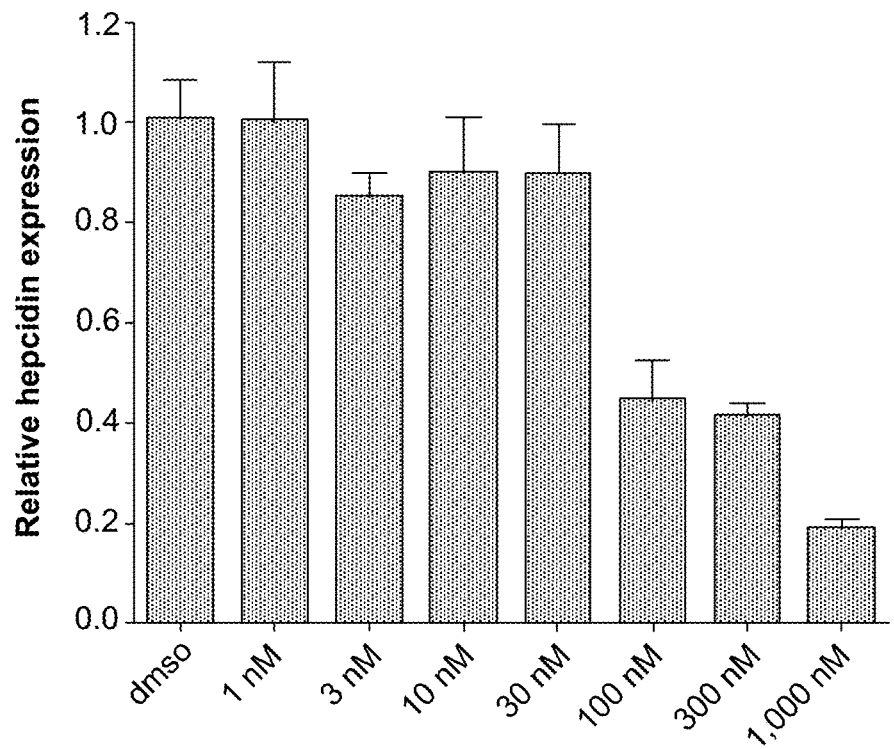

To evaluate the in vitro efficacy of Compound 2, HepG2 cells were stimulated with the ALK2 ligand BMP-2 in the presence or absence of various concentrations of Compound 2 and the resulting levels of hepcidin expression were measured by qPCR. The results shown in FIG. 2A, reveal a strong, dose responsive inhibition of hepcidin transcription by Compound 2 ($EC_{50}$<1 nM). Effects on basal hepcidin transcription were also measured (in the absence of BMP-2 stimulation) and the results are shown in FIG. 2B. Under these experimental conditions, Compound 2 inhibited hepcidin expression in a dose responsive manner ($IC_{50}$~100 nM).

Figure 3:
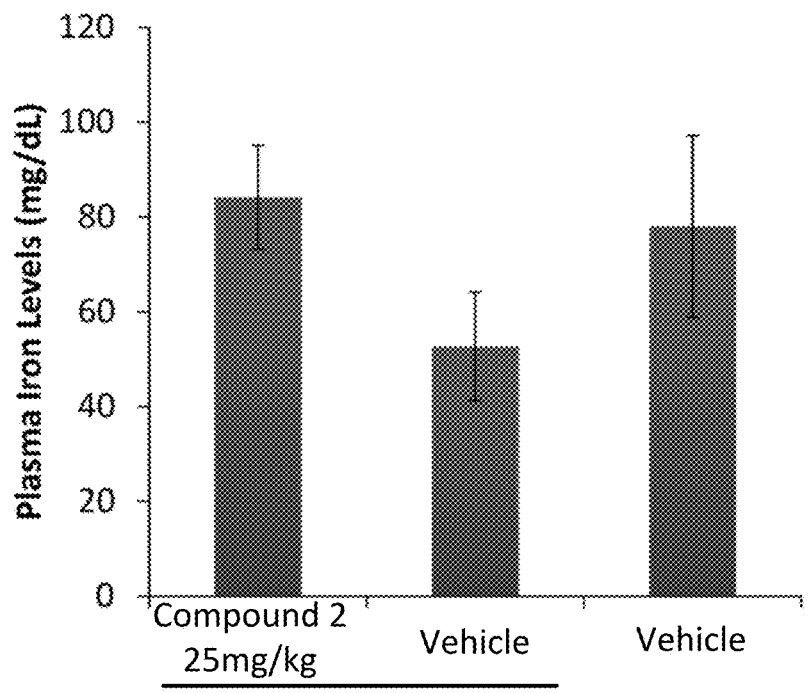
FIG. 3 shows the plasma iron levels for the group given Compound 2. The black bar indicates the groups administered turpentine oil.

Turpentine oil (TO) is known to induce an acute inflammatory response with associated dip in mice, including elevated hepcidin levels. We used this model to evaluate test compounds for in vivo efficacy (FIG. 3).

These data suggest that hepcidin may be a valuable predictive and/or prognostic marker when assessed before and/or during treatment with Compound 2.

Proliferation Assay Against DIPG Cell Lines

Compound 2 was tested in a proliferation assay against ACVR1 mutant (G328V mutated cell line) and wild type DIPG cell lines in vitro. The results demonstrate selective activity against the mutated cell line, similar to the values observed in pSMAD1/5 inhibition assays.

Example 2

Pharmacodynamic and Toxicology Testing of ACVR1 Inhibitors

Figure 4A:
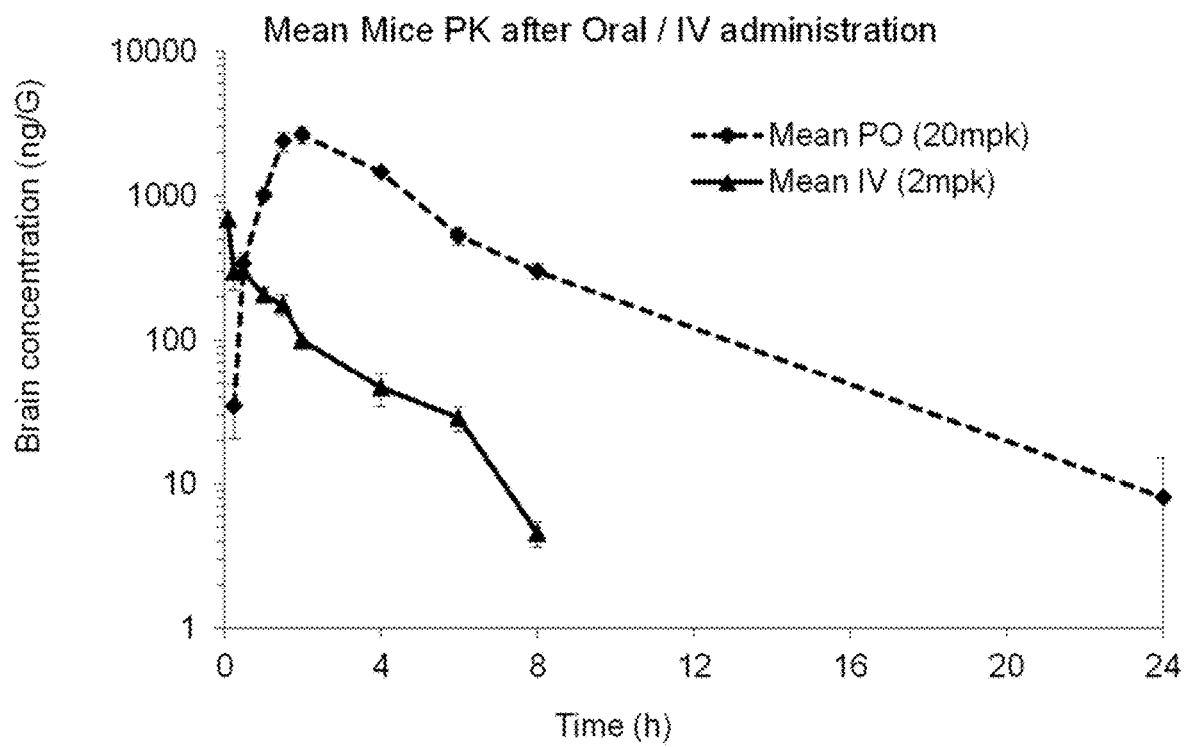
FIG. 4A show brain pharmacokinetics of Compound 2 delivered intravenously and orally in mice and FIG. 4B shows the concentration of Compound 2 in plasma and brain tissues.

In order to be an effective treatment for DIPG, Compound 2 needs to distribute to the brain and more importantly, achieve fairly deep penetration to the pons region of the brain. To assess the general distribution of Compound 2 to the brain, a preliminary brain PK study was conducted. Brain tissue concentrations show very good distribution to the brain (FIG. 4A). The calculated PK parameters are shown in Table 4 and Table 5.

TABLE 4

| PK Parameters | Value |
| --- | --- |
| $AUC_{(inf)}$ (hr * ng/mL) | 758 |
| $AUC_{(0-t)}$ (hr * ng/mL) | 750 |
| $C_{max}$ (ng/g) | 691 |
| $T_{max}$ (h) | 0.083 |
| $T_{1/2}$ (h) | 1.23 |

TABLE 5

| PK Parameters | Value |
| --- | --- |
| $AUC_{(inf)}$ (hr * ng/mL) | 10336 |
| $AUC_{(0-t)}$ (hr * ng/mL) | 10302 |
| $C_{max}$ (ng/g) | 2742 |
| $T_{max}$ (h) | 1.8 |
| $T_{1/2}$ (h) | 2.57 |

Figure 4B:
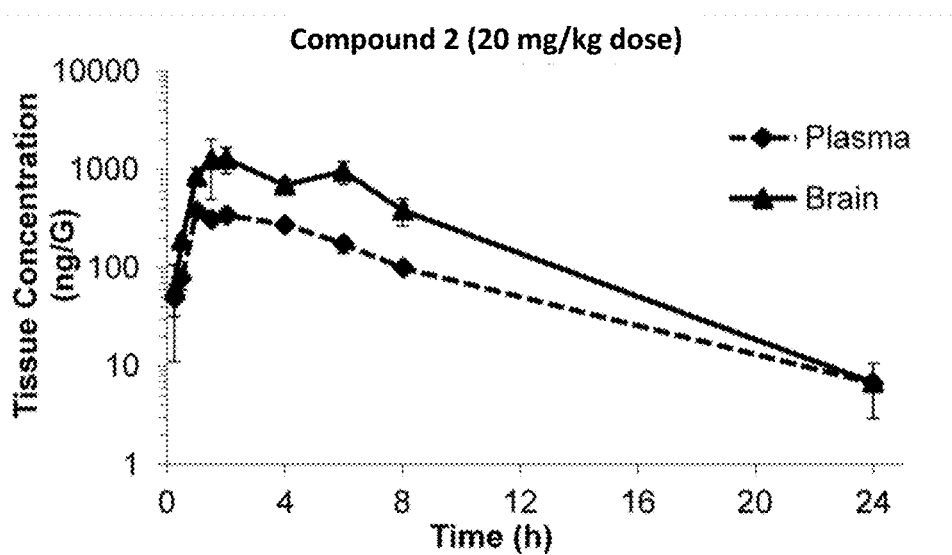

Additionally, a comparison of Compound 2 concentration in the plasma and brain tissue was made, the results of which are in FIG. 4B and Table 6.

TABLE 6

| Compound 2 | Plasma* | Brain |
| --- | --- | --- |
| Dose (mg/kg) | 20 | 20 |
| $C_{max}$ (ng/mL or ng/g) | 378 | 1,686 |
| AUC (ng/mL · hr) or (ng/g · hr) | 2,344 | 7,765 |

To further explore the penetration of Compound 2 into the brain, another study was conducted. In this study, mice were administered a single oral dose of Compound 2 and brain tissues were collected at 1 and 2 hours after dosing. Compound 2 concentrations were measured in tissue sections of the brain by MALDI-TOF mass spectrometry.

1 gram of murine brain cells were mixed with known concentrations of Compound 2 ranging from 0.5 μg to 50 μg. Four mice were treated with orally administered Compound 2 at 100 mg/kg. Samples were taken before treatment and 1, 2, and 4 hours after treatment. The murine mimetic model and actual samples treated with Compound 2 were then analyzed together.

An additional pharmacokinetic and tissue distribution study was conducted to comprehensively evaluate Compound 2 exposure in multiple mouse organs. CD-1 male mice were dosed 20 mg/kg, PO with Compound 2 formulated in 20% solutol and 80% saline. Plasma and organs were collected at nine (9) time points and the drug concentrations were determined by LC-MS/MS. Compound 2 was detectable in all tissues collected, and the majority of tissues demonstrated elevated drug concentrations compared to plasma. The results confirmed exposure in clinically relevant target organs, including brain and liver (Table 7).

TABLE 7

| Compound 2 Tissue Distribution in Mice (20 mg/kg, PO) | | | | | | | | | | | |
| --- | --- | --- | --- | --- | --- | --- | --- | --- | --- | --- | --- |
| PK Parameters | Bone marrow* | Plasma* | Brain | Bladder | Pancreas | Adrenals | Stomach | Lung | Intestine | Kidney | Spleen | Liver |
| $C_{max}$ (ng/mL or/G) | 240 | 378 | 1686 | 2221 | 10575 | 13812 | 17339 | 18259 | 20215 | 31074 | 36232 | 79864 |
| $T_{max}$ (h) | 4.5 | 1.0 | 3.2 | 3.0 | 3.2 | 1.3 | 0.5 | 1.3 | 1.8 | 2.3 | 6.0 | 0.8 |
| $AUC_{Last}$ (ng*h/mL or/G) | 1945 | 2344 | 7729 | 17386 | 53163 | 75782 | 32467 | 76622 | 51891 | 152492 | 406119 | 284827 |
| $AUC_{0-?}$ (ng*h/mL or/G) | 2023 | 2382 | 7756 | 17546 | 53297 | 76421 | 32717 | 76908 | 52421 | 152790 | 627382 | 286210 |
| Half life (h) | 4.6 | 3.8 | 2.6 | 3.1 | 2.6 | 3.3 | 3.6 | 2.8 | 3.6 | 2.5 | 13.3 | 3.3 |

Note:
Results are expressed in Mean, n = 3 animals/group (discrete method);
*Plasma and Bone marrow samples were represented as ng/mL.

Compound 2 free base was tested in humans. Oral pharmacokinetics of Compound 2 were determined in a single human patient for the treatment of DIPG. The formulation was free base Compound 2 by gelatin capsule daily for 15 days, followed by a 20-day suspension period. Dosing was resumed by dissolving in juice and administering via nasogastric tube for 9 days. The nominal dose is 240 mg/m2 (PO). Blood samples were collected at four (4) time points and the drug concentrations are determined by LC-MS/MS.

Compound 2 dosed orally was absorbed and detected in plasma 24 hours post-dosing in a single human, with a prolonged return to baseline. Additional PK parameters were evaluated.

Figure 5:
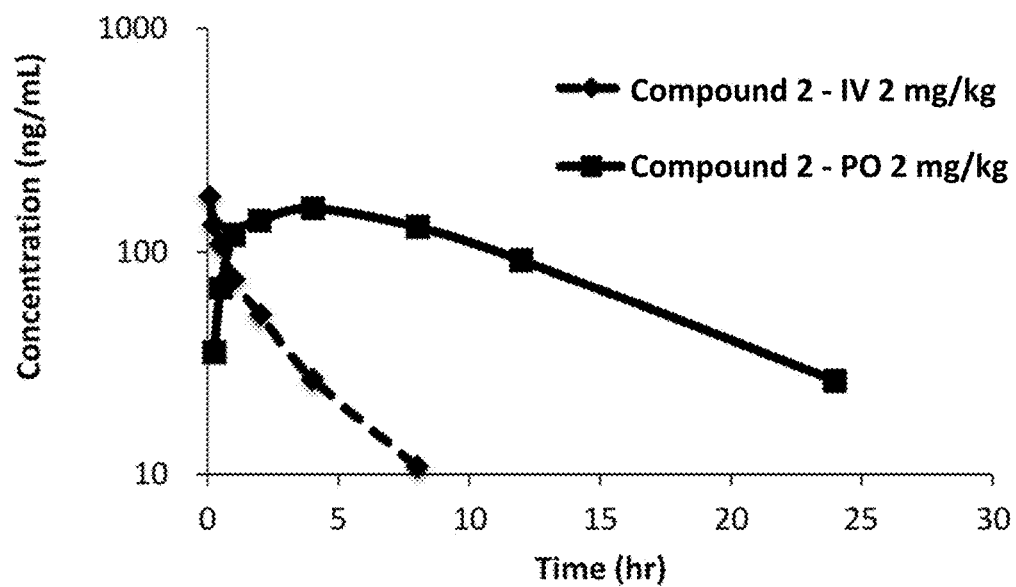
FIG. 5 shows results of pharmacokinetic and toxicity testing of Compound 2.

Pharmacokinetic and toxicology of Compound 2 were tested in rats. The intravenous (IV) and oral (PO) pharmacokinetics of Compound 2 were determined in plasma in fasted female Sprague-Dawley (SD) rats. The formulation used was 20% solutol and 80% saline for both administration routes. The nominal dose was 2 mg/kg (IV) and 20 mg/kg (PO). Samples were taken at 8 time points and the drug concentrations were determined by LC-MS/MS. Plasma concentrations for IV and PO administrations are shown in FIG. 5 and PK calculations from this data are in Table 8.

TABLE 8

|  | Compound 2 |
| --- | --- |
| Dose (mg/kg) | 20 |
| $C_{max}$ (ng/mL) | 159 |
| $T_{max}$ (hr) | 5.33 |
| $T_{1/2}$ (hr) | 6.58 |
| AUC (ng/mL · hr) | 2519 |
| Oral Bioavailability (% F) | 60.8 |

In a non-GLP toxicology study, SD rats were administered 400, 200 or 100 mg/kg Compound 2 HCl salt in 20% solutol or vehicle control for 7 days.

Example 3

Comparative Testing of Dose Response

The effect of Compound 2 on cell viability on 7 cell lines was investigated. The 50% inhibition concentration ($IC_{50}$) was determined in selected cell lines using CellTiter-Glo luminescent cell viability assay after incubation with different test articles concentrations.

The cell lines were treated with Compound 2 with 9 concentrations in triplicate, Cisplatin was used as a reference compound and 0.5% (v/v) DMSO added in culture medium as vehicle control.

Material and Reagents
  General cell culture reagents and plastic.
  96-Well Flat Clear Bottom Black Polystyrene TC-Treated Microplates (Cat #3340, Corning).
  Backseal black adhesive bottom seal (Cat #6005189, Perkin Elmer).
  CellTiter-Glo® Luminescent Cell Viability Assay (Cat. #.: G7572, Promega. Store at −20° C.)
  Substrate is sufficient for 1,000 assays at 100 µl per assay in 96-well plates.
  Including:
    1×100 mL CellTiter-Glo® Buffer
    1×vial CellTiter-Glo® Substrate (lyophilized)

Reagent Preparation
  Thawed the CellTiter-Glo Buffer, and equilibrated to room temperature prior to use.
  Equilibrated the lyophilized CellTiter-Glo Substrate to room temperature prior to use.
  Transferred the appropriate volume (100 mL) of CellTiter-Glo Buffer into the amber bottle containing CellTiter-Glo Substrate to reconstitute the lyophilized enzyme/substrate mixture. This formed the CellTiter-Glo Reagent.
  Mixed by gently vortexing, swirling or by inverting the contents to obtain a homogeneous solution.

Determination of the Half Maximal Inhibition Concentration $IC_{50}$
  Harvested cells during the logarithmic growth period and counted cell number using Count-star.
  Adjusted cell concentrations to $3.33 \times 10^4$ cells/mL with culture medium.
  Added 90 µL cell suspensions to three 96-well plates (plates A and B) with the final cell density of $3 \times 10^3$ cells/well. (cell concentration will be adjusted according to the data base or density optimization assay.)

For the Plates of T0 Reading:
  Added 10 µL culture medium to each well of plate A for T0 reading.
  Equilibrated the plate and its contents at room temperature for approximately 30 mins.
  Placed black sticker on bottom of plates to block light.
  Added 100 µL CellTiter-Glo to each well.
  Mixed contents for 2 mins on an orbital shaker to induce cell lysis.
  Allowed the plate to incubate at room temperature for 10 mins to stabilize luminescent signal.
  Recorded luminescence (T0) using EnVision Multi Label Reader.

For the Plates of Test Reading:
  Prepared 10× solution (working concentration: 10 µM of test article in media with 3.16-fold serial dilutions to achieve 10 dose levels.
  Dispensed 10 µL (10×) drug solution of both test article and reference control in each well (triplicate for each drug concentration) of the plate B. (Solvent final concentration in culture medium: 0.5% [v/v]).
  Incubated the test plate B for 72 hrs in the humidified incubator at 37° C. with 5% $CO_2$, and then measured by means of CTG assay.
  Equilibrated the plate and its contents at RT for approximately 30 mins.
  Placed black sticker on bottom of plates to block light.
  Added 100 µL CellTiter-Glo to each well.
  Mixed contents for 2 mins on an orbital shaker to induce cell lysis.
  Allowed the plate to incubate at room temperature for 10 mins to stabilize luminescent signal.
  Recorded luminescence.

Data Analysis
  The data was displayed graphically using GraphPad Prism 5.0.
  In order to calculate absolute $IC_{50}$ ($EC_{50}$), a dose-response curve was fitted using nonlinear regression model with a sigmoidal dose response. The formula for calculating surviving rate is shown below and the absolute $IC_{50}$ ($EC_{50}$)

was calculated according to the dose-response curve generated by GraphPad Prism 5.0.

The surviving rate (%)=(LumTest article−LumMedium control)/(LumNone treated−LumMedium control)×100%.

Figure 6A:
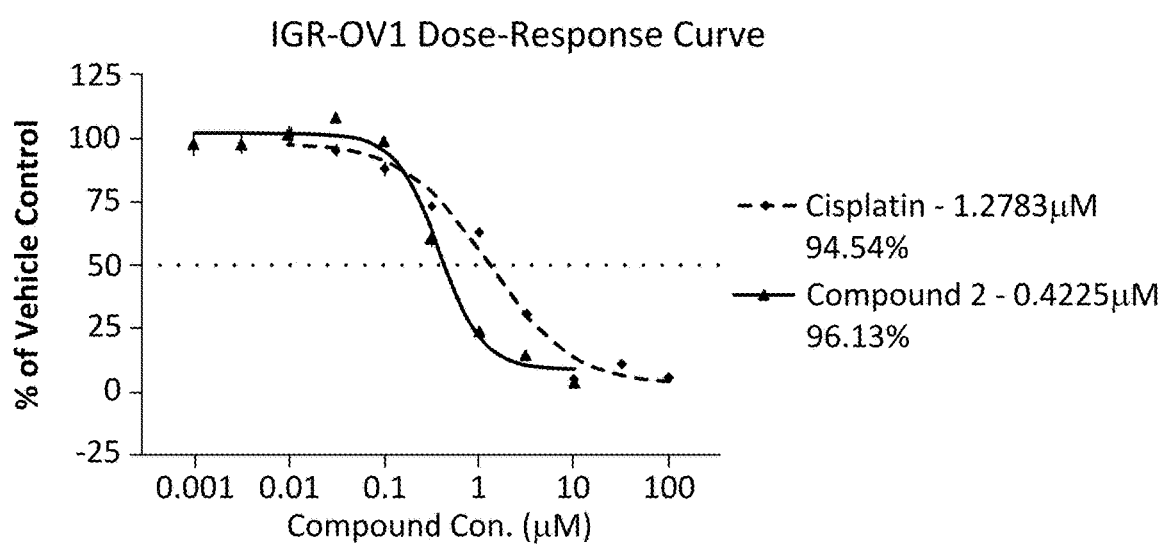
FIG. 6A shows a dose-response curve for Compound 2 in IGR-OV1 cells.
Figure 6B:
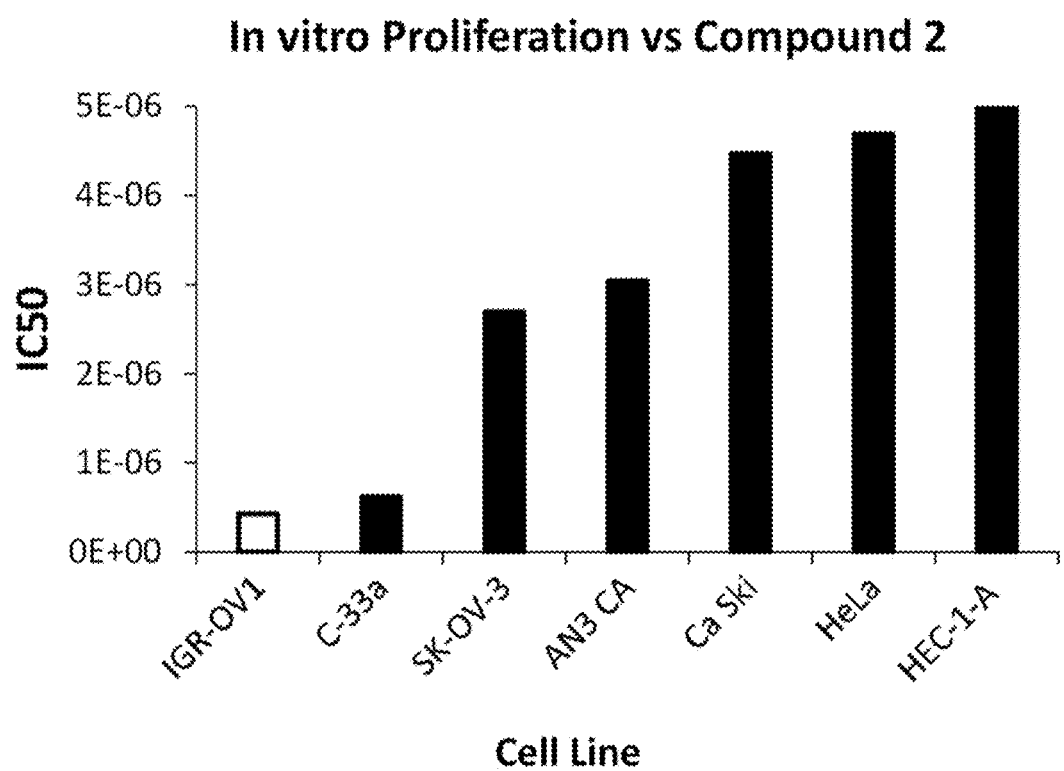
FIG. 6B shows comparative $IC_{50}$ data for seven cell lines.

FIG. 6A shows the dose-response curve for the IGR-OV1 cell line. IGR-OV1 is an ACVR1 mutant (P455A) cell line. FIG. 6B shows a comparison of the results for the IGR-OV1 (mutant ACVR1) cell line to C-33a, SK-OV-3, AN3-CA, CaSki, HeLa, and HEC-1-A (wild type ACVR1).

Example 4

In Vivo Jurkat Xenograft Model

The effect of Compound 2 on tumor volume in a xenograft model was investigated. The animals were housed with the following conditions:

Animals were housed in a ventilated mouse caging system (Animal Care Systems, Centennial, Colo.) with regulated temperature and light/dark cycles.

Temperature: 22.7-23.9° C.
Humidity: 10%
Bedding: Corn cob (Animal Care Systems, ¼" irradiated)
Diet: Irradiated global, soy protein-free, extruded rodent diet (Envigo, Cat. No: 2920X.CS)
Water: RO water, ad libitum Jurkat cells were cultured in RPMI1640 media supplemented with 10% FBS and incubated at 37° C. with 5% $CO_2$. Cells were subcultured twice per week, or as needed.

Cells were washed in serum free media, then suspended in a solution of 1:1, serum free media:matrigel. Injection volume was 200 µL. Mice were injected subcutaneously in the hind flank with $1 \times 10^7$ cells/mouse.

Animal tumor volumes and body weights were measured and recorded twice weekly. Treatment initiated once average tumor volumes reached >100 mm$^3$. Mice were stratified by tumor volume to yield similar average starting tumor volumes in each animal cage, and then each cage was randomly selected for placement into treatment groups.

Tumor volume measurements were made twice weekly using a caliper measuring both length (longest diameter) and width (perpendicular to longest diameter). Tumor volumes were calculated as L×W×W/2.

Figure 7:
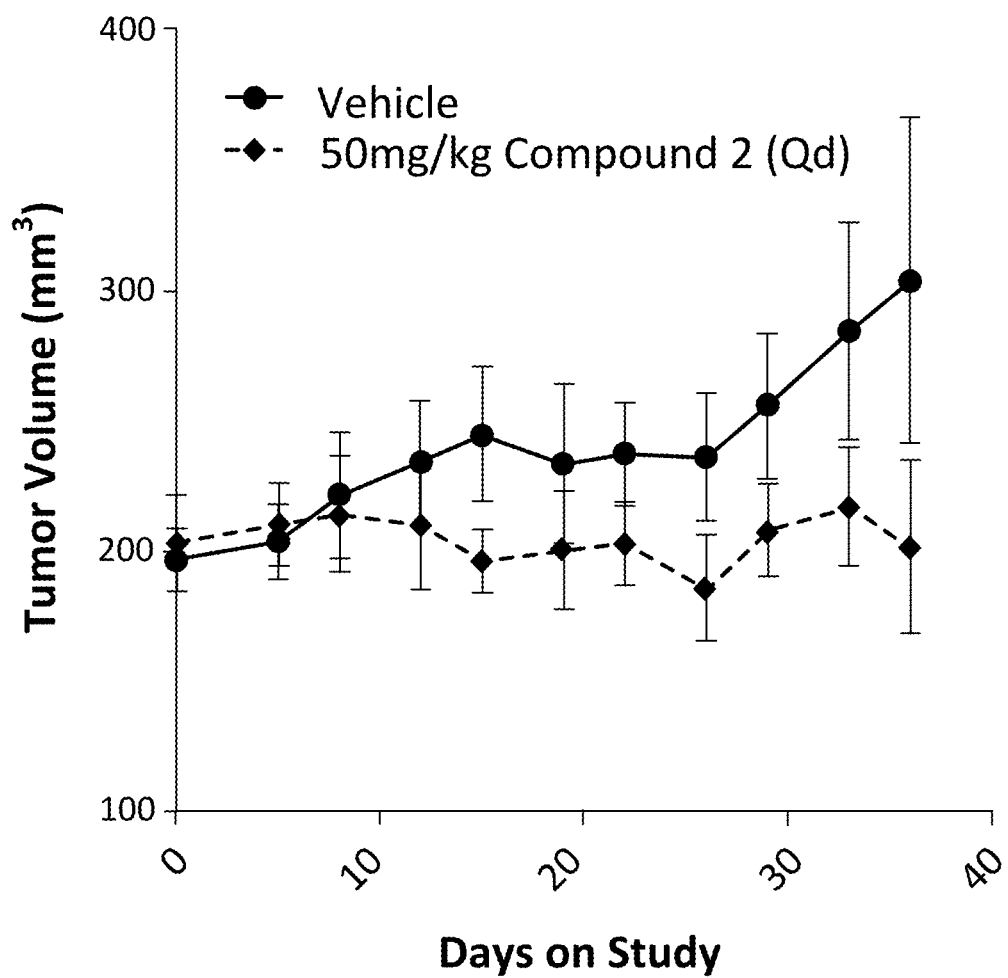
FIG. 7 shows the effect of Compound 2 on tumor volume in a xenograft model.

50 mg/kg (Qd) of an HCl salt of Compound 2 was formulated in 20% Solutol, 80% Dextrose (5% dextrose solution) administered to mice. The results are shown in FIG. 7.

Example 5

Analysis of ACVR1 Mutations in Adult Human Cancers

Genetic make-up of ACVR1 mutations was analyzed to evaluate which mutations may portend benefit from treatment with the compound of structure (I). Using publicly available sequence databases and the analysis tools at cBioPortal.org, ACVR1 mutations in tissues of cancer patients were analyzed. Results were compared to the known mutations of ACVR1 in the literature associated with various cancers or gain-of-function activity. Multiple mutations were found within ACVR1. The FOP community has done extensive work to identify and understand mutations that can drive aberrant activation of ACVR1. These mutations include L196P, R206H, Q207E, R258S, G328E/R, and G356D. ACVR1 mutations identified in adult cancers include most of the known FOP mutations, but also demonstrate more diversity in their ACVR1 mutational profile with fewer "hotspots" and many alterations of unknown significance. The results from surveying these rare mutations in multiple cancer types are herein presented.

Figure 8:
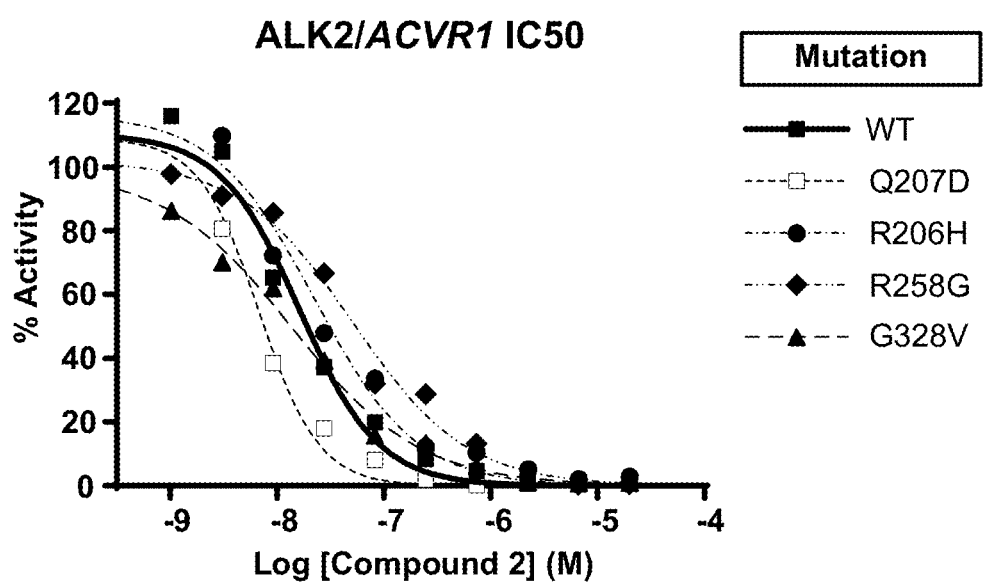
FIG. 8 shows activity of Compound 2 on ALK2/ACVR1 having various mutations.

Biochemical Studies indicate that mutations in the intracellular domain can have activating effects on ACVR1/ALK2 kinase activity. Many of the known mutations enhance the activity of the receptor in response to the receptor ligand. As shown in FIG. 8, Compound 2 was effective in inhibiting ALK2 receptors having various mutations.

Figures 9A, 9B:
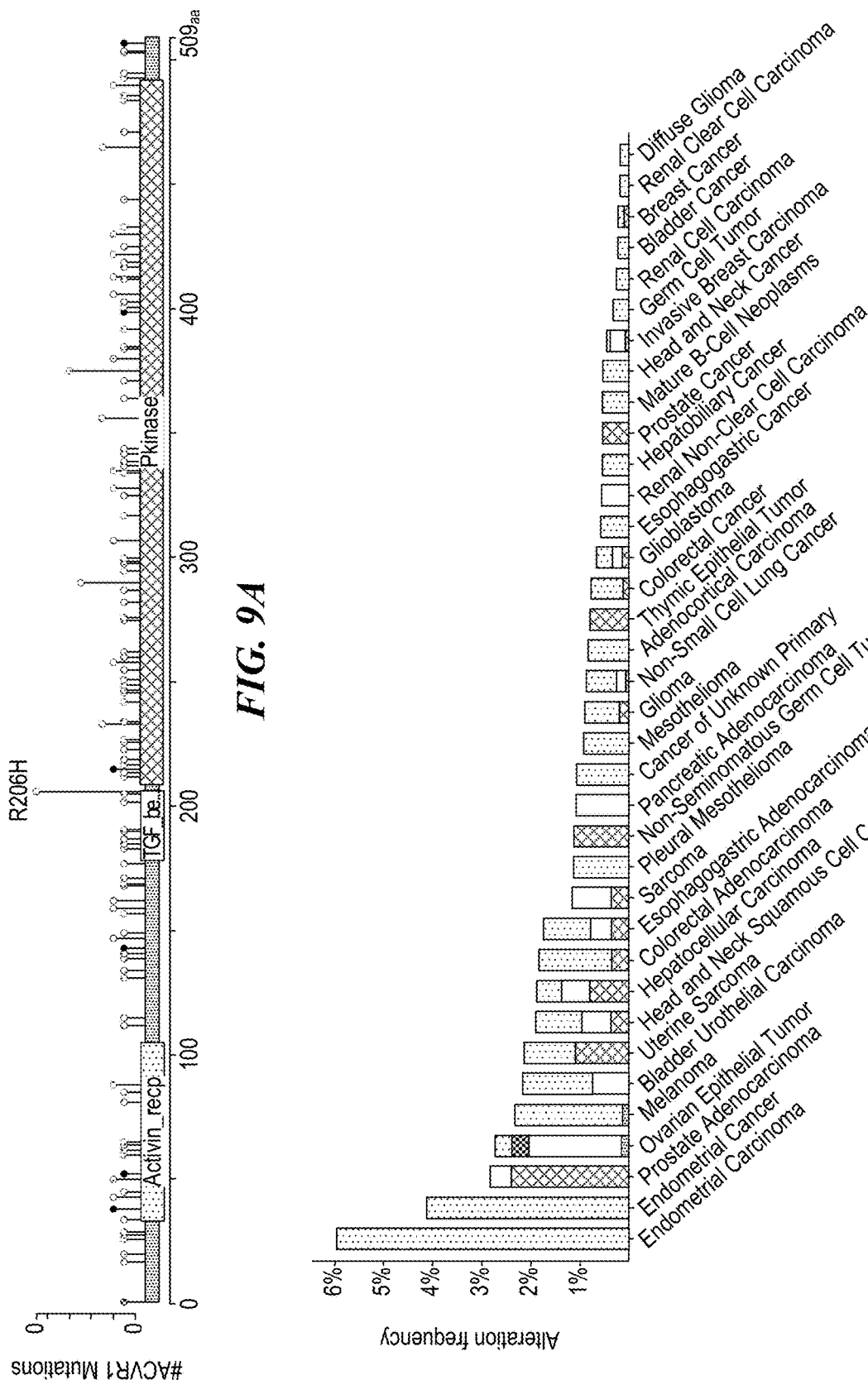
FIG. 9A shows a lollipop diagram of the distribution of ACVR1 mutations in The Cancer Genome Atlas (TCGA) pan cancer and the Memorial Sloan Kettering (MSK) IMPACT databases.
FIG. 9B shows distribution of chromosomal abnormalities found across different adult tumor types in the TCGA pan cancer and MSK IMPACT databases.
Figure 9C:
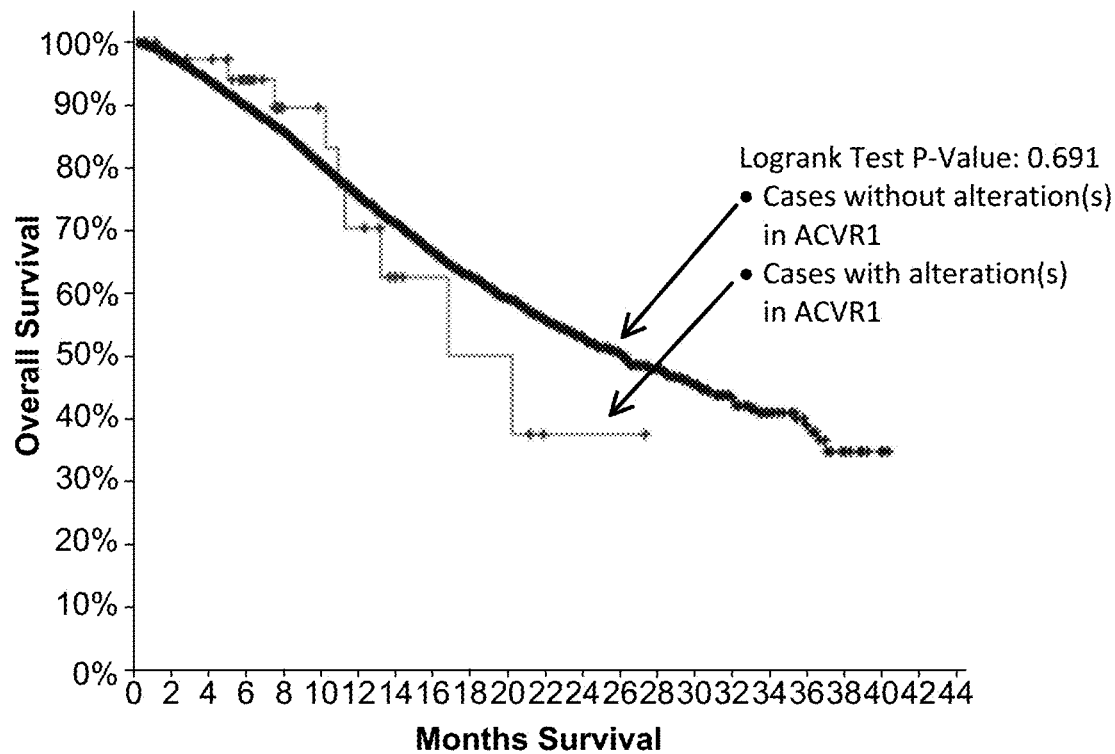
FIG. 9C shows a Kaplan-Meier curve indicating that subjects with genetic abnormalities in ACVR1 have shorter survival time by 6 months compared to subjects without ACVR1 alterations.

Using the cBioPortal.org browser, The Cancer Genome Atlas (TCGA) pan cancer and the Memorial Sloan Kettering (MSK) IMPACT databases were probed for mutations in ACVR1. FIG. 9A shows a Lollipop diagram showing distribution of ACVR1 mutations; including some replicate mutations (hotspots) in the glycine-serine regulatory domain and the protein kinase domain thought to play a role in the regulation of ALK2 activity. FIG. 9B shows distribution of chromosomal abnormalities of several types (mutations, amplifications, deletions and fusions) found across different adult tumor types. FIG. 9C shows a Kaplan-Meier curve indicating that subjects with genetic abnormalities in ACVR1 have shorter survival time by 6 months compared to subjects without ACVR1 alterations. The analysis was focused on mutations and fusions in the ACVR1 gene.

As shown in Table 9, MSK Impact and TCGA database statistics indicate an ACVR1 overall mutation rate of 0.69% found in 147 unique subjects from a population of 21289 patients.

TABLE 9

| Number | Category |
|---|---|
| 21912 | Total samples |
| 21289 | Patients represented |
| 158 | Mutations |
| 1 | Patients with 3 mutations |
| 9 | Patients with 2 mutations |
| 147 | Patients with mutations |
| 0.69% | Percentage of patients with mutations |

Analysis of mutations by tumor type showed that of the 147 unique patients having ACVR1 mutations, 34% had a gynecological cancer, 18% had a gastrointestinal cancer, 14% had a thoracic cancer, 13% had melanoma, 6% had a genitourinary cancer, 5% had a neurological cancer, 4% had a head and neck cancer, 3% had other cancers, and 2% had breast cancer.

Table 10 shows the top mutation frequencies categorized by amino acid position.

TABLE 10

| Protein Change | Count | Published | Region |
|---|---|---|---|
| R206H | 9 | R206H | GS |
| R375C/H | 6 | R375P | PK |
| S290L | 5 | | |
| G356D | 3 | G356D | PK |
| A233V/S | 3 | | |
| P465L/= | 3 | | |
| G328V | 2 | G328V | PK |
| R258G/W | 2 | R258G/S | PK |
| A406G/S | 2 | | |
| ACVR1-NFATC1 | 2 | | |
| E38Vfs*21 | 2 | | |
| E413K/Q | 2 | | |

TABLE 10-continued

| Protein Change | Count | Published | Region |
|---|---|---|---|
| G43D/S | 2 | | |
| G50C/V | 2 | | |
| G88D/V | 2 | | |
| P159L/S | 2 | | |
| P430L/S | 2 | | |
| R147Q | 2 | | |
| R307Q | 2 | | |
| R335Q | 2 | | |
| R380C/H | 2 | | |
| R490H | 2 | | |
| V162M | 2 | | |
| X215_splice | 2 | | |
| R202I | 1 | R202I | GS |
| G325E | 1 | R325A | PK |

In total 117 unique mutations were found across the tumor types in the databases used. Many of the canonical mutations associated with FOP and DIPG were among the most common mutations found in the same positions among the various adult cancers such as R206H, R375C/H, G356D, G328W/E/V/R, R258G/W. Many novel mutations of unknown significance were also detected suggesting additional genetic alterations that may play a role in cancer. Impact assessments from cBioPortal.org, using Mutation Assessor, SIFT, and PolyPhen2 algorithms were conducted to predict the impact of mutations on protein function.

Table 11 shows ACVR1 mutations identified in the data set that were predicted by the SIFT algorithm to have a deleterious impact. The SIFT algorithm predicted 55% of the mutations as deleterious, 35% of the mutations as tolerated, and 10% of the mutations as having an unidentified impact.

TABLE 11

| SIFT impact | Database Mutation | Literature Mutation | Protein Region |
|---|---|---|---|
| deleterious | G238E/V | G328W/E/V/R | PK |
| deleterious | G325E | R325A | PK |
| deleterious | G356D | G356D | PK |
| deleterious | R202I | R202I | GS |
| deleterious | R206H | R206H | GS |
| deleterious | R258G/W | R258G/S | PK |
| deleterious | R375C/H | R375P | PK |

Table 12 shows ACVR1 mutations identified in the data set that were predicted by the Polyphen 2 algorithm to have a possibly damaging or probably damaging impact. The Polyphen2 algorithm predicted 48% of the mutations as having a probably damaging impact, 10% of the mutations as having a possibly damaging impact, 31% of the mutations as benign, and 11% of the mutations as having an unidentified impact.

TABLE 12

| Polyphen-2 Impact | Database Mutation | Literature Mutation | Protein Region |
|---|---|---|---|
| possibly damaging | R375C/H | R375P | PK |
| probably damaging | G325E | R325A | PK |
| probably damaging | G328E/V | G328W/E/V/R | PK |
| probably damaging | G356D | G356D | PK |
| probably damaging | R202I | R202I | GS |
| probably damaging | R206H | R206H | GS |
| probably damaging | R258G/W | R258G/S | PK |

Table 13 shows ACVR1 mutations identified in the data set that were predicted by the Mutation Assessor algorithm to have a high, medium, or low impact. The Mutation Assessor algorithm predicted that 8% of the mutations have a high impact, 28% of the mutations have a medium impact, 35% of the mutations have a low impact, 19% of the mutations have a neutral impact, and 10% of the mutations have an undefined impact.

TABLE 13

| MA impact | Database Mutation | Literature Mutation | Protein Region |
|---|---|---|---|
| high | G356D | G356D | PK |
| medium | G325E | R325A | PK |
| medium | R202I | R202I | GS |
| medium | R206H | R206H | GS |
| medium | R258G/W | R258G/S | PK |
| low | R375C/H | R375P | PK |
| low | G328E/V | G328W/E/V/R | PK |

These algorithms indicate that both canonical and unique mutations could impact protein function. Using the SIFT algorithm, all the canonical mutations found within our search were categorized as deleterious suggesting this may be a useful tool in predicting activating mutations in the ACVR1 gene. In some cases, different amino acid substitutions at a specific site had different effects on mutational impact. Further investigation of these predictive algorithms is warranted.

Next, specific cancer subtypes were analyzed for the presence of the most common mutations or known activating mutations for the various anatomical sites, and SIFT impact scores were computed by cancer subtype.

Gynecological Cancers. Gynecological cancers accounted for the most mutations (43) and included many of the canonical mutations found in FOP and DIPG. The SIFT algorithm predicted that, of patients having ACVR1 mutations and gynecological cancers (n=50), 45% of the patients have a mutation with a deleterious impact, 40% have a mutation with a tolerated impact, and 15% have a mutation with an undefined impact. Known activating and/or common mutations identified in the gynecological cancer subset are shown in Table 14.

TABLE 14

| Protein Change | Count | Literature |
|---|---|---|
| R206H | 8 | R206H |
| R375C/H | 4 | R375P |
| G356D | 3 | G356D |
| P465L/= | 3 | |
| R147Q | 2 | |
| R258W | 1 | R258G/S |
| G328V | 1 | G328 W/E/F//R |
| R202I | 1 | R202I |

Gastrointestinal Cancers. The SIFT algorithm predicted that, of patients having ACVR1 mutations and gastrointestinal cancers (n=27), 52% of the patients have a mutation with a deleterious impact, 40% have a mutation with tolerated impact, and 8% have a mutation with an undefined impact. Known activating and/or common mutations identified in the gastrointestinal cancer subset are shown in Table 15.

TABLE 15

| Protein Change | Count | Literature |
|---|---|---|
| S290L | 3 | |
| A233S/V | 2 | |
| R375C | 1 | R375P |

Thoracic Cancers. The SIFT algorithm predicted that, of patients having ACVR1 mutations and thoracic cancers (n=21), 76% of the mutations have a deleterious impact, 14% have a tolerated impact, and 10% have an undefined impact. A known activating and/or common mutation identified in the thoracic cancer subset is shown in Table 16.

TABLE 16

| Protein Change | Count | Literature |
|---|---|---|
| R380C/H | 2 | |

Melanoma. The SIFT algorithm predicted that, of patients having ACVR1 mutations and melanoma (n=19), 58% of the patients have a mutation with a deleterious impact, 32% have a mutation with a tolerated impact, and 11% have a mutation with an undefined impact. Known activating and/or common mutations identified in the melanoma subset are shown in Table 17.

TABLE 17

| Protein Change | Count | Literature |
|---|---|---|
| P430L/S | 2 | |
| R375C | 1 | R375P |

Neurological Cancers. Neurological cancers demonstrated a high occurrence (30%) of the canonical mutations. The SIFT algorithm predicted that, of patients having ACVR1 mutations and neurological cancers (n=7), 100% of the patients have a mutation with a deleterious impact. Known activating and/or common mutations identified in the neurological cancer subset are shown in Table 18.

TABLE 18

| Protein Change | Count | Literature |
|---|---|---|
| G328E | 1 | G328W/E/V/R |
| R206H | 1 | R206H |
| R258G | 1 | R258GS |

Example 6

Clinical Trial Study Design for the First-in-Human Study of a Compound of Formula 2 Orally Administered to Patients with Advanced Solid Tumors The phase Ia portion of the trial will include a 3+3 modified dose escalation for patients with advanced or progressive solid tumors. Dosing will be calculated based on body surface area, and dosing will be performed for 21 continuous days on a 28-day treatment cycle. Up to twenty subjects will be enrolled. Archival tissue will be requested for genetic testing of patients enrolled in the phase Ia portion of the trial, and next generation sequencing will be performed on the archival tissues to determine ACVR1 mutation status.

Following the determination of the maximum tolerated dose, additional subjects will be enrolled in the phase Ib portion of the trial. Enrolled patients will have histologically confirmed diagnosis of advanced metastasis or progressive solid tumors. Enrolled patients will also be refractory to, or intolerant of, established therapy known to provide clinical benefit for their condition. For the phase Ib portion, dosing will be calculated based on body surface area and dosing will be performed for 21 continuous days on a 28-day treatment cycle. Archival tissue will be requested for genetic testing of patients enrolled in the phase Ib portion of the trial, and next generation sequencing will be performed on the archival tissues to determine ACVR1 mutation status.

An alternative regimen, based on the potency and half-life of Compound 2 is once weekly. Other alternative regimens are 2 doses per week, 3 dose per week, 4 doses per week, 5 doses per week, or 6 doses per week. Each such regimen includes dosing on a cycle of 4 weeks. One regimen, therefore, is once weekly over a four week cycle, which would result in continuous dosing weekly, without a holiday. Alternative cycles include one or more holiday, such as three weeks of dosing and one week of holiday, two weeks of dosing and two weeks of holiday, one week of dosing and three weeks of holiday, or alternatively, alternating weeks of dosing and holiday, namely one week of dosing and one week of holiday or bi-weekly dosing. For all of these embodiments, the dose of Compound 2 may be level or escalating. One starting dose may be in a range of about 24 to 30 mg. One starting dose, or an escalation dose, may be in a range of about 48 to 60 mg. Additional escalation doses may be in a range of about 72 to 90 mg and about 96 to 120 mg. In one embodiment, a starting dose may be about 60 mg weekly, which is either maintained or escalates to about 90 mg weekly. An about 90 mg weekly dose may be maintained or escalated to about 120 mg weekly.

Example 7

Oral Solid Formulation

The hydrochloride salt of Compound 2 was formulated into three (3) oral dose strengths (5, 25, and 125 mg dose [based on free base]). Increasing amounts of active pharmaceutical ingredient were formulated into three similar blends, see, Table 19. The product was formulated for immediate release using common excipients in the blend. The drug was placed in #3, hard gelatin capsules.

TABLE 19

Excipients in the Blend, 5, 25, and 125 mg Strength Capsules

| Excipient | Purpose |
|---|---|
| Microcrystalline Cellulose | Diluent |
| Lactose Monohydrate | Diluent |
| Croscarmellose Sodium | Disintegrant |
| Magnesium Stearate | Lubricant |

Example 8

Oral Liquid Formulation

In consideration of a pediatric population for DIPG therapy, an oral liquid formulation was developed for Compound 2, rather than, for example, a tablet or capsule form.

Compound 2 is marked by bitterness, therefore the liquid formulation required considerable analysis and evaluation.

First, as noted in Table 20, a variety of excipients were screened as buffering agents under storage conditions (Initial, 60° C. 1,2,4W, 40° C. 2,4W, 5, 25° C. 4W)

TABLE 20

Buffering Agents

| pH | Buffer | API conc. |
|---|---|---|
| 3.0/4.0/5.0 | 25 mM Citrate buffer | 10 mg/mL |
| | 10 mM Citrate buffer | |
| | 25 mM Tartrate buffer | |
| | 10 mM Tartrate buffer | |
| | 25 mM Malate buffer | |
| | 10 mM Malate buffer | |
| | 25 mM Acetate buffer | |
| | 10 mM Acetate buffer | |

The excipients were screened for precipitation and degradation impurities. Regarding precipitants, almost no change was observed in pH 3 conditions, but precipitation was found in many samples in pH 4 and pH 5 conditions. Regarding impurities, degradation appears to be pH-dependent, where pH 5 and pH 4 caused more degradation than pH3. The least degradation was observed in 10 mM malate buffer at pH 3. The malate buffer was more chemically and physicochemically stable compared to other tested buffers.

Next, as noted in Table 21, a variety of excipients were screened as preservatives under storage conditions (Initial, 60° C. 1,2,4W, 40° C. 2,4W, 25° C. 4W, 5° C. 4W), where the pH of each sample was adjusted to the target pH with NaOH or HCl after dissolution of the Compound 2.

TABLE 21

Preservatives

| Preservative | Conc. | Buffer | API conc. |
|---|---|---|---|
| Benzoic acid | 0.2% | 10 mM Citrate | 10 mg/mL |
| Sodium Benzoate | 0.2% | buffer (pH 3) | |
| Methyl Parahydroxy-benzoate | 0.2% | | |
| Propyl Parahydroxy-benzoate | 0.05% | | |
| Propylene glycol | 5.0% | | |
| Benzoic acid | 0.2% | 10 mM Malate | |
| Sodium Benzoate | 0.2% | buffer (pH 3) | |
| Methyl Parahydroxy-benzoate | 0.2% | | |
| Propyl Parahydroxy-benzoate | 0.05% | | |
| Propylene glycol | 5.0% | | |

The excipients were screened for precipitation and degradation impurities. Precipitation was found in the samples containing sodium benzoate in citrate and malate buffers. Regarding degradation, the preservatives did not demonstrate much difference, but propylene glycol appeared to result in the least degradation. Benzoic acid was believed to be the most suitable among the preservatives based on its chemical stability and preservative effect under acidic conditions.

Next, as noted in Table 22, a variety of excipients were screened as taste masking agents under storage conditions (Initial, 60° C. 1,2,4W, 40° C. 2,4W, 25° C. 4W, 5° C. 4W), where the pH of each sample was adjusted to the target pH with NaOH or HCl after dissolution of the Compound 2.

TABLE 22

| Masking agents | Conc. | Buffer | API conc. |
|---|---|---|---|
| Sucralose | 0.1% | 10 mM Citrate buffer (pH 3) | 10 mg/mL |
| | 1.0% | | |
| Glycerin | 10% | | |
| | 50% | | |
| HP-β-Cyclodextrin | 1.0% | | |
| | 15% | | |
| Sucralose | 0.1% | 10 mM Malate buffer (pH 3) | |
| | 1.0% | | |
| Glycerin | 10% | | |
| | 50% | | |
| HP-β-Cyclodextrin | 1.0% | | |
| | 15% | | |

The excipients were screened for precipitation and degradation impurities. Regarding precipitants, glycerin resulted in the least precipitation, but overall the excipients appeared roughly similar. Regarding degradation, glycerin resulted in the least degradation, but overall the excipients appeared roughly similar. The results of the screening did not produce a preferred agent, therefore an in vitro sensory study was performed among all of the taste-masking agents. Detailed information regarding the taste sensor may be found from the manufacturer of Insent™, Intelligent Sensor Technology, Inc., at, for example, http://www.insent.co.jp/en/index.html. Further reference may be made to the published review article by Tahara and Toko, *Electronic Tongues—A Review*, IEEE Sensors Journal, Volume 13, No. 8, pp 3001-11, August 2013. Each of which is hereby incorporated by reference with regard to the taste sensor technology.

Table 23 provides the test samples studied in the in vitro sensory study, which estimated the bitterness with a "Relative value" and "CPA value" and then converted to Quinine concentration for each of the test samples.

TABLE 23

| Sample No. | Masking agents/conc. | | Buffering agent | API conc. |
|---|---|---|---|---|
| 1 | — | — | 10 mM Malate buffer | 10 mg/mL |
| 2 | Glycerin | 10% | | |
| 3 | | 20% | | |
| 4 | | 50% | | |
| 5 | HP-β-CD | 5% | | |
| 6 | | 15% | | |
| 7 | Glycerin | 50% | | |
| | Sucralose | 0.1% | | |
| 8 | HP-β-CD | 15% | | |
| | Sucralose | 0.1% | | |

Figure 10:
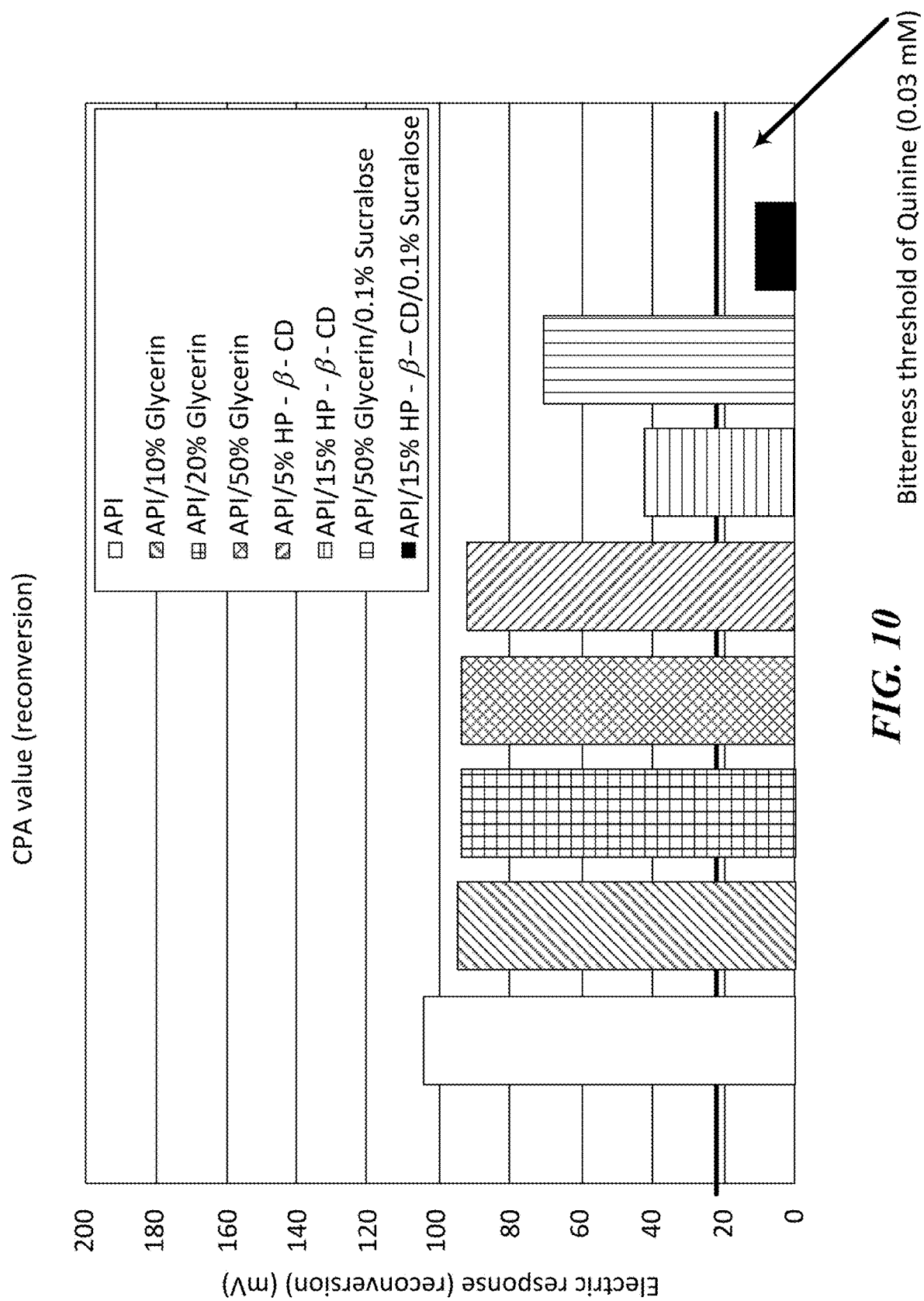
FIG. 10 illustrates the results of an in vitro sensory study of an oral liquid formulation comprising Compound 2. Bitterness was measured and converted for comparison to quinine.

The results of the testing are provided in FIG. 10. The quinine threshold is about 0.03 mM (3.00E-02). Bitterness masking by artificial sweeteners, such as Sucralose, is believed to be "sensual masking" and, therefore, the change in sensor output is poor. However, if the artificial sweetener concentration in the solution is known, it is possible to calculate the predicted value as to how much the bitterness is suppressed and the virtual sensor output at that time. Based on the sensor response, 15% HP-β-CD/0.1% Sucralose has taste-masking ability.

Table 24 provides a second set of test samples studies in the in vitro sensory study.

TABLE 24

| Sample No. | Masking agents/conc. | | Buffering agent | API conc. |
|---|---|---|---|---|
| 1 | — | | 10 mM | 10 mg/mL |
| 2 | HP-β-CD | 10% | Malate buffer | |
| | Sucralose | 0.1% | | |
| 3 | HP-β-CD | 15% | | |
| | Sucralose | 0.1% | | |
| 4 | α-CD Sucralose | 1% | | |
| | | 0.1% | | |
| 5 | α-CD Sucralose | 2% | | |
| | | 0.1% | | |
| 6 | β-CD Sucralose | 1% | | |
| | | 0.1% | | |
| 7 | β-CD Sucralose | 1.5% | | |
| | | 0.1% | | |
| 8 | — | | Apple juice | 1 mg/mL |
| 9 | — | | | 10 mg/mL |

Figure 11:
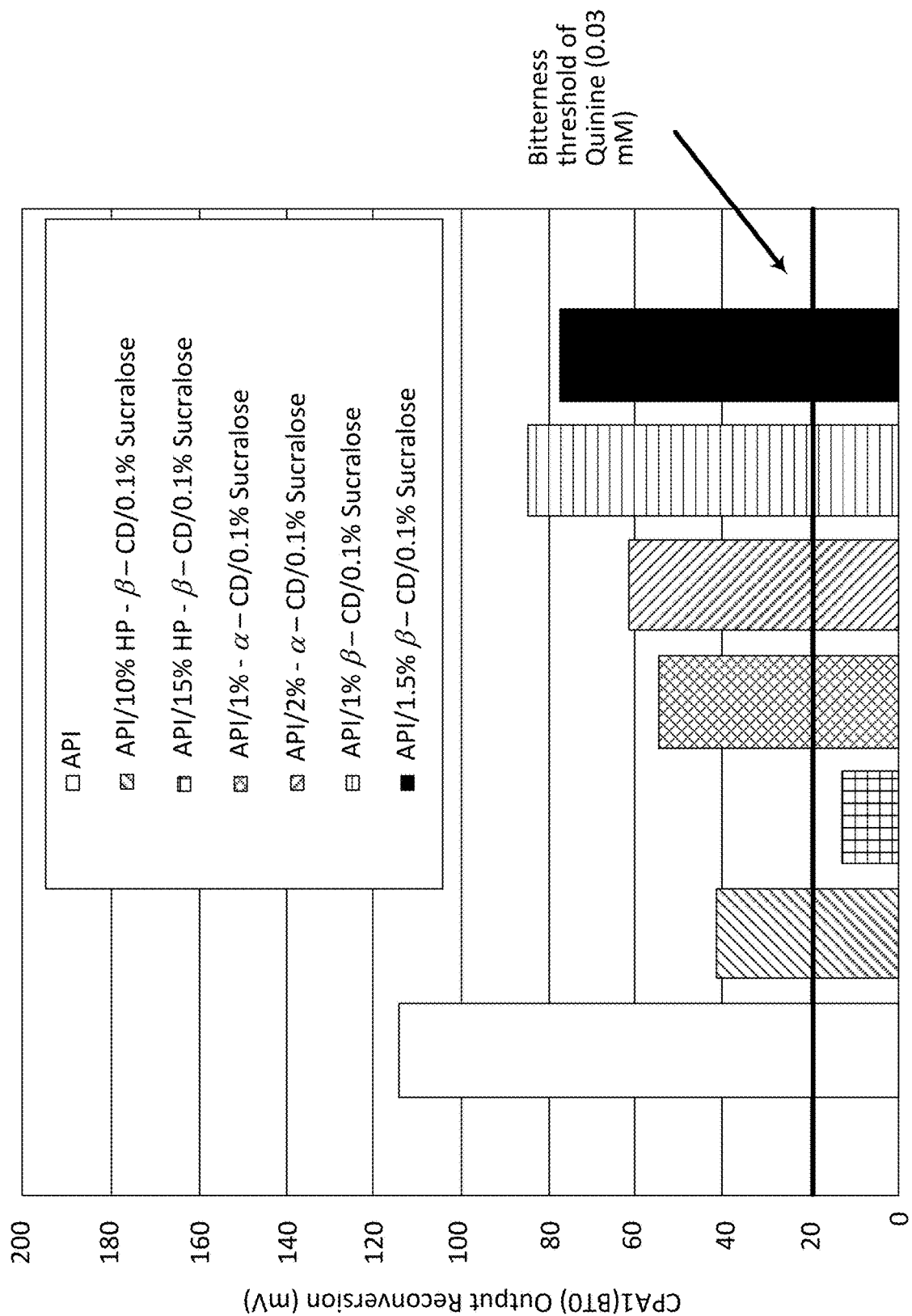
FIG. 11 illustrates the results of an in vitro sensory study of an oral liquid formulation comprising Compound 2. Bitterness was measured and converted for comparison to quinine.

The results of the testing are provided in FIG. 11. Based on the sensor response, 15% HP-β-CD/0.1% Sucralose has taste-masking ability.

A study of preservative efficacy was conducted with reference to USP40, herein incorporated by reference with regard to such protocol. All prototype formulations passed the criteria of antimicrobial effectiveness required for a category 3 product. Viable counts, however, of *Aspergillus brasiliensis* were monitored, therefore additional formulation study and preservative testing was performed. Again, reference is made to USP40. The formulation is set forth in Table 25.

TABLE 25

| Sample | 1 | 2 | 3 | 4 | 5 | 6 | 7 | 8 | 9 |
|---|---|---|---|---|---|---|---|---|---|
| Compound 2 | | | | | 10 mg/mL | | | | |
| HP-β-CD | | | | | 15% | | | | |
| Sucralose | | | | | 0.1% | | | | |
| Benzoic Acid | | 0.20% | | | | | 0.30% | | |
| p-hydroxybenzoate | — | 0.18 | — | — | — | 0.18 | 0.18 | | |
| Propyl-p-hydroxybenzoate | — | 0.02 | — | — | — | — | 0.02 | | |
| pH | 3 | 3 | 3 | 2 | 1 | 3 | 3 | 2 | 1 |

All prototype formulations passed the 14 day and 28 day criteria of antimicrobial effectiveness required for a category 3 product. Preservative efficacy was found to be pH-dependent. A formulation with 0.2% benzoic acid and a pH of 2 is believed to provide better preservative effect.

One embodiment of an oral liquid formulation is set forth in Table 26.

TABLE 26

| Ingredient | Conc. |
|---|---|
| Compound 2 | 10 mg/mL |
| Malic acid | 10 mM |
| HP-β-CD | 15% |
| Sucralose | 0.1% |
| Benzoic acid | 0.2% |
| pH adjusted by HCl | 2 |

Alternative embodiments for an oral liquid formulation are set forth in Table 27.

TABLE 27

| Ingredient | Function | Table 26 Amount per mL | Alternative Embodiments (range) | Alternate Embodiment (example) |
|---|---|---|---|---|
| Compound 2 | Active ingredient | 10 mg | N/A | 10 mg |
| DL-Malic Acid | Buffering agent | 1.341 mg | 0-6.705 mg | 1.341 mg |
| HP-β-CD | Taste masking agent | 150 mg | 0-300 mg | 150 mg |
| Sucralose | Sweetener | 1.0 mg | 0-2.0 mg | 1.0 mg |
| Benzoic Acid | Preservative | 2.0 mg | 0-3.0 mg | n/a |
| Hydrochloric acid | pH adjustment | Proper dose | Proper dose | Proper dose |
| Sterile Purified Water | Solvent | to 1 mL | 0.5-5.0 mL | To 1 mL |
| pH | | 2.0 | 2.0-3.5 | 3.0 |

Example 9

Salt Evaluation and Polymorph Screen

A salt screening evaluated the basic compound, Compound 2, to assess whether a salt form would provide benefits over the freebase form. For any suitable salt candidate identified, a preliminary polymorph screening would be performed to evaluate its polymorphism risk.

Summary

Salt screening was performed under 33 conditions using 10 acids (two molar ratios of HCl) and three solvent systems. From all the screening experiments, a total of 12 crystalline hits were isolated and characterized by X-ray powder diffraction (XRPD), thermo-gravimetric analysis (TGA), and differential scanning calorimetry (DSC). The stoichiometric ratio of salt hits was determined by proton nuclear magnetic resonance ($^1$H NMR) or high-performance liquid chromatography (HPLC) combined with ion chromatography (IC). Based on the physical properties of the hits, anhydrous HCl salt Form A and fumarate Form A were selected as salt leads for evaluation.

The salt leads of HCl salt Form A and fumarate Form A were prepared to 300 mg scale and evaluated on hygroscopicity, kinetic solubility in pH 2, 5, and 7 buffers, and solid-state stability under 40° C./75% RH for one week. As shown by the evaluation results (using freebase Form A as reference):

a) Freebase Form A, HCl salt Form A, and fumarate Form A were all slightly hygroscopic with no form change after DVS tests;

b) Compared with freebase Form A, HCl salt Form A showed increased solubility in pH 2, 5 and 7 buffers, and disproportionation was observed in pH 7 buffer. Fumarate Form A showed decreased solubility in pH 2 and 5 buffers with form change observed, but increased solubility was observed in pH 7 buffer with no form change; and c) Freebase Form A, HCl salt Form A and fumarate Form A all showed good physicochemical properties under 40° C./75% RH for one week. The characterization and evaluation results are summarized in Table 28.

Figure 12:
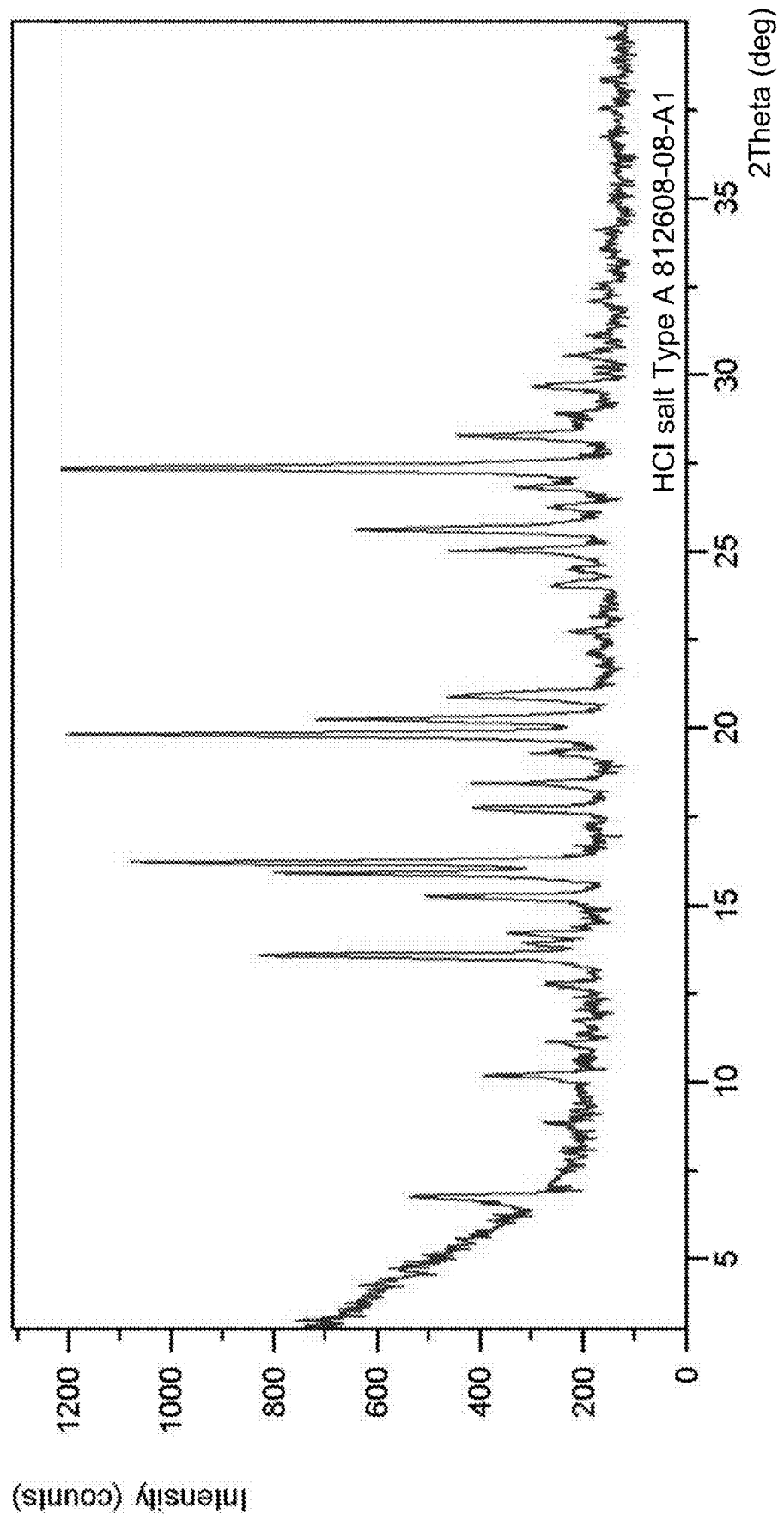
FIG. 12 is an XRPD pattern of Compound 2 mono-HCl salt Form A (812608-08-A1)
Figure 13A:
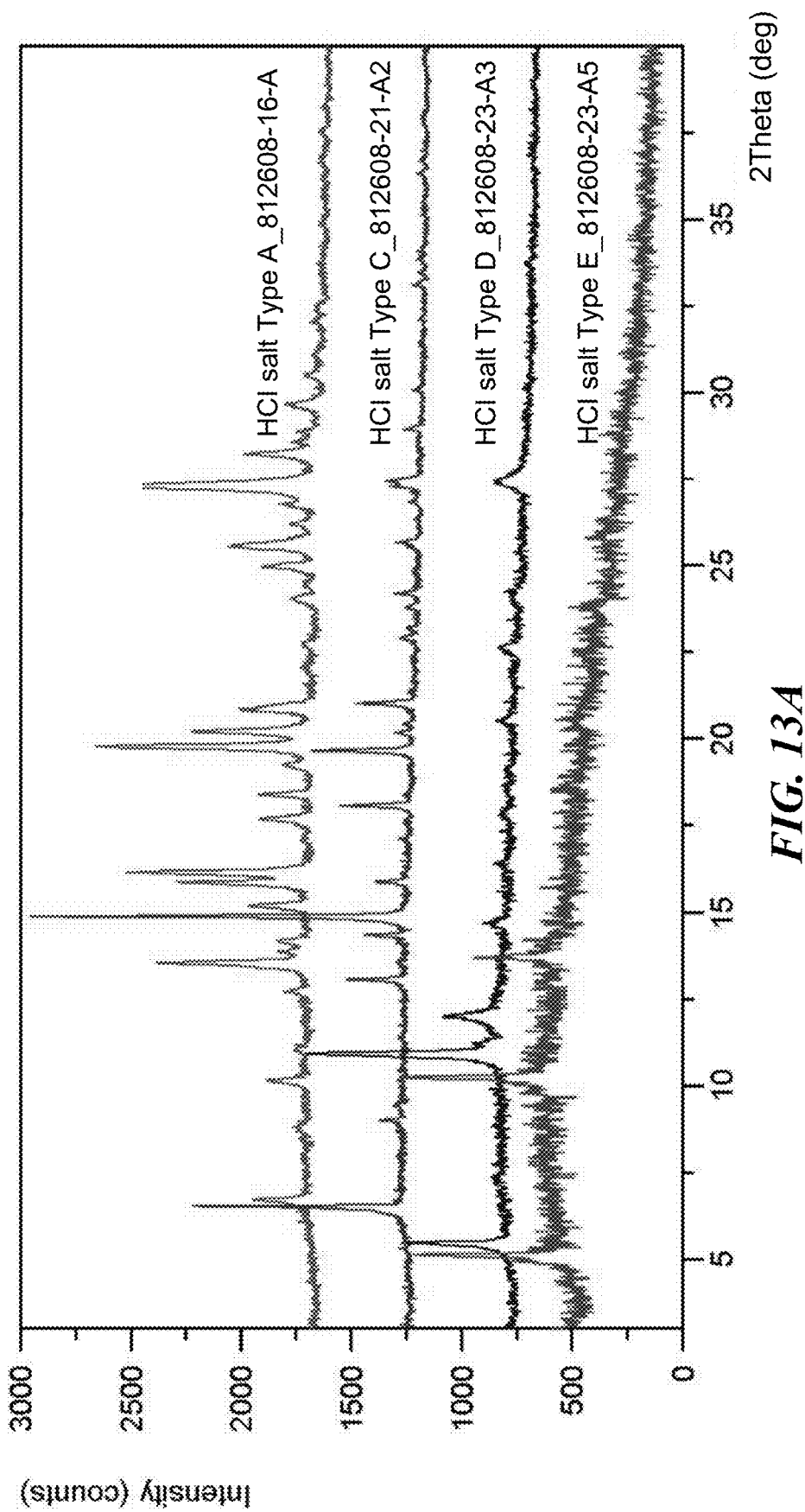
FIGS. 13A and 13B are XRPD overlays of Compound 2 HCl salt crystal forms.
Figure 13B:
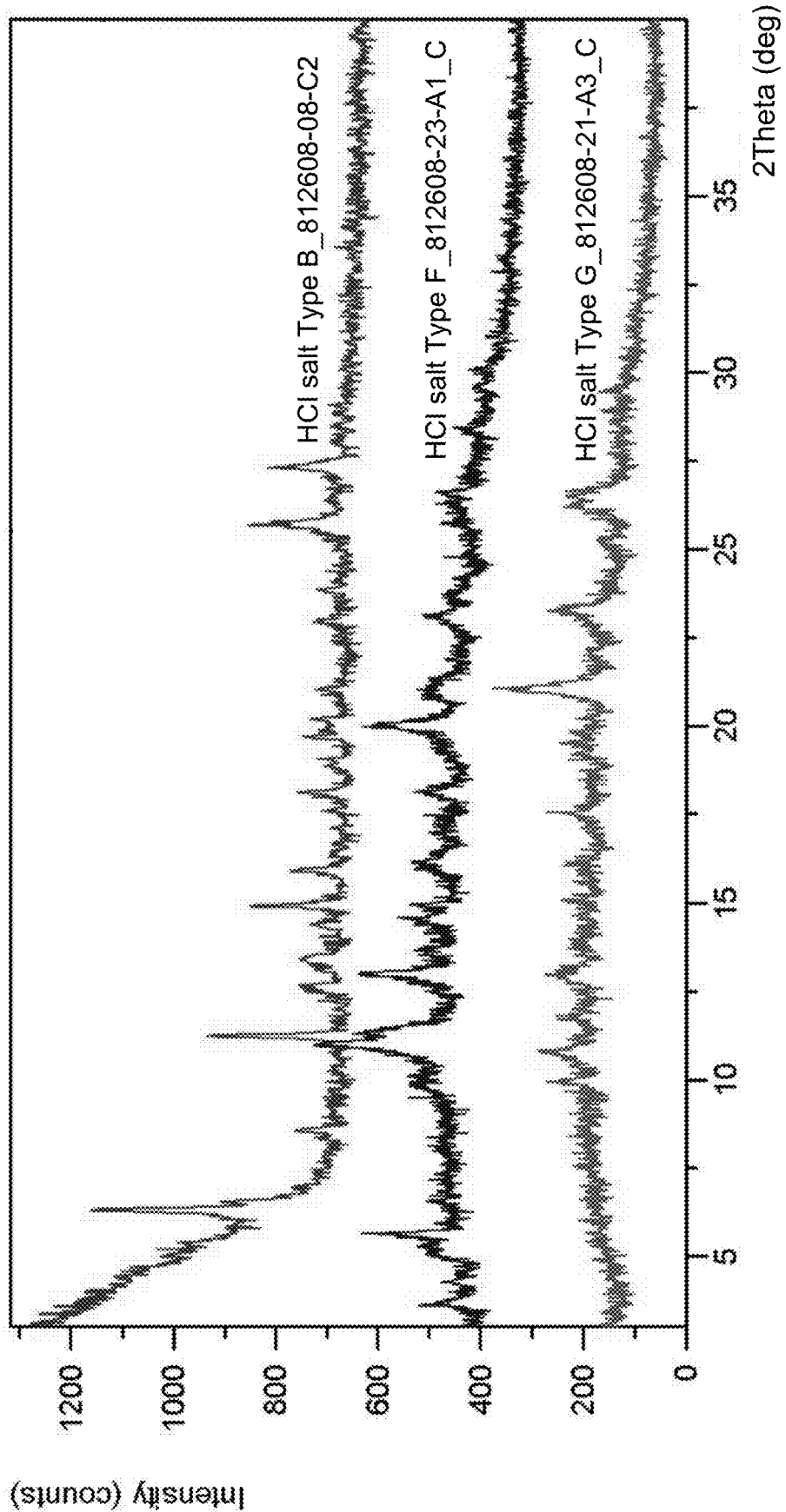

Based on results collected, HCl salt Form A is a preferred candidate form. Therefore, a polymorphism evaluation study was performed on the HCl salt (mono). Starting with HCl salt Form A, a preliminary polymorph screening was conducted under 32 conditions using different methods of slurry conversion, evaporation, slow cooling and anti-solvent addition. Based on XRPD comparison, besides HCl salt Form A, five additional crystalline forms (HCl salt Form C~G) were obtained from screening and characterized by TGA and DSC. Based on investigation results, HCl salt Form A and C were speculated to be anhydrate and hydrate, respectively. Re-preparation of HCl salt Form D and E by evaporation resulted in mixtures containing HCl salt Form C+D and C+E, respectively. As a result of $^1$H NMR and heating experiments of the mixtures, HCl salt Form D and E might be hydrates. Due to limited amount of material, the potential HCl salt Form F and G were not identified. Detailed characterization data and XRPD overlay of HCl salt forms obtained from both salt and polymorph screening are summarized in Table 29A, FIG. 12, and FIGS. 13A and 13B. FIG. 12 depicts an XRPD pattern of HCl salt Form A. FIG. 13A depicts an overlay of HCl salt crystal forms A, C, D, and E. FIG. 13B depicts forms B, F, and G. Each form may also be referred to as a "type" and the terms are used interchangeably.

TABLE 28

Characterization and evaluation summary of salt leads and freebase

| Salt Form (Batch No.) | Freebase Form A (812608-05-A) | HCl Salt Form A (812608-12-A) | Fumarate Form A (812608-12-B) |
|---|---|---|---|
| Stoichiometry (acid/freebase) | — | 0.97 (by IC/HPLC) | 0.94 (by $^1$H NMR) |
| Safety Class of Acid | — | I | I |
| HPLC Purity (area %) | 99.17 | 99.63 | 99.43 |
| Speculated Form | Anhydrate | Anhydrate | Anhydrate |
| Weight Loss (%) | 1.8 | 1.7 | 1.0 |
| Endotherm (° C., peak) | 200.2 | 198.9*, 218.0, 275.9 | 228.5, 233.9 |
| Hygroscopicity (%)** | Slightly hygroscopic (0.60) | Slightly hygroscopic (0.86) | Slightly hygroscopic (1.04) |
| Kinetic Solubility | Compared with freebase Form A, HCl Form A showed increased solubility in pH 2, 5 and 7 buffers; fumarate Form A showed decreased solubility in pH 2 and 5 buffers, but increased solubility in pH 7 buffer. | | |
| Solid-state Stability | Good physicochemical properties under 40° C./75% RH for at least one week. | | |

—: not available.
*might be caused by a very small amount of freebase Form A remaining.
**based on water uptake at 25° C./80% RH: very hygroscopic - >15%, hygroscopic - 2~15%, slightly hygroscopic - 0.2~2%, non-hygroscopic - <0.2%.

TABLE 29A

Characterization of HCl salt forms

| Crystal Form | Sample ID | Weight Loss in TGA (%) | Endotherm in DSC (° C., peak) | Stoichiometry (acid/FB)* | Speculated Form |
|---|---|---|---|---|---|
| Form A | 812608-16-A | 2.0 | 223.5, 276.4 | 1.01 | Anhydrate |
| Form C | 812608-21-A2 | 3.1 | 98.8, 267.5, 275.5 | 1.01** | Hydrate |
| Form D | 812608-23-A2 | 2.4 | 99.4, 157.1, 276.4 | 1.02** | Possibly Hydrate |
| Form E | 812608-23-A5 | 13.5 | 105.8, 273.6 | — | |
| Form B | 812608-08-C2 | 8.1 | 102.2, 144.6, 240.0, 281.6 | 1.71 | Unidentified |
| Form F | 812608-23-A6_C | 7.3 | 120.6, 274.7 | — | |
| Form G | 812608-21-A3_C | 8.9 | 117.3, 169.7, 273.3 | — | |

*the stoichiometric ratio was determined by HPLC/IC.
**sample was obtained from evaporation.
—: not measured due to limited amount of sample.

As noted, FIG. 12 depicts an XRPD pattern of HCl salt Form A. A tabulated version of the XRPD for Form A is as follows in Table 29B, noting an error range +/− of about 0.2° 2θ as appreciated by those skilled in the art:

TABLE 29B

Compound 2 HCl salt Form A

| Pos. [°2θ] | Height [cts] | Area [cts °2θ] | d-spacing [Å] | Rel. Int. [%] |
|---|---|---|---|---|
| 3.9059 | 298.79 | 37.70 | 22.62205 | 2.85 |
| 6.7125 | 2201.43 | 222.23 | 13.16854 | 20.97 |
| 8.8145 | 454.58 | 51.63 | 10.03229 | 4.33 |
| 10.1413 | 1672.42 | 211.04 | 8.72261 | 15.93 |
| 11.0558 | 561.23 | 70.82 | 8.00302 | 5.35 |
| 12.7048 | 1080.46 | 136.34 | 6.96775 | 10.29 |
| 13.5347 | 6642.71 | 922.04 | 6.54234 | 63.28 |
| 13.8769 | 1131.77 | 142.81 | 6.38178 | 10.78 |
| 14.1755 | 1620.14 | 224.88 | 6.24800 | 15.43 |
| 15.1840 | 3546.33 | 537.00 | 5.83520 | 33.78 |
| 15.8491 | 5585.02 | 775.23 | 5.59182 | 53.21 |
| 16.1455 | 8599.25 | 1193.62 | 5.48981 | 81.92 |
| 17.2245 | 162.88 | 26.72 | 5.14828 | 1.55 |
| 17.6770 | 2882.25 | 436.44 | 5.01749 | 27.46 |
| 18.3807 | 2578.71 | 390.48 | 4.82696 | 24.57 |
| 19.2499 | 1100.51 | 166.64 | 4.61093 | 10.48 |
| 19.7721 | 9580.62 | 1450.74 | 4.49032 | 91.27 |
| 20.2054 | 5072.51 | 896.12 | 4.39499 | 48.32 |
| 20.8140 | 3168.56 | 399.83 | 4.26782 | 30.19 |
| 20.9432 | 2000.42 | 227.18 | 4.24178 | 19.06 |
| 22.0018 | 366.67 | 64.72 | 4.04003 | 3.49 |
| 22.6847 | 604.86 | 76.32 | 3.91994 | 5.76 |
| 23.9816 | 1024.54 | 181.00 | 3.71080 | 9.76 |
| 24.4538 | 531.66 | 80.51 | 3.64021 | 5.06 |
| 24.9644 | 2159.45 | 326.99 | 3.56690 | 20.57 |
| 25.5118 | 4541.08 | 802.23 | 3.49160 | 43.26 |
| 26.1922 | 763.31 | 86.69 | 3.40242 | 7.27 |
| 26.7501 | 1326.52 | 200.87 | 3.33272 | 12.64 |
| 27.2385 | 10497.03 | 1854.42 | 3.27406 | 100.0 |
| 28.1817 | 2992.14 | 528.60 | 3.16659 | 28.50 |
| 28.5514 | 789.98 | 109.65 | 3.12642 | 7.53 |
| 28.8497 | 599.52 | 90.78 | 3.09477 | 5.71 |
| 29.6008 | 1378.42 | 260.91 | 3.01793 | 13.13 |
| 30.4479 | 633.83 | 103.97 | 2.93586 | 6.04 |
| 31.0671 | 347.19 | 52.57 | 2.87875 | 3.31 |
| 31.9977 | 365.28 | 92.19 | 2.79712 | 3.48 |
| 32.4347 | 376.35 | 80.73 | 2.76042 | 3.59 |
| 33.3026 | 174.88 | 26.48 | 2.69045 | 1.67 |
| 33.6159 | 293.68 | 44.47 | 2.66608 | 2.80 |
| 34.0326 | 123.70 | 18.73 | 2.63439 | 1.18 |
| 34.7780 | 211.12 | 42.62 | 2.57961 | 2.01 |
| 35.5705 | 123.93 | 25.02 | 2.52394 | 1.18 |
| 36.6319 | 310.89 | 86.31 | 2.45321 | 2.96 |
| 37.4707 | 246.78 | 43.60 | 2.40020 | 2.35 |
| 38.1695 | 235.29 | 71.26 | 2.35785 | 2.24 |
| 40.1011 | 135.41 | 34.18 | 2.24862 | 1.29 |
| 40.7471 | 678.30 | 77.03 | 2.21445 | 6.46 |
| 41.2836 | 367.58 | 74.21 | 2.18690 | 3.50 |
| 41.9985 | 284.08 | 64.53 | 2.15132 | 2.71 |
| 43.6795 | 124.43 | 31.40 | 2.07234 | 1.19 |
| 44.5269 | 137.92 | 34.81 | 2.03485 | 1.31 |
| 45.4240 | 143.20 | 36.14 | 1.99673 | 1.36 |
| 46.4339 | 166.33 | 58.77 | 1.95563 | 1.58 |
| 47.3800 | 176.53 | 53.46 | 1.91877 | 1.68 |

As a result of preliminary salt screening of Compound 2 and polymorph screening of HCl salt (mono), the mono-HCl salt Form A is a preferred candidate for further development.

Detail: Salt Screening and Lead Re-Preparation

According to estimated pKa values of 7.5 and 5.1 and approximate solubility of freebase (812608-05-A) at room temperature (RT, 25±3° C.), 10 salt formers and three solvent systems were used for the screening. Freebase (~15 mg) was dispersed with selected solvent in a glass vial and corresponding salt former was added with a molar charge ratio of 1:1 (for HCl/freebase, two ratios of both 1:1 and 2:1 were used). The mixtures of freebase and acid were stirred at RT for 3.5 days. To obtain more solid hits, clear solutions obtained (812608-08-B0/B5/B10) were transferred to 5° C. and stirred for another 2.5 days. Finally, to clear solutions of 812608-08-B0/B10, 0.5 mL of n-heptane was added and stirred at 5° C. for another two days.

All the resulted solids were isolated and analyzed by XRPD after being dried at 50° C. for 2.5 hours. As summarized in Table 30, a total of 12 crystalline hits were obtained and characterized by XRPD, TGA, and DSC with the stoichiometry determined by $^1$H NMR or HPLC/IC. The characterization data were summarized in Table 31.

TABLE 30

Summary of salt screening results

| | | Solvent | | |
|---|---|---|---|---|
| | Acid | A<br>EtOH | B<br>THF | C<br>EtOAc |
| 0 | Blank | FB Form A | FB Form A | FB Form A |
| 1 | HCl (1:1) | HCl salt Form A | HCl salt Form A | HCl salt Form A |
| 2 | HCl (2:1) | HCl salt Form B | FB Form A + HCl salt Form A + HCl salt Form B | HCl salt Form B |
| 3 | H₂SO₄ | Sulfate Form A | Amorphous | Amorphous |
| 4 | H₃PO₄ | Amorphous | Phosphate Form A | Amorphous |
| 5 | Succinic acid | FB Form A | Succinate Form A | FB Form A |
| 6 | Fumaric acid | Fumarate Form A | Fumarate Form A | Fumarate Form A |
| 7 | Citric acid | Yellow Gel | FB Form A | FB Form A |
| 8 | Maleic acid | Maleate Form A | Maleate Form B | Maleate Form C |
| 9 | L-Tartaric acid | Amorphous | Amorphous | Tartrate Form A |
| 10 | Hippuric acid | FB Form A | Hippurate Form A | Hippurate Form A |
| 11 | L-Malic acid | Malate Form A | Yellow Gel | FB Form A |

FB: freebase.

TABLE 31

Characterization summary of crystalline hits

| Hit | | Sample ID | Wt Loss (TGA, %) | Endotherm (DSC, ° C., peak) | Molar Ratio (acid/base) |
|---|---|---|---|---|---|
| HCl Salt | Form A | 812608-08-A1 | 1.2 | 227.0, 276.2 | 1.00 |
| | Form B | 812608-08-C2 | 8.1 | 102.2, 144.6, 240.0, 281.6 | 1.71 |
| Sulfate* | Form A | 812608-08-A3 | 7.9 | 62.6, 98.1, 128.1, 132.6, 135.0 | 3.00 |
| Phosphate | Form A | 812608-08-B4 | 3.9 | 137.7, 193.9, 209.1, 221.3 | 1.44 |
| Succinate | Form A | 812608-08-B5 | 8.4 | 92.1, 195.0 | 1.30 |
| Fumarate | Form A | 812608-08-A6 | 1.3 | 229.7, 234.6 | 0.91 |
| Maleate | Form A | 812608-08-A8 | 3.5 | 132.8, 167.4 | 0.82 |
| | Form B | 812608-08-B8 | 2.0 | 126.8, 170.3 | 0.84 |
| | Form C | 812608-08-C8 | 3.0 | 74.7, 126.9, 141.8 | 0.84 |
| Tartrate | Form A | 812608-08-C9 | 4.9 | 66.4, 206.8 | 1.11 |
| Hippurate | Form A | 812608-08-C10 | 0.4 | 155.6, 162.2 | 1.05 |
| Malate | Form A | 812608-08-A11 | 3.7 | 71.7, 161.8 | 1.07 |

*yellow powder was obtained with an HPLC purity of 99.61 area % for sulfate, and all the other hits were white powder.

Re-Preparation and Characterization of Salt Leads

Based on the characterization results, two salt leads (HCl salt Form A and fumarate Form A) were agreed as salt leads and re-prepared to hundreds of milligrams. The selection criteria include but not limited to: 1) sharp XRPD peaks without apparent amorphous halo, 2) negligible weight loss in TGA, 3) neat thermal event with a sharp melting peak in DSC. The detailed preparation procedures were described in Table 32 and the characterization data were summarized above in Table 28.

HCl Salt Form A

Figure 14:
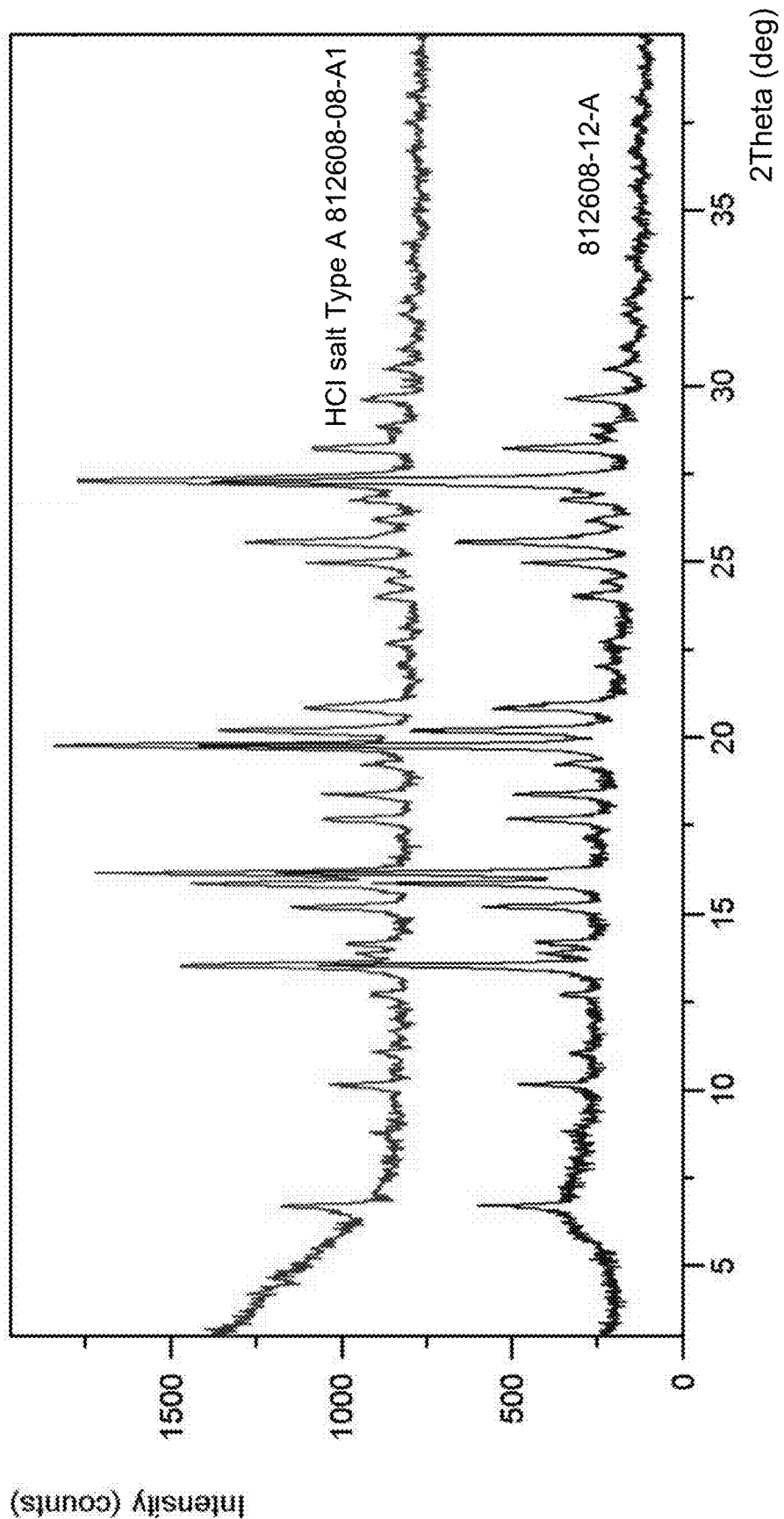
FIG. 14 is an XRPD overlay of Compound 2 HCl salt Form A batches to demonstrate equivalence.
Figure 15:
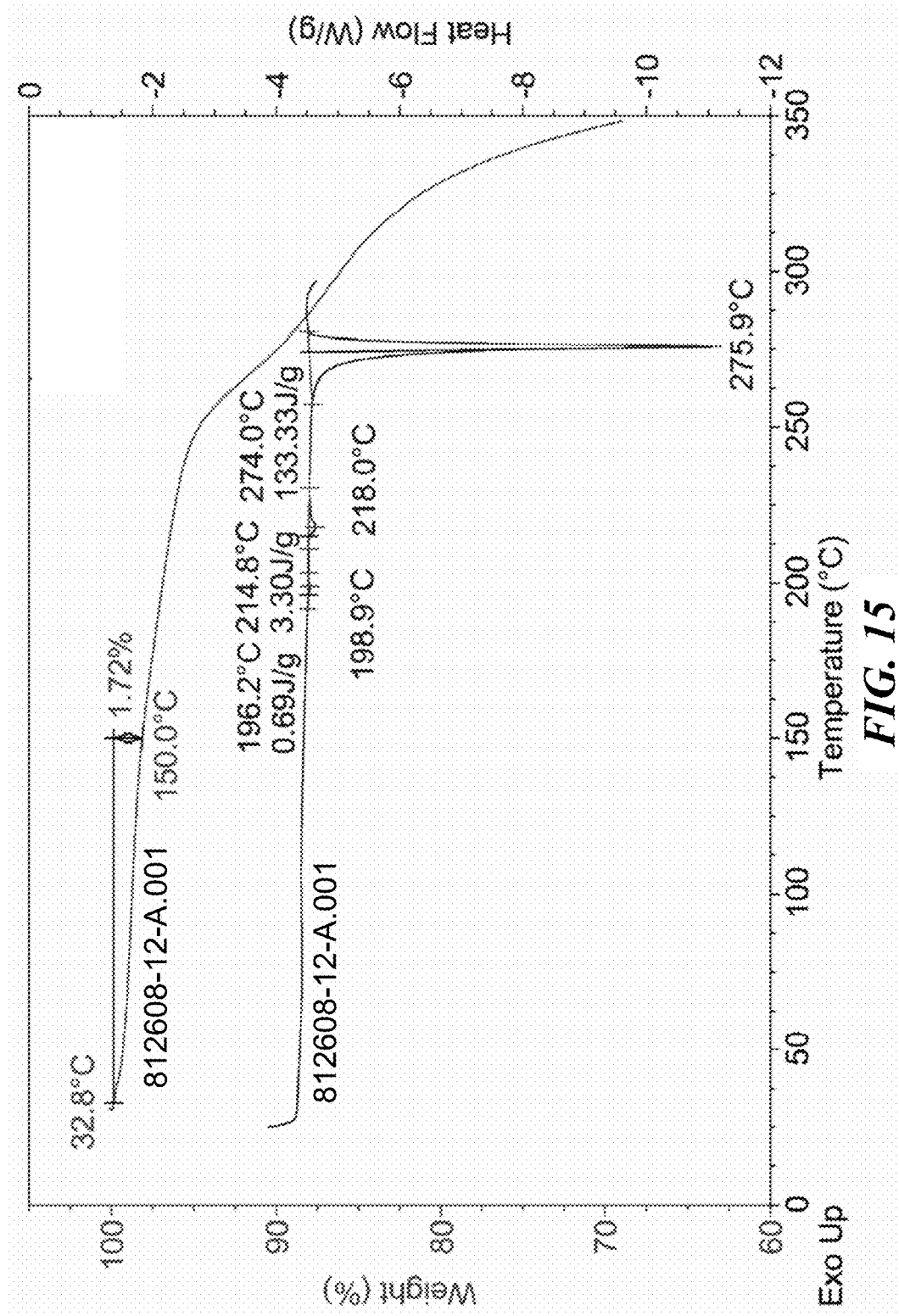
FIG. 15 shows TGA/DSC curves of Compound 2 HCl Form A (812608-12-A)
Figure 16:
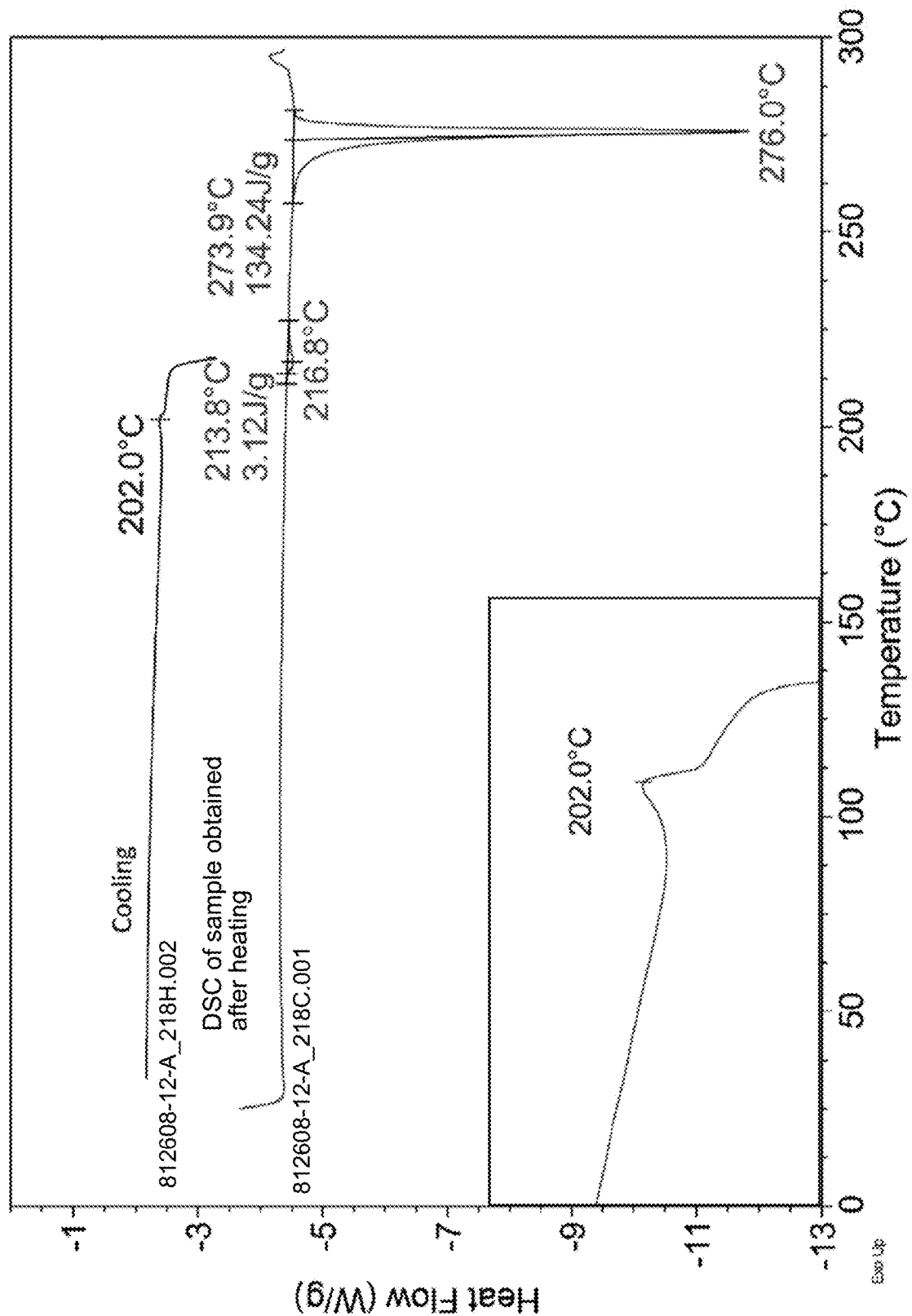
FIG. 16 shows a DSC of Compound 2 HCl Form A after heating (812608-12A_218C)

HCl salt Form A was successfully re-prepared as evidenced by XRPD results in FIG. 14. As per TGA and DSC data in FIG. 15, the sample showed a weight loss of 1.7% up to 150° C. and three endotherms at 196.2, 214.8 and 274.0° C. (onset temperature). The small endotherm at 196.2° C. might be caused by the melting of a very small amount of freebase Form A remaining. As shown in FIG. 16, after heating the HCl salt Form A sample to 218° C., an exotherm around 202.0° C. was observed during cooling and DSC of the sample obtained after heating still showed endotherms at 213.8 and 273.9° C. (onset temperature). Combined with the fact that no form change was observed after heating the sample to 218° C., cooling back to RT and exposed to ambient conditions, the signal at 213.8° C. was speculated to be caused by form transition. The stoichiometric ratio was determined as 0.97 (acid/base) by HPLC/IC. As limited gradual TGA weight loss before 150° C. and no significant thermal event in DSC before 190° C. was observed, the sample is speculated to be an anhydrous HCl salt.

Fumarate Form A

Figure 17:
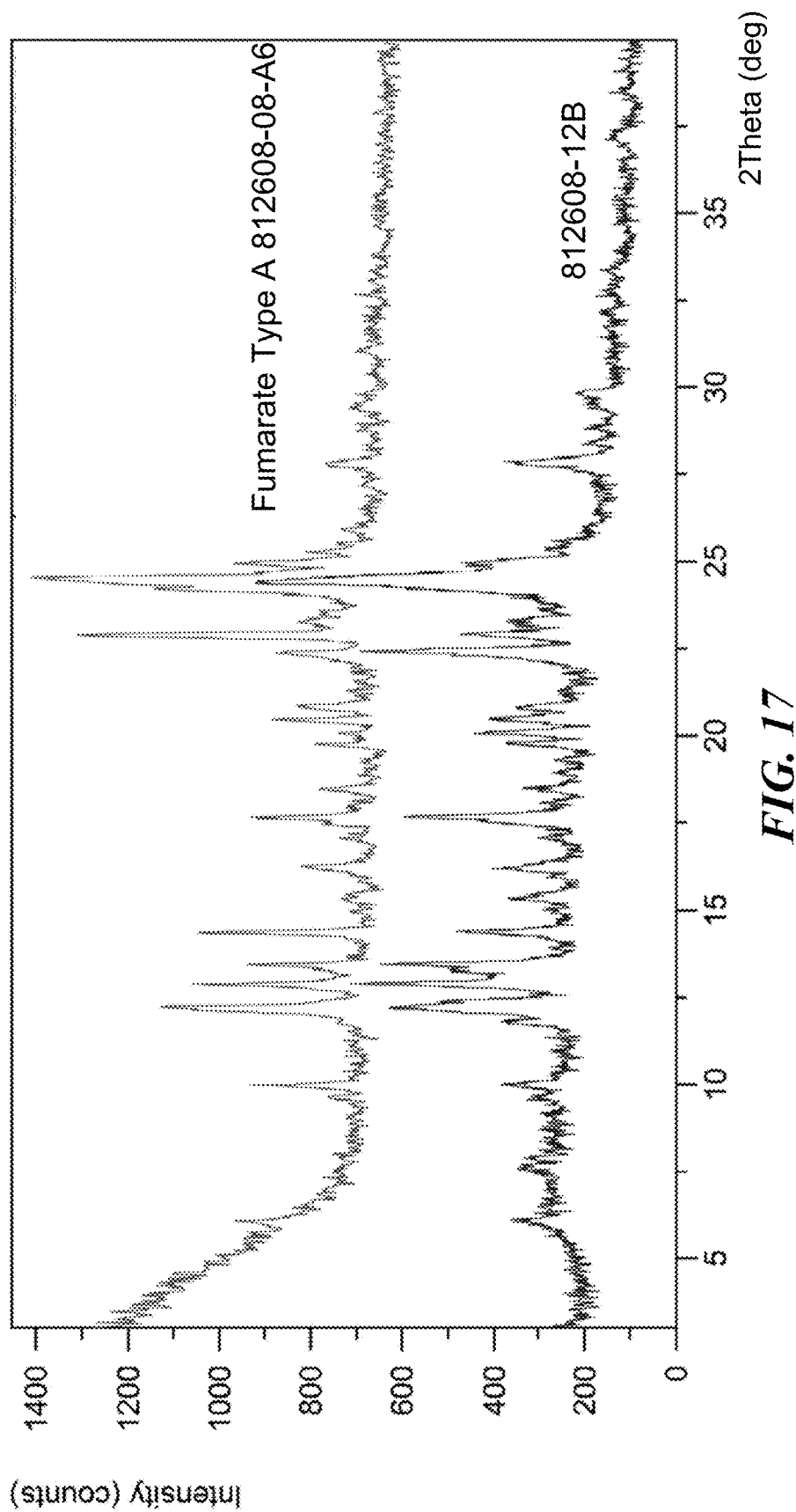
FIG. 17 shows an XRPD overlay of Compound 2 HCl salt Form A pre- and post-heating to demonstrate stability.
Figure 18:
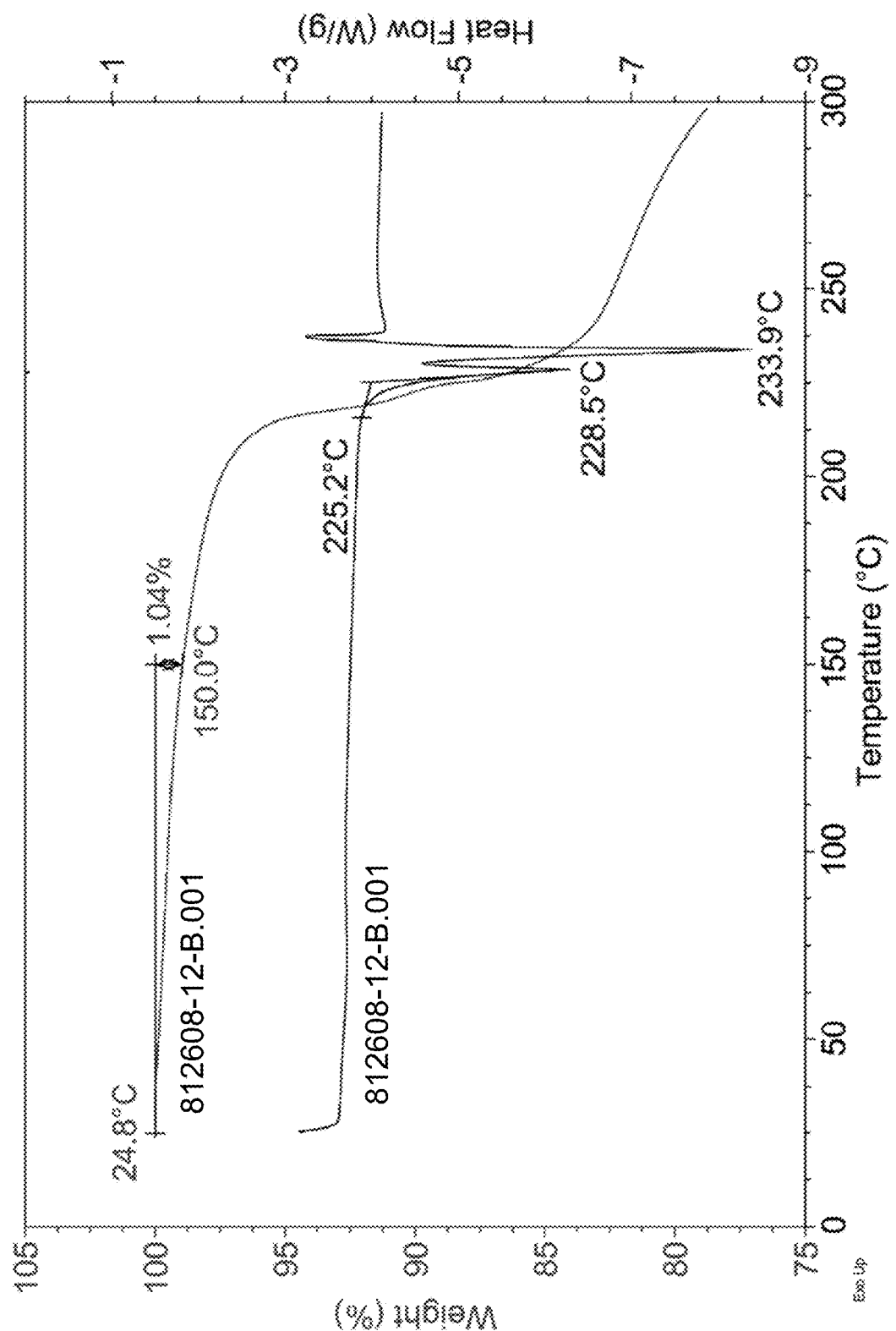
FIG. 18 shows TGA/DSC curves of Compound 2 fumarate Form A (812608-12-B).
Figure 19:
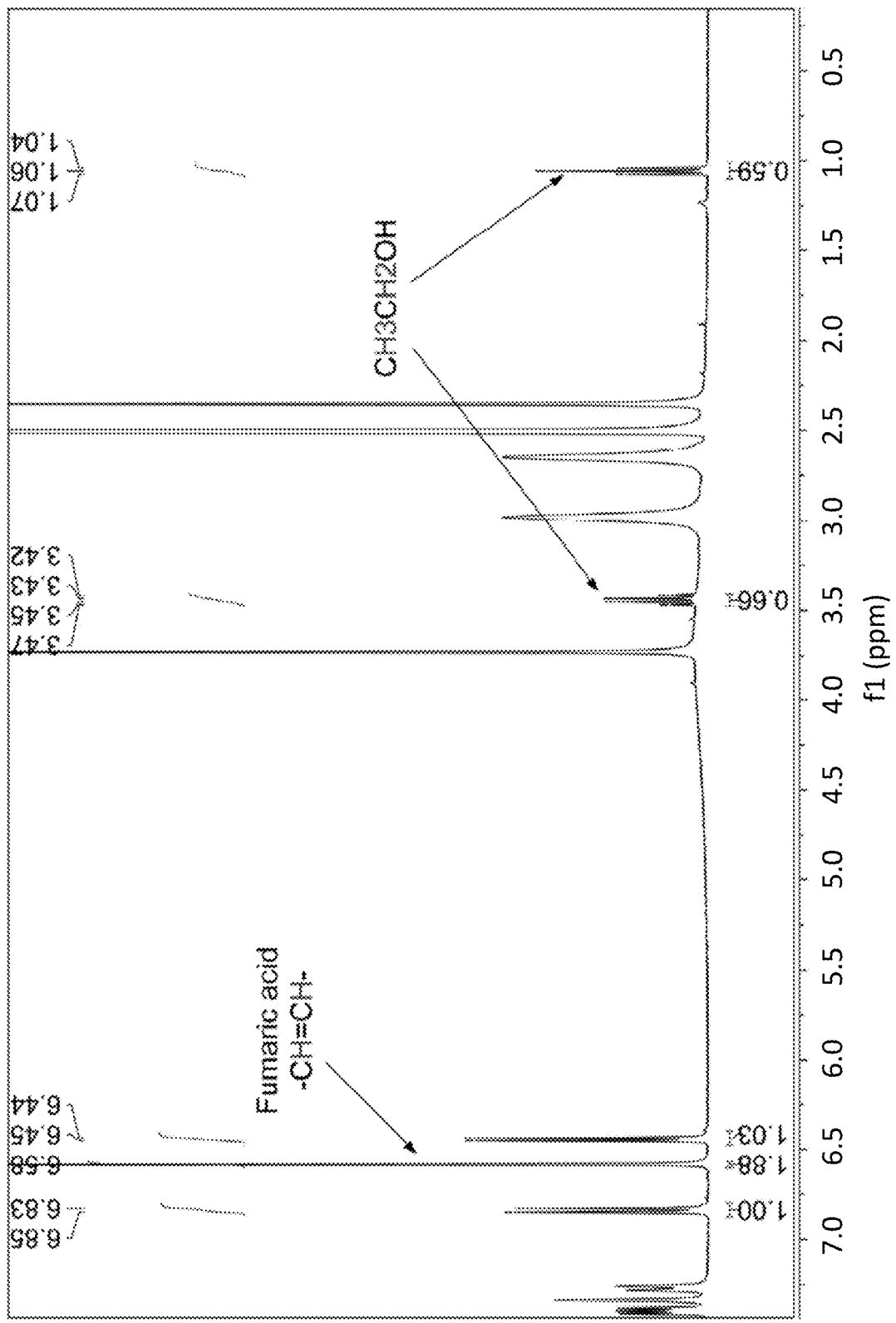
FIG. 19 shows an 1H-NMR spectrum of Compound 2 fumarate Form A (812608-12-B), where limited EtOH residual was detected (about 1.6%).
Figure 20A:
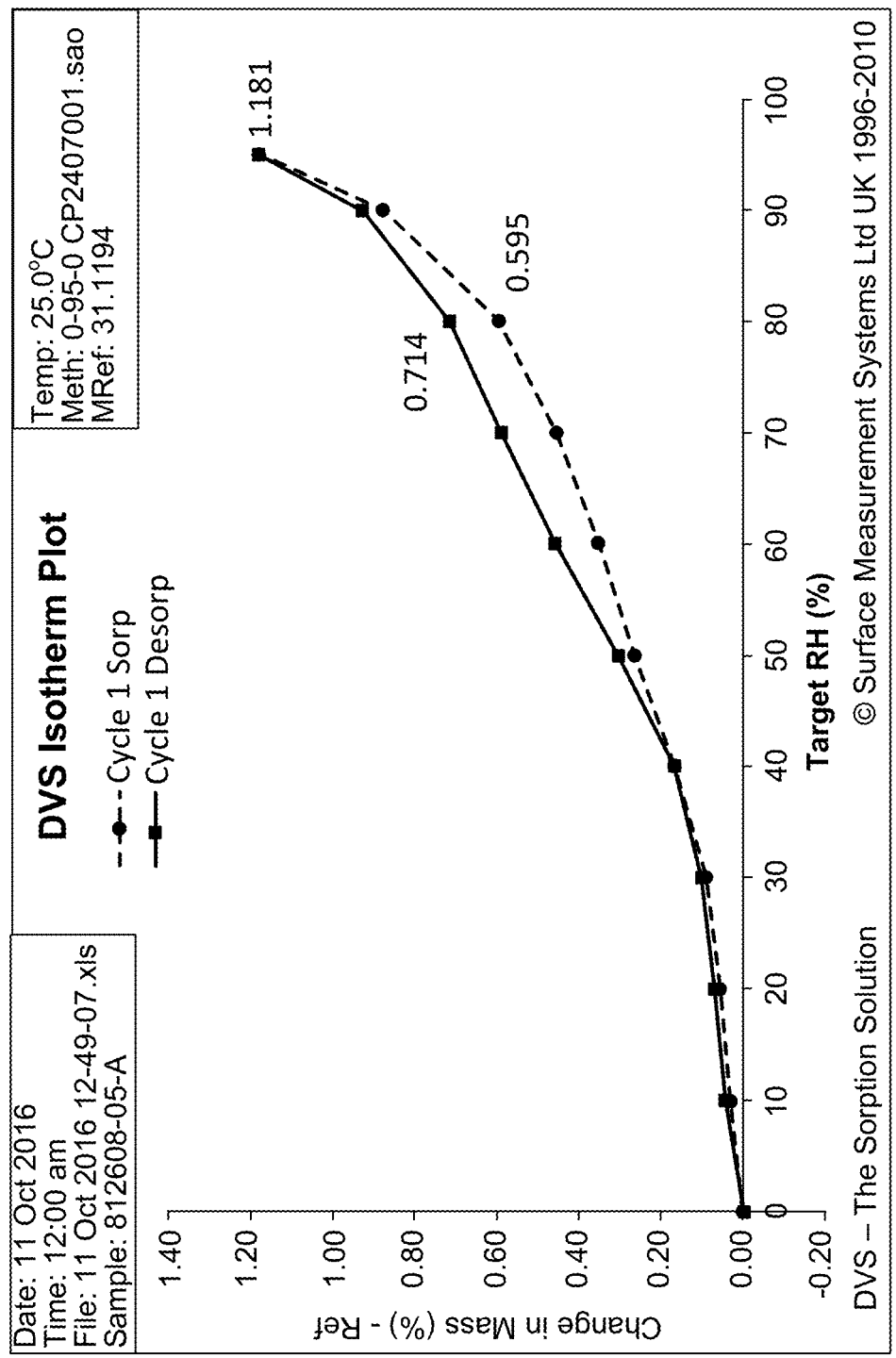
FIG. 20A shows a DVS plot of Compound 2 freebase Form A (812608-05-A)
Figure 20B:
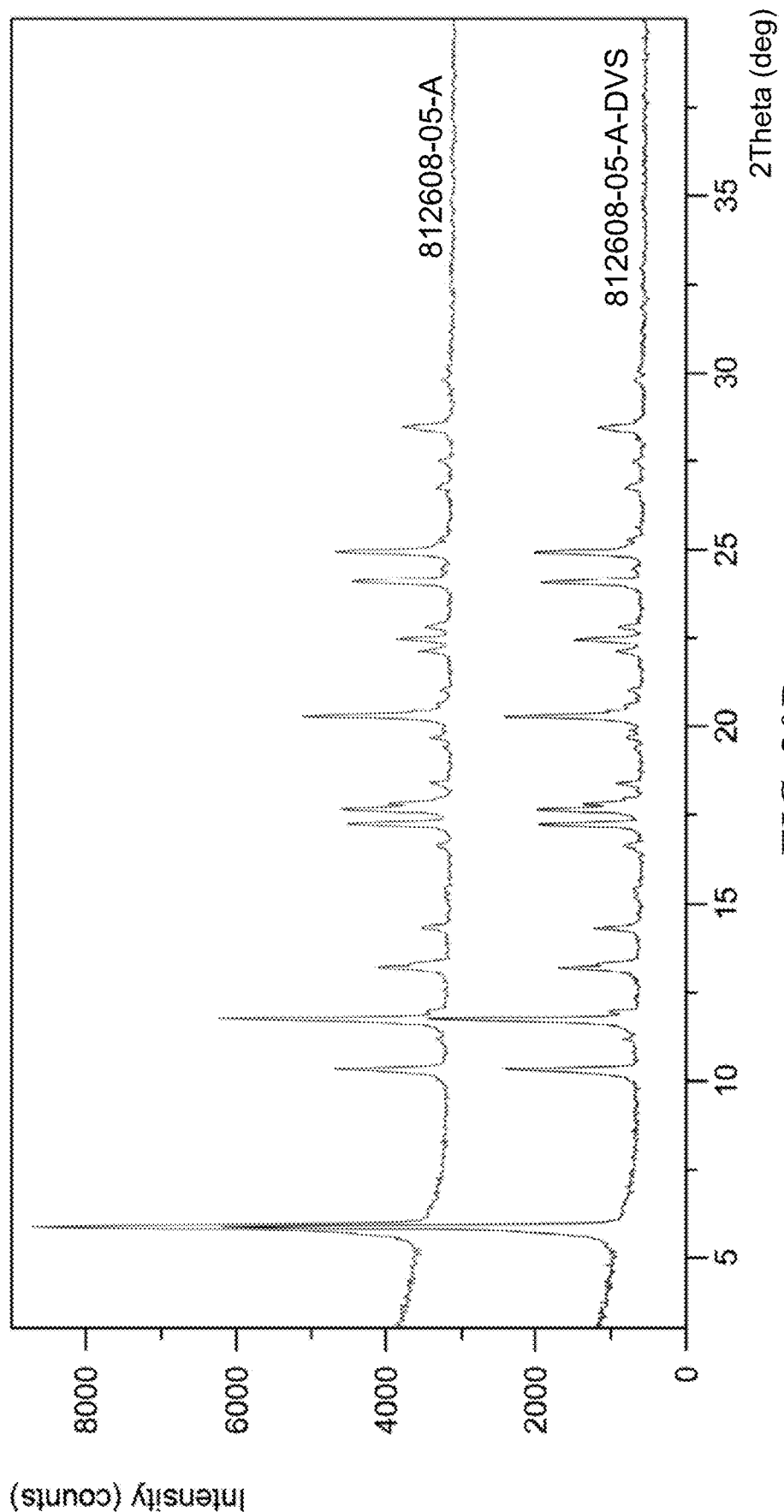
FIG. 20B shows an XRPD overlay of Compound 2 freebase Form A, pre- and post-DVS testing.
Figure 20C:
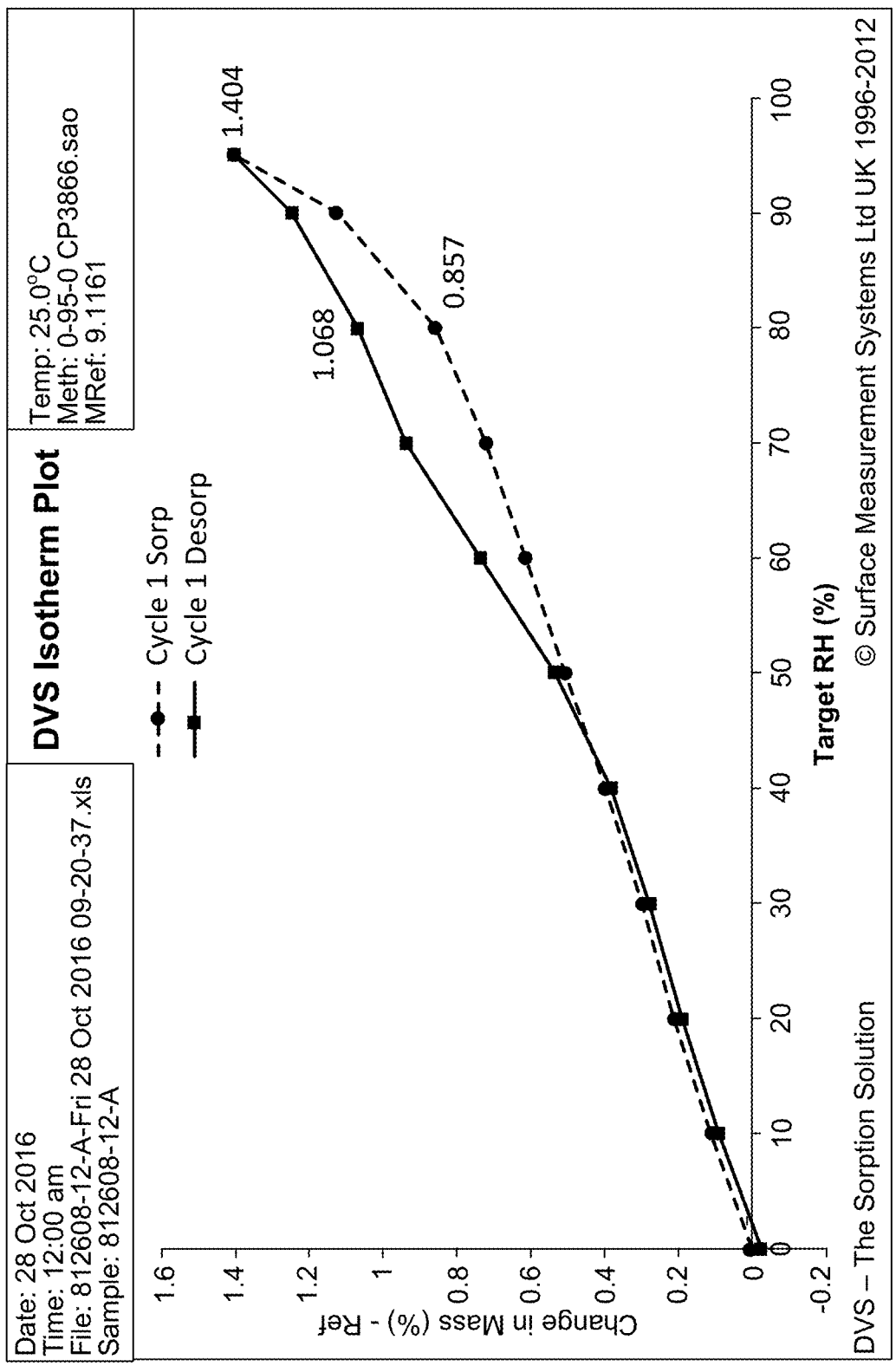
FIG. 20C shows a DVS plot of Compound 2 HCl salt Form A (812608-12-A)
Figure 20D:
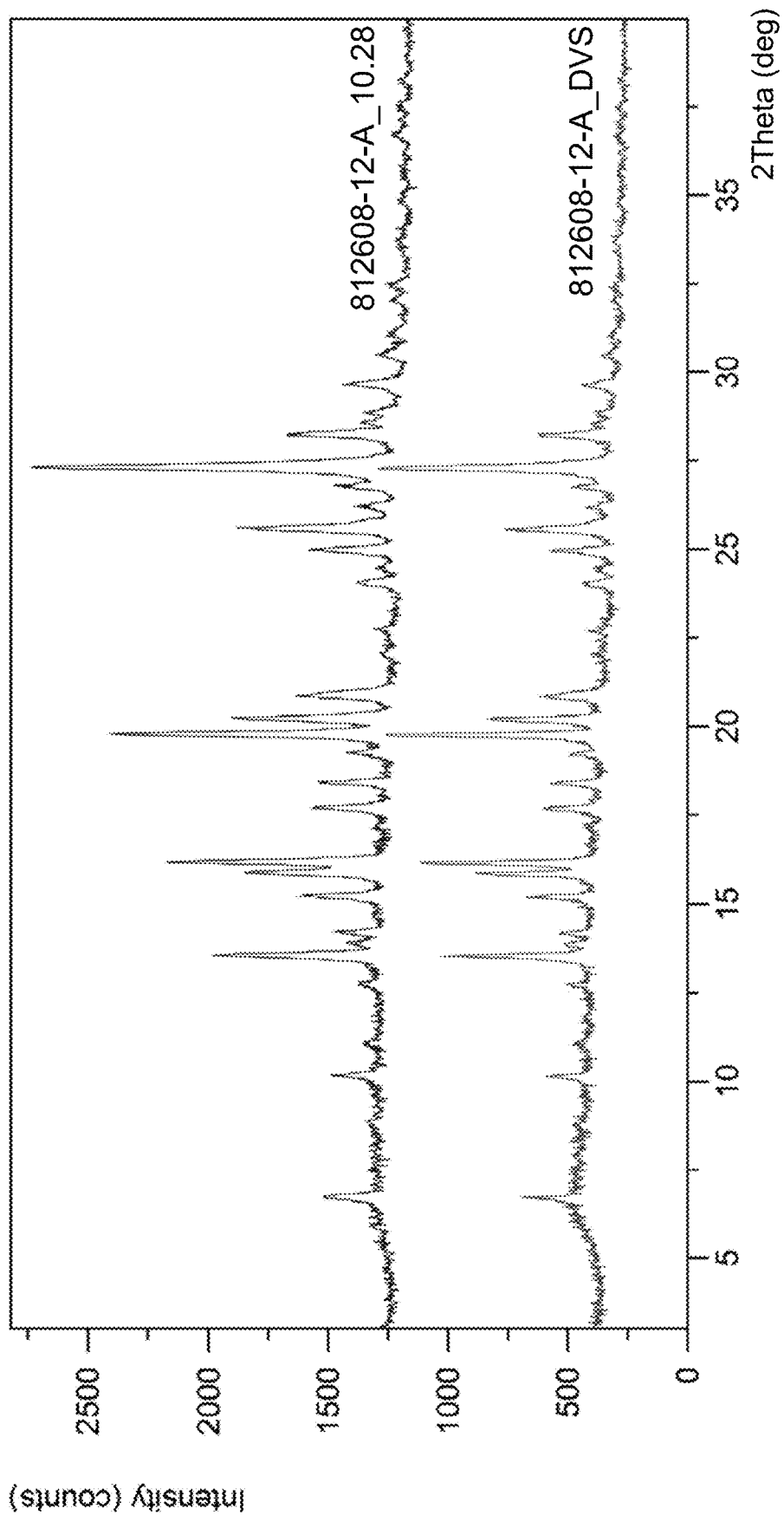
FIG. 20D shows an XRPD overlay of Compound 2 HCl salt Form A, pre- and post-DVS testing.
Figure 20E:
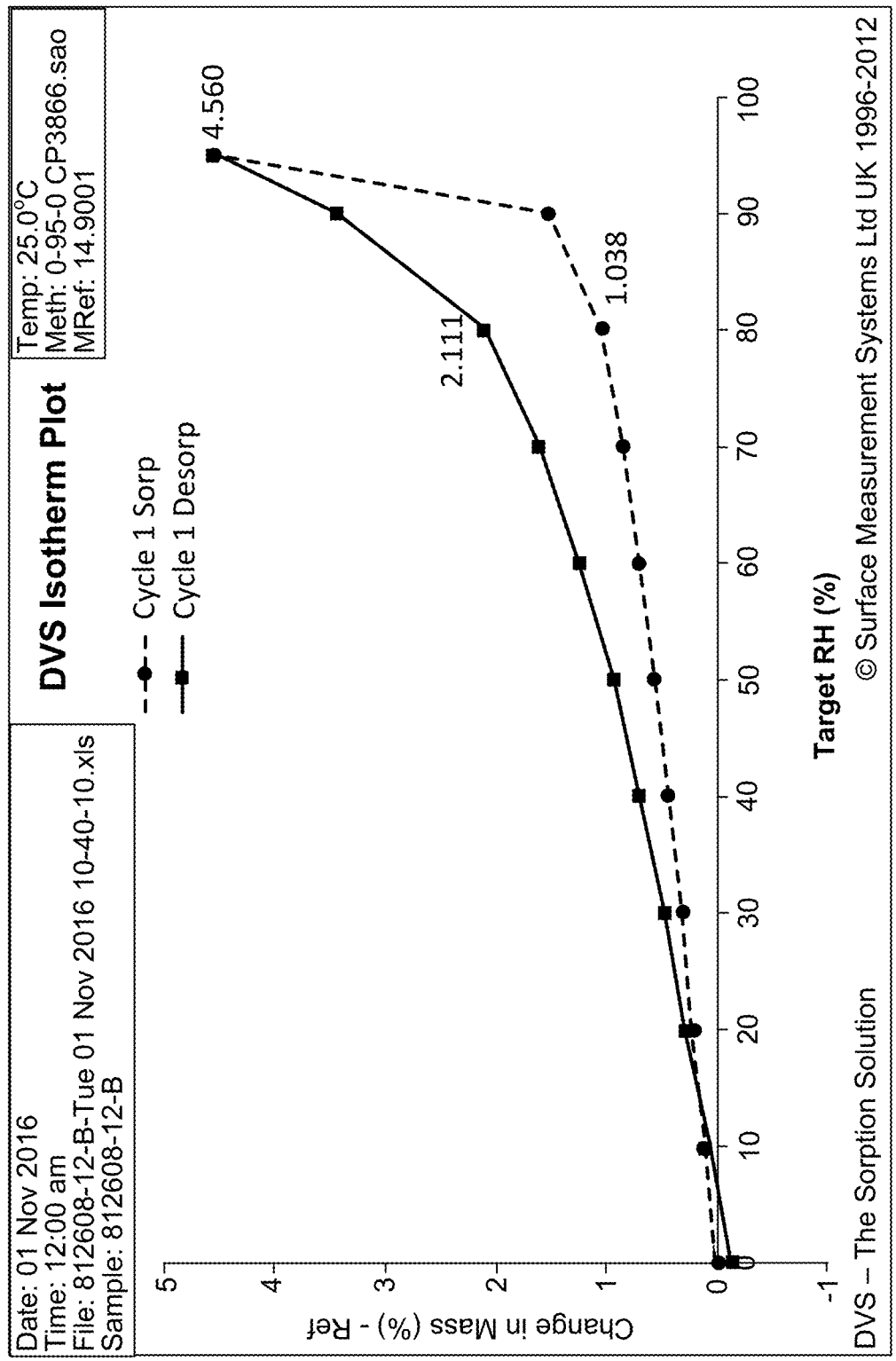
FIG. 20E shows a DVS plot of Compound 2 fumarate Form A (812608-12-B)
Figure 20F:
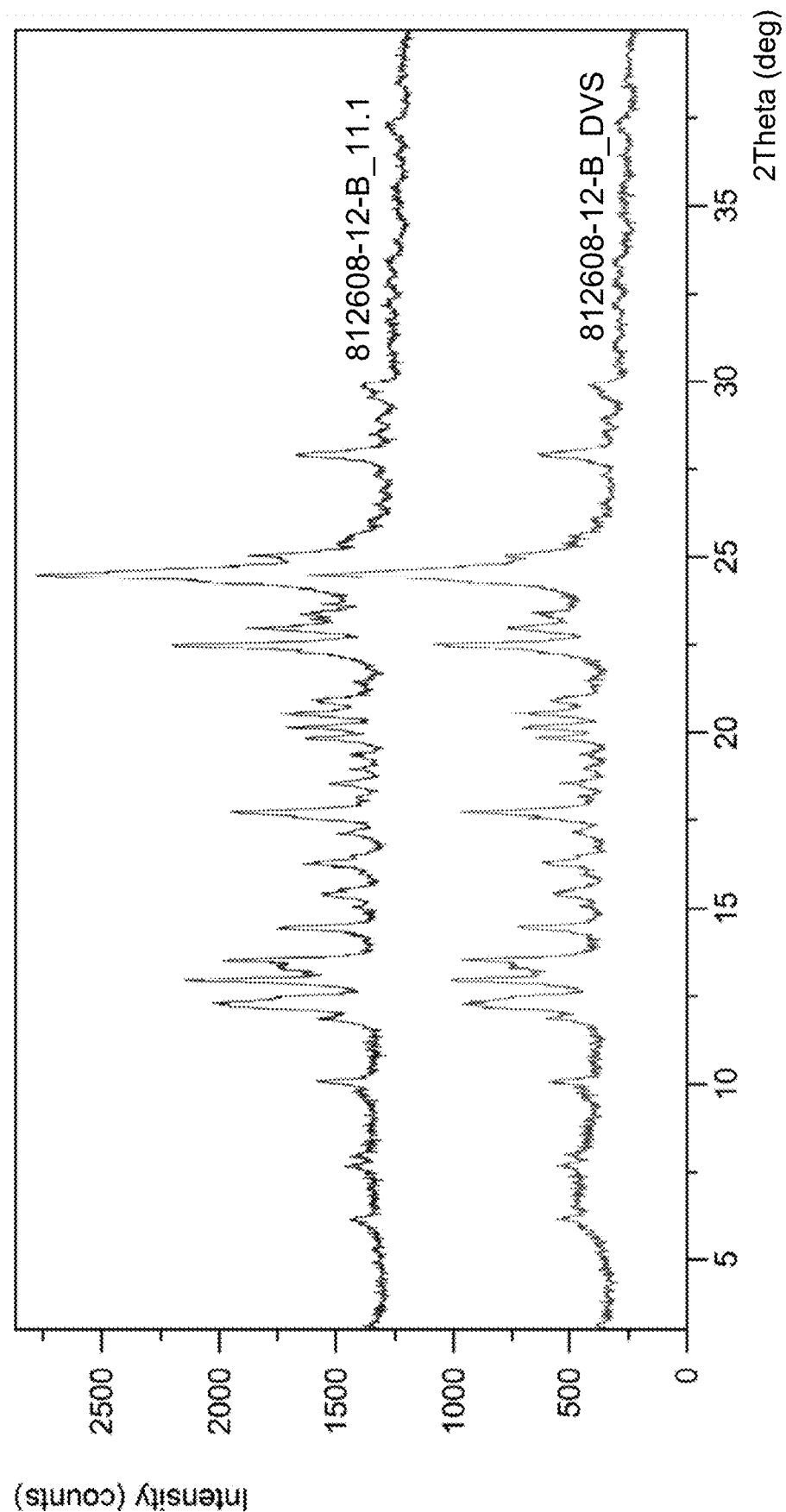
FIG. 20F shows an XRPD overlay of Compound 2 fumarate Form A, pre- and post-DVS testing.

Fumarate Form A was successfully re-prepared as evidenced by XRPD results in FIG. 17, which depicts an XRPD overlay of fumarate Form A batches. As per TGA and DSC data in FIG. 18, the sample showed a weight loss of 1.0% up to 150° C. and two endotherms at 228.5 and 233.9° C. (peak temperature). The stoichiometric ratio was determined as 0.94 (acid/base) by $^1$H NMR (FIG. 19) and limited EtOH residual was detected (~1.6%). As limited TGA weight loss before 150° C., no significant thermal event in DSC before 200° C. and limited solvent residual was observed, the sample is speculated to be an anhydrous fumarate.

Evaluation of Salt Leads

Further evaluation study on hygroscopicity, kinetic solubility, and solid-state stability was conducted to better under-

TABLE 32

Preparation procedures of salt leads

| Crystal Form | Preparation Procedures |
|---|---|
| HCl Salt Form A (812608-12-A) | 1. Add 53.2 µL HCl to 5.0 mL EtOH in a 20-mL glass vial.<br>2. Weigh 300.2 mg freebase into a 20-mL glass vial, and add 5.0 mL EtOH. A suspension was obtained.<br>3. Pipette the acid stock solution into the 20-mL vial and magnetically stir at RT.<br>4. Add ~5 mg of HCl salt Form A seed (812608-08-A1).<br>5. Sample for XRPD after stirring for 1 day, and the pattern conformed to HCl salt Form A.<br>6. Centrifuge the suspension obtained and dry the wet cake at 50° C. for 2.5 hrs.<br>7. Collect solids of 255.4 mg, with a yield of ~79.8%. |
| Fumarate Form A (812608-12-B) | 1. Weigh 74.7 mg fumaric acid into a 20-mL glass vial, and add 5.0 mL EtOH. A clear solution was obtained.<br>2. Weigh 300.6 mg freebase into a 20-mL glass vial, and add 5.0 mL EtOH. A suspension was obtained.<br>3. Add the acid solution into the 20-mL vial and magnetically stir at RT.<br>4. Add ~5 mg of fumarate Form A seed (812608-08-A6).<br>5. Sample for XRPD after stirring for 1 day, and the pattern conformed to fumarate Form A.<br>6. Centrifuge the suspension obtained and dry the wet cake at 50° C. for 2.5 hrs.<br>7. Collect solids of 300.1 mg, with a yield of ~80.0%. | stand the physicochemical properties of the two salt leads, using freebase Form A as reference.

Hygroscopicity

A DVS isotherm plot was collected at 25° C. to investigate the solid form stability as a function of humidity. All the anhydrous samples were pre-equilibrated at 0% RH to remove the unbounded solvent or water before getting started. As evidenced by the water uptake of 0.601.04% up to 80% RH, freebase Form A and both two salt forms were slightly hygroscopic, and no solid form change was observed after DVS evaluation (FIGS. 20A, 20B, 20C, 20D, 20E, and 20F).

Significant water uptake increase (4.56%) was observed for fumarate Type A at 95% RH, but for HCl salt Type A, for which only 1.40% water uptake was observed at 95% RH.

Kinetic Solubility

Kinetic solubility of two salt leads was measured in pH 2, 5, and 7 buffers to evaluate their solubility and disproportionation risk, using freebase Form A (812608-05-A) as control. All the solubility samples (initial solid loading of ~10 mg/mL) were kept rolling on a rolling incubator at a speed of 25 rpm, and sampled at 1, 2, 4, and 24 hours at RT (19±3° C.), respectively. After centrifugation, supernatants were collected for HPLC and pH tests, and wet cakes were collected for XRPD characterization. If clear solutions were obtained, accurate concentration was measured for the solutions.

Figure 21:
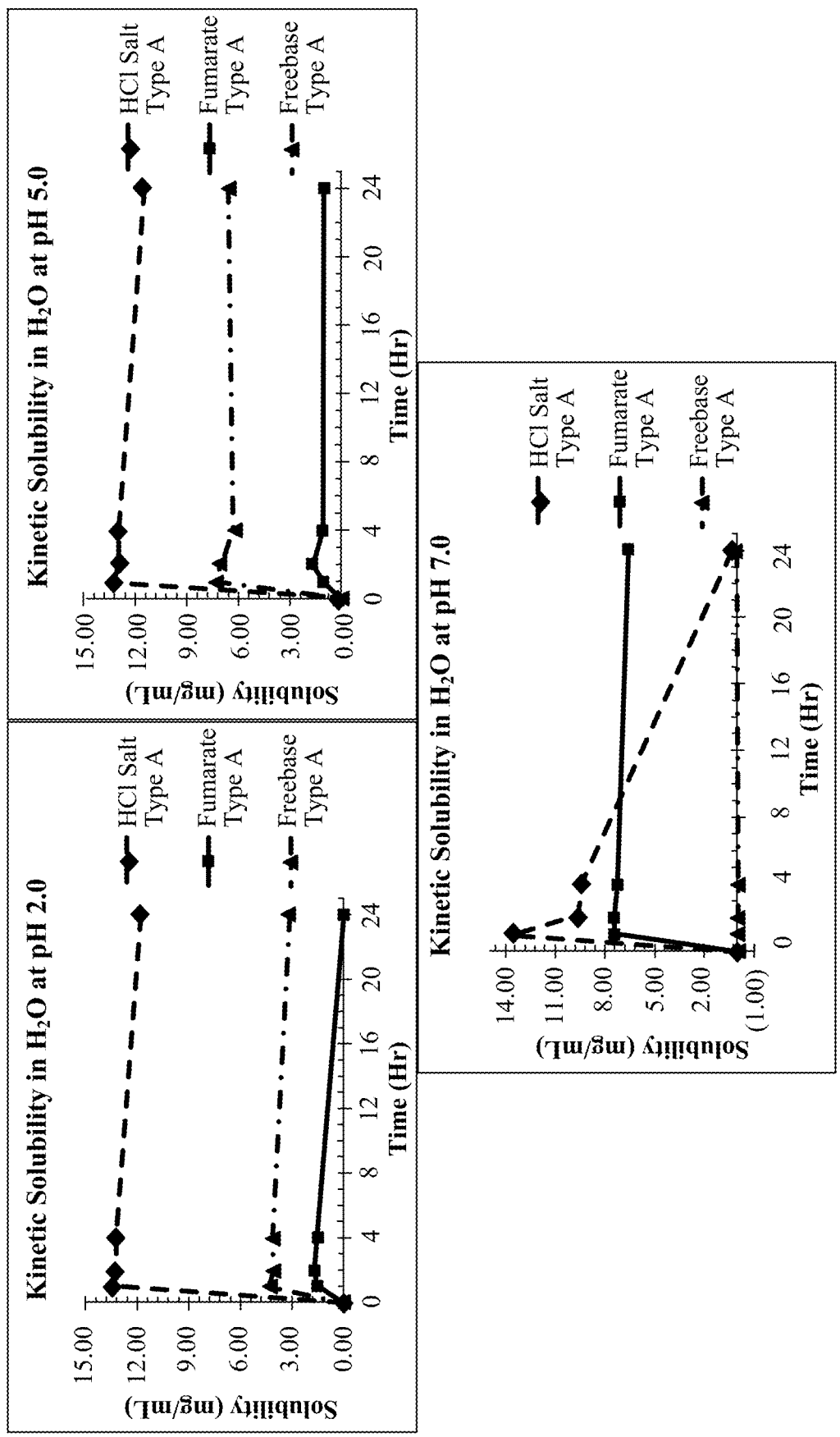
FIG. 21 shows kinetic solubility files of two salts and the freebase of Compound 2 at room temperature.

The results are summarized in Table 33A, and the kinetic solubility profiles are displayed in FIG. 21 (dashed line indicates clear solutions were obtained). Compared with freebase Form A, HCl salt Form A showed increased solubility in pH 2, 5, and 7 buffers. In pH 2 and 5 buffers, no solid was obtained. In pH 7 buffer, a form change to freebase Form A was observed after HCl salt Type A was suspended for 1, 2, and 4 hrs (limited solids were obtained at 1 and 2 hrs time points and one extra broad peak was observed at 2 hrs time point). New diffraction peaks were observed after 24 hrs. Fumarate Form A showed decreased solubility in pH 2 and 5 buffers with form change observed, but increased solubility was observed in pH 7 buffer with no form change. For freebase Form A, no form change was observed except that after suspending freebase Form A in pH 5, one extra broad peak (highlighted) was observed at 1 and 2 hrs time points.

TABLE 33A

Summary of kinetic solubility results at RT
Kinetic Solubility in pH 2 Buffer

| Solid Form | 1 hr | | | 2 hrs | | | 4 hrs | | | 24 hrs | | |
|---|---|---|---|---|---|---|---|---|---|---|---|---|
| | S | pH | FC | S | pH | FC | S | pH | FC | S | pH | FC |
| Freebase Type A | 4.3 | 6.2 | No | 4.1 | 6.2 | No | 4.1 | 6.2 | No | 3.2 | 6.1 | No |
| HCl Salt Type A | 13.4 | 5.5 | N/A | 13.3 | 5.6 | N/A | 13.2 | 5.6 | N/A | 11.8 | 5.6 | N/A |
| Fumarate Type A | 1.6 | 3.7 | Yes | 1.7 | 3.8 | Yes | 1.5 | 3.8 | Yes | G | G | Yes |

Kinetic Solubility in pH 5 Buffer

| Solid Form | 1 hr | | | 2 hrs | | | 4 hrs | | | 24 hrs | | |
|---|---|---|---|---|---|---|---|---|---|---|---|---|
| | S | pH | FC | S | pH | FC | S | pH | FC | S | pH | FC |
| Freebase Type A | 7.4 | 6.2 | No* | 7.2 | 6.3 | No* | 6.3 | 6.4 | No | 6.6 | 6.4 | No |
| HCl salt Type A | 13.2 | 5.7 | N/A | 13.0 | 5.7 | N/A | 13.0 | 5.7 | N/A | 11.6 | 5.7 | N/A |
| Fumarate Type A | 1.1 | 5.1 | Yes | 1.7 | 5.0 | Yes | 1.1 | 5.1 | Yes | 1.0 | 5.1 | Yes |

Kinetic Solubility in pH 7 Buffer

| Solid Form | 1 hr | | | 2 hrs | | | 4 hrs | | | 24 hrs | | |
|---|---|---|---|---|---|---|---|---|---|---|---|---|
| | S | pH | FC | S | pH | FC | S | pH | FC | S | pH | FC |
| Freebase Type A | 0.0004 | 7.0 | No | 0.0010 | 6.9 | No | 0.0004 | 7.0 | No | 0.0089 | 7.0 | No |
| HCl salt Type A | 13.5 | 7.0 | Yes | 9.6 | 6.9 | Yes | 9.4 | 6.9 | Yes | 0.21 | 6.4 | Yes |
| Fumarate Type A | 7.4 | 6.3 | No | 7.4 | 6.3 | No | 7.2 | 6.3 | No | 6.6 | 6.3 | No |

S: solubility in mg/mL,
pH: final pH of supernatant,
FC: solid form change.
G: no data was collected as gel-like material was obtained.
N/A: no solid for analysis.
*one extra broad peak was observed at 2θ≈7.6°.

Solid-State Stability

Figure 22:
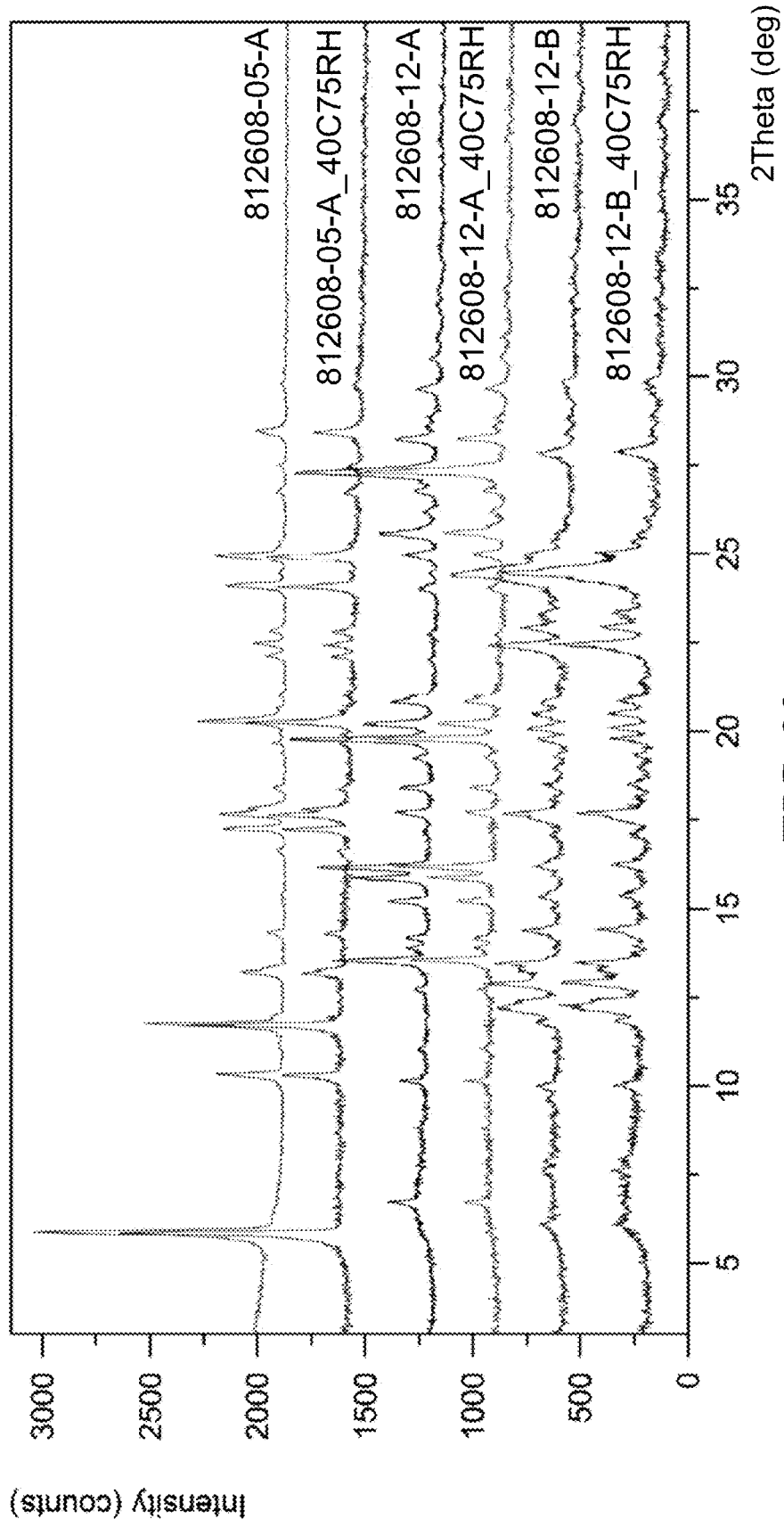
FIG. 22 shows an XRPD overlay of samples pre- and post-stability testing.

Solid-state stability of freebase Form A, HCl salt Form A and fumarate Form A was evaluated under 40° C./75% RH for one week. Stability samples were characterized by XRPD to check any solid form change and by HPLC to check purity change. All the results are summarized in Table 33B and XRPD data is displayed in FIG. 22, which showed that no form change or significant HPLC purity decrease was observed after stability tests, indicating good physicochemcial stability of freebase Form A and both two salts under the tested condition.

TABLE 33B

Stability evaluation summary of freebase and salt leads

| | | 40° C./75% RH, one week | | |
|---|---|---|---|---|
| Solid form (Batch No.) | Initial purity (area %) | Purity (area %) | Purity vs. Initial (%) | FC |
| Freebase Type A (812608-05-A) | 99.17 | 99.18 | 100.0 | No |
| HCl Salt Type A (812608-12-A) | 99.63 | 99.54 | 99.9 | No |
| Fumarate Type A (812608-12-B) | 99.43 | 99.36 | 99.9 | No |

FC: form change based on XRPD results.

Based on results collected, the HCl salt Form A is the candidate form.

Polymorphism Evaluation for HCl Salt (Mono)

Therefore, polymorphism evaluation study was conducted on HCl salt (mono). A preliminary polymorph screening was conducted under 32 conditions using methods of slurry conversion, evaporation, slow cooling and anti-solvent addition. Based on XRPD comparison, besides HCl salt Form A, five new crystalline forms (HCl salt Forms C~G) were obtained from screening and characterized by TGA and DSC. Based on investigation results, HCl salt Form C was speculated to a hydrate. Re-preparation of HCl salt Forms D and E by evaporation resulted in mixtures containing HCl salt Forms C+D and C+E, respectively. As a result of $^1$H NMR and heating experiments of the mixtures, HCl salt Forms D and E might be hydrates. Due to limited amount of material, the potential HCl salt Forms F and G were not identified fully.

Anhydrate HCl Salt Form A

Figure 23:
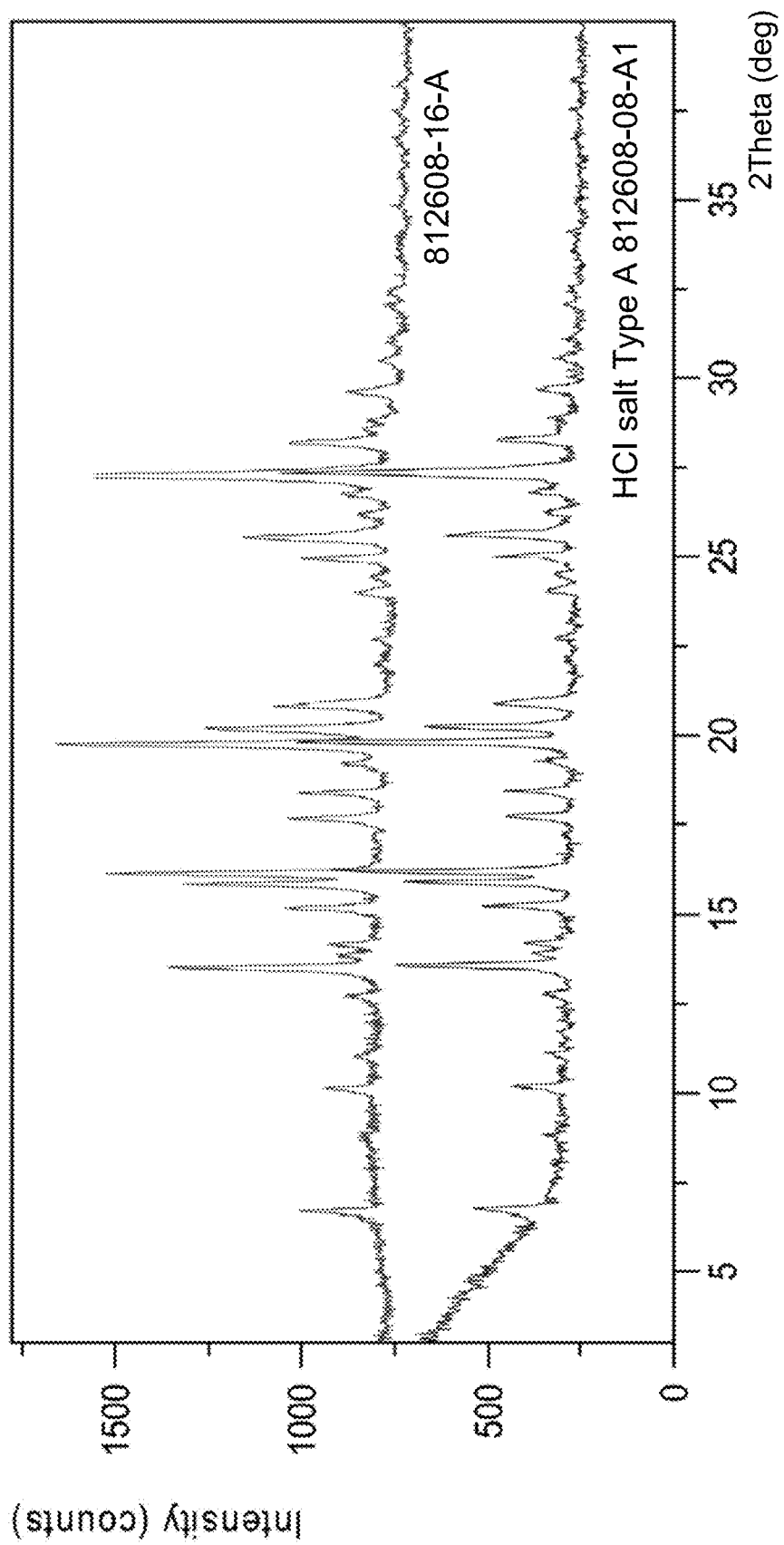
FIG. 23 shows an XRPD overlay of Compound 2 HCl salt Form A samples.
Figure 24:
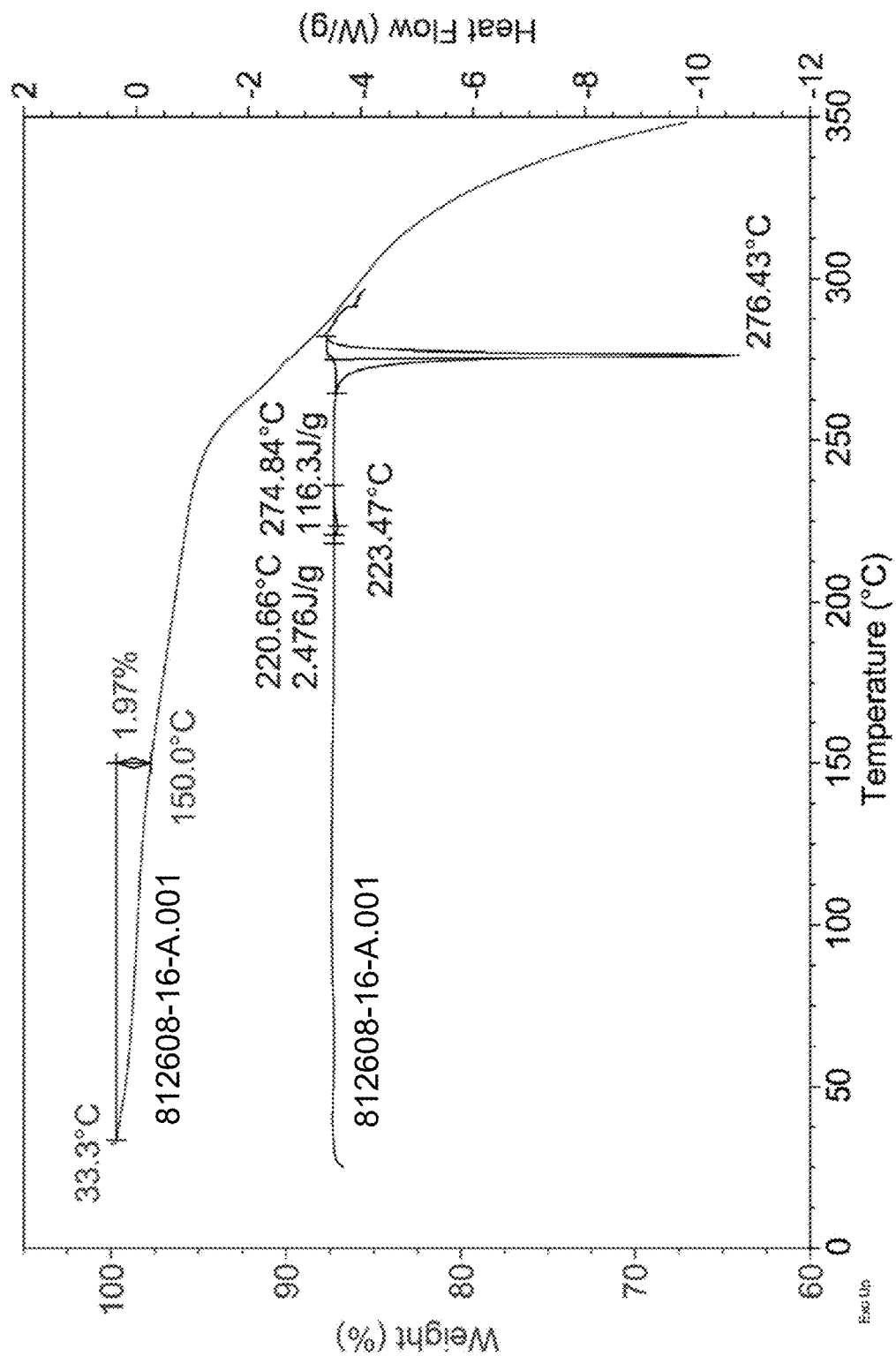
FIG. 24 shows TGA/DSC curves of Compound 2 HCl salt Form A (812608-16-A).

The HCl salt Form A (812608-16-A) was re-prepared for polymorph screening and detailed preparation procedure was shown in Table 34. As shown in FIG. 23, the HCl salt Type A was successfully re-prepared. As shown by TGA and DSC data in FIG. 24, 2.0% weight loss up to 150° C. and two endothermic peaks at 220.7 and 274.8° C. (onset temperature) were observed. The stoichiometry of acid/freebase was determined to be 1.01 by HPLC/IC. Due to the limited TGA weight loss and neat DSC curve, FIG. 24, HCl salt Form A was speculated to be an anhydrate.

TABLE 34

Preparation procedures of HCl salt Type A

| Crystal Form | Preparation Procedures |
|---|---|
| HCl Salt Form A (812608-16-A) | 1. Weigh 519.5 mg freebase solid into a 20-mL glass vial, and add 8.6 mL EtOH. A suspension was obtained.<br>2. Add 94.0 μL HCl acid into 8.6 mL EtOH in a 20-mL glass vial.<br>3. Add the acid solution into the 20-mL vial and magnetically stir at RT.<br>4. Add ~10 mg of HCl salt Form A seed (812608-12-A).<br>5. Sample for XRPD after stirring for about 1 day, and the pattern conformed to HCl salt Form A.<br>6. Centrifuge the suspension obtained and dry the wet cake at 50° C. for 3.0 hrs.<br>7. Collect 474.5 mg solids, with a yield of ~84.5%. |

Hydrate HCl Salt Form C

Figure 25:
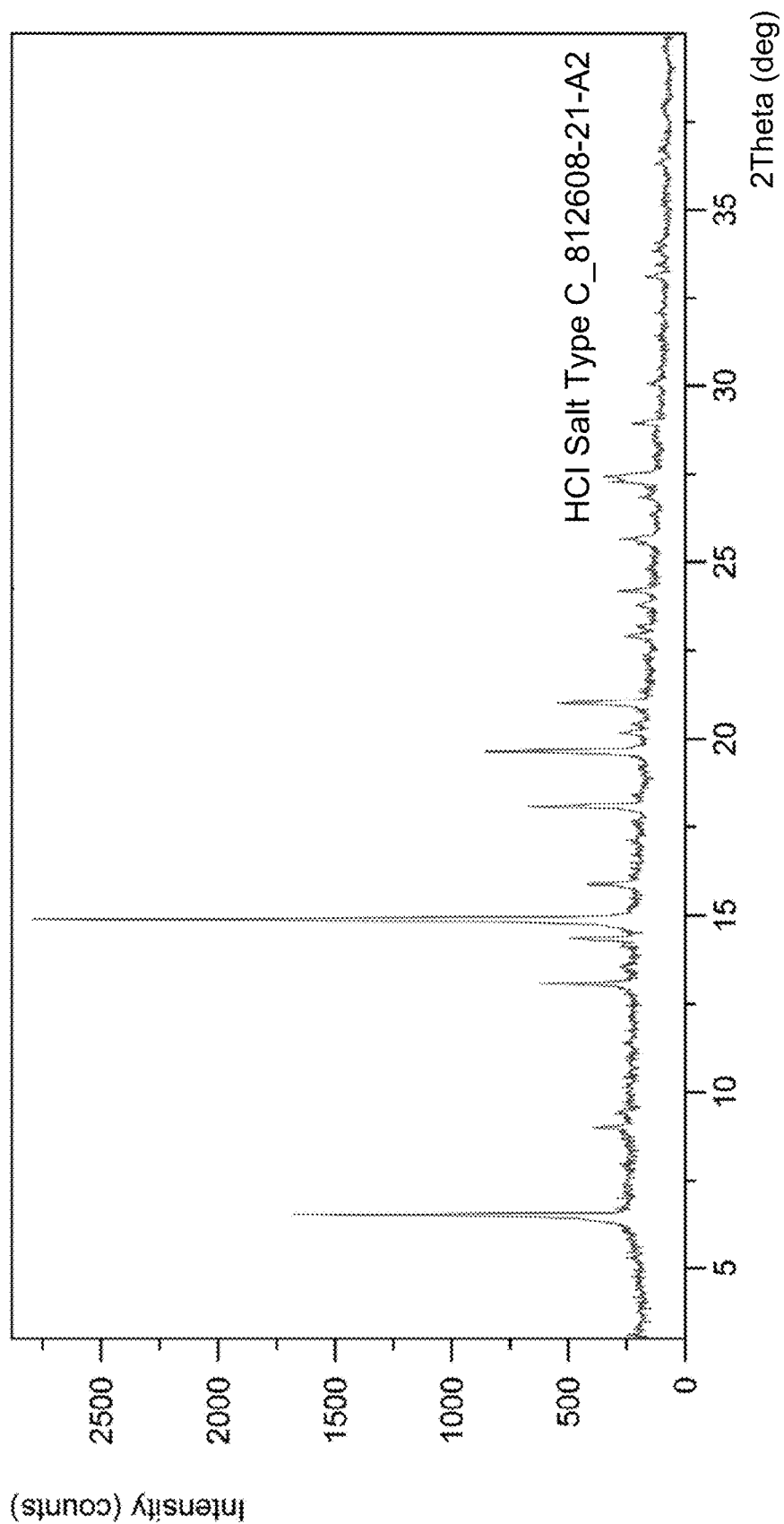
FIG. 25 shows an XRPD pattern of Compound 2 HCl salt Form C (812608-21-A2).
Figure 26:
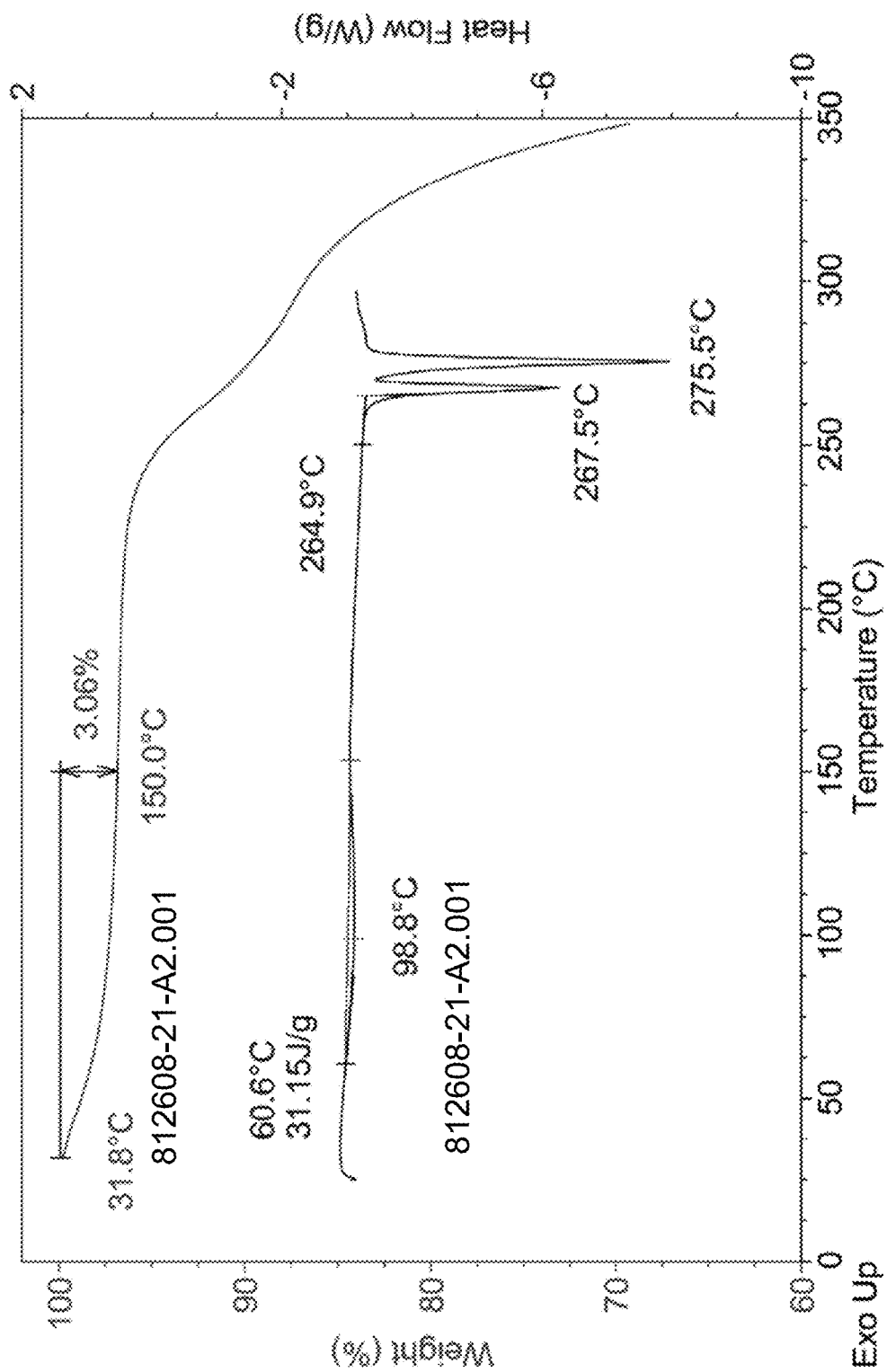
FIG. 26 shows TGA/DSC curves for Compound 2 HCl salt Form C (812608-21-A2).

HCl salt Form C (812608-21-A2) was obtained from evaporation of CHCl$_3$/MeOH (1:1, v/v) solution (FIG. 25). As shown by TGA and DSC data in FIG. 26, 3.1% weight loss up to 150° C., a broad endothermic peak at 98.8° C. and two sharp peaks at 267.5° C. and 275.5° C. (peak temperature) were observed. The stoichiometry of acid/freebase was determined to be 1.01 by HPLC/IC.

Figure 27:
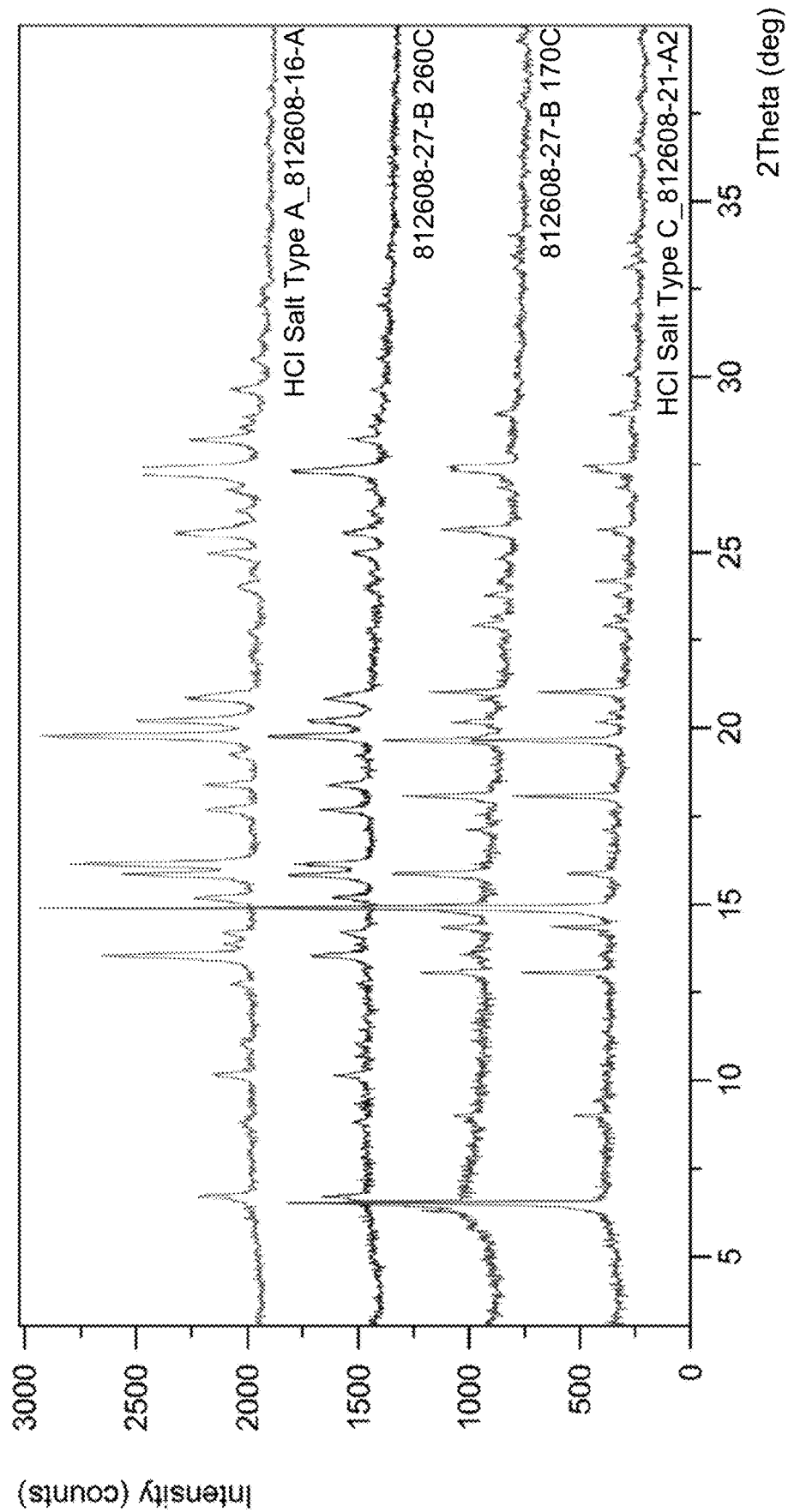
FIG. 27 shows an XRPD overlay of Compound 2 HCl salt Form C (812608-27-B) pre- and post-heating.
Figure 28:
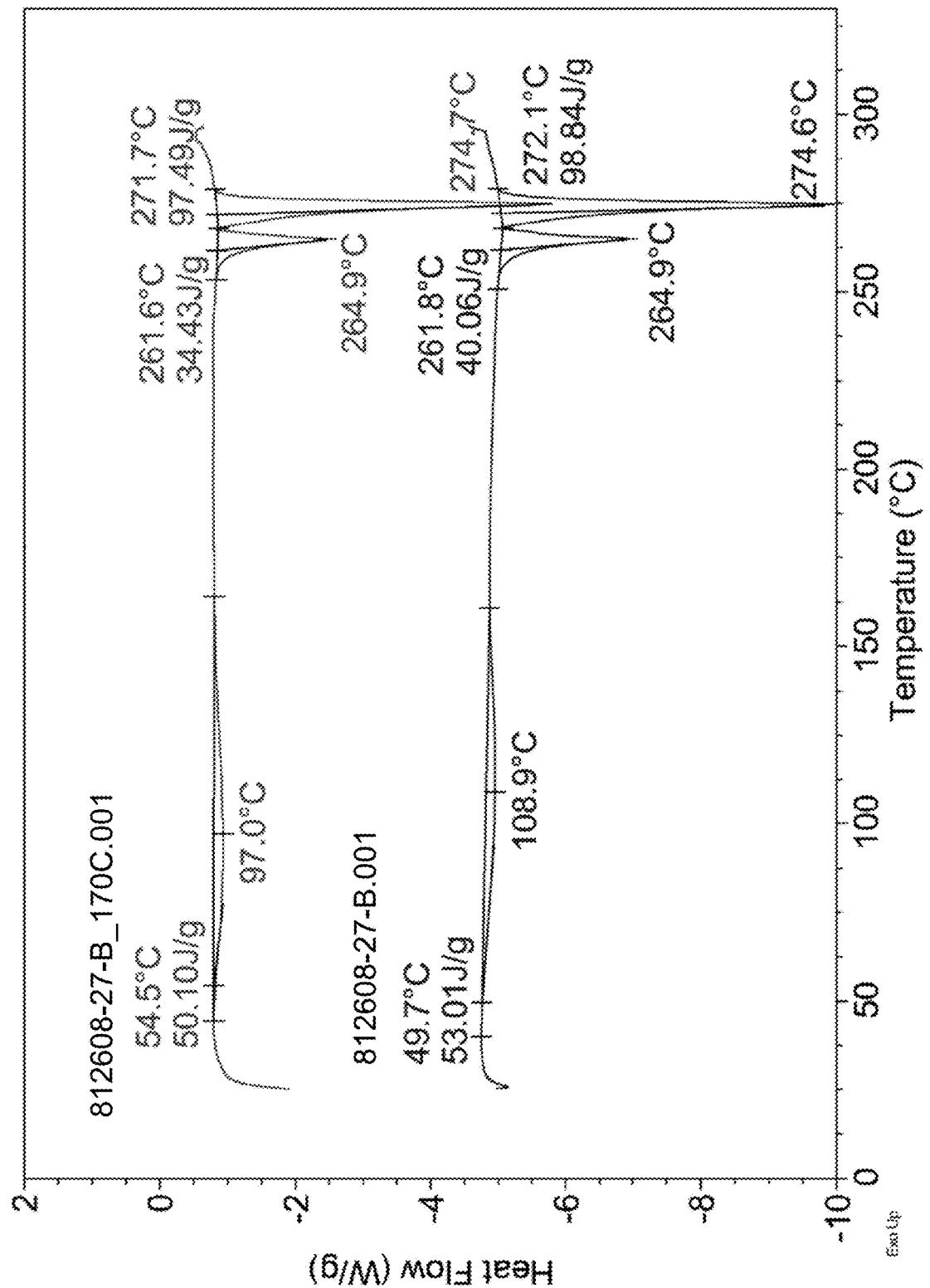
FIG. 28 shows a DSC overlay of Compound 2 HCl salt Form C (812608-27-B) pre- and post-heating.

To identify HCl salt Form C, heating experiments were performed. No form change was observed after HCl salt Type C (812608-27-B) was heated to 170° C. under N$_2$, cooled to 30° C. and exposed to ambient conditions. But, HCl salt Form C turned to HCl salt Form A after being heated to 260° C. with open lid (over the endotherm at 264.9° C. with crimped lid). See, FIG. 27. Furthermore, after HCl salt Form C (812608-27-B) was heated to 170° C., cooled back to 30° C. and exposed to ambient conditions, a broad peak was still observed in DSC, which may be caused by re-absorption of moisture. Combined with XPRD result and the fact that Form C can be obtained in different aqueous systems, HCl salt Form C was speculated to be a hydrate (theoretical water content of mono HCl salt mono-hydrate was 3.4%). FIG. 28 shows a DSC overlay of HCL Form C pre- and post-heating.

Forms Not Identified Fully (D-G)

Reference is made to the XRPD overlays of FIGS. 13A and 13B. The HCl salt Form D (812608-23-A2) was obtained from anti-solvent addition in DCM/MeOH (good solvent)/DCM (anti-solvent), and the clear solution obtained was transferred to 5° C. and −20° C. first, followed by evaporation at RT. As demonstrated by TGA and DSC data, 2.4% weight loss up to 150° C. and multiple endotherms were observed. The stoichiometry of acid/freebase was determined to be 1.02 by HPLC/IC.

Figure 29:
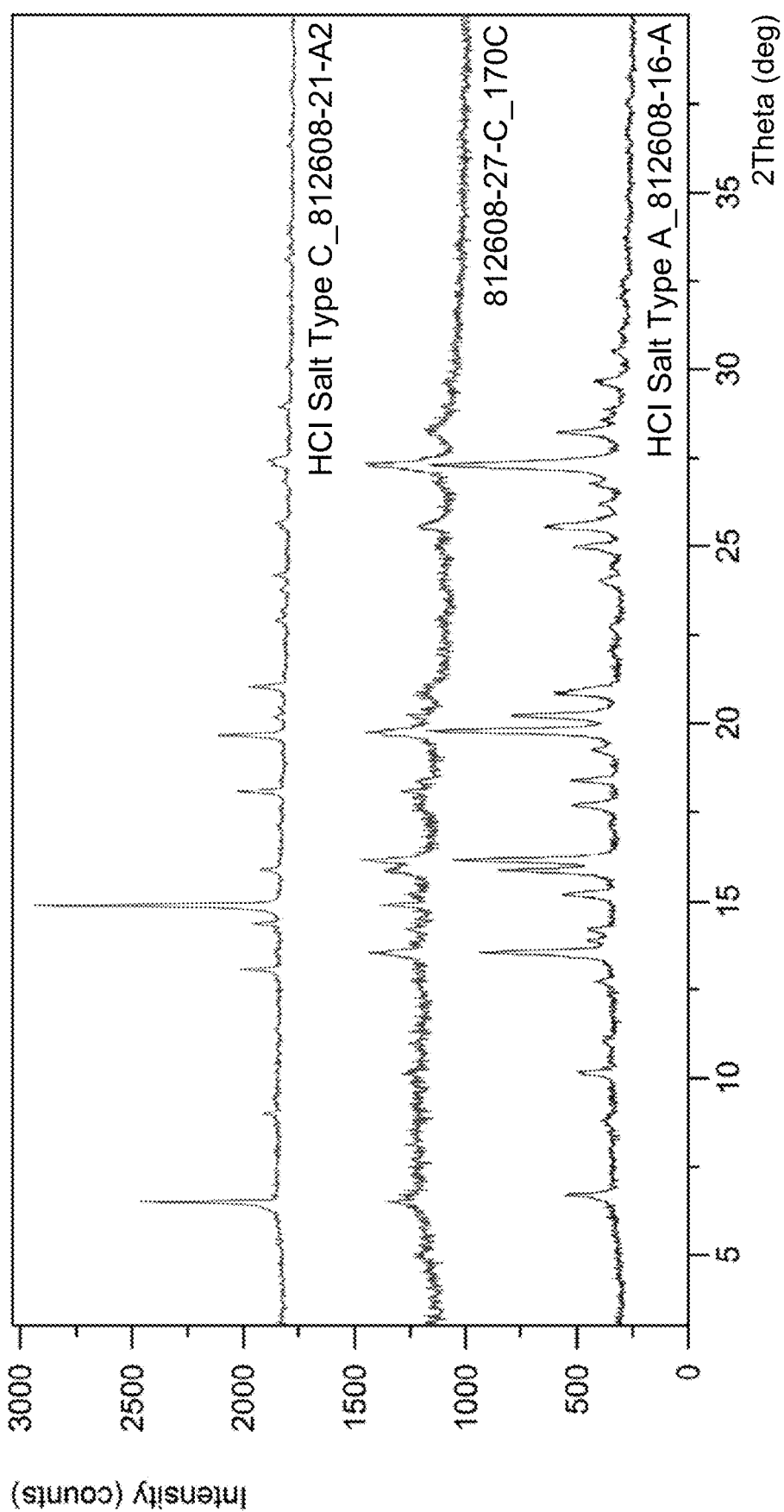
FIG. 29 shows an XRPD overlay of sample (812608-27-C) pre- and post-heating, showing that when heated to about 170° C. under $N_2$, cooled to 30° C. and exposed to ambient conditions, the sample that contained a mixture of HCl salt Forms C+D coverts to a mixture of Forms A+C.

To identify HCl salt Form D, re-preparation was attempted by anti-solvent addition in DCM/MeOH (good solvent)/DCM (anti-solvent), followed by evaporation at RT. As determined by XRPD, a mixture of HCl salt Type C+D (812608-27-C) was obtained from re-preparation. A few extra peaks were observed, which might be attributed to a new form or due to the relatively lower crystallinity of the reference sample of HCl salt Form D. TGA and DSC demonstrate a two-step weight loss of 4.8% up to 150° C. and multiple endotherms were observed. After the sample that contained a mixture of HCl salt Form C+D was heated to 170° C. under $N_2$, cooled to 30° C. and exposed to ambient conditions, a mixture of Form A+C was observed (FIG. 29). As no MeOH and limited DCM was detected by NMR, Form D might be a hydrate.

Again with reference to FIGS. 13A and 13B, the HCl salt Form E (812608-23-A5) was obtained from anti-solvent addition in THF/$H_2O$ (good solvent)/EtOH (anti-solvent), followed by evaporation at RT. As demonstrated by TGA and DSC, 13.5% weight loss up to 150° C. and two endothermic peaks at 105.8° C. and 273.6° C. (peak temperature) were observed. The stoichiometry of acid/freebase was not determined due to limited amount of the sample.

Figure 30:
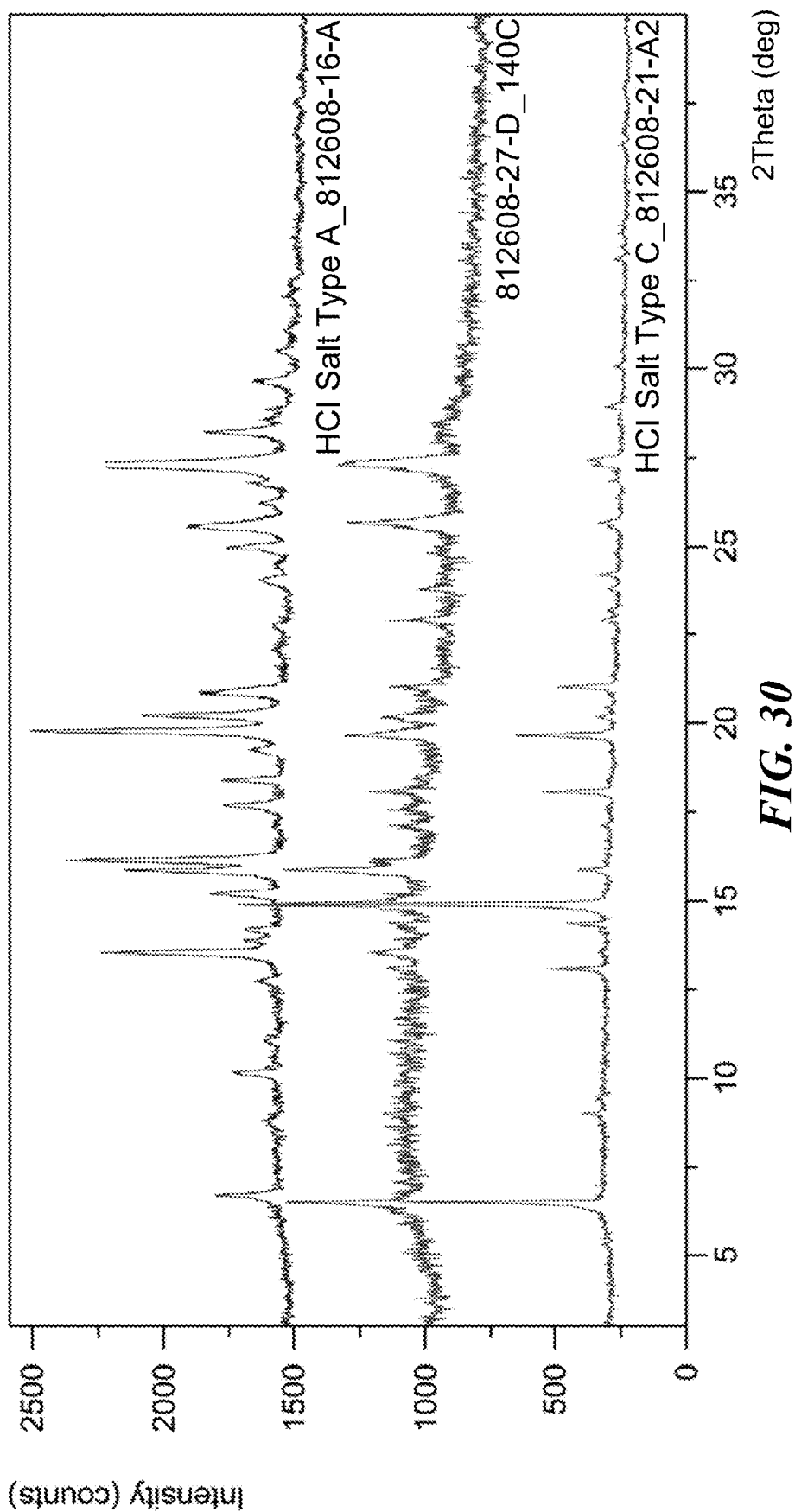
FIG. 30 shows an XRPD overlay of sample (812608-27-D) pre- and post-heating, showing that when heated to about 140° C., under $N_2$, cooled to 30° C. and exposed to ambient conditions, the sample that contained a mixture of HCl salt Forms C+E converts to a mixture of Forms A+C.

To identify HCl salt Form E, re-preparation was attempted by anti-solvent addition in THF/$H_2O$ (good solvent)/EtOH (anti-solvent), followed by evaporation at RT. As determined by XRPD, a mixture of HCl salt Forms C+E (812608-27-D) was obtained from re-preparation. A few extra peaks were observed (highlighted), which might be attributed to a new form or due to the relatively lower crystallinity of the reference sample of HCl salt Form E. As demonstrated by TGA and DSC, a two-step weight loss of 7.8% up to 150° C. and multiple thermal events were observed. After the sample that contained a mixture of HCl salt Forms C+E was heated to 140° C. under $N_2$, cooled to 30° C. and exposed to ambient conditions, a mixture of Forms A+C was observed (FIG. 30). As no THF and limited EtOH was detected by NMR, Type E might be a hydrate.

Again with reference to FIGS. 13A and 13B, a new form with low crystallinity was obtained from anti-solvent addition in $H_2O$/acetone, followed by evaporation at RT (812608-23-A6) or after HCl salt Form C (812608-23-A1, obtained by evaporation from MeOH/$H_2O$) was exposed to ambient conditions (21±1.5° C., 60±20% RH) for 6 days, named as HCl salt Form F. As demonstrated by TGA and DSC, 7.3% weight loss up to 150° C. and two endothermic peaks at 120.6 and 274.7° C. (peak temperature) were observed.

Figure 31:
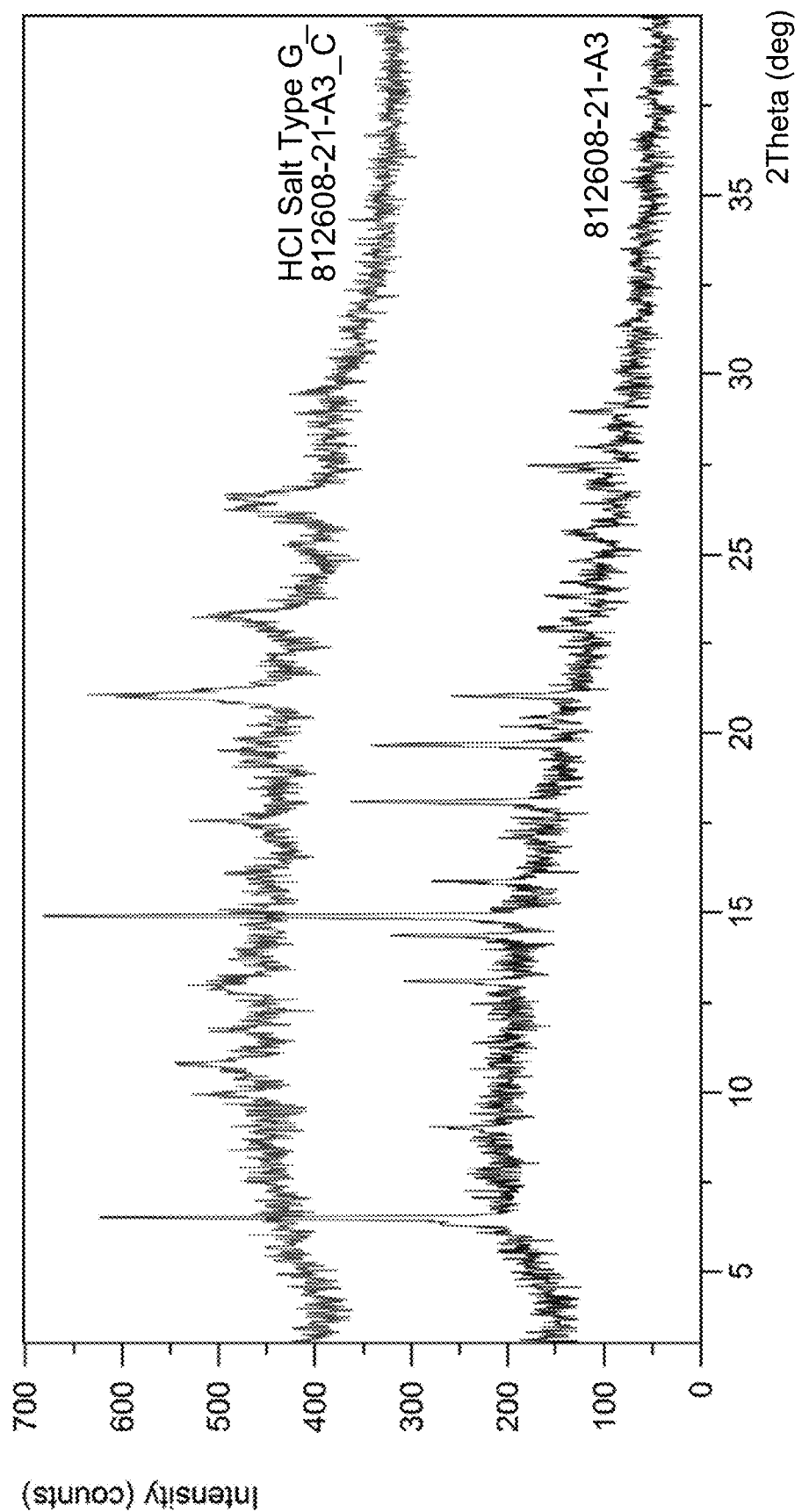
FIG. 31 shows an XRPD overlay for Compound 2 HCl salt Form G (812608-21-A3_C). A form change was observed after HCl salt Form C (812608-21-A3, obtained by evaporation from THF/$H_2O$) was exposed to ambient conditions (21±1.5° C., 60±20% RH) for 6 days, named as HCl salt Form G.
Figure 32A:
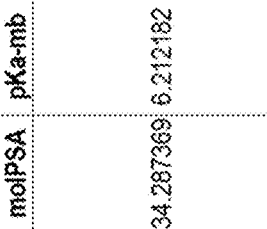
Figure 32A:
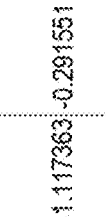
Figure 32A:
Figure 32A:
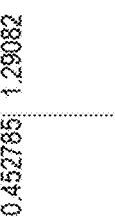
Figure 32A:
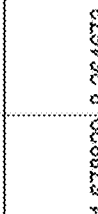

Lastly, with reference to FIGS. 13A and 13B and also to FIG. 31, a form change was observed after HCl salt Form C (812608-21-A3, obtained by evaporation from THF/$H_2O$) was exposed to ambient conditions (21±1.5° C., 60±20% RH) for 6 days, named as HCl salt Form G. As demonstrated by TGA and DSC, 8.9% weight loss up to 150° C. and multiple thermal events were observed for this Form G.

Results

Salt screening was conducted on freebase Compound 2. A total of 12 salt hits were obtained from 33 salt screening experiments. Anhydrates HCl salt Form A and fumarate Form A were selected as salt leads for further evaluation, including hygroscopicity, kinetic solubility in different pH buffers, and solid-state stability. As a result, both HCl salt Form A and fumarate Form A were slightly hygroscopic and showed good physicochemical stability under condition of 40° C./75% RH/1 week. Compared with freebase Form A, HCl Form A showed increased solubility in pH 2, 5, and 7 buffers although disproportionation and form change were observed in pH 7 buffer.

Based on the characterization and evaluation results, anhydrate HCl salt Form A is a preferred salt candidate, and polymorph screening was conducted on HCl salt (mono). Based on XRPD comparison, besides anhydrous HCl salt Form A, five new crystalline forms (hydrous HCl salt Form C and HCl salts Forms D~G) were obtained from a preliminary polymorph screening under 32 conditions and new forms were characterized by TGA and DSC.

As a result of preliminary salt screening of Compound 2 and polymorph screening of HCl salt (mono), HCl salt Form A is a preferred embodiment for development as an active pharmaceutical ingredient.

Instruments and Methods for Salt and Polymorphism Screening

Approximate Solubility

Approximate solubility of freebase Form A (812608-05-A) was measured in 12 solvents at RT. For each experiment, approximately 2 mg of sample was added into a 3 mL glass vial. Solvents in Table 35 were then added step wise (50, 50, 200, 200, 500 µL) into the vials until the solids were dissolved visually or a total volume of 1 mL was reached. Solubility results summarized in Table 35 were used to guide the solvent selection in salt screening design.

TABLE 35

Approximate solubility of starting freebase at RT

| Solvent | Solubility (mg/mL) | Solvent | Solubility (mg/mL) |
|---|---|---|---|
| MeOH | 2.4 < S < 4.8 | IPAc* | S < 2.4 |
| EtOH | 2.1 < S < 4.2 | ACN* | S < 2.0 |
| IPA* | S < 2.4 | THF | 3.6 < S < 6.0 |
| Acetone* | S < 2.4 | n-Heptane | S < 2.1 |
| MIBK | 1.9 < S < 3.8 | $H_2O$ | S < 1.9 |
| EtOAc* | S < 2.5 | Toluene | 2.0 < S < 4.0 |

*solids dissolved at 50° C.

Abbreviations for Solvents Used

The solvent abbreviations are listed in Table 36.

TABLE 36

Solvent abbreviation list

| Abbreviation | Solvent | Abbreviation | Solvent |
|---|---|---|---|
| MeOH | Methanol | THF | Tetrahydrofuran |
| EtOH | Ethanol | 2-MeTHF | 2-Methyltetrahydrofuran |
| IPA | Isopropyl alcohol | ACN | Acetonitrile |
| MIBK | Methyl isobutyl ketone | DCM | Dichloromethane |
| EtOAc | Ethyl acetate | DMSO | Dimethyl sulfoxide |
| IPAc | Isopropyl acetate | $CHCl_3$ | Chloroform |
| MTBE | Methyl tert-butyl ether | — | — |

Instruments and Methods

XRPD

For XRPD analysis, PANalytical X-ray powder diffractometers in reflection mode were used. The XRPD parameters are listed in Table 37.

TABLE 37

Parameters for XRPD test

| Parameters | PANalytical | PANalytical |
|---|---|---|
| Model | Empyrean | X' Pert[3] |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA |
| Divergence slit | Automatic | 1/8° |
| Scan mode | Continuous | Continuous |
| Scan range (°2TH) | 3°-40° | 3°-40° |

TABLE 37-continued

Parameters for XRPD test

| Parameters | PANalytical | PANalytical |
| --- | --- | --- |
| Scan step time (s) | 17.8 | 46.7 |
| Step size (°2TH) | 0.0167 | 0.0263 |
| Test Time | 5 min 30 s | 5 min 4 s |

TGA and DSC

TGA data were collected using a TA Q500/Q5000 TGA from TA Instruments and DSC was performed using a TA Q200/Q2000 DSC from TA Instruments. Detailed parameters used are listed in Table 38.

TABLE 38

Parameters for TGA and DSC test

| Parameters | TGA | DSC |
| --- | --- | --- |
| Method | Ramp | Ramp |
| Sample pan | Aluminum, open | Aluminum, crimped |
| Temperature | RT-desired temperature | 25° C.-desired temperature |
| Heating rate | 10° C./min | 10° C./min |
| Purge gas | $N_2$ | $N_2$ |

HPLC

Agilent 1100/1260 HPLC was utilized and detailed chromatographic conditions for purity and solubility measurement are listed in Table 39.

TABLE 39

Chromatographic conditions and parameters for purity/solubility test

| Parameters | Purity | Solubility |
| --- | --- | --- |
| Column | COSMOSIL 5C18-MS-II, 250 × 4.6 mm, 5.0 μm | |
| Mobile phase | A: 0.1% TFA in $H_2O$ | |
| | B: 0.1% TFA in ACN | |

| Gradient table | Time (min) | % B | Time (min)* | % B | Time (min)# | % B |
| --- | --- | --- | --- | --- | --- | --- |
| | 0.0 | 5 | 0.0 | 20 | 0.0 | 5 |
| | 5.0 | 5 | 8.0 | 90 | 3.0 | 20 |
| | 20.0 | 40 | 9.0 | 90 | 8.0 | 25 |
| | 30.0 | 90 | 9.1 | 20 | 12.0 | 90 |
| | 30.1 | 5 | 12.0 | 20 | 12.1 | 5 |
| | 35.0 | 5 | — | — | 15.0 | 5 |
| Run time | 35.0 min | | 12.0 min | | 15.0 min | |
| Post time | 0.0 min | | 0.0 min | | 0.0 min | |

| Parameters | Purity | Solubility |
| --- | --- | --- |
| Flow rate | 1.0 mL/min | |
| Injection volume | 5 μL | |
| Detector wavelength | UV at 254 nm | |
| Column temperature | 40° C. | |
| Sampler temperature | RT | |
| Diluent | ACN:$H_2O$ (4:6, v:v) | |

*Used for kinetic solubility test and stoichiometric ratio for sample 812608-12-A.
Used for stoichiometric ratio for samples 812608-08-A1/08-C2/08-A3/08-B4/16-A/21-A2/23-A2.

Ion Chromatography

Ion chromatography (IC) method for counter ion (anion) content measurement to determine stoichiometric ratio was listed in Table 40.

TABLE 40

IC method for $PO_4^{3-}$, $Cl^-$, $SO_4^{2-}$ content measurement

| Parameters | Value |
| --- | --- |
| Column | Dionex Ionpac ™ CS12A RFIC ™ 4 × 250 mm Analytical |
| Mobile Phase | 25 mM NaOH |
| Injection volume | 25 μL |
| Flow rate | 1.0 mL/min |
| Cell temperature | 35° C. |
| Column temperature | 35° C. |
| Current | 80 mA |
| Run Time | $PO_4^{3-}$, $SO_4^{2-}$: 28.0 min; |
| | $Cl^-$: 28 min for samples 812608-08-A1/A3/B4/C2, |
| | 6.0 min for samples 812608-12-A/16-A/21-A2/ |
| | 23-A2/14-A3_D |

Dynamic Vapor Sorption

Dynamic Vapor Sorption (DVS) was measured via a SMS (Surface Measurement Systems) DVS Intrinsic. The relative humidity at 25° C. were calibrated against deliquescence point of LiCl, $Mg(NO_3)_2$ and KCl. Actual parameters for DVS test were listed in Table 41.

TABLE 41

Parameters for DVS test

| Parameters | Value |
| --- | --- |
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH |
| | 5% RH from 90% RH to 95% RH |

Solution NMR

Solution NMR was collected on Bruker 400M NMR Spectrometer using DMSO-d6.

Preparation Procedure for pH Buffers

Stock Solution Preparation 0.2 M Hydrochloric acid: Add 8.25 mL of concentrated hydrochloric acid into a 500 mL volumetric flask. Dilute to volume with purified water and mix well.

0.2 M Sodium hydroxide: Weigh 2.0 g of sodium hydroxide into a 250 mL volumetric flask. Dissolve it with appropriate volume of purified water and dilute to volume. Mix well.

0.2 M Potassium chloride: Weigh 2.98 g of potassium chloride into a 200 mL volumetric flask. Dissolve it with appropriate volume of purified water and dilute to volume. Mix well.

0.2 M Potassium phosphate monobasic: Weigh 5.44 g of monobasic potassium phosphate ($KH_2PO_4$) into a 200 mL volumetric flask. Add appropriate volume of purified water and sonicate until all the solids are completely dissolved. Dilute to volume with purified water and mix well.

0.2 M Potassium biphthalate solution: Weigh 8.17 g of potassium biphthalate [$KHC_6H_4(COO)_2$] into a 200 mL volumetric flask. Add appropriate volume of purified water and sonicate until all solids are completely dissolved. Dilute to volume with purified water and mix well.

pH 2.0 Buffer: Transfer 25 mL of 0.2 M potassium chloride solution to a 100 mL volumetric flask, add 6.5 mL of 0.2 M hydrochloric acid solution. Add sufficient purified water closely to the target volume and adjust to pH 2.0. Dilute to volume with purified water, mix well and check the pH with a pH meter.

pH 5.0 Buffer: Transfer 12.5 mL of 0.2 M potassium biphthalate solution and 5.6 mL of 0.2 M sodium hydroxide solution in a 50 mL volumetric flask. Add sufficient purified water closely to the target volume and adjust to pH 5.0. Dilute to volume with purified water, mix well and check the pH with a pH meter.

pH 7.0 Buffer: Transfer 12.5 mL of 0.2 M potassium phosphate monobasic solution and 7.28 mL of 0.2 M sodium hydroxide solution to a 50 mL volumetric flask. Add sufficient purified water closely to the target volume and adjust to pH 7.0. Dilute to volume with purified water, mix well and check the pH with a pH meter.

Example 10

Predictive Modeling for Brain Penetration

Compound 2 was evaluated for predictive characteristics that would allow for entry of the compound through the blood brain barrier (BBB). A multiple parameter score ("myMPO") factored physico-chemical properties to predict BBB penetration. The exercise was performed with a number of CNS drugs as comparators. The higher the score (5 being ideal) the better the chance of CNS penetration. Although different conclusions may be drawn from the exercise, one conclusion is that Compound 2 is toward the bottom of this list, yet it does overlap with drugs that do cross the barrier well enough to be effective. Table 42 provides the analysis for Compound 2, in particular, and reference is made to FIG. 32 for the comparators. Thus, predictive modeling suggests Compound 2 to be a brain penetrant, although relatively weak.

TABLE 42

| MPO | NAME | molLogP | molWeight | nof_HBD | molPSA | pKa_mb |
|---|---|---|---|---|---|---|
| 3.389315 | Cpd 2 | 3.660375 | 468.238617 | 2 | 70.923172 | 8.196222 |

Example 11

Pharmacokinetics and Relative Bioavailability of Two Suspension Formulations of Compound 2 Following a Single Oral Dose in Beagle Dogs The purpose of the study is to dose two suspension formulations of Compound 2 at two dose levels by gavage to Beagle dogs and to collect blood samples for the determination of plasma concentrations, derivation of pharmacokinetic parameters and to determine the relative bioavailability of the two suspension formulations. The pharmacokinetics of Compound 2 would be evaluated following oral administration in capsules and the relative bioavailability of this dosage form to the oral liquid formulations was determined.

This study involves the dosing of the test item by the oral route over three periods separated by a 7 days washout period as outlined in Table 43, Table 44, and Table 45. The third period of the study outlined in Table 45 is considered to be optional and will only be performed at the Sponsor's request. Prior to the day of dosing, food will be removed from the dogs at 4:00 pm and reintroduced 2 hrs after dosing.

TABLE 43

| Period 1 Compound 2 Formulation 1 (pH about 2) | | | | | | | |
|---|---|---|---|---|---|---|---|
| Dose Sequence | Dose (mg/kg) | Dosing Day | Dose Volume (mL/kg) | Dosing Solution Concentration (mg/mL) | Number of Animals and Sex* | Frequency of Dosing | Observation Period |
| 1 | 2 | 1 | 0.2 | 10 | 3 males ID #'s 001, 002, 003 | Once | 24-hrs |
| 2 | 5 | | 0.5 | 10 | 3 males ID #'s 004, 005, 006 | Once | 24-hrs |

TABLE 44

Period 2 Compound 2 Formulation 2 (pH about 3)

| Dose Sequence | Dose (mg/kg) | Dosing Day | Dose Volume (mL/kg) | Dosing Solution Concentration (mg/mL) | Number of Animals and Sex* | Frequency of Dosing | Observation Period |
|---|---|---|---|---|---|---|---|
| 1 | 2 | At least a 7 day washout | 0.2 | 10 | 3 males ID #'s 001, 002, 003 | Once | 24-hrs |
| 2 | 5 | from Period 1 | 0.5 | 10 | 3 males ID #'s 004, 005, 006 | Once | 24-hrs |

TABLE 45

Period 3 Compound 2 in Capsule Form

| Dose Sequence | Dose (mg/kg) | Dosing Day | Capsules for Dosing | Number of Animals and Sex* | Frequency of Dosing | Observation Period |
|---|---|---|---|---|---|---|
| 1 | 2 | At least a 7 day washout | The appropriate amount of Compound 2 powder will be loaded into capsules | 3 males ID #'s 001, 002, 003 | Once | 24-hrs |
| 2 | 5 | out from Period 1 | | 3 males ID #'s 004, 005, 006 | Once | 24-hrs |

For oral administration of the formulations, the test item was administered via a stomach tube followed by the administration of 10 mL of tap water. For oral administration of capsules, the capsule was placed on the back of the tongue to encourage swallowing followed by administration of 10 mL of tap water. The oral cavity was then be inspected to make sure the capsule was swallowed. The actual volume of dosing formulation administered will be calculated based on the animal's most recently scheduled body weight.

More specifically, male beagle dogs were administered oral doses of 2 and 5 mg/kg of Compound 2 as solutions in Formulation #1 (Table 43) and Formulation #2 (Table 44) tolerated dosing well with mild vomiting observed in only one dog administered 5 mg/kg Compound 2 in Formulation #2 (Table 44).

The pharmacokinetic parameters for Compound 2 in solution as Formulation #1 (Table 43) and Formulation #2 (Table 44) along with data for the dosing of Compound 2 powder in capsule (Table 45) are presented in Table 46.

TABLE 46

Pharmacokinetic Parameters for Compound 2 in Male Beagle Dogs Following Oral Dosing with Two (2) Liquid Formulations (Table 43 and 44) or Powder in Capsule (Table 45)

| Dog ID | $C_{max}$ ng/ml | $T_{max}$ hr | $AUC_{0-TLast}$ ng-hr/mL | $AUC_{0-\infty}$ ng-hr/mL | $K_{el}$ $hr^{-1}$ | $t_{1/2}$ hr | Vz/F L/Kg | CL/F L/hr/kg | $MRT_{obs}$ hr |
|---|---|---|---|---|---|---|---|---|---|
| Formulation #1 (Table 43), 2 mg/k | | | | | | | | | |
| 001 | 8.69 | 4 | 87 | 92 | 0.133 | 5.2 | 165 | 22 | 8.64 |
| 002 | 7.27 | 5 | 77 | 82 | 0.124 | 5.6 | 197 | 24 | 9.26 |
| 003 | 4.37 | 5 | 45 | 49 | 0.116 | 6.0 | 350 | 41 | 10.05 |
| Mean | 6.78 | 4.7 | 70 | 74 | 0.124 | 5.6 | 237 | 29 | 9.32 |
| SD | 2.20 | 0.6 | 22 | 22 | 0.008 | 0.4 | 99 | 10 | 0.71 |
| % CV | 32 | 12 | 31 | 30 | 7 | 7 | 42 | 35 | 8 |
| Formulation #1 (Table 43), 5 mg/kg | | | | | | | | | |
| 004 | 15.51 | 4 | 190 | 204 | 0.115 | 6.0 | 213 | 25 | 9.72 |
| 005 | 46.76 | 3 | 453 | 475 | 0.136 | 5.1 | 77 | 11 | 8.6 |
| 006 | 21.15 | 4 | 198 | 204 | 0.162 | 4.3 | 152 | 25 | 7.82 |
| Mean | 27.81 | 3.7 | 280 | 294 | 0.138 | 5.1 | 147 | 20 | 8.71 |
| SD | 16.65 | 0.6 | 149 | 157 | 0.023 | 0.9 | 68 | 8 | 0.96 |
| % CV | 60 | 16 | 53 | 53 | 17 | 17 | 46 | 41 | 11 |
| Formulation #2 (Table 44), 2 mg/kg | | | | | | | | | |
| 001 | 19.72 | 4 | 146 | 148 | 0.179 | 3.9 | 75 | 13 | 7.31 |
| 002 | 10.43 | 5 | 115 | 120 | 0.145 | 4.8 | 114 | 17 | 9.2 |
| 003 | 4.59 | 5 | 44 | 47 | 0.125 | 5.5 | 341 | 43 | 8.96 |

TABLE 46-continued

| | | | | | | | | | |
|---|---|---|---|---|---|---|---|---|---|
| Mean | 11.58 | 4.7 | 102 | 105 | 0.150 | 4.7 | 177 | 24 | 8.49 |
| SD | 7.63 | 0.6 | 52 | 52 | 0.027 | 0.8 | 143 | 16 | 1.03 |
| % CV | 66 | 12 | 52 | 50 | 18 | 18 | 81 | 66 | 12 |
| Formulation #2 (Table 44), 5 mg/kg | | | | | | | | | |
| 004 | 17.70 | 3 | 151 | 159 | 0.129 | 5.4 | 243 | 31 | 8.44 |
| 005 | 34.08 | 5 | 342 | 357 | 0.142 | 4.9 | 98 | 14 | 8.7 |
| 006 | 14.91 | 3 | 141 | 146 | 0.153 | 4.5 | 223 | 34 | 7.71 |
| Mean | 22.23 | 3.7 | 211 | 221 | 0.142 | 4.9 | 188 | 27 | 8.28 |
| SD | 10.36 | 1.2 | 113 | 118 | 0.012 | 0.4 | 79 | 11 | 0.51 |
| % CV | 47 | 31 | 54 | 54 | 9 | 9 | 42 | 41 | 6 |
| Powder in Capsule (Table 45), 2 mg/kg | | | | | | | | | |
| 006 | 9.55 | 3 | 53 | 58 | 0.293 | 2.4 | 118 | 35 | 5.15 |
| 007 | 13.83 | 3 | 49 | ND | ND | ND | ND | ND | ND |
| 008 | 21.31 | 3 | 112 | 122 | 0.314 | 2.2 | 52 | 16 | 5.30 |
| Mean | 14.90 | 3.0 | 71 | 90 | 0.304 | 2.3 | 85 | 25 | 5.23 |
| SD | 5.95 | 0.0 | 35 | 45 | 0.015 | 0.1 | 47 | 13 | 0.10 |
| % CV | 40 | 0 | 49 | 51 | 5 | 5 | 55 | 51 | 2 |
| Powder in Capsule (Table 45), 5 mg/kg | | | | | | | | | |
| 011 | 43.79 | 3 | 191 | 215 | 0.255 | 2.7 | 91 | 23 | 5.79 |
| 012 | 14.66 | 6 | 139 | 142 | 0.183 | 3.8 | 192 | 35 | 7.62 |
| 013 | 18.21 | 3 | 107 | 122 | 0.261 | 2.7 | 156 | 41 | 5.92 |
| Mean | 25.55 | 4.3 | 146 | 160 | 0.233 | 3.1 | 147 | 33 | 6.44 |
| SD | 15.89 | 1.5 | 42 | 49 | 0.043 | 0.6 | 51 | 9 | 1.02 |
| % CV | 62 | 35 | 29 | 31 | 19 | 21 | 35 | 28 | 16 |

ND-Not determine, due to an inadequate number of time points to define the terminal phase. The linear correlation coefficient for the terminal phase ranged from 0.98-1.00. The extrapolation of $AUC_{0-TLast}$ to $AUC_{0-\infty}$ ranged from 1.84-12.48%.
The descriptive statistics were recalculated to match the format presented for the data with Formulations #1 (Table 43) and #2 (Table 44).

Following oral administration of Compound 2 at doses of 2 and 5 mg/kg as solutions in each of Formulation #1 (Table 43) and Formulation #2 (Table 44) and as powder in capsule (Table 45), the plasma concentrations of Compound 2 above the limit of quantitation (0.5 ng/mL) were observed in all dogs, as a single representative species, by 0.5 hr post dosing.

$T_{max}$ values that were similar for Formulation #1 (Table 43), Formulation #2 (Table 44), and powder in capsule (Table 45) at both doses and ranged from 3.0-4.7 hrs. Mean plasma half lives ($t_{1/2}$), systemic clearance (CL/F), volume of distribution (Vz/F) and mean residence times for Formulation #1 (Table 43), Formulation #2 (Table 44), and powder in capsule (Table 45) at both doses ranging from 2.3-5.6 hrs, 20-33 L/kg/hr, 85-237 L/kg and 5.23-9.32 hrs, respectively.

For each formulation, the increase of the mean $C_{max}$ and $AUC_{0-\infty}$ was compared for a dose increase of 2 mg/kg to 5 mg/kg (2.5-fold). The values for $C_{max}$ and $AUC_{0-\infty}$ were 4.1 and 4.0 for Formulation #1 (Table 43), 1.9 and 2.1 for Formulation #2 (Table 44), and 1.7 and 1.8 for powder in capsule (Table 45), respectively.

The plasma exposure to Compound 2 at doses of 2 mg/kg and 5 mg/kg for Formulation #1 (Table 43), Formulation #2 (Table 44), and powder in capsule (Table 45) were compared by using both the $C_{max}$ and $AUC_{0-\infty}$ of Compound 2. No statistically significant difference was observed between the mean $C_{max}$ and $AUC_{0-\infty}$ values at each dose when comparing Formulation #1 (Table 43), Formulation #2 (Table 44), and powder in capsule (Table 45). Variable plasma concentrations, however, were observed between the three dogs at each dose level and formulation.

The relative bioavailability of Compound 2, based on $C_{max}$ and $AUC_{0-\infty}$ for Formulation #1 (Table 43) to Formulation #2 (Table 44), may be compared for individual dogs, because the same individual dogs received both Formulation #1 (Table 43) and Formulation #2 (Table 44). For $C_{max}$ and $AUC_{0-\infty}$ the mean relative bioavailability was 0.70±0.26 and 0.78±0.24 at a dose of 2 mg/kg and 1.22±0.30 and 1.34±0.06 at a dose of 5 mg/kg, respectively (n=3, ±SD).

In summary, the present disclosure includes a study of oral dosing of beagle dogs by oral gavage with Compound 2, prepared in Formulation #1 (Table 43), Formulation #2 (Table 44), and as a powder in capsules (Table 45). Compound 2 appeared in the plasma by 0.5 hr post dosing, with mean $C_{max}$ values ranging from 6.78-14.90 ng/mL and 22.23-27.81 ng/mL at doses of 2 and 5 mg/kg, respectively and mean $T_{max}$ values ranging from 3.0-4.7 hrs across both doses. The plasma half-lives, clearance, volume of distribution, and mean residence time did not display apparent statistically significant differences across doses and formulations. Additional review, however, may demonstrate an unexpected benefit. Nevertheless, the data demonstrate that Increasing the dose by 2.5-fold resulted in greater than (synergistic) dose proportional increases in the mean $C_{max}$ and mean $AUC_{0-\infty}$ for Compound 2 for Formulation #1 (Table 43) and close to dose proportional increases for Formulation #2 (Table 44) and powder in capsule (Table 45).

There were no significant differences between Formulation #1 (Table 43), Formulation #2 (Table 44), and powder in capsule (Table 45) when comparing the mean $C_{max}$, $AUC0-_{TLast}$, and $AUC_{0-\infty}$ values at doses of 2 and 5 mg/kg. Calculation of the relative bioavailability of Compound 2 in Formulation #1 (Table 43) compared to Formulation #2 (Table 44) based on $C_{max}$ and $AUC_{0-\infty}$ resulted in mean values of 0.70 and 0.78 at a dose of 2 mg/kg and 1.22 and 1.34 at a dose of 5 mg/kg, respectively.

Figure 33A:
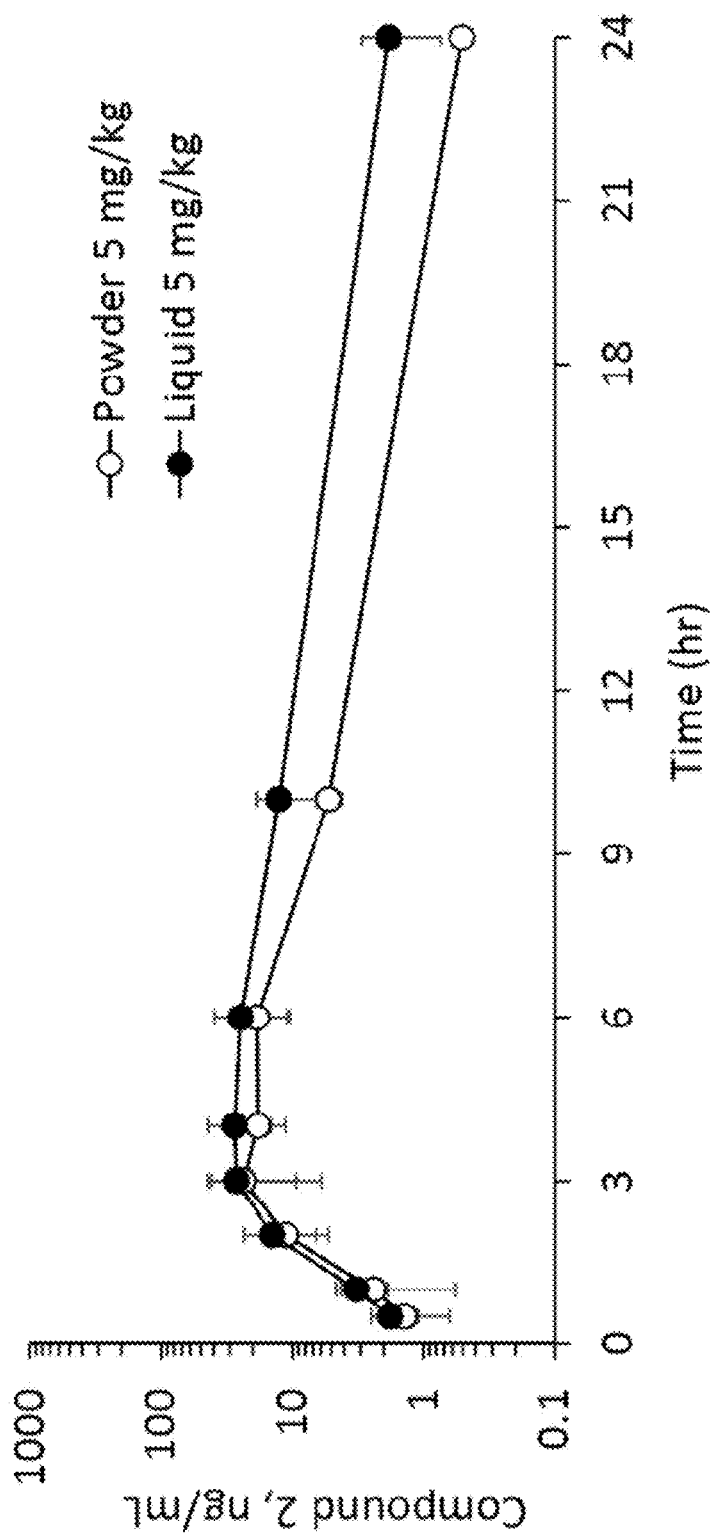
FIG. 33A and FIG. 33B show the results of a comparison made between a powder capsule formulation and a liquid formulation of Compound 2, demonstrating comparable a plasma concentration as between the two formulations in a single species.
Figure 33B:
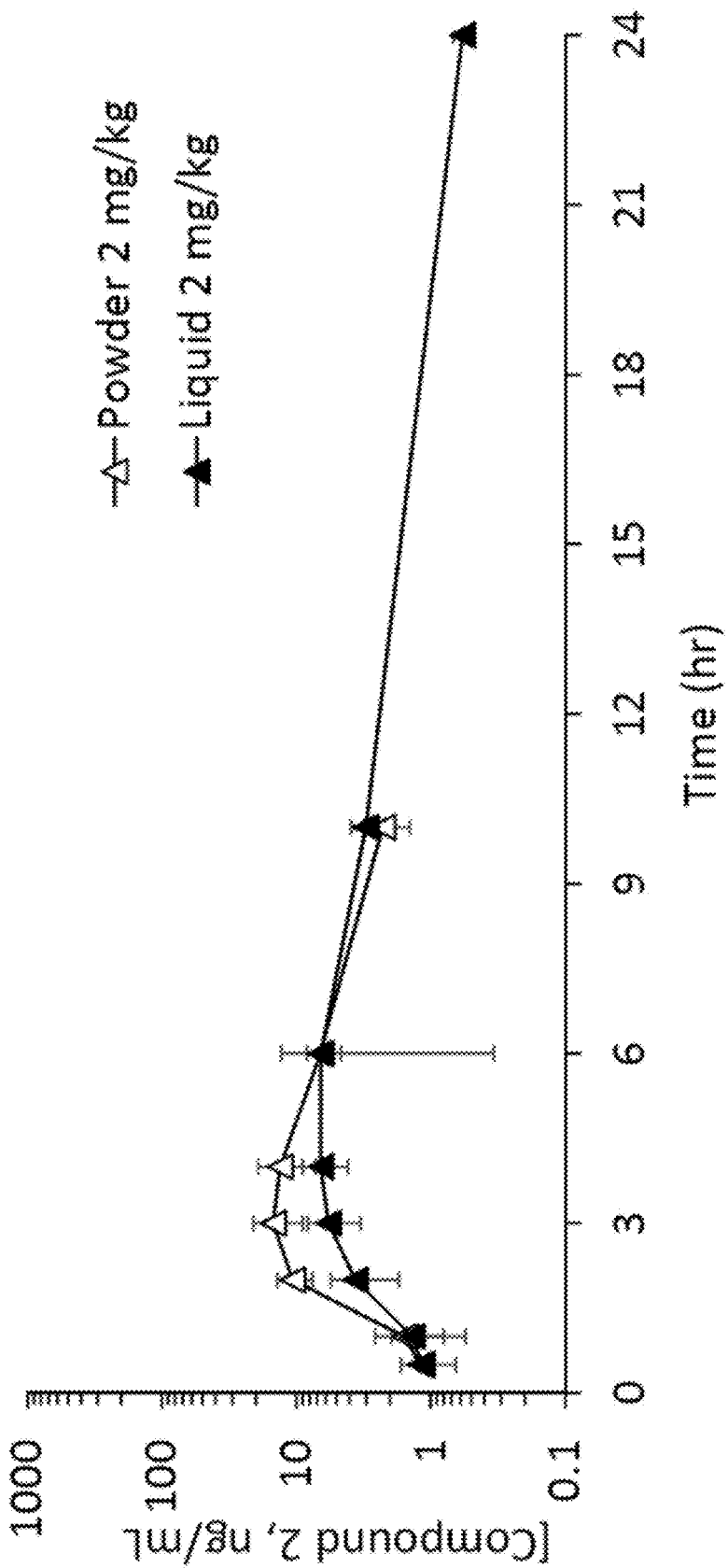

Thus, while a direct correlation from dog-to-human pharmacokinetics may not be available, the results of a direct comparison of dog-to-dog pharmacokinetics upon administration of an oral capsule formulation to an oral liquid formulation may be made. The results demonstrate bioavailability of a capsule formulation to be similar to the two oral liquid formulations. As shown in FIGS. 33A and 33B, the plasma concentration of Compound 2 in the tested species is comparable between the powder formulation (Table 45) and the liquid formulation (Table 43). The plasma half-lives, clearance, volume of distribution and mean residence time did not display substantial differences across doses and formulations.

Embodiments and Aspects

Embodiments and aspects of the present disclosure, which may be incorporated in various combinations, include:

1. A method of treating diffuse intrinsic pontine glioma (DIPG) in a subject in need thereof, the method comprising: administering a therapeutically effective amount of a compound of formula (2):

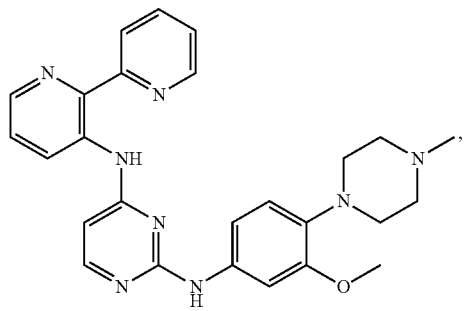

(2)

or a crystalline salt thereof.

2. The method of Embodiment 1, wherein the crystalline salt is an acid addition salt.

3. The method of Embodiment 2, wherein the acid addition salt is a hydrochloric acid salt.

4. The method of Embodiment 3, wherein the hydrochloric acid salt is monovalent.

5. The method of any one of Embodiments 1-4, wherein the crystalline salt form is anhydrous.

6. The method of any one of Embodiments 1-5, wherein the subject is a pediatric patient.

7. The method of any one of Embodiments 1-5, wherein the subject is about 1 week of age to about 22 years of age.

8. The method of any one of Embodiments 1-7, wherein the subject is about 18 years of age or less.

9. The method of any one of Embodiments 1-8, wherein the subject is about 10 years of age or less.

10. The method of any one of Embodiments 1-9, wherein the subject is about 8 years of age or less.

11. The method of any one of Embodiments 1-10, wherein the subject is about 6 years of age or less.

12. The method of any one of Embodiments 1-11, wherein the DIPG is newly diagnosed or recurrent.

13. The method of any one of Embodiments 1-12, wherein the DIPG is characterized as a pontine tumor with a histologic diagnosis of infiltrating glioma, grades II to IV.

14. The method of any one of Embodiments 1-13, further comprising administering radiation therapy.

15. The method of Embodiment 14, wherein the administration of radiation occurs prior to administration of the compound or crystalline salt thereof. 16. The method of Embodiment 15, wherein the administration of radiation occurs after the administration of the compound or crystalline salt thereof.

17. The method of Embodiment 16, wherein the administration of radiation occurs both prior to and after administration of the compound or crystalline salt thereof.

18. The method of any one of Embodiments 1-17, further comprising administering one or more additional therapeutic agent.

19. The method of any one of Embodiments 1-18, wherein the administration of the compound or crystalline salt thereof reduces or alleviates one or more signs or symptoms associated with DIPG.

20. The method of Embodiment 19, wherein the one or more signs or symptoms are selected from the group consisting of modifications of speech or speech patterns, loss of ability to move one side of the subject's face or body, loss of balance, loss of coordination, trouble with walking or movement, vision problems, hearing problems, headache, nausea, vomiting, unusual sleepiness, modification in energy level, behavioral changes, and change in performance in school.

21. The method of any one of Embodiments 1-20, wherein the administration of the compound or crystalline salt thereof achieves progression free survival.

22. The method of Embodiment 21, wherein the progression free survival is one month or more, two months or more, three months or more, four months or more, five months or more, six months or more, seven months or more, eight months or more, nine months or more, ten months or more, eleven months or more, one year or more, two years or more, three years or more, or five years or more.

23. The method of any one of Embodiments 1-22, further comprising one or more of debulking of tumor growth or cerebrospinal fluid diversion.

24. The method of any one of Embodiments 1-23, wherein the subject has a predetermined genetic profile comprising one or more mutations in an ACVR1 gene.

25. The method of Embodiment 24, wherein the one or more mutations in an ACVR1 gene is an activating mutation.

26. The method of Embodiment 25, wherein the one or more mutations in the ACVR1 gene encode an ACVR1 polypeptide comprising an amino acid substitution at one or more amino acid residues selected from R206H, G328V, R258G, or a combination thereof.

27. The method of Embodiment 26, wherein the amino acid substitution in the ACVR1 polypeptide comprises R206H.

28. The method of any one of Embodiments 1-27, wherein the compound or crystalline salt thereof is administered orally.

29. The method of any one of Embodiments 1-28, wherein the compound or crystalline salt thereof is administered in a dose ranging from about 10 mg to about 320 mg per week.

30. The method of Embodiment 29, wherein the dose ranges from about 30 mg to about 240 mg per week.

31. The method of Embodiment 29, wherein the dose ranges from about 60 mg to about 180 mg per week.

32. The method of Embodiment 29, wherein the dose ranges from about 30 mg to about 120 mg per week.

33. The method of Embodiment 29, wherein the dose ranges from about 60 mg to about 120 mg per week.

34. The method of Embodiment 29, wherein the dose is about 60 mg per week.

35. The method of Embodiment 29, wherein the dose is about 90 mg per week.

36. The method of Embodiment 29, wherein the dose is about 120 mg per week.

37. The method of Embodiment 29, wherein the dose is about 180 mg per week.

38. The method of Embodiment 29, wherein the dose is about 210 mg per week.

39. The method of Embodiment 29, wherein the dose is about 240 mg per week.

40. The method of any one of Embodiments 1-28, wherein the compound or crystalline salt thereof is administered in a weekly dose of about 320 mg or less, about 240 mg or less, about 210 or less, about 180 or less, about 120 or less, about 90 or less, about 60 or less, or about 30 or less.

41. The method of Embodiment 40, wherein the dose is about 60 mg or less per week.

42. The method of Embodiment 40, wherein the dose is about 90 mg or less per week.

43. The method of Embodiment 40, wherein the dose is about 120 mg or less per week.

44. The method of Embodiment 40, wherein the dose is about 180 mg or less per week.

45. The method of Embodiment 40, wherein the dose is about 210 mg or less per week.

46. The method of Embodiment 40, wherein the dose is about 240 mg or less per week.

47. The method of any one of Embodiments 29-46, wherein the dose is administered once a week.

48. The method of any one of Embodiments 29-46, wherein the dose is administered in two or more sub-doses, three or more sub-doses, four or more sub-doses, five or more sub-doses, six or more sub-doses, or daily sub-doses over the course of a week.

49. The method of any one of Embodiments 29-48, wherein the subject is a pediatric patient and the dose is between about 80% to 100% of the dose range.

50. The method of Embodiment 49, wherein the dose is adjusted to about 80%, 85%, 90%, or 95% of the dose range.

51. The method of Embodiment 49, wherein the dose ranges from about 8 mg to about 320 mg per week.

52. The method of Embodiment 49, wherein the dose ranges from about 24 mg to about 240 mg per week.

53. The method of Embodiment 49, wherein the dose ranges from about 24 mg to about 120 mg per week.

54. The method of Embodiment 49, wherein the dose ranges from about 48 mg to about 120 mg per week.

55. The method of Embodiment 49, wherein the dose ranges from about 72 mg to about 120 mg per week.

56. The method of Embodiment 49, wherein the dose ranges from about 96 mg to about 120 mg per week 57. The method of any one of Embodiments 1-56, wherein the subject has a predetermined hepcidin level of at least about 0.1 ng/mL.

58. The method of Embodiment 57, wherein the predetermined hepcidin level ranges from about 10 ng/mL to about 200 ng/mL.

59. The method of any one of Embodiments 1-58, further comprising determining a hepcidin level in the subject after the compound or crystalline salt thereof is administered.

60. The method of any one of Embodiments 1-59, further comprising determining a transferrin saturation level in the subject after the compound or crystalline salt thereof is administered.

61. The method of Embodiment 60, wherein the transferrin saturation level is less than about 50%.

62. The method of Embodiment 60, wherein the transferrin saturation level is less than about 45%.

63. The method of Embodiment 60, wherein the transferrin saturation level is less than about 40%.

64. The method of any one of Embodiments 1-63, wherein the compound or crystalline salt thereof is administered over one or more treatment cycles, wherein each cycle comprises four weeks.

65. The method of Embodiment 64, wherein the method further comprises one or more treatment holidays between treatment cycles.

66. The method of Embodiment 65, wherein the treatment holiday is selected from one day, two days, three days, four days, five days, six days, one week, two weeks, three weeks, or four weeks.

67. A method for treating a disease or disorder susceptible to inhibition of ACVR1 comprising administering to a subject in need thereof a therapeutically effective amount of a compound of formula (2):

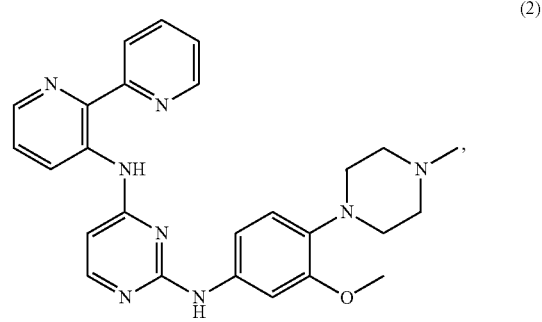 [SMILES: COc1cc(Nc2nccc(Nc3cccnc3-c3ccccn3)n2)ccc1N1CCN(C)CC1]

(2)

or a crystalline salt thereof, wherein the compound is administered in a dose ranging from about 10 mg to about 320 mg per week.

68. The method of Embodiment 67, wherein the dose ranges from about 30 mg to about 240 mg per week.

69. The method of Embodiment 67, wherein the dose ranges from about 60 mg to about 180 mg per week.

70. The method of Embodiment 67, wherein the dose ranges from about 30 mg to about 120 mg per week.

71. The method of Embodiment 67, wherein the dose ranges from about 60 mg to about 120 mg per week.

72. The method of Embodiment 67, wherein the dose is about 60 mg per week.

73. The method of Embodiment 67, wherein the dose is about 90 mg per week.

74. The method of Embodiment 67, wherein the dose is about 120 mg per week.

75. The method of Embodiment 67, wherein the dose is about 180 mg per week.

76. The method of Embodiment 67, wherein the dose is about 210 mg per week.

77. The method of Embodiment 67, wherein the dose is about 240 mg per week.

78. The method of any one of Embodiments 67-77, wherein the compound or crystalline salt thereof is administered in a weekly dose of about 320 mg or less, about 240 mg or less, about 210 or less, about 180 or less, about 120 or less, about 90 or less, about 60 or less, or about 30 or less.

79. The method of Embodiment 78, wherein the dose is about 60 mg or less per week.

80. The method of Embodiment 78, wherein the dose is about 90 mg or less per week.

81. The method of Embodiment 78, wherein the dose is about 120 mg or less per week.

82. The method of Embodiment 78, wherein the dose is about 180 mg or less per week.

83. The method of Embodiment 78, wherein the dose is about 210 mg or less per week.

84. The method of Embodiment 78, wherein the dose is about 240 mg or less per week.

85. The method of any one of Embodiments 67-84, wherein the subject is a pediatric patient and the dose is between about 80% to 100% of the dose range.

86. The method of Embodiment 85, wherein the dose is about 80%, 85%, 90%, or 95% of the dose range.

87. The method of Embodiment 85, wherein the dose ranges from about 8 mg to about 320 mg per week.

88. The method of Embodiment 85, wherein the dose ranges from about 24 mg to about 240 mg per week.

89. The method of Embodiment 85, wherein the dose ranges from about 24 mg to about 120 mg per week.

90. The method of Embodiment 85, wherein the dose ranges from about 48 mg to about 120 mg per week.

91. The method of Embodiment 85, wherein the dose ranges from about 72 mg to about 120 mg per week.

92. The method of Embodiment 85, wherein the dose ranges from about 96 mg to about 120 mg per week 93. The method of any one of Embodiments 67-92, wherein the dose is administered once a week.

94. The method of any one of Embodiments 67-92, wherein the dose is administered in two sub-doses over the course of a week.

95. The method of any one of Embodiments 67-92, wherein the dose is administered in three sub-doses over the course of a week.

96. The method of any one of Embodiments 67-92, wherein the dose is administered in four sub-doses over the course of a week.

97. The method of any one of Embodiments 67-92, wherein the dose is administered in five sub-doses over the course of a week.

98. The method of any one of Embodiments 67-92, wherein the dose is administered in six sub-doses over the course of a week.

99. The method of any one of Embodiments 67-92, wherein the dose is administered in daily sub-doses.

100. The method of any one of Embodiments 67-99, wherein the subject has a predetermined genetic profile comprising one or more mutations in an ACVR1 gene.

101. The method of Embodiment 100, wherein the one or more mutations in an ACVR1 gene is an activating mutation.

102. The method of Embodiment 101, wherein the one or more mutations in the ACVR1 gene encode an ACVR1 polypeptide comprising an amino acid substitution at one or more amino acid residues selected from R206H, G328V, R258G, or a combination thereof.

103. The method of Embodiment 102, wherein the amino acid substitution in the ACVR1 polypeptide comprises R206H.

104. The method of any one of Embodiments 67-103, wherein the compound or crystalline salt thereof is administered orally.

105. The method of any one or Embodiments 67-104, wherein the disease or disorder is selected from one or more of diffuse intrinsic pontine glioma, a pontine tumor with a histologic diagnosis of infiltrating glioma of grades II to IV, a solid tumor, fibrodysplasia ossificans progressiva, and anemia of chronic disease.

106. The method of Embodiment 105, wherein the compound or crystalline salt thereof is administered as a solid dose formulation.

107. The method of Embodiment 105, wherein the compound or crystalline salt thereof is administered as a liquid dose formulation.

108. The method of any one of Embodiments 67-107, wherein the subject is monitored for hepcidin levels to determine any modification of dose.

109. The method of any one of Embodiments 67-108, wherein the subject is monitored for accumulation of the compound in one or more organ.

110. The method of any one of Embodiments 67-109, wherein the crystalline salt is an acid addition salt.

111. The method of Embodiment 110, wherein the acid addition salt is a hydrochloric acid salt.

112. The method of Embodiment 111, wherein the hydrochloric acid salt is monovalent.

113. The method of any one of Embodiments 110-112, wherein the crystalline salt form is anhydrous.

114. An oral solid pharmaceutical composition comprising one or more pharmaceutically acceptable excipient and a compound of formula (2):

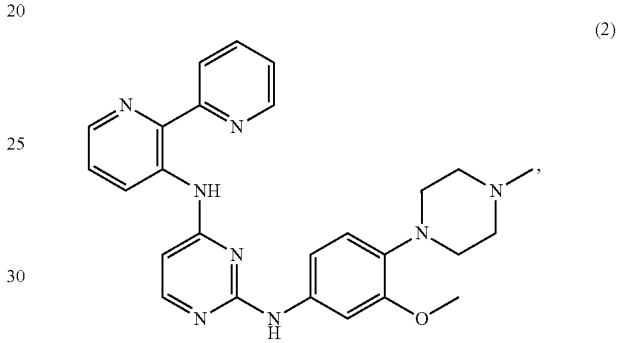

or a crystalline salt thereof, wherein the compound is formulated in a strength of between about 5 mg to about 125 mg based on free base weight.

115. The pharmaceutical composition of Embodiment 114, wherein the crystalline salt is an acid addition salt.

116. The pharmaceutical composition of Embodiment 115, wherein the acid addition salt is a hydrochloric acid salt.

117. The pharmaceutical composition of Embodiment 116, wherein the hydrochloric acid salt is monovalent.

118. The pharmaceutical composition of any one of Embodiments 115-117, wherein the crystalline salt form is anhydrous.

119. The pharmaceutical composition of any one of Embodiments 114-118, wherein the pharmaceutical composition is a gelatin capsule.

120. The pharmaceutical composition of Embodiment 119, wherein the gelatin capsule is (i) 5 mg, (ii) 25 mg, or (iii) 125 mg strength, based on free base weight.

121. The pharmaceutical composition of Embodiment 119, wherein the gelatin capsule is (i) 30 mg, (ii) 60 mg, (iii) 90 mg, or (iv) 120 mg strength, based on free base weight.

122. The pharmaceutical composition of any one of Embodiments 114-121, wherein the one or more pharmaceutical excipients are selected from microcrystalline cellulose, lactose monohydrate, croscarmellose sodium, magnesium stearate, or a combination thereof.

123. An oral liquid pharmaceutical composition comprising a compound of formula (2):

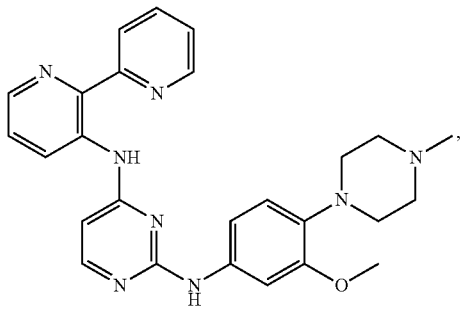

or a crystalline salt thereof; and
(i) one or more buffering agents;
(ii) optionally, one or more preservatives;
(iii) optionally, one or more solvents;
(iv) optionally, one or more taste masking agents; and
(v) optionally, one or more further pH-adjusting agent.

124. The pharmaceutical composition of Embodiment 123, wherein the crystalline salt is an acid addition salt.

125. The pharmaceutical composition of Embodiment 124, wherein the acid addition salt is a hydrochloric acid salt.

126. The pharmaceutical composition of Embodiment 125, wherein the hydrochloric acid salt is monovalent.

127. The pharmaceutical composition of any one of Embodiments 124-126, wherein the crystalline salt form is anhydrous.

128. The pharmaceutical composition of any one of Embodiments 123-127, wherein the composition has a pH of between about 2.0 and about 5.0.

129. The pharmaceutical composition of Embodiment 128, wherein the composition has a pH of between about 2.0 and about 3.5.

130. The pharmaceutical composition of Embodiment 128, wherein the composition has a pH of about 2.0.

131. The pharmaceutical composition of any one of Embodiments 123-130, wherein the buffering agent is selected from citric acid, tartaric acid, malic acid, or acetic acid.

132. The pharmaceutical composition of Embodiment 131, wherein the buffering agent is malic acid.

133. The pharmaceutical composition of Embodiment 132, wherein the malic acid is DL-malic acid.

134. The pharmaceutical compositions of any one of Embodiments 123-133 comprising one or more preservatives.

135. The pharmaceutical composition of Embodiment 134, wherein the preservative is selected from benzoic acid, sodium benzoate, methyl para-hydroxy benzoate, propyl para-hydroxy benzoate, or propylene glycol.

136. The pharmaceutical composition of Embodiment 135, wherein the preservative is benzoic acid.

137. The pharmaceutical composition of Embodiment 136, wherein the benzoic acid is a preservative and a buffering agent.

138. The pharmaceutical composition of any one of Embodiments 123-137 comprising one or more taste masking agent.

139. The pharmaceutical composition of Embodiment 138, wherein the taste masking agent is selected from sucralose, glycerin, cyclodextrin, HP-β-cyclodextrin, α-cyclodextrin, β-cyclodextrin, or a combination thereof.

140. The pharmaceutical composition of Embodiment 138, wherein the taste masking agent is a combination of HP-β-cyclodextrin and sucralose.

141. The pharmaceutical composition of any one of Embodiments 123-140, wherein the composition comprises a compound of formula (2) or a crystalline salt thereof in a concentration of about 10 mg/mL.

142. The pharmaceutical composition of any one of Embodiments 123-141, wherein the composition comprises malic acid in a concentration up to about 6.7 mg/mL.

143. The pharmaceutical composition of Embodiment 142, wherein the composition comprises malic acid in a concentration of about 1.3 mg/mL.

144. The pharmaceutical composition of any one of Embodiments 123-143, wherein the composition comprises HP-β-cyclodextrin in a concentration of up to about 300 mg/mL.

145. The pharmaceutical composition of Embodiment 144, wherein the composition comprises HP-β-cyclodextrin in a concentration of up to about 150 mg/mL.

146. The pharmaceutical composition of any one of Embodiments 123-145, wherein the composition comprises sucralose in a concentration of up to about 2.0 mg/mL.

147. The pharmaceutical composition of Embodiment 146, wherein the composition comprises sucralose in a concentration of about 1.0 mg/mL.

148. The pharmaceutical composition of any one of Embodiments 123-147, wherein the composition comprises benzoic acid in a concentration of up to about 3.0 mg/mL.

149. The pharmaceutical composition of Embodiment 148, wherein the composition comprises benzoic acid in a concentration of up to about 2.0 mg/mL.

150. The pharmaceutical composition of any one of Embodiments 123-149, wherein the pH is adjusted to about 2.0 with hydrochloric acid.

151. The pharmaceutical composition of any one of Embodiments 123-150, wherein the solvent is water.

152. A crystalline form of a salt of compound (2)

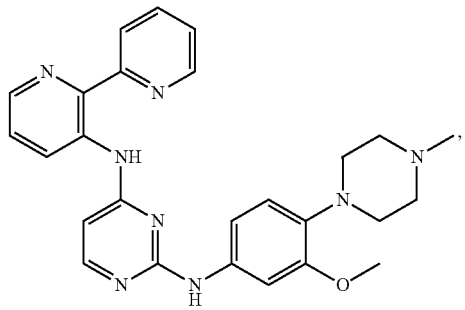

$N^4$-(2,2'-bipyridin-3-yl)-$N^2$-(3-methoxy-4-(4-methylpiperazin-1-yl)phenyl)pyrimidine-2,4-diamine.

153. The crystalline form of Embodiment 152, wherein the salt is a pharmaceutically acceptable salt.

154. The crystalline form of Embodiment 153, wherein the pharmaceutically acceptable salt is an HCl salt.

155. The crystalline form of any one of Embodiments 152-154, comprising Form A.

156. The crystalline form of any one of Embodiments 152-154, consisting essentially of Form A.

157. The crystalline form of Embodiment 155 or 156, wherein the Form A is substantially free from impurities.

158. A compound Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt.

159. A compound Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) comprising one or more 2θ values selected from: 13.53, 16.14, 17.67, 18.38, 24.96, and 28.18.

160. The Form A of Embodiment 159, wherein the form is characterized by two or more of the listed 2θ values.

161. The Form A of Embodiment 159, wherein the form is characterized by three or more of the listed 2θ values.

162. The Form A of Embodiment 159, wherein the form is characterized by four or more of the listed 2θ values.

163. The Form A of Embodiment 159, wherein the form is characterized by five or more of the listed 2θ values.

164. The Form A of Embodiment 159, wherein the form is characterized by all six of the listed 2θ values.

165. The Form A of any one of Embodiments 157-164, further characterized by one or more 2θ values selected from: 6.71, 19.25, 23.98, and 29.60.

166. The Form A of Embodiment 165, wherein the form is characterized by two or more of the listed 2θ values.

167. The Form A of Embodiment 165, wherein the form is characterized by three or more of the listed 2θ values.

168. The Form A of Embodiment 165, wherein the form is characterized by all four of the listed 2θ values.

169. The Form A of any one of Embodiments 158-168, wherein the X-ray powder diffractometer is used in reflection mode with an X-ray wavelength of Cu kα, Kα1 (Å): 1.540598, Kα2 (Å): 1.544426, with a Kα2/Kα1 intensity ratio of 0.50, and an X-ray tube setting of 45 kV, 40 mA.

170. The Form A of any one of Embodiments 158-169, wherein the 2θ values are within +/-0.2 2θ.

171. A compound Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) substantially the same as FIG. 12.

172. A compound Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an endotherm at one or more of 196.2° C., 214.8° C., and 274.0° C.

173. The Form A of Embodiment 172, further characterized by a peak endotherm at one or more of 198.9° C., 218.0° C., and 275.9° C.

174. The Form A of Embodiment 172 or 173, further characterized by an onset temperature of 274.0° C.

175. The Form A of any one of Embodiments 172-174, further characterized by weight loss of 1.7% up to 150° C.

176. A compound Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by a TGA-DSC thermogram substantially the same as FIG. 15.

177. A pharmaceutical composition comprising the crystalline form of any one of Embodiments 152-176.

178. The pharmaceutical composition of Embodiment 176, as a solid dose formulation.

179. The oral solid pharmaceutical composition of any one of Embodiments 114-122, wherein the compound is the crystalline form of any one of Embodiments 152-176.

180. The pharmaceutical composition of Embodiment 176, as a liquid dose formulation.

181. The oral liquid pharmaceutical composition of any one of Embodiments 123-151, wherein the compound is the crystalline form of any one of Embodiments 152-176.

182. The method of any one of Embodiments 1-113, wherein the compound is the crystalline form of any one of Embodiments 152-176.

Further embodiments and aspects of the present disclosure, which may be incorporated in various combinations, include:

1'. A method of treating a disease in a subject in need thereof, the method comprising:
administering a treatment regimen comprising an ACVR1 inhibitor to the subject having a predetermined genetic profile comprising one or more mutations in an ACVR1 gene, the ACVR1 inhibitor having the following structure (I):

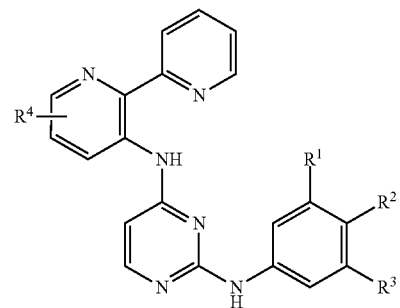

or a stereoisomer, pharmaceutically acceptable salt, tautomer or prodrug thereof,
wherein:
$R^1$ is H or $C_1$-$C_6$ alkoxy;
$R^2$ is $C_1$-$C_6$ alkoxy or heterocyclyl;
$R^3$ is halo or $C_1$-$C_6$ alkoxy; and
$R^4$ is H or $C_1$-$C_6$ alkyl.

2'. The method of Embodiment 1', wherein the disease is cancer.

3'. The method of Embodiment 2', wherein the cancer is a solid cancer.

4'. The method of Embodiment 2' or 3', wherein the cancer is a brain cancer, a uterine cancer, an ovarian cancer, a cervical cancer, a lung cancer, a breast cancer, a colon cancer, a gastrointestinal cancer, a hematopoietic or lymphoid cancer, a skin cancer, or a bone cancer.

5'. The method of any one of Embodiments 2'-4', wherein the cancer is a brain cancer.

6'. The method of Embodiment 5', wherein the brain cancer is a brain stem glioma.

7'. The method of Embodiment 5' or 6', wherein the brain cancer is diffuse intrinsic pontine glioma (DIPG).

8'. The method of any one of Embodiments 2'-4', wherein the cancer is a uterine, ovarian, or cervical cancer.

9'. The method of Embodiment 8', wherein the uterine cancer is an endometrial cancer.

10'. The method of any one of Embodiments 2'-4', wherein the cancer is a lung cancer.

11'. The method of Embodiment 10', wherein the lung cancer is a non-small cell lung cancer.

12'. The method of any one of Embodiments 2'-4', wherein the cancer is a breast cancer.

13'. The method of any one of Embodiments 2'-4', wherein the cancer is a colon cancer.

14'. The method of any one of Embodiments 2'-4', wherein the cancer is a melanoma.

15'. The method of Embodiment 1', wherein the disease is fibrodysplasia ossificans progressiva.

16'. A method of treating diffuse intrinsic pontine glioma (DIPG) in a subject in need thereof, the method comprising:
administering a treatment regimen comprising an ACVR1 inhibitor to the subject the ACVR1 inhibitor having the following structure (I):

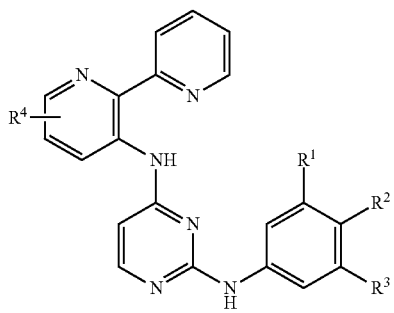

(I)

or a stereoisomer, pharmaceutically acceptable salt, tautomer or prodrug thereof,
wherein:
$R^1$ is H or $C_1$-$C_6$ alkoxy;
$R^2$ is $C_1$-$C_6$ alkoxy or heterocyclyl;
$R^3$ is halo or $C_1$-$C_6$ alkoxy; and
$R^4$ is H or $C_1$-$C_6$ alkyl.

17'. The method of any one of Embodiments 1'-16', wherein the treatment regimen further comprises administering a therapeutic agent.

18'. The method of any one of Embodiments 1'-17', wherein the subject is a pediatric subject.

19'. A method of treating fibrodysplasia ossificans progressiva (FOP) in a subject in need thereof, the method comprising:
administering a treatment regimen to the subject, the treatment regimen comprising an ACVR1 inhibitor and a therapeutic agent, the ACVR1 inhibitor having the following structure (I):

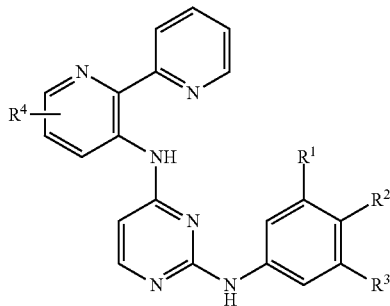

(I)

or a stereoisomer, pharmaceutically acceptable salt, tautomer or prodrug thereof,
wherein:
$R^1$ is H or $C_1$-$C_6$ alkoxy;
$R^2$ is $C_1$-$C_6$ alkoxy or heterocyclyl;
$R^3$ is halo or $C_1$-$C_6$ alkoxy; and
$R^4$ is H or $C_1$-$C_6$ alkyl.

20'. The method of any one of Embodiments 16'-19', wherein the subject has a predetermined genetic profile comprising one or more mutations in an ACVR1 gene.

21'. The method of any one of Embodiments 1'-15' or 20', wherein the one or more mutations in the ACVR1 gene comprise a missense mutation, a frameshift mutation, a splice site mutation, or a combination thereof.

22'. The method of any one of Embodiments 1'-15', 20', or 21', wherein the one or more mutations comprise (P197F198)L, C509S, D185G, D185N, D433N, E38FS, F265S, G225D, G264S, G328E, G328R, G328V, G328W, G356D, G50C, H320Y, I323V, K31E, K345Q, L196P, L251S, M34I, N100D, N481I, P115S, P455A, Q207E, Q278P, R201I, R206C, R206H, R258G, R258S, R307Q, R325A, R375C, R375P, R401M, R490H, S130F, S226N, S41F, S440G, S469C, S56L, T298S, V234M, V91M, W98R, or a combination thereof.

23'. The method of any one of Embodiments 1'-15' or 20', wherein the one or more mutations in the ACVR1 gene comprise a missense mutation.

24'. The method of Embodiment 21' or 23', wherein the missense mutation is C509S, D185N, D433N, F265S, G225D, H320Y, I323V, K31E, K345Q, M34I, N100D, N481I, P115S, P455A, Q278P, R206C, R401M, S130F, S226N, S41F, S41F, S440G, S469C, S56L, T298S, V234M, V91M, or W98R.

25'. The method of any one of Embodiments 1'-16' or 20', wherein the one or more mutations in the ACVR1 gene comprise a frameshift mutation.

26'. The method of Embodiment 21' or 25', wherein the frameshift mutation is E38fs.

27'. The method of any one of Embodiments 1'-15' or 20', wherein the one or more mutations in the ACVR1 gene comprise a splice site mutation.

28'. The method of Embodiment 21' or 27', wherein the splice site mutation is G264S.

29'. The method of any one of Embodiments 1'-15' or 20'-22', wherein the one or more mutations in the ACVR1 gene comprise R206H, G328V, R258G, or a combination thereof.

30'. The method of any one of Embodiments 1'-15', 20'-22', or 29', wherein the one or more mutations in the ACVR1 gene comprise R206H.

31'. The method of any one of Embodiments 1'-30', wherein the subject has a predetermined hepcidin level of at least about 0.1 ng/mL.

32'. The method of Embodiment 31', wherein the predetermined hepcidin level ranges from about 10 ng/mL to about 35 ng/mL.

33'. The method of any one of Embodiments 1'-32', further comprising determining a hepcidin level after the ACVR1 inhibitor is administered.

34'. The method of any one of Embodiments 1'-33', wherein the subject has a predetermined transferrin saturation level of less than about 50%.

35'. The method of any one of Embodiments 1'-33', wherein the subject has a predetermined transferrin saturation level of less than about 45%.

36'. The method of any one of Embodiments 1'-33', wherein the subject has a predetermined transferrin saturation level of less than about 40%.

37'. The method of any one of Embodiments 1'-36', wherein the ACVR1 inhibitor is administered in a dose ranging from about 10 mg to about 320 mg per day.

38'. The method of Embodiment 37', wherein the dose ranges from about 30 mg to about 240 mg per day.

39'. The method of Embodiment 37' or 38', wherein the dose ranges from about 60 mg to about 180 mg per day.

40'. The method of any one of Embodiments 37'-39', wherein the dose is about 25 mg per day; about 30 mg per day; about 60 mg per day; about 120 mg per day; about 125 mg per day; about 180 mg per day; about 240 mg per day; about 250 mg per day; about 320 mg per day; or about 325 mg per day.

41'. The method of any one of Embodiments 1'-40', wherein $R^1$ is H.

42'. The method of any one of Embodiments 1'-40', wherein $R^1$ is $C_1$-$C_6$ alkoxy.

43'. The method of Embodiment 42', wherein the $C_1$-$C_6$ alkoxy is methoxy.

44'. The method of any one of Embodiments 1'-43', wherein $R^2$ is $C_1$-$C_6$ alkoxy.

45'. The method of Embodiment 44', wherein the $C_1$-$C_6$ alkoxy is methoxy.

46'. The method of any one of Embodiments 1'-45', wherein $R^2$ is heterocyclyl.

47'. The method of Embodiment 46', wherein the heterocyclyl is optionally substituted piperazinyl.

48'. The method of Embodiment 47', wherein the optionally substituted piperazinyl is substituted with $C_1$-$C_6$ alkyl or $C_1$-$C_6$ hydroxylalkyl.

49'. The method of any one of Embodiments 1'-48', wherein $R^3$ is halo.

50'. The method of Embodiment 49', wherein the halo is chloro.

51'. The method of any one of Embodiments 1'-48', wherein $R^3$ is $C_1$-$C_6$ alkoxy.

52'. The method of Embodiment 51', wherein the $C_1$-$C_6$ alkoxy is methoxy.

53'. The method of any one of Embodiments 1'-52', wherein $R^4$ is H.

54'. The method of any one of Embodiments 1'-52', wherein $R^4$ is $C_1$-$C_6$ alkyl.

55'. The method of Embodiment 54', wherein the $C_1$-$C_6$ alkyl is methyl.

56'. The method of any one of Embodiments 1'-40', having the following structure:

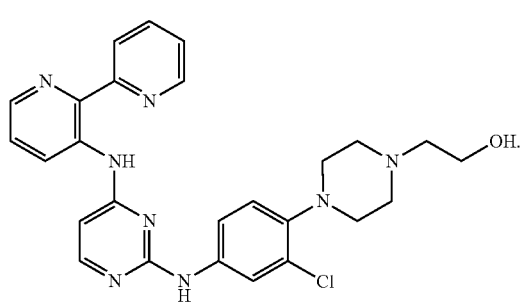 [SMILES: OCCN1CCN(c2ccc(Nc3nccc(Nc4cccnc4-c4ccccn4)n3)cc2Cl)CC1]

57'. The method of any one of Embodiments 1'-40', having the following structure:

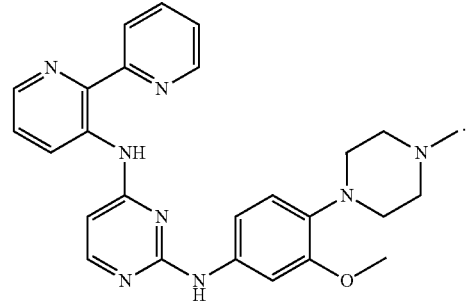 [SMILES: COc1cc(Nc2nccc(Nc3cccnc3-c3ccccn3)n2)ccc1N1CCN(C)CC1]

58'. The method of any one of Embodiments 1'-40', having the following structure:

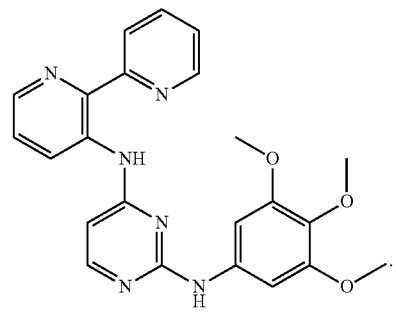 [SMILES: COc1cc(Nc2nccc(Nc3cccnc3-c3ccccn3)n2)cc(OC)c1OC]

59'. The compound of any one of Embodiments 1'-40', having the following structure:

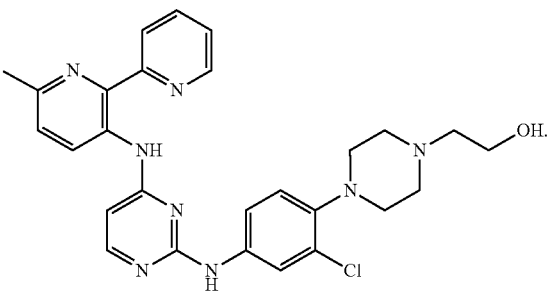 [SMILES: Cc1ccc(Nc2ccnc(Nc3ccc(N4CCN(CCO)CC4)c(Cl)c3)n2)c(-c2ccccn2)n1]

60'. The method of any one of Embodiments 1'-40', having the following structure:

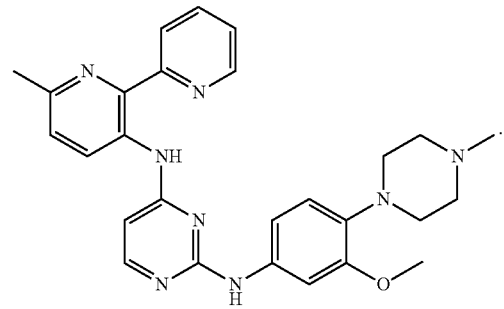

61'. The method of any one of Embodiments 1'-40', having the following structure:

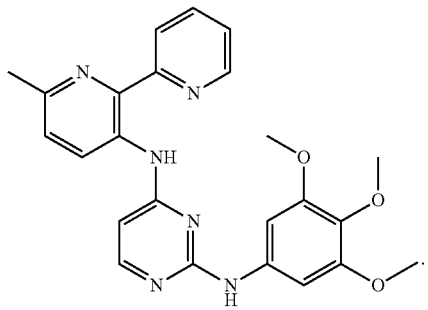

62'. The method of any one of Embodiments 17'-61', wherein the therapeutic agent is selected from:
a retinoic acid receptor gamma agonist; an mTOR inhibitor; an Activin A antibody; a kinase inhibitor; an ACVR1 antibody; a TAK1 inhibitor; a phosphodiesterase inhibitor; a HDAC inhibitor; a chemotherapy agent; an immunotherapeutic agent; a cell therapy; a peptide or tumor lysate vaccine; irinotecan; a TTRNA-DC vaccine with GM-CSF, TTRNA-xALT; an integrin inhibitor; an IL-12 therapy; an antineoplaston therapy; Imiquimod; an oncolytic adenovirus; a WEE1 inhibitor; a WT1 protein derived peptide vaccine; a pegylated Interferon Alfa 2b; a kinase antibody; a smoothened inhibitor; a tubulin inhibitor; a telomerase inhibitor; a CD40 agonist; a GM-CSF agonist; an IDO inhibitor; and
a radioactive Iodine labeled monoclonal antibody 8H9.64.

63'. The method of any one of Embodiments 17'-62', wherein the therapeutic agent is selected from:
a retinoic acid receptor gamma agonist; an mTOR inhibitor; an Activin A antibody; a kinase inhibitor; an ACVR1 antibody; a TAK1 inhibitor; and a phosphodiesterase inhibitor.

64'. The method of any one of Embodiments 17'-62', wherein the therapeutic agent is selected from:
a HDAC inhibitor; a chemotherapy agent; an immunotherapeutic agent; a cell therapy; a peptide or tumor lysate vaccine; irinotecan; a TTRNA-DC vaccine with GM-CSF, TTRNA-xALT; an integrin inhibitor; an IL-12 therapy; an antineoplaston therapy; Imiquimod; an oncolytic adenovirus; a WEE1 inhibitor; a WT1 protein derived peptide vaccine;
a pegylated Interferon Alfa 2b; a kinase antibody; a kinase inhibitor; a smoothened inhibitor; a tubulin inhibitor; a telomerase inhibitor; a CD40 agonist; a GM-CSF agonist;
an IDO inhibitor; and a radioactive Iodine labeled monoclonal antibody 8H9.

65'. The method of any one of Embodiments 17'-64', wherein the kinase inhibitor inhibits cyclin dependent kinase (CDK).

66'. The method of Embodiment 65', wherein the CDK is CDK9 or CDK7.

67'. The method of Embodiment 65', wherein the CDK is CDK9.

68'. The method of Embodiment 66' or 67', wherein the CDK9 inhibitor is a siRNA, alvocidib, or a prodrug thereof, dinaciclib, or a combination thereof.

69'. The method of any one of Embodiments 17'-64', wherein the kinase inhibitor inhibits phosphoinositide 3-kinase (PI3K).

70'. The method of any one of Embodiments 17'-62' or 64', wherein the immunotherapeutic agent is an immune checkpoint inhibitor.

71'. The method of Embodiment 70', wherein the immune checkpoint inhibitor is a PD-1 inhibitor.

72'. The method of Embodiment 71', wherein the PD-1 inhibitor is Pembrolizumab, Nivolumab, or a combination thereof.

73'. The method of Embodiment 70', wherein the immune checkpoint inhibitor is a PD-L1 inhibitor.

74'. The method of Embodiment 73', wherein the PD-L1 inhibitor is Atezolizumab, Avelumab, Durvalumab, or a combination thereof.

75'. The method of any one of Embodiments 17'-64', wherein the kinase antibody comprises a drug conjugate.

76'. The method of any one of Embodiments 17'-65', wherein:
the retinoic acid receptor gamma agonist is Palovarotene; the mTOR inhibitor is Rapamycin or everolimus; the Activin A antibody is REGN2447; the kinase inhibitor is saracatinib, momelotinib, dorsomorphin, imatinib, Crizotinib, Dasatinib, bevacizumab, erlotinib, vandetanib, ribociclib, crenolanib, abemaciclib, ONC201, Cilengitide, alvocidib, or a prodrug thereof; the phosphodiesterase inhibitor is Dipyridamole; the HDAC inhibitor is SAHA, vorinostat, or panobinostat; the chemotherapy agent is melphalan, gemcitabine, temozolomide, cyclophosphamide, fludarabine, doxorubicin, irinotecan, lenalidomide, valproic acid, chloroquine, carboplatin, etoposide, ifosfamide, pomalidomide, or lomustine;
the immunotherapeutic agent is MDV9300; the cell therapy comprises autologous dendritic cells; the peptide or tumor lysate vaccine comprises a K27M peptide or Rindopepimut; the irinotecan is administered with convection enhanced delivery; the integrin inhibitor is cilengitide; the antineoplaston therapy is Atengenal or Astugenal; the oncolytic adenovirus is DNX-2401; the WEE1 inhibitor is AZD1775; the WT1 protein derived peptide vaccine is DSP-7888; the kinase antibody is Nimotuzumab, erbitux, or ABT-414; the smoothened inhibitor is Vismodegib; the tubulin inhibitor is Mebendazole;
the telomerase inhibitor is Imetelstat; the CD40 agonist is APX005M; the GM-CSF agonist is Sargramostim with reovirus; or the DO inhibitor is indoximod.

77'. The method of any one of Embodiments 1'-76', wherein the treatment regimen further comprises surgical resection, radiation therapy, or a combination thereof.

78'. The method of any one of Embodiments 1'-77', wherein the pharmaceutically acceptable salt is an acid addition salt.

79'. The method of Embodiment 78', wherein the acid addition salt is a hydrochloric acid salt.

The various embodiments described above may be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments may be modified, if necessary, to employ concepts of the various patents, applications, and publications to provide yet further embodiments.

Test compounds for the experiments described herein were employed in free or salt form, as noted.

The specific responses observed may vary according to and depending on the particular active compound selected or whether there are present carriers, as well as the type of formulation and mode of administration employed, and such expected variations or differences in the results are contemplated in accordance with practice of the present invention.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) comprising one or more 2θ values selected from: 13.53, 16.14, 17.67, 18.38, 24.96, and 28.18.

2. The Form A of claim 1, wherein the form is substantially free from impurities.

3. The Form A of claim 1, wherein the form is characterized by an XRPD selected from the group consisting of:
   (a) an XRPD comprising two or more of the listed 2θ values;
   (b) an XRPD comprising three or more of the listed 2θ values;
   (c) an XRPD comprising four or more of the listed 2θ values;
   (d) an XRPD comprising five or more of the listed 2θ values; and
   (e) an XRPD comprising each of the six listed 2θ values.

4. The Form A of claim 1, further characterized by one or more 2θ values selected from: 6.71, 19.25, 23.98, and 29.60.

5. The Form A of claim 4, wherein the form is characterized by an XRPD selected from the group consisting of:
   (a) an XRPD comprising two or more of the listed 2θ values;
   (b) an XRPD comprising three or more of the listed 2θ values; and
   (c) an XRPD comprising each of the four listed 2θ values.

6. Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an x-ray diffraction pattern (XRPD) substantially the same as FIG. 12.

7. Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by an endotherm at one or more of 196.2° C., 214.8° C., and 274.0° C.

8. The Form A of claim 7, further characterized by a peak endotherm at one or more of 198.9° C., 218.0° C., and 275.9° C.

9. The Form A of claim 8, further characterized by an onset temperature of 274.0° C.

10. The Form A of claim 9, further characterized by weight loss of 1.7% up to 150° C.

11. Form A of $N^4$-(2,2'-bipyridin-3-yl)-$N^2$-(3-methoxy-4-(4-methylpiperazin-1-yl)phenyl)pyrimidine-2,4-diamine anhydrous hydrochloric acid salt characterized by a TGA-DSC thermogram substantially the same as FIG. 15.

* * * * *